United States Patent
Taggi et al.

(10) Patent No.: US 8,288,375 B2
(45) Date of Patent: Oct. 16, 2012

(54) FUNGICIDAL BICYCLIC PYRAZOLES

(75) Inventors: Andrew Edmund Taggi, Newark, DE (US); Thomas Martin Stevenson, Newark, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 190 days.

(21) Appl. No.: 12/746,827

(22) PCT Filed: Dec. 10, 2008

(86) PCT No.: PCT/US2008/086227
§ 371 (c)(1),
(2), (4) Date: Jun. 8, 2010

(87) PCT Pub. No.: WO2009/076440
PCT Pub. Date: Jun. 18, 2009

(65) Prior Publication Data
US 2010/0273775 A1 Oct. 28, 2010

Related U.S. Application Data

(60) Provisional application No. 61/007,410, filed on Dec. 12, 2007.

(51) Int. Cl.
| C07D 471/04 | (2006.01) |
| C07D 487/04 | (2006.01) |
| C07D 498/04 | (2006.01) |
| A01N 43/90 | (2006.01) |
| A01P 3/00 | (2006.01) |

(52) U.S. Cl. .................. 514/230.2; 544/91; 544/105
(58) Field of Classification Search .......... 544/91, 544/105; 514/230.2
See application file for complete search history.

(56) References Cited

FOREIGN PATENT DOCUMENTS
| EP | 0531901 A2 | 3/1993 |
| WO | 97/02262 A1 | 1/1997 |
| WO | 02/094833 A1 | 11/2002 |
| WO | 2006/052568 A2 | 5/2006 |

OTHER PUBLICATIONS

J.A. Townes et al., The Development of New Bicyclic Pyrazole-Based Cytokine Synthesis Inhibitors, Bioorganic & Medicinal Chemistry Letters, vol. 14, No. 19, p. 4945-4948, (2004).

*Primary Examiner* — Kahsay T Habte
(74) *Attorney, Agent, or Firm* — Charlene Gross Sternberg

(57) ABSTRACT

Disclosed are compounds of Formulae 1 and 1a, N-oxides, and salts thereof,

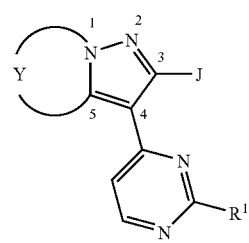

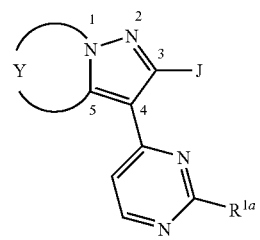

wherein $R^1$, $R^{1a}$, Y, and J are as defined in the disclosure.

Also disclosed are compositions containing the compounds of Formula 1 and methods for controlling plant disease caused by a fungal pathogen comprising applying an effective amount of a compound or a composition of the invention. Further disclosed is a method for preparing compounds of Formula 1 from compounds of Formula 1a.

14 Claims, No Drawings

FUNGICIDAL BICYCLIC PYRAZOLES

FIELD OF THE INVENTION

This invention relates to certain bicyclic pyrazoles, their N-oxides, salts and compositions, and methods of their use as fungicides.

BACKGROUND OF THE INVENTION

The control of plant diseases caused by fungal plant pathogens is extremely important in achieving high crop efficiency. Plant disease damage to ornamental, vegetable, field, cereal, and fruit crops can cause significant reduction in productivity and thereby result in increased costs to the consumer. Many products are commercially available for these purposes, but the need continues for new compounds which are more effective, less costly, less toxic, environmentally safer or have different sites of action.

Certain bicyclic pyrazoles have been previously described. World Patent Publication WO 02/094833 discloses pyrrole derivatives of Formula i as anti-cancer agents

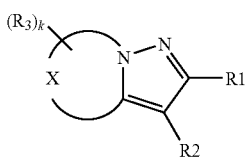

(i)

wherein, inter alia, the ring containing X is a five or six membered saturated ring; X is C, O or S; $R_3$ is independently, H or alkyl; k is 1 to 8; R1 is unsubstituted or substituted phenyl and R2 is pyrimidine optionally substituted with alkoxy and alkylamino.

SUMMARY OF THE INVENTION

This invention is directed to compounds of Formula 1 (including all geometric and stereoisomers), N-oxides, and salts thereof, agricultural compositions containing them and their use as fungicides:

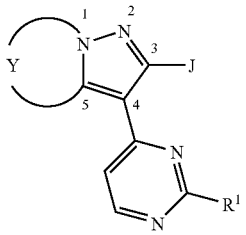

1 wherein
Y is taken together with the contiguous nitrogen and carbon linking atoms (which are identified with "1" and "5" respectively) to form a 5-to 7-membered fused nonaromatic heterocyclic ring, including ring members, in addition to the contiguous nitrogen and carbon linking atoms, selected from the group consisting of $C(R^2)_2$, O, S, $NR^3$, —$C(R^2)$=$C(R^2)$—, —$C(R^2)$=N—, —N=N—, C(=O), C(=S), C(=$NR^4$), S(=O)$_p$ (=$NR^4)_q$ and $SiR^{5a}R^{5b}$;

each $R^2$ is independently H, halogen, cyano, hydroxy, —CHO, —NHCHO, —$N_3$, —N=C=O, —N=C=S, —SH, —C(=O)$NH_2$, —C(=O)NHCN, —C(=O)$OR^6$, —C(=O)NHOR$^{6a}$, $C_1$-$C_5$ alkyl, $C_2$-$C_5$ alkenyl, $C_2$-$C_5$ alkynyl, $C_3$-$C_6$ cycloalkyl, $C_3$-$C_6$ halocycloalkyl, $C_3$-$C_6$ cycloalkenyl, $C_1$-$C_5$ haloalkyl, $C_1$-$C_5$ alkoxy, $C_1$-$C_5$ haloalkoxy, $C_3$-$C_6$ cycloalkoxy, $C_2$-$C_5$ alkenyloxy, $C_3$-$C_5$ haloalkenyloxy, $C_2$-$C_5$ alkynyloxy, $C_2$-$C_5$ alkylcarbonyl, $C_2$-$C_5$ alkylcarbonyloxy, $C_2$-$C_5$ haloalkylcarbonyloxy, $C_3$-$C_5$ alkoxycarbonylalkoxy, $C_1$-$C_5$ alkylthio, $C_1$-$C_5$ haloalkylthio, $C_3$-$C_6$ cycloalkylthio, $C_2$-$C_5$ alkyl(thiocarbonyl), $C_2$-$C_5$ alkylthio(thiocarbonyl), $C_1$-$C_5$ alkylsulfinyl, $C_1$-$C_5$ haloalkylsulfinyl, $C_3$-$C_6$ cycloalkylsulfinyl, $C_1$-$C_5$ alkylsulfonyl, $C_1$-$C_5$ haloalkylsulfonyl, $C_3$-$C_6$ cycloalkylsulfonyl, $C_3$-$C_5$ trialkylsilyl, $C_3$-$C_5$ halotrialkylsilyl, $C_1$-$C_5$ alkylamino, $C_2$-$C_5$ haloalkylamino, $C_3$-$C_6$ cycloalkylamino, $C_2$-$C_5$ dialkylamino or $C_3$-$C_5$ halodialkylamino; or two $R^2$ attached to adjacent ring carbon atoms are taken together to form a 5-to 7-membered fused carbocyclic or heterocyclic ring, optionally substituted with 1-3 substituents selected from $C_1$-$C_4$ alkyl, $C_1$-$C_4$ haloalkyl, $C_1$-$C_4$ alkoxy, $C_1$-$C_4$ haloalkoxy, halogen, hydroxy, amino, cyano and nitro;

each $R^3$ is independently H, —CN, —C(=O)$NH_2$, —C(=O)NHCN, —CHO, —NHCHO, —C(=O)$OR^6$, —C(=O)NHOR$^{6a}$, hydroxy, $C_1$-$C_5$ alkyl, $C_2$-$C_5$ alkenyl, $C_2$-$C_5$ alkynyl, $C_3$-$C_6$ cycloalkyl, $C_3$-$C_6$ halocycloalkyl, $C_3$-$C_6$ cycloalkenyl, $C_4$-$C_{10}$ cycloalkylalkyl, $C_4$-$C_7$ alkylcycloalkyl, $C_5$-$C_7$ alkylcycloalkylalkyl, $C_1$-$C_5$ haloalkyl, $C_2$-$C_5$ alkylcarbonyl, $C_2$-$C_5$ haloalkylcarbonyl, $C_4$-$C_7$ cycloalkylcarbonyl, $C_2$-$C_6$ alkoxycarbonyl, $C_2$-$C_6$ haloalkoxycarbonyl, $C_4$-$C_7$ cycloalkoxycarbonyl, $C_3$-$C_6$ alkoxyalkylcarbonyl, $C_3$-$C_6$ alkoxyalkoxycarbonyl, $C_2$-$C_6$ (alkylthio)carbonyl, $C_2$-$C_6$ alkoxy(thiocarbonyl), $C_2$-$C_6$ alkyl(thiocarbonyl), $C_2$-$C_6$ alkylthio(thiocarbonyl), $C_2$-$C_6$ alkylaminocarbonyl, $C_4$-$C_7$ cycloalkylaminocarbonyl, $C_3$-$C_6$ dialkylaminocarbonyl, $C_2$-$C_6$ alkylamino(thiocarbonyl), $C_3$-$C_6$ dialkylamino(thiocarbonyl), $C_3$-$C_6$ alkoxy(alkyl)aminocarbonyl, $C_1$-$C_5$ alkoxy, $C_1$-$C_5$ haloalkoxy, $C_1$-$C_5$ alkylthio, $C_1$-$C_5$ haloalkylthio, $C_3$-$C_6$ cycloalkylthio, $C_1$-$C_5$ alkylaminosulfonyl, $C_3$-$C_5$ trialkylsilyl or $C_3$-$C_5$ halotrialkylsilyl;

each $R^4$ is independently H, cyano, amino, hydroxy, $C_1$-$C_6$ alkyl, $C_3$-$C_{10}$ cycloalkyl, $C_2$-$C_6$ alkylcarbonyl, $C_2$-$C_6$ haloalkylcarbonyl, $C_1$-$C_6$ alkoxy, phenyl or benzoyl;

each $R^{5a}$ and $R^{5b}$ is independently $C_1$-$C_5$ alkyl, $C_2$-$C_5$ alkenyl, $C_2$-$C_5$ alkynyl, $C_3$-$C_5$ cycloalkyl, $C_3$-$C_6$ halocycloalkyl, $C_4$-$C_{10}$ cycloalkylalkyl, $C_4$-$C_7$ alkylcycloalkyl, $C_5$-$C_7$ alkylcycloalkylalkyl, $C_1$-$C_5$ haloalkyl, $C_1$-$C_5$ alkoxy or $C_1$-$C_5$ haloalkoxy;

each $R^6$ is independently H, $C_1$-$C_6$ alkyl, $C_1$-$C_6$ haloalkyl, $C_3$-$C_6$ cycloalkyl, $C_4$-$C_7$ cycloalkylalkyl, $C_4$-$C_7$ alkylcycloalkyl or benzyl;

each $R^{6a}$ is independently $C_1$-$C_6$ alkyl, $C_1$-$C_6$ haloalkyl, $C_3$-$C_6$ cycloalkyl, $C_4$-$C_7$ cycloalkylalkyl or $C_4$-$C_7$ alkylcycloalkyl;

J is a phenyl or 5-or 6-membered heteroaromatic ring or a naphthalenyl or 8-to 10-membered heteroaromatic bicyclic ring system, each ring or ring system optionally substituted with up to 5 substituents independently selected from $R^7$ on carbon atom ring members and $R^8$ on nitrogen atom ring members; or J is a 5-or 6-membered nonaromatic carbocyclic or heterocyclic ring, optionally including ring members selected from the group consisting of C(=O), C(=S), C(=NR$^4$), SiR$^{5a}$R$^{5b}$ and S(=O)$_p$(=NR$^4$)$_q$, each ring optionally substituted with 1 to 5 substituents independently selected from R$^7$ on carbon atom ring members and R$^8$ on nitrogen atom ring members;

each R$^7$ is independently halogen, C$_1$-C$_6$ alkyl, C$_2$-C$_6$ alkenyl, C$_2$-C$_6$ alkynyl, C$_3$-C$_6$ cycloalkyl, C$_3$-C$_6$ halocycloalkyl, C$_4$-C$_7$ alkylcycloalkyl, C$_1$-C$_6$ haloalkyl, C$_2$-C$_6$ haloalkenyl, cyano, nitro, C$_1$-C$_6$ alkoxy, C$_1$-C$_6$ haloalkoxy, C$_1$-C$_6$ alkylthio, C$_1$-C$_6$ alkylsulfinyl, C$_1$-C$_6$ alkylsulfonyl, C$_1$-C$_6$ haloalkylthio, C$_1$-C$_6$ haloalkylsulfinyl, C$_1$-C$_6$ haloalkylsulfonyl, C$_1$-C$_6$ alkylamino, C$_2$-C$_6$ dialkylamino, C$_2$-C$_6$ alkylcarbonyl, C$_2$-C$_6$ alkoxycarbonyl, C$_2$-C$_6$ alkylaminocarbonyl, C$_3$-C$_6$ dialkylaminocarbonyl or C$_3$-C$_6$-trialkylsilyl;

R$^8$ is C$_1$-C$_3$ alkyl;

R$^1$ is H, —NR$^{9a}$R$^{9b}$, —NR$^{10}$—NR$^{11a}$R$^{11b}$, OR$^{12}$, —N=CR$^{13a}$R$^{13b}$ or —NR$^{10}$N=CR$^{14a}$R$^{14b}$;

each R$^{9a}$ and R$^{11a}$ is independently H, C$_1$-C$_{10}$ alkyl, C$_2$-C$_{10}$ alkenyl, C$_2$-C$_{10}$ alkynyl, C$_1$-C$_{10}$ haloalkyl, C$_2$-C$_{10}$ haloalkenyl, C$_2$-C$_{10}$ haloalkynyl, C$_2$-C$_{10}$ alkoxyalkyl, C$_3$-C$_{10}$ alkoxyalkoxyalkyl, C$_3$-C$_{10}$ alkoxyalkenyl, C$_3$-C$_{10}$ alkoxyalkynyl, C$_3$-C$_{10}$ dialkoxyalkyl, C$_4$-C$_{10}$ trialkoxyalkyl, C$_2$-C$_{10}$ haloalkoxyalkyl, C$_2$-C$_{10}$ alkoxyhaloalkyl, C$_2$-C$_{10}$ haloalkoxyhaloalkyl, C$_1$-C$_{10}$ hydroxyalkyl, C$_2$-C$_{10}$ cyanoalkyl, C$_2$-C$_{10}$ alkylthioalkyl, C$_2$-C$_{10}$ alkylsulfinylalkyl, C$_3$-C$_{10}$ alkylaminoalkyl, C$_3$-C$_{10}$ haloalkylaminoalkyl, C$_5$-C$_{10}$ cycloalkylaminoalkyl, C$_4$-C$_{10}$ dialkylaminoalkyl, C$_4$-C$_{10}$ halodialkylaminoalkyl, C$_6$-C$_{10}$ cycloalkyl(alkyl)aminoalkyl, C$_2$-C$_{10}$ alkylcarbonyl, C$_2$-C$_{10}$ haloalkylcarbonyl, C$_4$-C$_{10}$ cycloalkylcarbonyl, C$_2$-C$_{10}$ alkoxycarbonyl, C$_2$-C$_{10}$ haloalkoxycarbonyl, C$_4$-C$_{10}$ cycloalkoxycarbonyl, C$_3$-C$_{10}$ alkoxyalkylcarbonyl, C$_3$-C$_{10}$ alkoxyalkoxycarbonyl, C$_2$-C$_{10}$ (alkylthio)carbonyl, C$_2$-C$_{10}$ alkoxy(thiocarbonyl), C$_2$-C$_{10}$ alkyl(thiocarbonyl), C$_2$-C$_{10}$ alkylthio(thiocarbonyl), C$_2$-C$_{10}$ alkylaminocarbonyl, C$_4$-C$_{10}$ cycloalkylaminocarbonyl, C$_3$-C$_{10}$ dialkylaminocarbonyl, C$_2$-C$_{10}$ alkylamino(thiocarbonyl), C$_3$-C$_{10}$ dialkylamino(thiocarbonyl), C$_2$-C$_{10}$ alkylsulfonylaminocarbonyl, C$_2$-C$_{10}$ haloalkylsulfonylaminocarbonyl, C$_3$-C$_{10}$ alkoxy(alkyl)aminocarbonyl, C$_1$-C$_{10}$ alkoxy, C$_1$-C$_{10}$ haloalkoxy, C$_3$-C$_{10}$ cycloalkoxy, C$_1$-C$_{10}$ alkylsulfonyl, C$_1$-C$_{10}$ haloalkylsulfonyl, C$_3$-C$_{10}$ cycloalkylsulfonyl, C$_1$-C$_{10}$ alkylaminosulfonyl, C$_2$-C$_{10}$ dialkylaminosulfonyl or —(CR$^{15a}$R$^{15b}$)$_m$R$^{16}$;

each R$^{9b}$ and R$^{11b}$ is independently H, C$_1$-C$_{10}$ alkyl, C$_2$-C$_{10}$ alkenyl, C$_2$-C$_{10}$ alkynyl, C$_1$-C$_{10}$ haloalkyl, C$_2$-C$_{10}$ haloalkenyl, C$_2$-C$_{10}$ haloalkynyl, C$_2$-C$_{10}$ alkoxyalkyl, C$_3$-C$_{10}$ alkoxyalkoxyalkyl, C$_3$-C$_{10}$ alkoxyalkenyl, C$_3$-C$_{10}$ alkoxyalkynyl, C$_3$-C$_{10}$ dialkoxyalkyl, C$_4$-C$_{10}$ trialkoxyalkyl, C$_2$-C$_{10}$ haloalkoxyalkyl, C$_2$-C$_{10}$ alkoxyhaloalkyl, C$_2$-C$_{10}$ haloalkoxyhaloalkyl, C$_1$-C$_{10}$ hydroxyalkyl, C$_2$-C$_{10}$ cyanoalkyl, C$_2$-C$_{10}$ alkylthioalkyl, C$_2$-C$_{10}$ alkylsulfinylalkyl, C$_3$-C$_{10}$ alkylaminoalkyl, C$_3$-C$_{10}$ haloalkylaminoalkyl, C$_5$-C$_{10}$ cycloalkylaminoalkyl, C$_4$-C$_{10}$ dialkylaminoalkyl, C$_4$-C$_{10}$ halodialkylaminoalkyl, C$_6$-C$_{10}$ cycloalkyl(alkyl)aminoalkyl, C$_2$-C$_{10}$ alkylcarbonyl, C$_2$-C$_{10}$ haloalkylcarbonyl, C$_4$-C$_{10}$ cycloalkylcarbonyl, C$_2$-C$_{10}$ alkoxycarbonyl, C$_2$-C$_{10}$ haloalkoxycarbonyl, C$_4$-C$_{10}$ cycloalkoxycarbonyl, C$_3$-C$_{10}$ alkoxyalkylcarbonyl, C$_3$-C$_{10}$ alkoxyalkoxycarbonyl, C$_2$-C$_{10}$ (alkylthio)carbonyl, C$_2$-C$_{10}$ alkoxy(thiocarbonyl), C$_2$-C$_{10}$ alkyl(thiocarbonyl), C$_2$-C$_{10}$ alkylthio(thiocarbonyl), C$_2$-C$_{10}$ alkylaminocarbonyl, C$_4$-C$_{10}$ cycloalkylaminocarbonyl, C$_3$-C$_{10}$ dialkylaminocarbonyl, C$_2$-C$_{10}$ alkylamino(thiocarbonyl), C$_3$-C$_{10}$ dialkylamino(thiocarbonyl), C$_2$-C$_{10}$ alkylsulfonylaminocarbonyl, C$_2$-C$_{10}$ haloalkylsulfonylaminocarbonyl, C$_3$-C$_{10}$ alkoxy(alkyl)aminocarbonyl, C$_1$-C$_{10}$ alkylsulfonyl, C$_1$-C$_{10}$ haloalkylsulfonyl, C$_3$-C$_{10}$ cycloalkylsulfonyl, C$_1$-C$_{10}$ alkylaminosulfonyl, C$_2$-C$_{10}$ dialkylaminosulfonyl or —(CR$^{15a}$R$^{15b}$)$_m$R$^{16}$;

each R$^{9a}$ and R$^{9b}$ pair, or R$^{11a}$ and R$^{11b}$ pair is independently taken together with the nitrogen to which it is attached to form a 3-to 6-membered ring containing ring members selected from carbon and heteroatoms, said ring optionally including ring members selected from the group consisting of NR$^3$, C(=O), C(=S), C(=NR$^4$), SiR$^{5a}$R$^{5b}$ and S(=O)$_p$(=NR$^4$)$_q$, and optionally substituted on carbon ring members with 1 to 4 substituents selected from the group consisting of halogen, —CN, C$_1$-C$_2$ alkyl and C$_1$-C$_2$ alkoxy;

R$^{12}$ is H, C$_1$-C$_{10}$ alkyl, C$_2$-C$_{10}$ alkenyl, C$_2$-C$_{10}$ alkynyl, C$_1$-C$_{10}$ haloalkyl, C$_2$-C$_{10}$ haloalkenyl, C$_2$-C$_{10}$ haloalkynyl, C$_2$-C$_{10}$ alkoxyalkyl, C$_3$-C$_{10}$ alkoxyalkoxyalkyl, C$_3$-C$_{10}$ alkoxyalkenyl, C$_3$-C$_{10}$ alkoxyalkynyl, C$_3$-C$_{10}$ dialkoxyalkyl, C$_4$-C$_{10}$ trialkoxyalkyl, C$_2$-C$_{10}$ haloalkoxyalkyl, C$_2$-C$_{10}$ alkoxyhaloalkyl, C$_2$-C$_{10}$ haloalkoxyhaloalkyl, C$_2$-C$_{10}$ hydroxyalkyl, C$_2$-C$_{10}$ cyanoalkyl, C$_2$-C$_{10}$ alkylthioalkyl, C$_2$-C$_{10}$ alkylsulfinylalkyl, C$_3$-C$_{10}$ alkylaminoalkyl, C$_3$-C$_{10}$ haloalkylaminoalkyl, C$_5$-C$_{10}$ cycloalkylaminoalkyl, C$_4$-C$_{10}$ dialkylaminoalkyl, C$_4$-C$_{10}$ halodialkylaminoalkyl, C$_6$-C$_{10}$ cycloalkyl(alkyl)aminoalkyl, C$_2$-C$_{10}$ alkylcarbonyl, C$_2$-C$_{10}$ haloalkylcarbonyl, C$_4$-C$_{10}$ cycloalkylcarbonyl, C$_2$-C$_{10}$ alkoxycarbonyl, C$_2$-C$_{10}$ haloalkoxycarbonyl, C$_4$-C$_{10}$ cycloalkoxycarbonyl, C$_3$-C$_{10}$ alkoxyalkylcarbonyl, C$_3$-C$_{10}$ alkoxyalkoxycarbonyl, C$_2$-C$_{10}$ (alkylthio)carbonyl, C$_2$-C$_{10}$ alkoxy(thiocarbonyl), C$_2$-C$_{10}$ alkyl(thiocarbonyl), C$_2$-C$_{10}$ alkylthio(thiocarbonyl), C$_2$-C$_{10}$ alkylaminocarbonyl, C$_4$-C$_{10}$ cycloalkylaminocarbonyl, C$_3$-C$_{10}$ dialkylaminocarbonyl, C$_2$-C$_{10}$ alkylamino(thiocarbonyl), C$_3$-C$_{10}$ dialkylamino(thiocarbonyl), C$_2$-C$_{10}$ alkylsulfonylaminocarbonyl, C$_2$-C$_{10}$ haloalkylsulfonylaminocarbonyl, C$_3$-C$_{10}$ alkoxy(alkyl)aminocarbonyl or —(CR$^{15a}$R$^{15b}$)$_m$R$^{16}$;

each R$^{15a}$ and R$^{15b}$ is independently H, halogen, C$_1$-C$_5$ alkyl, C$_1$-C$_5$ haloalkyl or C$_1$-C$_5$ alkoxy; or a geminal pair of R$^{15a}$ and R$^{15b}$ are taken together with the carbon atom to which they are attached to form —C(=O)— or a C$_3$-C$_6$ cycloalkyl or C$_3$-C$_6$ halocycloalkyl ring; or R$^{15a}$ and R$^{15b}$ attached to adjacent carbon atoms are taken together with the carbon atoms to which they are attached to form a C$_3$-C$_6$ cycloalkyl or C$_3$-C$_6$ halocycloalkyl ring;

each R$^{16}$ is independently phenyl, C$_3$-C$_8$ cycloalkyl, C$_3$-C$_8$ cycloalkenyl, C$_3$-C$_8$ cycloalkoxy, C$_3$-C$_8$ cycloalkenyloxy, 5-or 6-membered heteroaromatic ring or naphthalenyl or 8-, 9-or 10-membered heteroaromatic bicyclic ring system; or a 5-or 6-membered heterocyclic nonaromatic ring, optionally including ring members selected from the group consisting of C(=O), C(=S), C(=NR$^4$), SiR$^{5a}$R$^{5b}$ and S(=O)$_p$(=NR$^4$)$_q$; each ring or ring system optionally substituted with up to 5 substituents independently selected from R$^{17}$ on carbon atom ring members and R$^8$ on nitrogen atom ring members; provided that when R$^{12}$ is —(CR$^{15a}$R$^{15b}$)$_m$R$^{16}$ and m is 0, then R$^{16}$ is other than C$_3$-C$_8$ cycloalkoxy or C$_3$-C$_8$ cycloalkenyloxy;

each R$^{17}$ is halogen, C$_1$-C$_6$ alkyl, C$_2$-C$_6$ alkenyl, C$_2$-C$_6$ alkynyl, C$_3$-C$_6$ cycloalkyl, C$_4$-C$_{10}$ alkylcycloalkyl, C$_3$-C$_6$ halocycloalkyl, C$_1$-C$_6$ haloalkyl, C$_2$-C$_6$ haloalkenyl, cyano, nitro, C$_1$-C$_6$ alkoxy, C$_3$-C$_8$ cycloalkoxy, $C_3$-$C_8$ halocycloalkoxy, $C_1$-$C_6$ haloalkoxy, $C_1$-$C_6$ alkylthio, $C_1$-$C_6$ alkylsulfinyl, $C_1$-$C_6$ alkylsulfonyl, $C_1$-$C_6$ haloalkylthio, $C_1$-$C_6$ haloalkylsulfinyl, $C_1$-$C_6$ haloalkylsulfonyl, $C_1$-$C_6$ alkylamino, $C_2$-$C_6$ dialkylamino, $C_2$-$C_6$ alkylcarbonyl, $C_2$-$C_6$ alkoxycarbonyl, $C_2$-$C_6$ alkylaminocarbonyl, $C_3$-$C_6$ dialkylaminocarbonyl, $C_3$-$C_6$ trialkylsilyl, phenyl, naphthalenyl or a 5-or 6-membered heteroaromatic ring;

each m is independently 0, 1 or 2;

each $R^{10}$ is independently H, $C_1$-$C_5$ alkyl, $C_2$-$C_5$ alkenyl, $C_2$-$C_5$ alkynyl, $C_3$-$C_6$ cycloalkyl, $C_3$-$C_6$ halocycloalkyl, $C_1$-$C_5$ haloalkyl, $C_2$-$C_5$ haloalkenyl, $C_2$-$C_5$ haloalkynyl, $C_2$-$C_5$ alkoxyalkyl, $C_2$-$C_5$ alkylcarbonyl or $C_1$-$C_5$ alkoxy;

each $R^{13a}$ and $R^{13b}$ is independently H, —CN, —C(=O)O$R^{18}$, $C_1$-$C_6$ alkyl, $C_2$-$C_6$ alkenyl, $C_2$-$C_6$ alkynyl, $C_3$-$C_8$ cycloalkyl, $C_3$-$C_8$ halocycloalkyl, $C_3$-$C_8$ cycloalkenyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ alkylamino, $C_2$-$C_6$ dialkylamino, $C_2$-$C_6$ alkylaminoalkyl, $C_2$-$C_6$ haloalkylaminoalkyl, $C_4$-$C_6$ cycloalkylaminoalkyl, $C_3$-$C_6$ dialkylaminoalkyl, $C_3$-$C_6$ halodialkylaminoalkyl, $C_5$-$C_{10}$ cycloalkyl(alkyl)aminoalkyl, $C_1$-$C_6$ alkoxy, $C_1$-$C_6$ haloalkoxy, $C_3$-$C_{10}$ cycloalkoxy, $C_1$-$C_{10}$ alkylthio, $C_1$-$C_{10}$ haloalkylthio, $C_3$-$C_{10}$ cycloalkylthio, $C_3$-$C_{10}$ trialkylsilyl or $C_3$-$C_{10}$ halotrialkylsilyl; or a phenyl or 5-or 6-membered heteroaromatic ring, a 8-, 9-or 10-membered heteroaromatic bicyclic ring system, or a 5-or 6-membered heterocyclic nonaromatic ring optionally including ring members selected from the group consisting of N$R^3$, C(=O), C(=S), C(=N$R^4$), SiR$^{5a}$R$^{5b}$ and S(=O)$_p$(=N$R^4$)$_q$, each ring or ring system optionally substituted on carbon ring members with 1 to 5 substituents selected from the group consisting of $C_1$-$C_3$ alkyl, halogen, —CN and $C_1$-$C_3$ alkoxy; or $R^{13a}$ and $R^{13b}$ are taken together with the carbon to which they are attached to form a 3-to 6-membered ring, said ring optionally including ring members selected from the group consisting of N$R^3$, C(=O), C(=S), C(=N$R^4$), SiR$^{5a}$R$^{5b}$ or S(=O)$_p$(=N$R^4$)$_q$ and optionally substituted on carbon ring members with 1 to 4 substituents selected from the group consisting of $C_1$-$C_2$ alkyl, halogen, —CN and $C_1$-$C_2$ alkoxy;

each $R^{14a}$ and $R^{14b}$ is independently H, —CN, —C(=O)O$R^{18}$, $C_1$-$C_6$ alkyl, $C_2$-$C_6$ alkenyl, $C_2$-$C_6$ alkynyl, $C_3$-$C_8$ cycloalkyl, $C_3$-$C_8$ halocycloalkyl, $C_3$-$C_8$ cycloalkenyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ alkylamino, $C_2$-$C_6$ dialkylamino, $C_2$-$C_6$ alkylaminoalkyl, $C_2$-$C_6$ haloalkylaminoalkyl, $C_4$-$C_6$ cycloalkylaminoalkyl, $C_3$-$C_6$ dialkylaminoalkyl, $C_3$-$C_6$ halodialkylaminoalkyl, $C_5$-$C_{10}$ cycloalkyl(alkyl)aminoalkyl, $C_1$-$C_6$ alkoxy, $C_1$-$C_6$ haloalkoxy, $C_3$-$C_{10}$ cycloalkoxy, $C_1$-$C_{10}$ alkylthio, $C_1$-$C_{10}$ haloalkylthio, $C_3$-$C_{10}$ cycloalkylthio, $C_3$-$C_{10}$ trialkylsilyl or $C_3$-$C_{10}$ halotrialkylsilyl; or a phenyl or 5-or 6-membered heteroaromatic ring, a 8-, 9-or 10-membered heteroaromatic bicyclic ring system, or a 5-or 6-membered heterocyclic nonaromatic ring, optionally including ring members selected from the group consisting of N$R^3$, C(=O), C(=S), C(=N$R^4$), SiR$^{5a}$R$^{5b}$ or S(=O)$_p$(=N$R^4$)$_q$, each ring or ring system optionally substituted on carbon ring members with 1 to 5 substituents selected from the group consisting of $C_1$-$C_3$ alkyl, halogen, —CN and $C_1$-$C_3$ alkoxy; or $R^{14a}$ and $R^{14b}$ are taken together with the carbon to which they are attached to form a 3-to 6-membered ring, said ring optionally including ring members selected from the group consisting of N$R^3$, C(=O), C(=S), C(=N$R^4$), SiR$^{5a}$R$^{5b}$ or S(=O)$_p$(=N$R^3$)$_q$ and optionally substituted on carbon ring members with 1 to 4 substituents selected from the group consisting of $C_1$-$C_2$ alkyl, halogen, —CN and $C_1$-$C_2$ alkoxy;

p and q are independently 0, 1 or 2 in each instance of S(=O)$_p$(=N$R^4$)$_q$, provided that the sum of p and q is 0, 1 or 2; and each $R^{18}$ is independently $C_1$-$C_6$ alkyl, $C_1$-$C_6$ haloalkyl, $C_3$-$C_6$ cycloalkyl, $C_4$-$C_7$ cycloalkylalkyl or $C_4$-$C_7$ alkylcycloalkyl.

This invention also relates to a compound of Formula 1a (including all geometric and stereoisomers), N-oxides, and salts thereof; and use of said compound to prepare compounds of Formula 1 (including N-oxides, and salts thereof),

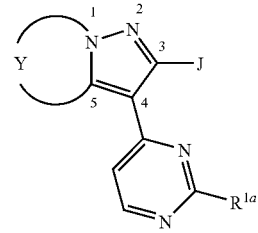

1a wherein $R^{1a}$ is halogen, —SCH$_3$, —S(=O)CH$_3$, —S(=O)$_2$CH$_3$, —OS(=O)$_2$CH$_3$, —S(=O)$_2$CF$_3$ or —OS(=O)$_2$Ph-p-CH$_3$; and J and Y are defined as above for Formula 1.

More particularly, this invention pertains to a compound of Formula 1 or 1a (including all geometric and stereoisomers), an N-oxide or salt thereof. This invention also relates to a fungicidal composition comprising a fungicidally effective amount of a compound of Formula 1 and at least one additional component selected from the group consisting of surfactants, solid diluents or liquid diluents.

This invention also relates to a fungicidal composition comprising a mixture of a compound of Formula 1 and at least one other fungicide (e.g., at least one other fungicide having a different site of action).

This invention further relates to a method for controlling plant diseases caused by fungal plant pathogens comprising applying to the plant or portion thereof, or to the plant seed, a fungicidally effective amount of a compound of the invention (i.e. as a composition described herein).

This invention also relates to a method for preparing a compound of Formula 1, as defined above, or an N-oxide, or salt thereof, comprising contacting a compound of Formula 1a, as defined above, with a compound of Formula 2

$R^1H$          2 or a reducing agent; wherein (a) when $R^1$ is other than hydrogen, then the compound of Formula 1a is contacted with the compound of Formula 2 in the presence of a base; and (b) when $R^1$ is hydrogen, then $R^{1a}$ is halogen and the compound of Formula 1a is contacted with the reducing agent.

DETAILS OF THE INVENTION

As used herein, the terms "comprises," "comprising," "includes," "including," "has," "having", "contains" or "containing" or any other variation thereof, are intended to cover a non-exclusive inclusion. For example, a composition, process, method, article, or apparatus that comprises a list of elements is not necessarily limited to only those elements but may include other elements not expressly listed or inherent to such composition, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to in the present disclosure and claims, "plant" includes members of Kingdom Plantae, particularly seed plants (Spermatopsida), at all life stages, including young plants (e.g., germinating seeds developing into seedlings) and mature, reproductive stages (e.g., plants producing flowers and seeds). Portions of plants include geotropic members typically growing beneath of the surface of the growing medium (e.g., soil), such as roots, tubers, bulbs and corms, and also members growing above the growing medium, such as foliage (including stems and leaves), flowers, fruits and seeds.

As referred to herein, the term "seedling", used either alone or in a combination of words means a young plant developing from the embryo of a seed.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl.

"Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkenyloxy" includes straight-chain or branched alkenyloxy moieties. Examples of "alkenyloxy" include $H_2C=CHCH_2O$, $(CH_3)_2C=CHCH_2O$, $(CH_3)CH=CHCH_2O$, $(CH_3)CH=C(CH_3)CH_2O$ and $CH_2=CHCH_2CH_2O$. "Alkynyloxy" includes straight-chain or branched alkynyloxy moieties. Examples of "alkynyloxy" include $HC\equiv CCH_2O$, $CH_3C\equiv CCH_2O$ and $CH_3C\equiv CCH_2CH_2O$. "Alkylthio" includes branched or straight-chain alkylthio moieties such as methylthio, ethylthio, and the different propylthio, butylthio, pentylthio and hexylthio isomers.

"Alkylcarbonyl" denotes a straight-chain or branched alkyl moieties bonded to a $C(=O)$ moiety. Examples of "alkylcarbonyl" include $CH_3C(=O)$—, $CH_3CH_2CH_2C(=O)$— and $(CH_3)_2CHC(=O)$—. Examples of "alkoxycarbonyl" include $CH_3C(=O)$—, $CH_3CH_2OC(=O)$—, $CH_3CH_2CH_2C(=O)$—, $(CH_3)_2CHOC(=O)$— and the different butoxy-or pentoxycarbonyl isomers. "Alkyl(thiocarbonyl)" denotes a straight-chain or branched alkyl moieties bonded to a $C(=S)$ moiety. Examples of "alkyl(thiocarbonyl)" include $CH_3C(=S)$—, $CH_3CH_2CH_2C(=S)$— and $(CH_3)_2CHC(=S)$—. "(Alkylthio)carbonyl" denotes a straight-chain or branched alkylthio moieties bonded to a $C(=O)$ moiety. Examples of "(alkylthio)carbonyl" include $CH_3SC(=O)$—, $CH_3CH_2CH_2SC(=O)$— and $(CH_3)_2CHSC(=O)$—. "Alkoxy(thiocarbonyl)" denotes a straight-chain or branched alkoxy moieties bonded to a $C(=S)$ moiety. Examples of "alkoxy(thiocarbonyl)" include $CH_3C(=S)$—, $CH_3CH_2CH_2OC(=S)$— and $(CH_3)_2CHOC(=S)$—. "Alkylthio(thiocarbonyl)" denotes a straight-chain or branched alkylthio moieties bonded to a $C(=S)$ moiety. Examples of "alkylthio(thiocarbonyl)" include $CH_3SC(=S)$—, $CH_3CH_2CH_2SC(=S)$— and $(CH_3)_2CHSC(=S)$—. Examples of "alkylaminocarbonyl" include $CH_3NHC(=O)$, $CH_3CH_2NHC(=O)$, $CH_3CH_2CH_2NHC(=O)$, $(CH_3)_2CHNHC(=O)$ and the different butylamino-or pentylaminocarbonyl isomers. Examples of "dialkylaminocarbonyl" include $(CH_3)_2NC(=O)$, $(CH_3CH_2)_2NC(=O)$, $CH_3CH_2(CH_3)NC(=O)$, $(CH_3)_2CH(CH_3)NC(=O)$ and $CH_3CH_2CH_2(CH_3)NC(=O)$. "Alkylamino(thiocarbonyl)" denotes a straight-chain or branched alkylamino moieties bonded to a $C(=S)$ moiety. Examples of "alkylamino(thiocarbonyl)" include $CH_3NHC(=S)$—, $CH_3CH_2NHC(=S)$— and $(CH_3)_2CHNHC(=S)$—. "Dialkylamino(thiocarbonyl)" denotes a straight-chain or branched dialkylamino moieties bonded to a $C(=S)$ moiety. Examples of "dialkylamino(thiocarbonyl)" include $(CH_3)_2NC(=S)$—, $CH_3CH_2CH_2(CH_3)NC(=S)$— and $(CH_3)_2C(CH_3)NC(=S)$—. "Alkoxy(alkyl)aminocarbonyl" denotes a straight-chain or branched alkyl and alkoxy moieties bonded to a nitrogen atom of aminocarbonyl moiety. Examples of "Alkoxy(alkyl)aminocarbonyl" include $CH_3O(CH_3)NC(=O)$—, $CH_3CH_2O(CH_3)NC(=O)$— and $(CH_3)_2CHO(CH_3)NC(=O)$—.

"Alkylsulfinyl" includes both enantiomers of an alkylsulfinyl group. Examples of "alkylsulfinyl" include $CH_3S(O)$—, $CH_3CH_2S(O)$—, $CH_3CH_2CH_2S(O)$—, $(CH_3)_2CHS(O)$— and the different butylsulfinyl, pentylsulfinyl and hexylsulfinyl isomers. Examples of "alkylsulfonyl" include $CH_3S(O)_2$—, $CH_3CH_2S(O)_2$—, $CH_3CH_2CH_2S(O)_2$—, $(CH_3)_2CHS(O)_2$—, and the different butylsulfonyl, pentylsulfonyl and hexylsulfonyl isomers. "Alkylthioalkyl" denotes alkylthio substitution on alkyl. Examples of "alkylthioalkyl" include $CH_3SCH_2$, $CH_3SCH_2CH_2$, $CH_3CH_2SCH_2$, $CH_3CH_2CH_2CH_2SCH_2$ and $CH_3CH_2SCH_2CH_2$. "Cyanoalkyl" denotes an alkyl group substituted with one cyano group. Examples of "cyanoalkyl" include $NCCH_2$, $NCCH_2CH_2$ and $CH_3CH(CN)CH_2$. "Alkylamino includes an NH radical substituted with straight-chain or branched alkyl. Examples of "alkylamino" include $CH_3CH_2NH$, $CH_3CH_2CH_2NH$, and $(CH_3)_2CHCH_2NH$. Examples of "dialkylamino" include $(CH_3)_2N$, $(CH_3CH_2CH_2)_2N$ and $CH_3CH_2(CH_3)N$. "Alkylaminoalkyl" denotes alkylamino substitution on alkyl. Examples of "alkylaminoalkyl" include $CH_3NHCH_2$, $CH_3NHCH_2CH_2$, $CH_3CH_2NHCH_2$, $CH_3CH_2CH_2NHCH_2$ and $CH_3CH_2NHCH_2CH_2$. Examples of "dialkylaminoalkyl" include $(CH_3)_2CH(CH_3)N$, $(CH_3CH_2CH_2)_2N$ and $CH_3CH_2(CH_3)N$.

"Cycloalkyl" includes, for example, cyclopropyl, cyclobutyl, cyclopentyl and cyclohexyl. The term "alkylcycloalkyl" denotes alkyl substitution on a cycloalkyl moiety and includes, for example, ethylcyclopropyl, i-propylcyclobutyl, 3-methylcyclopentyl and 4-methylcyclohexyl. The term "cycloalkylalkyl" denotes cycloalkyl substitution on an alkyl moiety. Examples of "cycloalkylalkyl" include cyclopropylmethyl, cyclopentylethyl, and other cycloalkyl moieties bonded to straight-chain or branched alkyl groups. The term "cycloalkoxy" denotes cycloalkyl linked through an oxygen atom such as cyclopentyloxy and cyclohexyloxy. "Cycloalkenyl" includes groups such as cyclopentenyl and cyclohexenyl as well as groups with more than one double bond such as 1,3-and 1,4-cyclohexadienyl. "Cycloalkylcarbonyl" denotes cycloalkyl bonded to a C(=O) group including, for example, cyclopropylcarbonyl and cyclopentylcarbonyl. "Cycloalkylaminocarbonyl" denotes cycloalkylamino bonded to a C(=O) group, for example, cyclopentylaminocarbonyl and cyclohexylaminocarbonyl. The term "cycloalkoxycarbonyl" means cycloalkoxy bonded to a C(=O) group, for example, cyclopropyloxycarbonyl and cyclopentyloxycarbonyl.

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include $F_3C-$, $ClCH_2-$, $CF_3CH_2-$ and $CF_3CCl_2-$. The terms "halocycloalkyl", "haloalkoxy", "haloalkylthio", "halodialkylaminoalkyl", "halotrialkylsilyl", "haloalkenyl", "haloalkynyl", and the like, are defined analogously to the term "haloalkyl". Examples of "haloalkoxy" include $CF_3O-$, $CCl_3CH_2O-$, $HCF_2CH_2CH_2O-$ and $CF_3CH_2O-$. Examples of "haloalkylthio" include $CCl_3S-$, $CF_3S-$, $CCl_3CH_2S-$ and $ClCH_2CH_2CH_2S-$. Examples of "haloalkylsulfinyl" include $CF_3S(O)-$, $CCl_3S(O)-$, $CF_3CH_2S(O)-$ and $CF_3CF_2S(O)-$. Examples of "haloalkylsulfonyl" include $CF_3S(O)_2-$, $CCl_3S(O)_2-$, $CF_3CH_2S(O)_2-$ and $CF_3CF_2S(O)_2-$. Examples of "haloalkylamino" include $CF_3(CH_3)CHNH$, $(CF_3)_2CHNH$ and $CH_2ClCH_2NH$. Examples of "halodialkylamino" include $CF_3(CH_3)N-$, $(CF_3)_2N-$ and $CH_2Cl(CH_3)N-$. Examples of "halodialkylaminoalkyl" include $(CF_3)_2NCH_2-$, $(CF_3)_2NC(CH_3)H-$ and $(CF_3)(CH_3)NCH_2-$. Examples of "halotrialkylsilyl" include $CF_3(CH_3)_2Si-$, $(CF_3)_3Si-$, and $CH_2Cl(CH_3)_2Si-$. Examples of "haloalkenyl" include $(Cl)_2C=CHCH_2-$ and $CF_3CH_2CH=CHCH_2-$. Examples of "haloalkynyl" include $HC\equiv CCHCl-$, $CF_3C\equiv C-$, $CCl_3C\equiv C-$ and $FCH_2C\equiv CCH_2-$.

"Trialkylsilyl" includes three branched and/or straight-chain alkyl radicals attached to and linked through a silicon atom such as trimethylsilyl, triethylsilyl and t-butyl-dimethylsilyl.

The total number of carbon atoms in a substituent group is indicated by the "$C_i$-$C_j$" prefix where i and j are numbers from 1 to 10. For example, $C_1$-$C_4$ alkylsulfonyl designates methylsulfonyl through butylsulfonyl; $C_2$ alkoxyalkyl designates $CH_3OCH_2-$; $C_3$ alkoxyalkyl designates, for example, $CH_3CH(OCH_3)-$, $CH_3OCH_2CH_2-$ or $CH_3CH_2OCH_2-$; and $C_4$ alkoxyalkyl designates the various isomers of an alkyl group substituted with an alkoxy group containing a total of four carbon atoms, examples including $CH_3CH_2CH_2OCH_2-$ and $CH_3CH_2OCH_2CH_2-$.

When a compound is substituted with a substituent bearing a subscript that indicates the number of said substituents can exceed 1, said substituents (when they exceed 1) are independently selected from the group of defined substituents (e.g., $(CR^{15a}R^{15b})_m$ wherein m is 0, 1 or 2, and $S(=O)_p(=NR^4)_q$ wherein p and q are independently 0, 1 or 2, provided that the sum of p and q is 0, 1 or 2). When a group contains a substituent which can be hydrogen, for example $R^1$, $R^2$, $R^3$, $R^4$, $R^6$, $R^{9a}$, $R^{9b}$, $R^{10}$, $R^{12}$, $R^{11a}$, $R^{11b}$, $R^{13a}$, $R^{13b}$, $R^{14a}$, $R^{14b}$, $R^{15a}$ or $R^{15b}$, then when this substituent is taken as hydrogen, it is recognized that this is equivalent to said group being unsubstituted. When a variable group is shown to be optionally attached to a position, for example $(R^\nu)_r$ in U-40 of Exhibit 1 wherein r may be 0, then hydrogen may be at the position even if not recited in the variable group definition. When one or more positions on a group are said to be "not substituted" or "unsubstituted", then hydrogen atoms are attached to take up any free valency.

As used herein, the terms "alkylate" and "alkylated" refer to a chemical reaction wherein a leaving group is displaced by a nucleophile from a carbon-containing radical bonded through a carbon atom to the leaving group. Unless otherwise indicated, the carbon-containing radical is not limited to alkyl; the carbon-containing radical can be, for example, pyridinyl, as present in the bromopyridine compounds of Formula 18 (see below).

Unless otherwise indicated, a "ring" or "ring system" as a component of Formula 1 (e.g., Y, J, $R^{13a}$, $R^{13b}$, $R^{14a}$, $R^{14b}$ and $R^{16}$) is carbocyclic or heterocyclic. The term "ring system" denotes two or more rings sharing common atoms. As is generally understood, the term "bicyclic ring system" denotes a ring system containing two rings that share two or more common atoms. If the common atoms are adjacent (i.e. there is a bond between the bridgehead carbons), the bicyclic ring system is a "fused bicyclic ring system". The term "heteroaromatic bicyclic ring system" denotes a ring system consisting of two fused rings, in which either or both rings can be aromatic, and containing at least one heteroatom (e.g., O, N) in at least one of the component rings. The term "ring member" refers to an atom or other moiety (e.g., C(=O), C(=S), S(O) or S(O)$_2$) forming the backbone of a ring or ring system.

The terms "carbocyclic ring", "carbocycle" or "carbocyclic ring system" denote a ring or ring system wherein the atoms forming the ring backbone are selected only from carbon.

Unless otherwise indicated, a carbocyclic ring can be a saturated, partially unsaturated, or fully unsaturated ring. When a fully unsaturated carbocyclic ring satisfies Hückel's rule, then said ring is also called an "aromatic ring". "Saturated carbocyclic" refers to a ring having a backbone consisting of carbon atoms linked to one another by single bonds; unless otherwise specified, the remaining carbon valences are occupied by hydrogen atoms.

The terms "heterocyclic ring", "heterocycle" or "heterocyclic ring system" denote a ring or ring system in which at least one atom forming the ring backbone is not carbon, e.g., nitrogen, oxygen or sulfur. Typically a heterocyclic ring contains no more than 4 nitrogens, no more than 2 oxygens and no more than 2 sulfurs. Unless otherwise indicated, a heterocyclic ring can be a saturated, partially unsaturated, or fully unsaturated ring. When a fully unsaturated heterocyclic ring satisfies Hückel's rule, then said ring is also called a "heteroaromatic ring" or "aromatic heterocyclic ring". A heterocyclic ring that does not satisfy Hückel's rule is described as a "nonaromatic heterocyclic ring".

"Aromatic" indicates that each of the ring atoms is essentially in the same plane and has a p-orbital perpendicular to the ring plane, and in which (4n+2) π electrons, where n is a positive integer, are associated with the ring to comply with Hückel's rule. The term "aromatic ring system" denotes a carbocyclic or heterocyclic ring system in which at least one ring of the ring system is aromatic. The term "aromatic carbocyclic ring system" denotes a carbocyclic ring system in which at least one ring of the ring system is aromatic. The term "aromatic heterocyclic ring system" denotes a heterocyclic ring system in which at least one ring of the ring system is aromatic. As is generally understood, the term "saturated ring" denotes a ring in which no ring member is bonded to an adjacent ring member through a double bond. Analogously, the term "saturated ring system" denotes a ring system in which no ring member is bonded to an adjacent ring member through a double bond.

The term "optionally substituted" means unsubstituted or substituted. Therefore an optionally substituted group (i.e. radical) is unsubstituted or has at least 1 non-hydrogen substituent. Unless a particular limit is recited, a group can be substituted with as many optional substituents as can be accommodated by replacing a hydrogen atom with a non-hydrogen substituent on any available carbon or nitrogen atom in the group. When the term "optionally substituted" is accompanied by a limit such as for the groups listed for J and $R^{16}$, the number of optional substituents cannot exceed the limit even if further positions for substitution are available. Therefore, for example, the phrase "optionally substituted with 1 to 5 substituents" means than no substituent may be present, 1 substituent may be present, or up to 5 substituents may be present if accommodated by the number of positions available for substitution.

As noted above, J, $R^{13a}$, $R^{13b}$, $R^{14a}$, $R^{14b}$ or $R^{16}$ can be (among others) phenyl optionally substituted with up to 5 substituents selected from a group of substituents as defined in the Summary of Invention. An example of phenyl optionally substituted with up to five substituents is the ring illustrated as U-1 in Exhibit 1, wherein $R^v$ is selected from a group of substituents as defined in the Summary of the Invention for J, $R^{13a}$, $R^{13b}$, $R^{14a}$, $R^{14b}$ or $R^{16}$ (i.e., $R^7$ and $R^{17}$) and r is an integer from 0 to 5.

As noted above, J or $R^{16}$ can be (among others) naphthalenyl optionally substituted with 1 to 5 substituents (independently selected from $R^7$ or $R^{17}$). As is well known in the art, the naphthalenyl ring system consists of two phenyl rings fused together at adjacent carbon atoms. The ring of naphthalenyl attached to the remainder of Formula 1 has 3 positions available for $R^7$ and $R^{17}$ substituents, and the other ring of naphthalenyl has 4 positions available for $R^7$ and $R^{17}$ substituents. As noted above, J, $R^{13a}$, $R^{13b}$, $R^{14a}$, $R^{14b}$ or $R^{16}$ can be (among others) a 5-or 6-membered heteroaromatic ring optionally substituted with one or more substituents selected from a group of substituents as defined in the Summary of Invention. Examples of a 5-or 6-membered heteroaromatic ring optionally substituted with from one or more substituents include the rings U-2 through U-61 illustrated in Exhibit 1 wherein $R^v$ is any substituent as defined in the Summary of the Invention for J, $R^{13a}$, $R^{13b}$, $R^{14a}$, $R^{14b}$ or $R^{16}$ (e.g., $R^7$ on carbon atom ring members and $R^8$ on nitrogen atom ring members) and r is an integer from 0 to 5, limited by the number of available positions on each U group. As U-29, U-30, U-36, U-37, U-38, U-39, U-40, U-41, U-42 and U-43 have only one available position, for these U groups r is limited to the integers 0 or 1, and r being 0 means that the U group is unsubstituted and a hydrogen is present at the position indicated by $(R^v)_r$.

Exhibit I

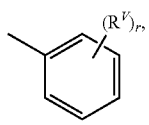
U-1

-continued

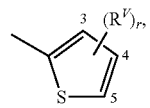
U-2

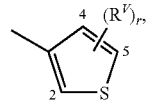
U-3

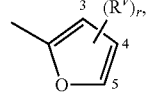
U-4

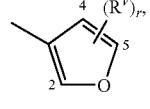
U-5

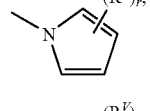
U-6

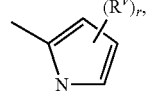
U-7

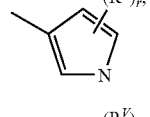
U-8

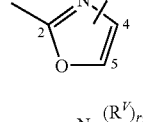
U-9

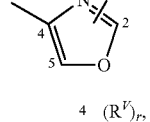
U-10

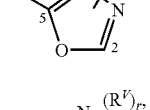
U-11

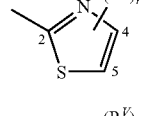
U-12

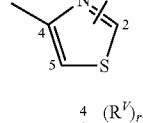
U-13

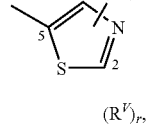
U-14

U-15

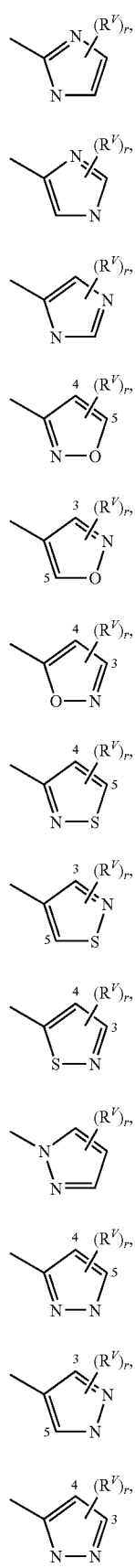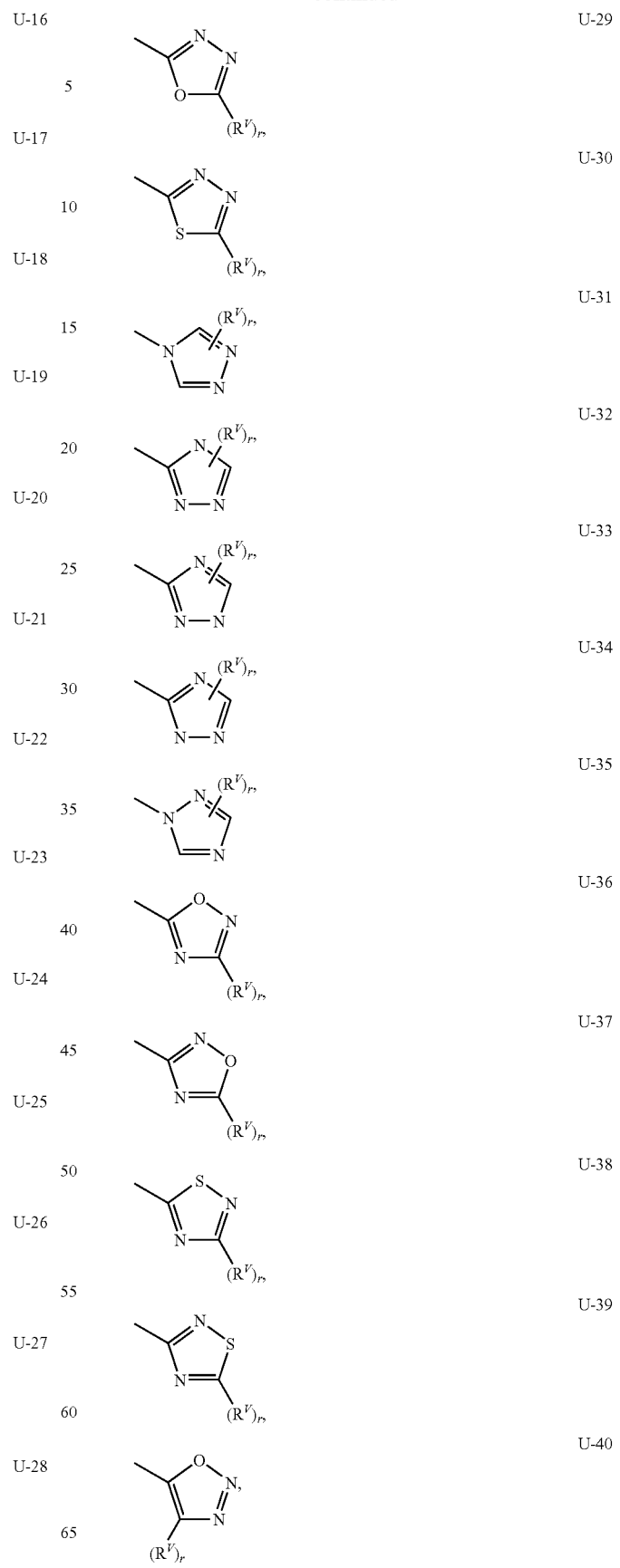

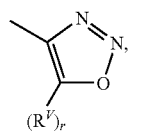 U-31

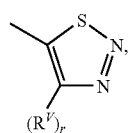 U-32

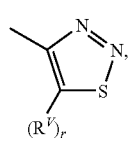 U-33

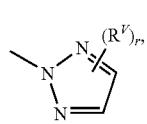 U-34

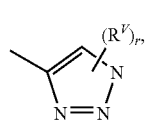 U-35

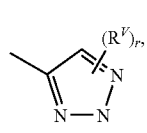 U-36

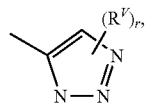 U-37

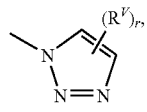 U-38

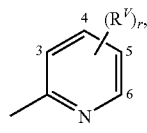 U-39

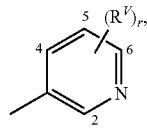 U-40

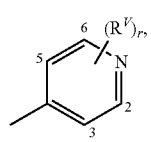 U-41

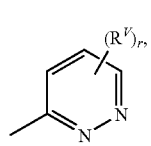 U-42

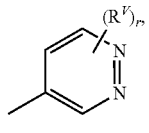 U-43

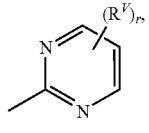 U-44

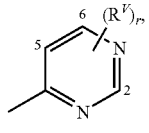 U-45

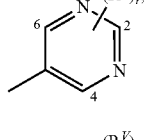 U-46

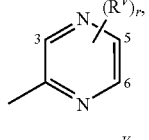 U-47

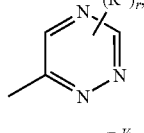 U-48

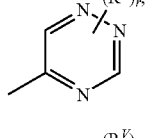 U-49

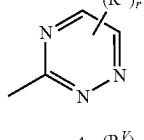 U-50

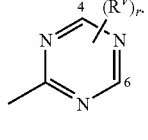 U-51

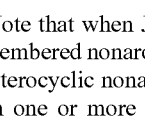 U-52 and

Note that when J, $R^{13a}$, $R^{13b}$, $R^{14a}$, $R^{14b}$ or $R^{16}$ is a 5-or 6-membered nonaromatic carbocyclic or heterocyclic ring or a heterocyclic nonaromatic ring; each optionally substituted with one or more substituents selected from the group of substituents as defined in the Summary of Invention for J, $R^{13a}$, $R^{13b}$, $R^{14a}$, $R^{14b}$ or $R^{16}$, one or two carbon ring members of the heterocycle can optionally be in the oxidized form of a carbonyl moiety.

Examples of 5-or 6-membered nonaromatic heterocyclic rings include the rings G-1 through G-38 as illustrated in Exhibit 2. Note that when the attachment point on the G group is illustrated as floating, the G group can be attached to the remainder of Formula 1 through any available carbon or nitrogen of the G group by replacement of a hydrogen atom. The optional substituents corresponding to $R^v$ can be attached to any available carbon or nitrogen by replacing a hydrogen atom. For these G rings, r is typically an integer from 0 to 5, limited by the number of available positions on each G group.

Note that when J, $R^{13a}$, $R^{13b}$, $R^{14a}$, $R^{14b}$ or $R^{16}$ comprises a ring selected from G-28 through G-35, $G^2$ is selected from O, S or N. Note that when $G^2$ is N, the nitrogen atom can complete its valence by substitution with either H or the substituents corresponding to $R^v$ as defined in the Summary of Invention for J, $R^{13a}$, $R^{13b}$, $R^{14a}$, $R^{14b}$ or $R^{16}$.

Exhibit 2

-continued

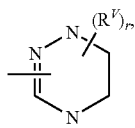 G-27

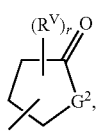 G-28

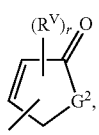 G-29

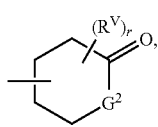 G-30

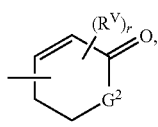 G-31

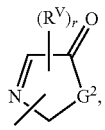 G-32

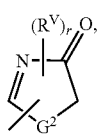 G-33

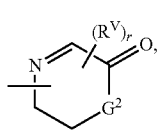 G-34

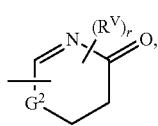 G-35

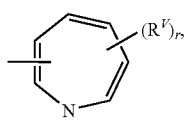 G-36

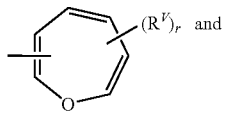 G-37 and

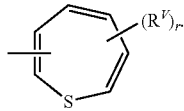 G-38

As noted above, J, $R^{13a}$, $R^{13b}$, $R^{14a}$, $R^{14b}$ or $R^{16}$ can be (among others) an 8-, 9-or 10-membered heteroaromatic bicyclic ring system optionally substituted with one or more substituents selected from a group of substituents as defined in the Summary of Invention (i.e. $R^7$ or $R^{17}$ on carbon atom ring members and $R^8$ on nitrogen atom ring members). Examples of 8-, 9-or 10-membered heteroaromatic bicyclic ring system optionally substituted with from one or more substituents include the rings U-81 through U-123 illustrated in Exhibit 3 wherein $R^V$ is any substituent as defined in the Summary of the Invention for J, $R^{13a}$, $R^{13b}$, $R^{14a}$, $R^{14b}$ or $R^{16}$ (i.e. $R^7$ or $R^{17}$ on carbon atom ring members and $R^8$ on nitrogen atom ring members), and r is typically an integer from 0 to 5.

U-81

U-82

U-83

U-84

U-85

U-86

U-87

U-88

U-89

U-90

U-91

| | |
|---|---|
| 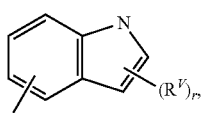 U-92 | 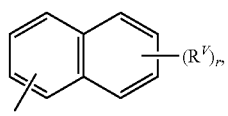 U-105 |
| 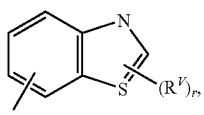 U-93 | 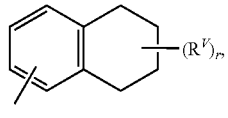 U-106 |
| 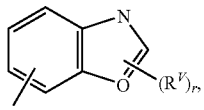 U-94 | 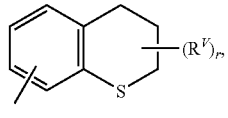 U-107 |
| 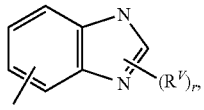 U-95 | 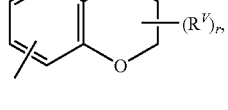 U-108 |
| 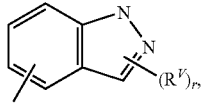 U-96 | 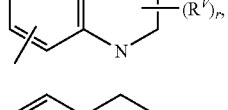 U-109 |
| 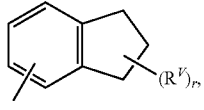 U-97 | 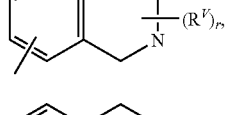 U-110 |
| 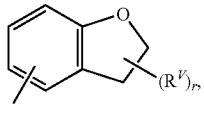 U-98 | 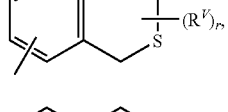 U-111 |
| 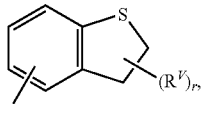 U-99 | 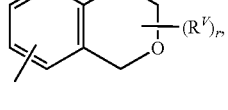 U-112 |
| 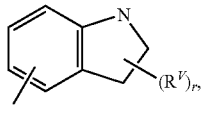 U-100 | 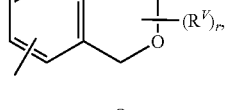 U-113 |
| 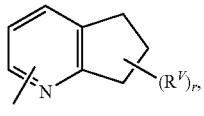 U-101 | 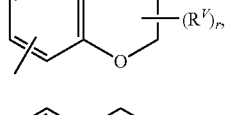 U-114 |
| 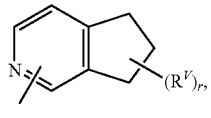 U-102 | 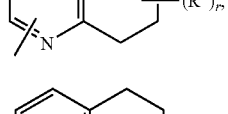 U-115 |
| 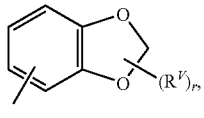 U-103 | 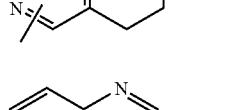 U-116 |
| 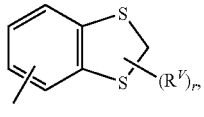 U-104 | 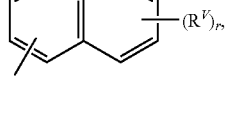 U-117 |

-continued

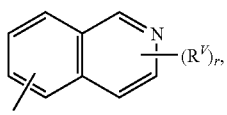 U-118

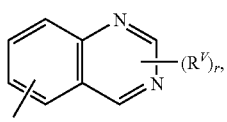 U-119

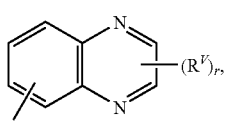 U-120

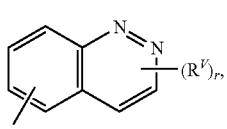 U-121

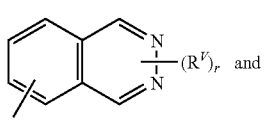 U-122 and

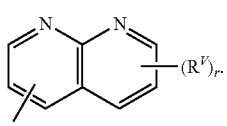 U-123

Although $R^v$ groups are shown in the structures U-1 through U-123 and G-1 through G-38, it is noted that they do not need to be present since they are optional substituents. Note that when $R^v$ is H when attached to an atom, this is the same as if said atom is unsubstituted. The nitrogen atoms that require substitution to fill their valence are substituted with H or $R^v$. Note that when the attachment point between $(R^v)_r$ and the U or G group is illustrated as floating, $(R^v)_r$ can be attached to any available carbon atom or nitrogen atom of the U or G group. Note that when the attachment point on the U or G group is illustrated as floating, the U or G group can be attached to the remainder of Formula 1 through any available carbon or nitrogen of the U or G group by replacement of a hydrogen atom. Note that some U or G groups can only be substituted with less than 4 $R^v$ groups (e.g., U-2 through U-5, U-7 through U-48, U-52 through U-61, G-32, and G-33).

As noted above, Y together with the contiguous nitrogen and carbon linking atoms to which it is attached forms a 5-to 7-membered fused nonaromatic heterocyclic ring including ring members as defined in the Summary of the Invention. Examples of fused rings formed by Y include the rings illustrated as H-1 to H-10 in Exhibit 4. Typically s is an integer from 0 to 4. $R^2$ can be attached to any available carbon of the ring formed by Y. The nitrogen atoms that require a substitutent to fill their valence are substituted with $R^3$. H-1 through H-10 of Exhibit 4 illustrate the portion of Formula 1 enclosed in brackets containing the fused rings formed by Y.

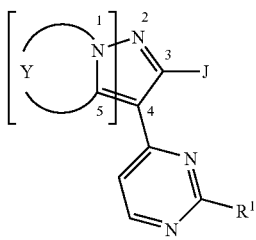 1

Exhibit 4

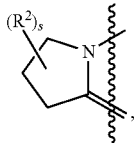 H-1

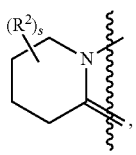 H-2

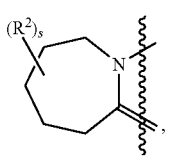 H-3

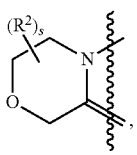 H-4

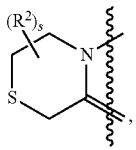 H-5

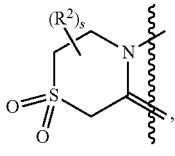 H-6

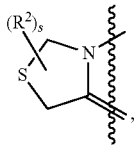 H-7

-continued

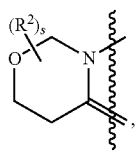
H-8

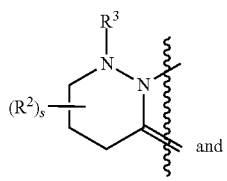
H-9
and

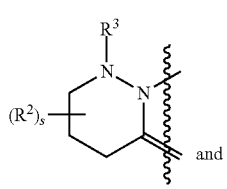
H-9
and

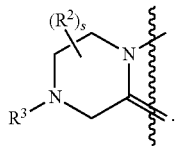
H-10

A wide variety of synthetic methods are known in the art to enable preparation of aromatic and nonaromatic heterocyclic rings and ring systems; for extensive reviews see the eight volume set of *Comprehensive Heterocyclic Chemistry*, A. R. Katritzky and C. W. Rees editors-in-chief, Pergamon Press, Oxford, 1984 and the twelve volume set of *Comprehensive Heterocyclic Chemistry II*, A. R. Katritzky, C. W. Rees and E. F. V. Scriven editors-in-chief, Pergamon Press, Oxford, 1996.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers or as an optically active form.

One skilled in the art will appreciate that not all nitrogen containing heterocycles can form N-oxides since the nitrogen requires an available lone pair for oxidation to the oxide; one skilled in the art will recognize those nitrogen containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA or 3-chloroperbenzoic acid), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. Thus a wide variety of salts of the compounds of Formula 1 are useful for control of plant diseases caused by fungal plant pathogens (i.e. are agriculturally suitable). The salts of the compounds of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of Formula 1 contains an acidic moiety such as a carboxylic acid or phenol, salts also include those formed with organic or inorganic bases such as pyridine, triethylamine or ammonia, or amides, hydrides, hydroxides or carbonates of sodium, potassium, lithium, calcium, magnesium or barium. Accordingly, the present invention comprises compounds selected from Formula 1, N-oxides and agriculturally suitable salts thereof.

Compounds of Formula 1 and Formula 1a typically exist in more than one form, and Formula 1 and Formula 1a thus include all crystalline and non-crystalline forms of the compounds they represent. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound of Formula 1 and Formula 1a can exhibit beneficial effects (e.g., suitability for preparation of useful formulations, improved biological performance) relative to another polymorph or a mixture of polymorphs of the same compound of Formula 1 and Formula 1a. Preparation and isolation of a particular polymorph of a compound of Formula 1 and Formula 1a can be achieved by methods known to those skilled in the art including, for example, crystallization using selected solvents and temperatures.

Embodiments of the present invention as described in the Summary of the Invention include those described below. In the following Embodiments, Formula 1 includes N-oxides and salts thereof, and reference to "a compound of Formula 1" includes the definitions of substituents specified in the Summary of the Invention unless further defined in the Embodiments.

Embodiment 1. A compound of Formula 1 wherein Y is taken together with the contiguous nitrogen and carbon linking atoms (which are identified with "1" and "5" respectively) to form a 5-to 7-membered fused nonaromatic heterocyclic ring, including ring members, in addition to the contiguous nitrogen and carbon linking atoms, selected from the group consisting of $C(R^2)_2$, O, S, $NR^3$, —$C(R^2)$=$C(R^2)$—, C(=O), C(=S) and $S(=O)_p(=NR^4)_q$.

Embodiment 1a. A compound of Formula 1 or Embodiment 1 wherein Y is taken together with the contiguous nitrogen and carbon linking atoms to form a 5-to 7-membered fused nonaromatic heterocyclic ring selected from the group consisting of H-1, H-2, H-3, H-4, H-5, H-6, H-7, H-8, H-9 and H-10 depicted in Exhibit 4 wherein s is an integer from 0 to 4.

Embodiment 2. A compound of Embodiment 1 wherein Y is taken together with the contiguous nitrogen and carbon linking atoms to form a 5-to 7-membered fused nonaromatic heterocyclic ring, including ring members, in addition to the contiguous nitrogen and carbon linking atoms, selected from the group consisting of $C(R^2)_2$, O, S and $NR^3$.

Embodiment 3. A compound of Embodiment 2 wherein Y is taken together with the contiguous nitrogen and carbon linking atoms to form a 5-to 7-membered fused nonaromatic heterocyclic ring, including ring members, in addition to the contiguous nitrogen and carbon linking atoms, selected from the group consisting of $C(R^2)_2$ and O.

Embodiment 4. A compound of Formula 1 or any one of Embodiments 1 through 3 wherein each $R^2$ is independently H, halogen, cyano, hydroxy, —CHO, —C(=O)$OR^6$, —C(=O)$NHOR^{6a}$, $C_1$-$C_5$ alkyl, $C_2$-$C_5$ alkenyl, $C_2$-$C_5$ alkynyl, $C_3$-$C_6$ cycloalkyl, $C_3$-$C_6$ halocycloalkyl, $C_3$-$C_6$ cycloalkenyl, $C_1$-$C_5$ haloalkyl, $C_1$-$C_5$ alkoxy, $C_1$-$C_5$ haloalkoxy, $C_3$-$C_6$ cycloalkoxy, $C_2$-$C_5$ alkenyloxy, $C_3$-$C_5$ haloalkenyloxy, $C_2$-$C_5$ alkynyloxy, $C_2$-$C_5$ alkylcarbonyl, $C_1$-$C_5$ alkylthio, $C_1$-$C_5$ haloalkylthio or $C_3$-$C_6$ cycloalkylthio.

Embodiment 5. A compound of Embodiment 4 wherein each $R^2$ is independently H, halogen, cyano, hydroxy, —CHO, —C(=O)$OR^6$, —C(=O)$NHOR^{6a}$, $C_1$-$C_3$ alkyl, $C_1$-$C_3$ haloalkyl, $C_3$-$C_6$ cycloalkyl, $C_1$-$C_3$ alkoxy, $C_1$-$C_3$ haloalkoxy, $C_3$-$C_6$ cycloalkoxy or $C_2$-$C_5$ alkylcarbonyl.

Embodiment 6. A compound of Embodiment 5 wherein each $R^2$ is independently H, halogen, cyano, hydroxy, —CHO, $C_1$-$C_3$ alkyl or $C_1$-$C_3$ alkoxy.

Embodiment 7. A compound of Embodiment 6 wherein $R^2$ is H.

Embodiment 8. A compound of Formula 1 or any one of Embodiments 1 through 7 wherein $R^3$ is independently H, —CN, —C(=O)$NH_2$, —C(=O)NHCN, —CHO, —C(=O)$OR^6$, —C(=O)$NHOR^{6a}$, $C_1$-$C_5$ alkyl, $C_1$-$C_5$ haloalkyl, $C_2$-$C_5$ alkylcarbonyl, $C_2$-$C_5$ haloalkylcarbonyl, $C_4$-$C_7$ cycloalkylcarbonyl, $C_2$-$C_6$ alkoxycarbonyl, $C_2$-$C_6$ haloalkoxycarbonyl, $C_4$-$C_7$ cycloalkoxycarbonyl, $C_3$-$C_6$ alkoxyalkylcarbonyl, $C_3$-$C_6$ alkoxyalkoxycarbonyl, $C_2$-$C_6$ (alkylthio)carbonyl, $C_2$-$C_6$ alkoxy(thiocarbonyl), $C_2$-$C_6$ alkyl(thiocarbonyl), $C_2$-$C_6$ alkylthio(thiocarbonyl), $C_2$-$C_6$ alkylaminocarbonyl, $C_4$-$C_7$ cycloalkylaminocarbonyl, $C_3$-$C_6$ dialkylaminocarbonyl, $C_2$-$C_6$ alkylamino(thiocarbonyl), $C_3$-$C_6$ dialkylamino(thiocarbonyl) or $C_3$-$C_6$ alkoxy(alkyl)aminocarbonyl.

Embodiment 9. A compound of Embodiment 8 wherein $R^3$ is independently H, —CN, —C(=O)$NH_2$, —C(=O)NHCN, —CHO, —C(=O)$OR^6$, —C(=O)$NHOR^{6a}$, $C_1$-$C_3$ alkyl, $C_2$-$C_4$ alkylcarbonyl, $C_2$-$C_4$ haloalkylcarbonyl, $C_2$-$C_4$ alkoxycarbonyl or $C_2$-$C_4$ haloalkoxycarbonyl.

Embodiment 10. A compound of Embodiment 9 wherein $R^3$ is independently H, —C(=O)$NH_2$, —CHO, —C(=O)$OR^6$, —C(=O)$NHOR^{6a}$, $C_2$-$C_3$ alkylcarbonyl or $C_2$-$C_3$ alkoxycarbonyl.

Embodiment 11. A compound of Formula 1 or any one of Embodiments 1 through 10 wherein $R^6$ is independently H or $C_1$-$C_3$ alkyl.

Embodiment 12. A compound of Formula 1 or any one of Embodiments 1 through 11 wherein $R^{6a}$ is independently $C_1$-$C_3$ alkyl.

Embodiment 13. A compound of Formula 1 or any one of Embodiments 1 through 12 wherein J is a phenyl or 5-or 6-membered heteroaromatic ring, a naphthalenyl ring system, or a 5-or 6-membered nonaromatic carbocyclic or heterocyclic ring, optionally including ring members selected from the group consisting of C(=O) or C(=S), each ring or ring system optionally substituted with 1 to 5 substituents independently selected from $R^7$ on carbon atom ring members and $R^8$ on nitrogen atom ring members.

Embodiment 14. A compound of Embodiment 13 wherein J is a phenyl or a 5-or 6-membered heteroaromatic ring; each ring optionally substituted with up to 3 substituents independently selected from $R^7$ on carbon atom ring members and $R^8$ on nitrogen atom ring members.

Embodiment 14a. A compound of Embodiment 14 wherein J is a phenyl or a 5-or 6-membered heteroaromatic ring, each ring optionally substituted with up to 2 substituents independently selected from $R^7$ on carbon atom ring members and $R^8$ on nitrogen atom ring members.

Embodiment 15. A compound of Embodiment 14a wherein J is a phenyl or thiophene ring optionally substituted with up to 2 substituents independently selected from $R^7$.

Embodiment 16. A compound of Embodiment 15 wherein J is a phenyl or thiophene ring optionally substituted with up to 1 substituents independently selected from $R^7$.

Embodiment 17. A compound of Embodiment 16 wherein J is a phenyl or thiophene ring optionally substituted up to 1 substituent selected from F and $CH_3$.

Embodiment 18. A compound of Formula 1 or Embodiment 13 wherein J is a 5-or 6-membered nonaromatic carbocyclic or heterocyclic ring, optionally including ring members selected from the group consisting of C(=O) or C(=S), and optionally substituted with up to 3 substituents independently selected from $R^7$ on carbon atom ring members and $R^8$ on nitrogen atom ring members.

Embodiment 19. A compound of Embodiment 18 wherein J is a 5-or 6-membered nonaromatic carbocyclic ring optionally substituted up to 2 substituents independently selected from $R^7$.

Embodiment 20. A compound of Formula 1 or any one of Embodiments 1 through 19 wherein each $R^7$ is independently halogen, $C_1$-$C_6$ alkyl, $C_3$-$C_6$ cycloalkyl, $C_3$-$C_6$ halocycloalkyl, $C_4$-$C_7$ alkylcycloalkyl, $C_1$-$C_6$ haloalkyl, cyano, $C_1$-$C_6$ alkoxy, $C_1$-$C_6$ haloalkoxy, $C_1$-$C_6$ alkylthio, $C_1$-$C_6$ alkylsulfinyl, $C_1$-$C_6$ alkylsulfonyl or $C_1$-$C_6$ haloalkylthio.

Embodiment 21. A compound of Embodiment 20 wherein each $R^7$ is independently halogen, $C_1$-$C_3$ alkyl or $C_1$-$C_3$ alkoxy.

Embodiment 22. A compound of Embodiment 21 wherein each $R^7$ is independently halogen or $C_1$-$C_3$ alkyl.

Embodiment 23. A compound of Embodiment 22 wherein each $R^7$ is independently F or $CH_3$.

Embodiment 24. A compound of Formula 1 or any one of Embodiments 1 through 23 wherein $R^1$ is —$NR^{9a}R^{9b}$, —$NR^{10}$—$NR^{11a}R^{11b}$ or —$OR^{12}$.

Embodiment 24a. A compound of Embodiment 24 wherein $R^1$ is —$NR^{9a}R^{9b}$ or —$NR^{10}$—$NR^{11a}R^{11b}$.

Embodiment 25. A compound of Embodiment 24a wherein $R^1$ is —$NR^{9a}R^{9b}$.

Embodiment 26. A compound of Embodiment 24a wherein $R^1$ is —$NR^{10}$—$NR^{11a}R^{11b}$.

Embodiment 27. A compound of Embodiment 24 wherein $R^1$ is —$OR^{12}$.

Embodiment 28. A compound of Formula 1 or any one of Embodiments 1 through 27 wherein each $R^{9a}$ and $R^{11a}$ is independently H, $C_1$-$C_{10}$ alkyl, $C_2$-$C_{10}$ alkenyl, $C_2$-$C_{10}$ alkynyl, $C_1$-$C_{10}$ haloalkyl, $C_2$-$C_{10}$ haloalkenyl, $C_2$-$C_{10}$ haloalkynyl, $C_2$-$C_{10}$ alkoxyalkyl, $C_3$-$C_{10}$ alkoxyalkoxyalkyl, $C_3$-$C_{10}$ alkoxyalkenyl, $C_3$-$C_{10}$ alkoxyalkynyl, $C_3$-$C_{10}$ dialkoxyalkyl, $C_2$-$C_{10}$ haloalkoxyalkyl, $C_2$-$C_{10}$ alkoxyhaloalkyl, $C_2$-$C_{10}$ haloalkoxyhaloalkyl, $C_1$-$C_{10}$ hydroxyalkyl, $C_2$-$C_{10}$ cyanoalkyl, $C_2$-$C_{10}$ alkylthioalkyl, $C_2$-$C_{10}$ alkylsulfinylalkyl, $C_3$-$C_{10}$ alkylaminoalkyl, $C_3$-$C_{10}$ haloalkylaminoalkyl, $C_5$-$C_{10}$ cycloalkylaminoalkyl, $C_4$-$C_{10}$ dialkylaminoalkyl, $C_4$-$C_{10}$ halodialkylaminoalkyl, $C_6$-$C_{10}$ cycloalkyl(alkyl)aminoalkyl or —$(CR^{15a}R^{15b})_m R^{16}$.

Embodiment 29. A compound of Embodiment 28 wherein each $R^{9a}$ and $R^{11a}$ is independently H, $C_1$-$C_{10}$ alkyl, $C_2$-$C_{10}$ alkenyl, $C_2$-$C_{10}$ alkynyl, $C_1$-$C_{10}$ haloalkyl, $C_2$-$C_{10}$ alkoxyalkyl, $C_1$-$C_{10}$ hydroxyalkyl or —$(CR^{15a}R^{15b})_m R^{16}$.

Embodiment 30. A compound of Embodiment 29 wherein each $R^{9a}$ and $R^{11a}$ is independently $C_1$-$C_6$ alkyl, $C_2$-$C_6$ alkoxyalkyl, $C_1$-$C_6$ hydroxyalkyl or —$(CR^{15a}R^{15b})_m R^{16}$.

Embodiment 31. A compound of Embodiment 30 wherein each $R^{9a}$ and $R^{11a}$ is independently isopropyl or cyclopropyl.

Embodiment 32. A compound of Embodiment 31 wherein each $R^{9a}$ and $R^{11a}$ is independently isopropyl.

Embodiment 33. A compound of Embodiment 31 wherein each $R^{9a}$ and $R^{11a}$ is independently cyclopropyl.

Embodiment 34. A compound of Formula 1 or any one of Embodiments 1 through 33 wherein each $R^{9b}$ and $R^{11b}$ is independently H, $C_1$-$C_{10}$ alkyl, $C_2$-$C_{10}$ alkenyl, $C_2$-$C_{10}$ alkynyl, $C_1$-$C_{10}$ haloalkyl or —$(CR^{15a}R^{15b})_m R^{16}$.

Embodiment 34a. A compound of Embodiment 34 wherein each $R^{9b}$ and $R^{11b}$ is independently H, $C_1$-$C_{10}$ alkyl, $C_1$-$C_{10}$ haloalkyl or —$(CR^{15a}R^{15b})_m R^{16}$.

Embodiment 35. A compound of Embodiment 34 wherein each $R^{9b}$ and $R^{11b}$ is independently H or $C_1$-$C_6$ alkyl.

Embodiment 36. A compound of Embodiment 35 wherein each $R^{9b}$ and $R^{11b}$ is independently H.

Embodiment 37. A compound of Formula 1 or any one of Embodiments 1 through 27 wherein when each $R^{9a}$ and $R^{9b}$ pair, or $R^{11a}$ and $R^{11b}$ pair is independently taken together with the nitrogen to which it is attached to form a 3- to 6-membered ring, said ring optionally includes ring members selected from the group consisting of $C(=O)$, $C(=S)$, $NR^3$ or $S(=O)_p(=NR^4)_q$ and is optionally substituted with 1 to 4 substituents selected from the group consisting of halogen, —CN, $C_1$-$C_2$ alkyl and $C_1$-$C_2$ alkoxy.

Embodiment 38. A compound of Embodiment 37 wherein when each $R^{9a}$ and $R^{9b}$ pair, or $R^{11a}$ and $R^{11b}$ pair is independently taken together with the nitrogen to which it is attached to form a 3- to 5-membered ring, said ring is optionally substituted with 1 to 2 substituents selected from the group consisting of halogen, —CN and $C_1$-$C_2$ alkyl.

Embodiment 39. A compound of Embodiment 38 wherein when each $R^{9a}$ and $R^{9b}$ pair, or $R^{11a}$ and $R^{11b}$ pair is independently taken together with the nitrogen to which it is attached to form a 3- to 5-membered ring, said ring is optionally substituted with 1 to 2 substituents selected from the group consisting of $C_1$-$C_2$ alkyl.

Embodiment 40. A compound of Formula 1 or any one of Embodiments 1 through 39 wherein $R^{12}$ is H, $C_1$-$C_{10}$ alkyl, $C_2$-$C_{10}$ alkenyl, $C_2$-$C_{10}$ alkynyl, $C_1$-$C_{10}$ haloalkyl, $C_2$-$C_{10}$ haloalkenyl or —$(CR^{15a}R^{15b})_m R^{16}$.

Embodiment 41. A compound of Embodiment 40 wherein $R^{12}$ is $C_1$-$C_3$ alkyl or —$(CR^{15a}R^{15b})_m R^{16}$.

Embodiment 42. A compound of Formula 1 or any one of Embodiments 1 through 41 wherein each $R^{15a}$ and $R^{15b}$ is independently H, halogen or $C_1$-$C_5$ alkyl.

Embodiment 43. A compound of Embodiment 42 wherein each $R^{15a}$ and $R^{15b}$ is independently H or halogen.

Embodiment 44. A compound of Embodiment 43 wherein each $R^{15a}$ and $R^{15b}$ is H.

Embodiment 45. A compound of Formula 1 or any one of Embodiments 1 through 41 wherein a pair of $R^{15a}$ and $R^{15b}$ are taken together with the carbon atom to which they are attached to form —$C(=O)$— or a $C_3$-$C_6$ cycloalkyl or $C_3$-$C_6$ halocycloalkyl ring.

Embodiment 46. A compound of Formula 1 or any one of Embodiments 1 through 41 wherein a pair of $R^{15a}$ and $R^{15b}$ attached to adjacent carbon atoms are taken together with the carbon atoms to which they are attached to form a $C_3$-$C_6$ cycloalkyl or $C_3$-$C_6$ halocycloalkyl ring.

Embodiment 47. A compound of Formula 1 or any one of Embodiments 1 through 46 wherein each $R^{16}$ is independently phenyl, $C_3$-$C_8$ cycloalkyl, $C_3$-$C_8$ cycloalkenyl, 5- or 6-membered heteroaromatic ring or naphthalenyl or 8-, 9- or 10-membered heteroaromatic bicyclic ring system; or a 5- or 6-membered heterocyclic nonaromatic ring, optionally including ring members selected from the group consisting of $C(=O)$, $C(=S)$, $C(=NR^4)$, $SiR^{5a}R^{5b}$ and $S(=O)_p(=NR^4)_q$; each ring or ring system optionally substituted with up to 3 substituents independently selected from $R^{17}$ on carbon atom ring members and $R^8$ on nitrogen atom ring members.

Embodiment 48. A compound of Embodiment 47 wherein each $R^{16}$ is independently $C_3$-$C_8$ cycloalkyl, $C_3$-$C_8$ cycloalkenyl, phenyl or naphthalenyl, each optionally substituted with up to 2 substituents independently selected from $R^{17}$.

Embodiment 49. A compound of Embodiment 48 wherein each $R^{16}$ is independently $C_3$-$C_8$ cycloalkyl or phenyl, each optionally substituted up to 2 substituents independently selected from $R^{17}$.

Embodiment 50. A compound of Embodiment 49 wherein each $R^{16}$ is independently $C_3$-$C_8$ cycloalkyl or phenyl, each optionally substituted with up to 1 substituent selected from $R^{17}$.

Embodiment 51. A compound of Formula 1 or any one of Embodiments 1 through 50 wherein each $R^{17}$ is independently halogen, $C_1$-$C_6$ alkyl, $C_2$-$C_6$ alkenyl, $C_2$-$C_6$ alkynyl, $C_3$-$C_6$ cycloalkyl, $C_4$-$C_{10}$ alkylcycloalkyl, $C_3$-$C_6$ halocycloalkyl, $C_1$-$C_6$ haloalkyl or cyano; or phenyl or 5-or 6-membered heteroaromatic ring.

Embodiment 52. A compound of Embodiment 51 wherein each $R^{17}$ is halogen, $C_1$-$C_6$ alkyl or cyano.

Embodiment 53. A compound of Formula 1 or any one of Embodiments 1 through 52 wherein m is 0 or 1.

Embodiment 54. A compound of Embodiment 53 wherein m is 0.

Embodiment 55. A compound of Formula 1 or any one of Embodiments 1 through 23 wherein $R^1$ is —N=$CR^{13a}R^{13b}$ or —$NR^{10}$N=$CR^{14a}R^{14b}$.

Embodiment 56. A compound of Embodiment 55 wherein $R^1$ is —N=$CR^{13a}R^{13b}$.

Embodiment 57. A compound of Embodiment 55 wherein $R^1$ is —$NR^{10}$N=$CR^{14a}R^{14b}$.

Embodiment 58. A compound of Formula 1 or any one of Embodiments 1 through 57 wherein each $R^{13a}$ and $R^{13b}$ is independently H, —CN, —C(=O)$OR^{18}$, $C_1$-$C_6$ alkyl, $C_2$-$C_6$ alkenyl, $C_2$-$C_6$ alkynyl, $C_3$-$C_8$ cycloalkyl, $C_3$-$C_8$ halocycloalkyl, $C_3$-$C_8$ cycloalkenyl, $C_4$-$C_{10}$ cycloalkylalkyl, $C_4$-$C_{10}$ alkylcycloalkyl or $C_5$-$C_{10}$ alkylcycloalkylalkyl.

Embodiment 59. A compound of Embodiment 58 wherein each $R^{13a}$ and $R^{13b}$ are independently H, —CN, —C(=O)$OR^{18}$ or $C_1$-$C_6$ alkyl.

Embodiment 60. A compound of Formula 1 or any one of Embodiments 1 through 57 wherein $R^{13b}$ is H, —CN, —(C=O)$OR^{18}$ or $C_1$-$C_6$ alkyl.

Embodiment 60a. A compound of Embodiment 60 wherein $R^{13b}$ is H.

Embodiment 60b. A compound of Formula 1 or any one of Embodiments 1 through 57, or 60 or 60a wherein $R^{13a}$ is a phenyl or 5-or 6-membered heteroaromatic ring or a 5-or 6-membered heterocyclic nonaromatic ring optionally including ring members selected from the group consisting of $NR^3$, C(=O), C(=S), C(=$NR^4$), $SiR^{5a}R^{5b}$ and S(=O)$_p$(=$NR^4$)$_q$; each ring optionally substituted on carbon ring members with 1 to 3 substituents selected from the group consisting of $C_1$-$C_3$ alkyl, halogen, —CN and $C_1$-$C_3$ alkoxy.

Embodiment 61. A compound of Embodiment 60b wherein $R^{13a}$ is independently a phenyl or 5-or 6-membered heteroaromatic ring; each ring optionally substituted on carbon ring members with 1 to 2 substituents selected from the group consisting of $C_1$-$C_3$ alkyl, halogen, —CN and $C_1$-$C_3$ alkoxy.

Embodiment 62. A compound of Formula 1 or any one of Embodiments 1 through 57 wherein $R^{13a}$ and $R^{13b}$ are taken together with the carbon to which they are attached to form a 5-or 6-membered carbocyclic ring optionally substituted with up to 4 substituents independently selected from the group consisting of $C_1$-$C_2$ alkyl, halogen, —CN and $C_1$-$C_2$ alkoxy.

Embodiment 63. A compound of Formula 1 or any one of Embodiments 1 through 62 wherein each $R^{14a}$ and $R^{14b}$ are independently H, —CN, —C(=O)$OR^{18}$, $C_1$-$C_6$ alkyl, $C_2$-$C_6$ alkenyl, $C_2$-$C_6$ alkynyl, $C_3$-$C_8$ cycloalkyl, $C_3$-$C_8$ halocycloalkyl, $C_3$-$C_8$ cycloalkenyl, $C_4$-$C_{10}$ cycloalkylalkyl, $C_4$-$C_{10}$ alkylcycloalkyl or $C_5$-$C_{10}$ alkylcycloalkylalkyl.

Embodiment 64. A compound of Embodiment 63 wherein each $R^{14a}$ and $R^{14b}$ are independently H, —CN, —C(=O)$OR^{18}$ or $C_1$-$C_6$ alkyl.

Embodiment 65. A compound of Formula 1 or any one of Embodiments 1 through 62 wherein $R^{14b}$ is H, —CN, —(C=O)$OR^{18}$ or $C_1$-$C_6$ alkyl.

Embodiment 65a. A compound of Embodiment 65 wherein $R^{14b}$ is H.

Embodiment 65b. A compound of Formula 1 or any one of Embodiments 1 through 62, or 65 or 65a wherein $R^{14a}$ is a phenyl or 5-or 6-membered heteroaromatic ring or a 5-or 6-membered heterocyclic nonaromatic ring optionally including ring members selected from the group consisting of $NR^3$, C(=O), C(=S), C(=$NR^4$), $SiR^{5a}R^{5b}$ and S(=O)$_p$(=$NR^4$)$_q$; each ring optionally substituted on carbon ring members with 1 to 3 substituents selected from the group consisting of $C_1$-$C_3$ alkyl, halogen, —CN and $C_1$-$C_3$ alkoxy.

Embodiment 66. A compound of Embodiment 65b wherein $R^{14a}$ is independently a phenyl or 5-or 6-membered heteroaromatic ring; each ring optionally substituted on carbon ring members with 1 to 2 substituents selected from the group consisting of $C_1$-$C_3$ alkyl, halogen, —CN and $C_1$-$C_3$ alkoxy.

Embodiment 67. A compound of Formula 1 or any one of Embodiments 1 through 62 wherein $R^{14a}$ and $R^{14b}$ are taken together with the carbon to which they are attached to form a 5-to 6-membered carbocyclic ring optionally substituted with up to 4 substituents independently selected from the group consisting of $C_1$-$C_2$ alkyl, halogen, —CN and $C_1$-$C_2$ alkoxy.

Embodiment 68. A compound of Formula 1 or any one of Embodiments 1 through 67 wherein each $R^{18}$ is independently $C_1$-$C_6$ alkyl, $C_1$-$C_6$ haloalkyl or $C_3$-$C_6$ cycloalkyl.

Embodiment 69. A compound of Embodiment 68 wherein each $R^{18}$ is independently $C_1$-$C_3$ alkyl or $C_1$-$C_3$ haloalkyl.

Embodiment 70. A compound of Embodiment 69 wherein each $R^{18}$ is independently $C_1$-$C_3$ alkyl.

Embodiment 71. A compound of Formula 1 or any one of Embodiments 1 through 69 wherein $R^{10}$ is H, $C_1$-$C_5$ alkyl or $C_1$-$C_5$ haloalkyl.

Embodiment 72. A compound of Embodiment 71 wherein $R^{10}$ is H or $C_1$-$C_5$ alkyl.

Embodiment 73. A compound of Embodiment 72 wherein $R^{10}$ is H or methyl.

Embodiment 74. A compound of Formula 1a wherein $R^{1a}$ is halogen, —$SCH_3$, —S(=O)$_2CH_3$, —OS(=O)$_2CF_3$ or —OS(=O)$_2$Ph-p-$CH_3$.

Embodiment 75. A compound of Embodiment 74 wherein $R^{1a}$ is halogen or —S(=O)$_2CH_3$.

Embodiment 76. A compound of Embodiment 75 wherein $R^{1a}$ is Cl or —S(=O)$_2CH_3$.

Embodiments of this invention, including Embodiments 1-76 above as well as any other embodiments described herein, can be combined in any manner, and the descriptions of variables in the embodiments pertain not only to the compounds of Formulae 1 and 1a but also to the starting compounds and intermediate compounds (including Formula 1a) useful for preparing the compounds of Formulae 1 and 1a. In addition, embodiments of this invention, including Embodiments 1-76 above as well as any other embodiments described herein, and any combination thereof, pertain to the compositions and methods of the present invention.

Combinations of Embodiments 1-76 are illustrated by:

Embodiment A1. A compound of Formula 1 wherein
Y is taken together with the contiguous nitrogen and carbon linking atoms (which are identified with "1" and "5" respectively) to form a 5-to 7-membered fused nonaromatic heterocyclic ring, including ring members, in addition to the contiguous nitrogen and carbon linking atoms, selected from the group consisting of $C(R^2)_2$, O, S, $NR^3$, —$C(R^2)$=$C(R^2)$—, C(=O), C(=S), —C≡C— and $S(=O)_p(=NR^4)_q$;

each $R^2$ is independently H, halogen, cyano, hydroxy, —CHO, $C_1$-$C_3$ alkyl or $C_1$-$C_3$ alkoxy;

$R^3$ is independently H, —CN, —C(=O)$NH_2$, —C(=O)NHCN, —CHO, —C(=O)$OR^6$, —C(=O)$NHOR^{6a}$, $C_1$-$C_3$ alkyl, $C_2$-$C_4$ alkylcarbonyl, $C_2$-$C_4$ haloalkylcarbonyl, $C_2$-$C_4$ alkoxycarbonyl or $C_2$-$C_4$ haloalkoxycarbonyl;

J is a phenyl or 5-or 6-membered heteroaromatic ring, a naphthalenyl ring system, or a 5-or 6-membered nonaromatic carbocyclic or heterocyclic ring, optionally including ring members selected from the group consisting of C(=O) or C(=S), each ring or ring system optionally substituted with 1 to 5 substituents independently selected from $R^7$ on carbon atom ring members and $R^8$ on nitrogen atom ring members;

each $R^7$ is independently halogen, $C_1$-$C_3$ alkyl or $C_1$-$C_3$ alkoxy;

$R^1$ is —$NR^{9a}R^{9b}$, —$NR^{10}$—$NR^{11a}R^{11b}$ or —$OR^{12}$;

each $R^{9a}$ and $R^{11a}$ is independently H, $C_1$-$C_{10}$ alkyl, $C_2$-$C_{10}$ alkenyl, $C_2$-$C_{10}$ alkynyl, $C_1$-$C_{10}$ haloalkyl, $C_2$-$C_{10}$ alkoxyalkyl, $C_1$-$C_{10}$ hydroxyalkyl or —$(CR^{15a}R^{15b})_mR^{16}$;

each $R^{9b}$ and $R^{11b}$ is independently H, $C_1$-$C_{10}$ alkyl, $C_2$-$C_{10}$ alkenyl, $C_2$-$C_{10}$ alkynyl, $C_1$-$C_{10}$ haloalkyl or —$(CR^{15a}R^{15b})_mR^{16}$;

$R^{12}$ is H, $C_1$-$C_{10}$ alkyl, $C_2$-$C_{10}$ alkenyl, $C_2$-$C_{10}$ alkynyl, $C_1$-$C_{10}$ haloalkyl, $C_2$-$C_{10}$ haloalkenyl or —$(CR^{15a}R^{15b})_mR^{16}$;

each $R^{15a}$ and $R^{15b}$ is independently H, halogen or $C_1$-$C_5$ alkyl;

each $R^{16}$ is independently phenyl, $C_3$-$C_8$ cycloalkyl, $C_3$-$C_8$ cycloalkenyl, 5-or 6-membered heteroaromatic ring or naphthalenyl or 8-, 9-or 10-membered heteroaromatic bicyclic ring system; or a 5-or 6-membered heterocyclic nonaromatic ring, optionally including ring members selected from the group consisting of C(=O), C(=S), C(=$NR^4$), $SiR^{5a}R^{5b}$ and $S(=O)_p(=NR^4)_q$; each ring or ring system optionally substituted with up to 3 substituents independently selected from $R^{17}$ on carbon atom ring members and $R^8$ on nitrogen atom ring members;

m is 0 or 1;

each $R^{17}$ is independently halogen, $C_1$-$C_6$ alkyl, $C_2$-$C_6$ alkenyl, $C_2$-$C_6$ alkynyl, $C_3$-$C_6$ cycloalkyl, $C_4$-$C_{10}$ alkylcycloalkyl, $C_3$-$C_6$ halocycloalkyl, $C_1$-$C_6$ haloalkyl or cyano; or phenyl or 5-or 6-membered heteroaromatic ring; and $R^{10}$ is H, $C_1$-$C_5$ alkyl or $C_1$-$C_5$ haloalkyl.

Embodiment A2. A compound of Embodiment A1 wherein

Y is taken together with the contiguous nitrogen and carbon linking atoms (which are identified with "1" and "5" respectively) to form a 5-to 7-membered fused nonaromatic heterocyclic ring, including ring members, in addition to the contiguous nitrogen and carbon linking atoms, selected from the group consisting of $C(R^2)_2$, O, S and $NR^3$;

$R^3$ is independently H, —C(=O)$NH_2$, —CHO, —C(=O)$OR^6$, —C(=O)$NHOR^{6a}$, $C_2$-$C_3$ alkylcarbonyl or $C_2$-$C_3$ alkoxycarbonyl;

J is a phenyl or a 5-or 6-membered heteroaromatic ring, each ring optionally substituted up to 2 substituents independently selected from $R^7$ on carbon atom ring members and $R^8$ on nitrogen atom ring members;

each $R^7$ is independently halogen or $C_1$-$C_3$ alkyl;

$R^1$ is —$NR^{9a}R^{9b}$ or —$NR^{10}$— $NR^{11a}R^{11b}$;

each $R^{9a}$ and $R^{11a}$ is independently $C_1$-$C_6$ alkyl, $C_2$-$C_6$ alkoxyalkyl, $C_1$-$C_6$ hydroxyalkyl or —$(CR^{15a}R^{15b})_mR^{16}$;

each $R^{9b}$ and $R^{11b}$ is independently H, $C_1$-$C_{10}$ alkyl, $C_1$-$C_{10}$ haloalkyl or —$(CR^{15a}R^{15b})_mR^{16}$;

m is 0;

each $R^{16}$ is independently $C_3$-$C_8$ cycloalkyl or phenyl, each optionally substituted up to 2 substituents independently selected from $R^{17}$;

$R^{17}$ is halogen, $C_1$-$C_6$ alkyl or cyano; and $R^{10}$ is H or methyl.

Embodiment A3. A compound of Embodiment A2 wherein $R^2$ is H;

J is a phenyl or thiophene ring optionally substituted with up to 2 substituents independently selected from $R^7$;

each $R^7$ is independently F or $CH_3$;

$R^1$ is —$NR^{9a}R^{9b}$;

$R^{9a}$ is independently isopropyl or cyclopropyl;

$R^{9b}$ is independently H.

Embodiment A4. A compound of Embodiment A3 wherein

Y is taken together with the contiguous nitrogen and carbon linking atoms (which are identified with "1" and "5" respectively) to form a 5-to 7-membered fused nonaromatic heterocyclic ring, including ring members, in addition to the nitrogen and carbon linking atoms, selected from the group consisting of $C(R^2)_2$ and O; and J is a phenyl or thiophene ring optionally substituted with up to 1 substituent selected from F and $CH_3$.

Embodiment B1. A compound of Formula 1a wherein $R^{1a}$ is halogen or —$S(=O)_2CH_3$; and J and Y are defined as above for Formula 1.

Embodiment B2. A compound of Embodiment B1 wherein $R^{1a}$ is Cl or —$S(=O)_2CH_3$.

Specific embodiments include compounds of Formulae 1 and 1a selected from the group consisting of:

4-[2-(4-fluorophenyl)-4,5,6,7-tetrahydropyrazolo[1,5-a]pyridin-3-yl]-N-(1-methylethyl)-2-pyrimidinamine (Compound 8), N-cyclopropyl-4-[2-(4-fluorophenyl)-6,7-dihydro-4H-pyrazolo[5,1-c][1,4]oxazin-3-yl]-2-pyrimidinamine (Compound 109), 4-[2-(4-fluorophenyl)-6,7-dihydro-4H-pyrazolo[5,1-c][1,4]oxazin-3-yl]-N-(1-methylethyl)-2-pyrimidinamine (Compound 107), 2-[[4-[2-(4-fluorophenyl)-6,7-dihydro-4H-pyrazolo[5,1-c][1,4]oxazin-3-yl]-2-pyrimidinyl]amino]-1-propanol (Compound 108), 2-[[4-[2-(4-fluorophenyl)-4,5,6,7-tetrahydropyrazolo[5,1-a]pyridin-3-yl]-2-pyrimidinyl]amino]-1-propanol (Compound 5), N-cyclopropyl-4-[2-(4-fluorophenyl)-4,5,6,7-tetrahydropyrazolo[1,5-a]pyridin-3-yl]-2-pyrimidinamine (Compound 12), N-(1-methylethyl)-4-(4,5,6,7-tetrahydro-2-phenylpyrazolo[1,5-a]pyridin-3-yl)-2-pyrimidinamine (Compound 26), N-cyclopropyl-4-(4,5,6,7-tetrahydro-2-phenylpyrazolo[1,5-a]pyridin-3-yl)-2-pyrimidinamine (Compound 27), (2S)-2-[[4-(4,5,6,7-tetrahydro-2-phenylpyrazolo[1,5-c]pyridine-3-yl)-2-pyrimidinyl]amino]-1-propanol (Compound 54), 4-(6,7-dihydro-2-phenyl-4H-pyrazolo[5,1-c][1,4]oxazin-3-yl)-N-(1-methylethyl)-2-pyrimidinamine (Compound 116), N-cyclopropyl-4-(6,7-dihydro-2-phenyl-4H-pyrazolo[5,1-c] [1,4]oxazin-3-yl)-2-pyrimidinamine (Compound 117),
N-cyclopropyl-4-[6,7-dihydro-2-(3-thienyl)-4H-pyrazolo[5,1-c][1,4]oxazin-3-yl]-2-pyrimidinamine (Compound 121),
2-(4-fluorophenyl)-4,5,6,7-tetrahydro-3-[2-(methylsulfonyl)-4-pyrimidinyl]pyrazolo[1,5-c]pyridine (Compound 174),
3-(2-chloro-4-pyrimidinyl)-2-(4-fluorophenyl)-4,5,6,7-tetrahydropyrazolo[1,5-c]pyridine (Compound 150),
3-(2-chloro-4-pyrimidinyl)-2-(4-fluorophenyl)-4,5,6,7-tetrahydropyrazolo[1,5-b]pyridazine (Compound 145), and
2-(4-fluorophenyl)-4,5-dihydro-3-[2-(methylsulfonyl)-4-pyrimidinyl]-7H-pyrazolo[1,5-c][1,3]oxazine (Compound 178).

Of note are the above embodiments, including Embodiments 1 through 76 and A1 through A4, wherein Formula 1 does not include N-oxides and salts thereof.

This invention provides a fungicidal composition comprising a compound of Formula 1 (including all geometric and stereoisomers, N-oxides, and salts thereof) and at least one other fungicide. Of note as embodiments of such compositions are compositions comprising a compound corresponding to any of the compound embodiments described above.

This invention provides a fungicidal composition comprising a fungicidally effective amount of a compound of Formula 1 (including all geometric and stereoisomers, N-oxides, and salts thereof), and at least one additional component selected from the group consisting of surfactants, solid diluents and liquid diluents. Of note as embodiments of such compositions are compositions comprising a compound corresponding to any of the compound embodiments described above.

This invention provides a method for controlling plant diseases caused by fungal plant pathogens comprising applying to the plant or portion thereof, or to the plant seed, a fungicidally effective amount of a compound of Formula 1 (including all geometric and stereoisomers, N-oxides, and salts thereof). Of note as embodiments of such methods are methods comprising applying a fungicidally effective amount of a compound corresponding to any of the compound embodiments described above. Of particular note are embodiments where the compounds are applied as compositions of this invention.

One or more of the following methods and variations as described in Schemes 1-10 can be used to prepare the compounds of Formulae 1 and 1a. The definitions of $R^1$, $R^2$, $R^{1a}$, Y and J in the compounds of Formulae 1-22 below are as defined above in the Summary of the Invention unless otherwise noted. Formulae 1b-1c are various subsets of Formula 1, and all substituents for Formulae 1b-1c are as defined above for Formula 1 unless otherwise indicated. Formula 7a is a subset of Formula 7, and Formula 11a is a subset of Formula 11.

As shown in Scheme 1, compounds of Formula 1 wherein $R^1$ is other than H can be prepared by the reaction of compounds of Formula 1a wherein $R^{1a}$ is a leaving group such as halogen, —$SCH_3$, —$S(=O)CH_3$, —$S(=O)_2CH_3$, —$OS(=O)_2CH_3$, —$OS(=O)_2CF_3$ or —$OS(=O)_2Ph$-p-$CH_3$ as defined in the Summary of the Invention with compounds of Formula 2 wherein $R^1$ is —$NR^{9a}R^{9b}$, $NR^{10}$—$NR^{11a}R^{11b}$, —$OR^{12}$, —$N=CR^{13a}R^{13b}$ or —$NR^{10}N=CR^{14a}R^{14b}$. This reaction is carried out by contacting a compound of Formula 1a with a compound of Formula 2 in the presence of a base such as a metal hydride, alkali metal hydroxide or alkali metal carbonate in the presence or absence of a suitable aprotic solvent such as N,N-dimethylformamide, dimethylsulfoxide or acetonitrile. Alternatively, the reaction can be carried out in an excess of compounds of Formula 2 when $R^1H$ is a primary or secondary amine, or an aniline. In this alternative the excess primary or secondary amine or aniline serves as the base. This reaction is typically run at 0-175° C. over a reaction time period of 1 to 48 h. Compounds of Formula 1 wherein $R^1$ is H can be prepared by the reaction of (resulting form contacting) compounds of Formula 1a wherein $R^{1a}$ is halogen with hydrogen gas in the presence of a catalyst such as palladium on activated carbon or Raney Ni.

Scheme 1

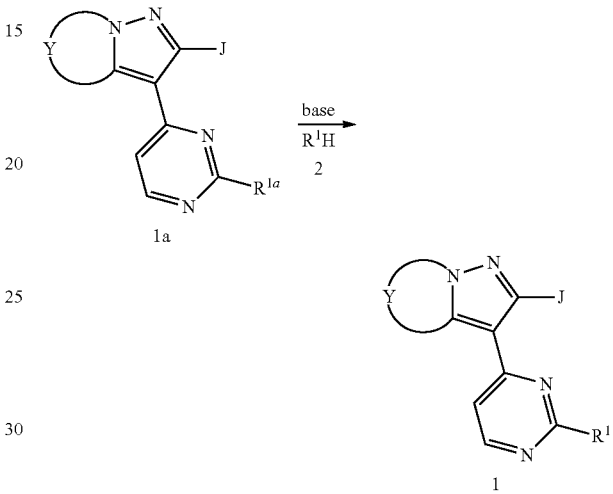

Scheme 2 describes how compounds of Formula 1a can be prepared by reaction of compounds of Formula 3 with appropriately substituted alkynes of Formula 4 at temperatures typically between 80 and 250° C. with reaction times ranging from 24 to 96 h. A variety of solvents can be employed; particularly useful solvents include aromatic hydrocarbons such as benzene, toluene, xylenes or mesitylene.

Scheme 2

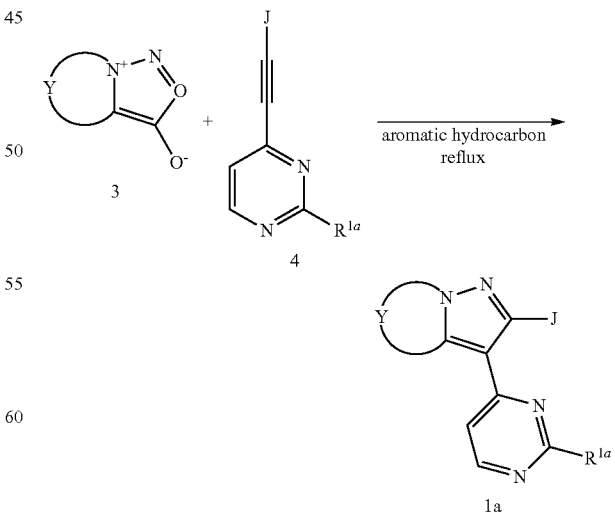

In the method of Scheme 3, commercially available pyrimidines of Formula 5 wherein $Z^1$ is Cl, Br or I and $R^{1a}$ is Cl, —SCH₃, —S(=O)CH₃ or —S(=O)₂CH₃ can be coupled with aryl alkynes of Formula 6 in the presence of catalysts comprising palladium(II) to obtain compounds of Formula 4. Appropriate catalysts and conditions are discussed by Heck, R. F. in *Palladium Reagents in Organic Synthesis*, Academic Press, New York, 1985.

Scheme 3

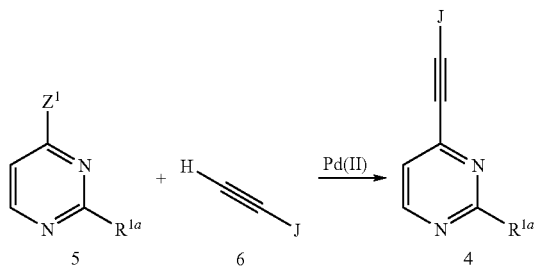

In Scheme 4, compounds of Formula 3 are prepared from amino acids of Formula 7 (wherein Y is H-1, H-2, H-5, H-7 and H-10 of Exhibit 4) such as commercially available proline, pipecolinic acid, thiomorpholine-3-carboxylic acid, thiazolidine-4-carboxylic acid and 4-N-BOC-piperazine-2-carboxylic acid. The described amino acids of Formula 7 can be nitrosated with sodium nitrite in aqueous acid such as hydrochloric acid and subsequently treated with dehydrating agents such as trifluoroacetic anhydride to prepare compounds of Formula 3. A representative dehydration procedure is described by Boyer, J. et al. in *Heterocycles* 1990, 31(3), 481-4 and Venkatesan, A. M. et al. in *J. Med. Chem.* 2006, 49, 4623-4637.

Scheme 4

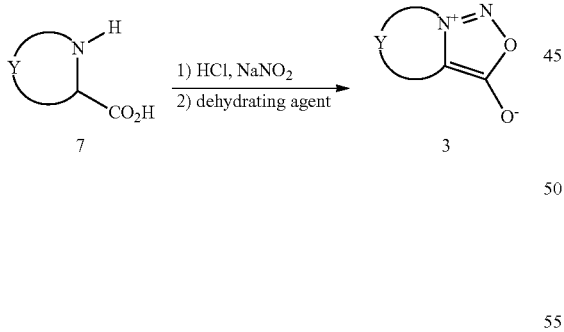

The amino acid of Formula 7 wherein Y is H-4 of Exhibit 4 can be prepared from morpholine as described by Asher, V. et al. in *Tetrahedron Lett.* 1981, 22, 141-144.

The synthetic procedure of Scheme 5 is a useful method for the preparation of compounds of Formula 7 wherein Y is H-8 of Exhibit 4. In Scheme 5a compound of Formula 7a, can be prepared from the commercially available homoserine lactone of Formula 8 and a 37% solution of formaldehyde in water in the presence of a catalytic amount of hydrochloric acid as described by Shiro, Y. et al. in *Tetrahedron* 2006, 62, 8687-8695.

Scheme 5

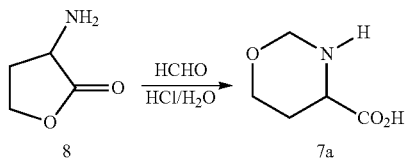

Certain compounds of Formula 1b (Formula 1 wherein Y comprises NR³ as a ring member and R³ is alkyl or alkylcarbonyl as defined in the Summary of the Invention) can be prepared by displacement of an appropriate leaving group Lv bonded to R³ in Formula 22 with the cyclic amine moiety of a compound of Formula 9 in the presence of a base as shown in Scheme 6. Suitable bases include organic bases such as triethylamine, pyridine and N,N-diisopropylethylamine, and inorganic bases such as potassium carbonate or sodium carbonate. The reaction is carried out in an aprotic organic solvent such as tetrahydrofuran, dichloromethane, chloroform, diethyl ether or N,N-dimethylformamide at temperatures between 0 and 100° C. with reaction times ranging from 1 to 72 h. Suitable leaving groups (i.e. Lv) in the compounds of Formula 22 include bromide, iodide, mesylate (OS(O)₂CH₃), triflate (OS(O)₂CF₃) and the like.

Scheme 6

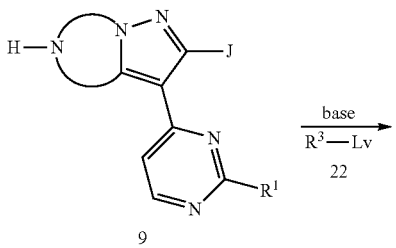

In Scheme 7, deprotection of compounds of Formula 10, wherein Z² is a protecting group such as a carbamoyl or a benzyl group, affords compounds of Formula 9 by a number of methods known to one skilled in the art. An overview of this art is described by Greene, T. W. et al. in *Protective Groups in Organic Synthesis*, Wiley-Interscience, New York, 1999. One skilled in the art will recognize that many compounds of Formula 10 can be prepared by methods analogous to those described in Schemes 1 through 4 above where the ring Y contains N—Z².

Scheme 7

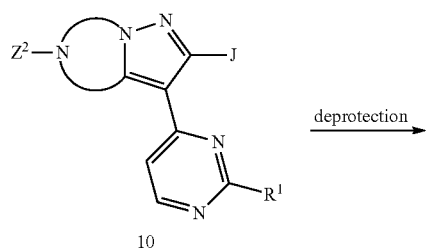

Compounds of Formula 1c wherein Y is taken together with the contiguous nitrogen and carbon linking atoms to form a 5-to 7-membered fused nonaromatic heterocyclic ring, including ring members selected from the group consisting of $C(R^2)_2$ can be prepared as shown in Scheme 8. Reaction of acetic anhydride or acetyl chloride with compounds of Formula 11 in the presence of Lewis acid catalysts such as aluminum chloride, $BF_3$-etherate or iron(III) chloride in solvents such as 1,2-dimethoxyethane over a time period of 1 to 18 h at reaction temperatures between 0 to 165° C. gives compounds of Formula 12. The acylation products of Formula 12 are reacted with neat N,N-dimethylformamide dimethylacetal (DMF-DMA) at temperatures between 50 and 150° C. over reaction times of 1 to 8 h to afford compounds of Formula 13. The compounds of Formula 1c can be prepared from the compounds of Formula 13 by reaction with guanidines of Formula 14, wherein $R^1$ is as described in the Summary of the Invention, in solvents such as N,N-dimethylformamide, tetrahydrofuran or dichloromethane in the presence of bases such as $K_2CO_3$, $Na_2CO_3$, $KHCO_3$ or $NaHCO_3$ at temperatures between 25 and 150° C.

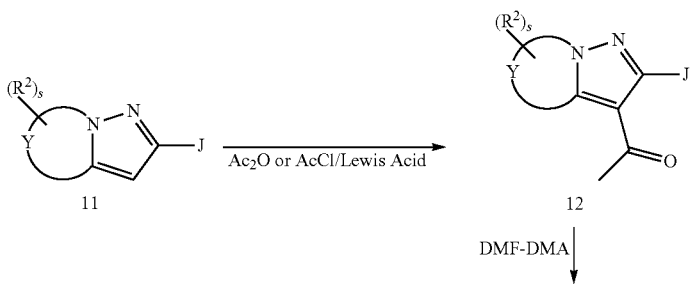

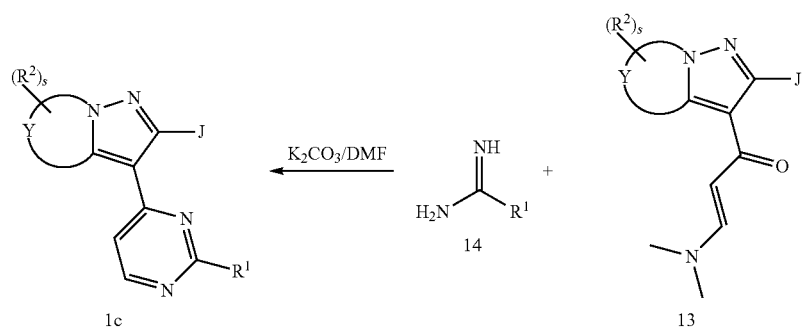

Compounds of Formula 11a (i.e. Formula 11 wherein s is 0 to 4) can be prepared as shown in Scheme 9. Compounds of Formula 15 can be reacted with hydroxylamine hydrochloride, followed by dehydration/cyclization to give compounds of Formula 16 as described in Stevens, K. et al. *Org. Lett.,* 2005, 21, 4753-56. Compounds of Formula 17 can be prepared by heating compounds of Formula 16 in solvent such as trichlorobenzene between 50 and 250° C. or by treating compounds of Formula 16 in solvent such as 1,2-dimethoxyethane in the presence of a catalytic amount of iron(II) chloride between 0 and 150° C. as described in Johns, B. et al. *Tetrahedron* 2003, 59, 9001-9011. Compounds of Formula 11a can be prepared by reacting compounds of Formula 17 with hydrogen gas in the presence of a catalyst such as palladium on activated carbon in alcoholic solvents such as methanol or ethanol as described in Elsner, J. et al. *J. Med. Chem.* 2005, 48, 5771-5779.

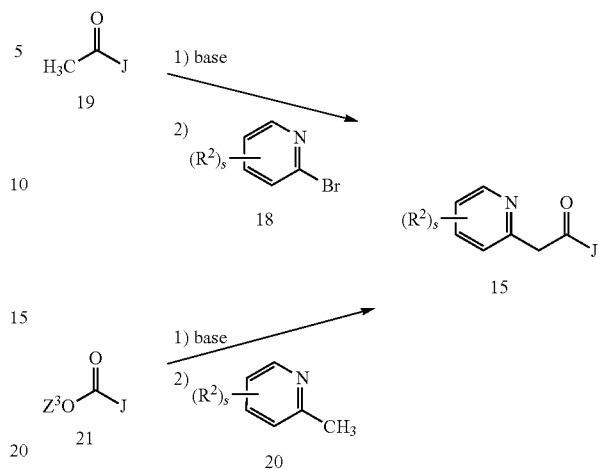

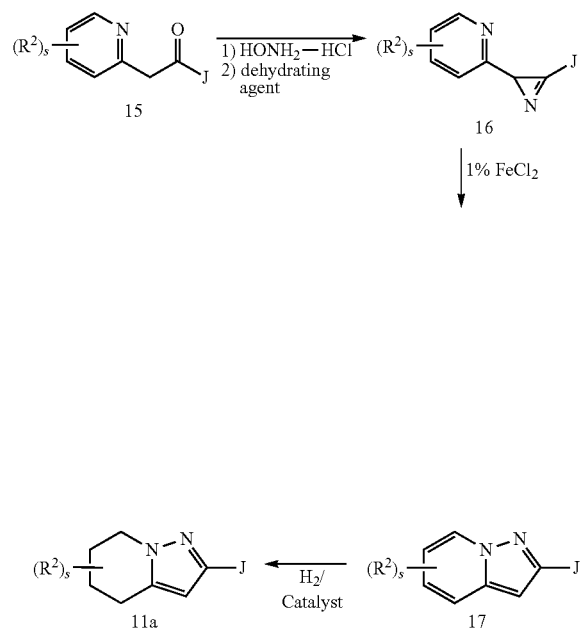

Compounds of Formula 15 can be prepared by two methods shown in Scheme 10. Commercially available substituted acetophenones of Formula 19 can be deprotonated with a base such as a lithium bis(trimethylsilyl)amide or lithium diisopropylamide, and then alkylated with an appropriately substituted bromo pyridine of Formula 18. Alternatively, the compounds of Formula 15 can also be prepared by deprotonation of substituted methyl pyridines of Formula 20 by bases such as sodium hydride, lithium bis(trimethylsilyl)amide or lithium diisopropylamide in solvents such as tetrahydrofuran or dioxane at temperatures between −50 to 80° C., followed by treatment with commercially available ester compounds of Formula 21 wherein $Z^3$ is methyl or ethyl to afford the compounds of Formula 15.

It is recognized that some reagents and reaction conditions described above for preparing compounds of Formulae 1 and 1a may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis,* 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formulae 1 and 1a. One skilled in the art will also recognize that it may be necessary to perform a combination of the steps illustrated in the above schemes in an order other than that implied by the particular sequence presented to prepare the compounds of Formulae 1 and 1a.

One skilled in the art will also recognize that compounds of Formulae 1 and 1a and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; "s" means singlet, "d" means doublet, "t" means triplet, "q" means quartet, "m" means multiplet, "dd" means doublet of doublets, "dt" means doublet of triplets, "br s" means broad singlet.

EXAMPLE 1

Preparation of 2-(4-fluorophenyl)-4,5,6,7-tetrahydro-3-[2-(methylsulfonyl)-4-pyrimidinyl]pyrazolo[1,5-a]pyridine (Compound 174) and N-(cyclopropylmethyl)-4-[2-(4-fluorophenyl)-4,5,6,7-tetrahydropyrazolo[1,5-a]pyridin-3-yl]-2-pyrimidinamine (Compound 24)

Step A: Preparation of 4-[2-(4-fluorophenyl)ethynyl]-2-(methylthio)pyrimidine 4-Iodo-2-(methylthio)pyrimidine (35.7 g, 142 mmol) and 1-ethynyl-4-fluorobenzene (17.0 g, 142 mmol) were added to triethylamine (200 mL) at room temperature. To the resulting solution were added dichlorobis(triphenylphosphine)palladium(II) (1.0 g, 1.4 mmol) and copper iodide (1.0 g, 5.2 mmol). Then the reaction mixture was stirred under a nitrogen atmosphere at room temperature for 18 h. The reaction mixture was concentrated under reduced pressure to remove excess triethylamine. The residue was partitioned between water (400 mL) and dichloromethane (400 mL). The organic layer was washed with water (2×400 mL) and dried (MgSO$_4$), and the solvent was evaporated under reduced pressure to give an oil. Flash chromatographic purification on silica gel with 0 to 50% ethyl acetate/hexanes as eluant gave 18.3 g of the title compound as a light brown solid.

$^1$H NMR (CDCl$_3$) δ 8.5 (d, 1H), 7.6 (m, 2H), 7.08 (m, 3H), 2.58 (s, 3H).

Step B: Preparation of 2-(4-fluorophenyl)-4,5,6,7-tetrahydro-3-[2-(methylthio)-4-pyrimidinyl]pyrazolo[1,5-a]pyridine A suspension of tetrahydropyrido[c]sydnone (5.57 g, 38.7 mmol) (prepared according to the procedure of *Heterocycles* 1990, 31(3), 481-4) and 4-[2-(4-fluorophenyl)ethynyl]-2-(methylthio)pyrimidine (i.e. the product of Step A) (9.44 g, 38.7 mmol) in mesitylene (100 mL) was stirred at 165° C. for 18 h. The solvent was evaporated under reduced pressure to leave an oil. This residue was purified by silica gel chromatography using a gradient of ethyl acetate/hexanes (0:1 to 2:4) to give 6.0 g of the title compound as a beige solid.

$^1$H NMR (CDCl$_3$) δ 8.2 (d, 1H), 7.4 (m, 2H), 7.0 (m, 2H), 6.6 (d, 1H), 4.2 (t, 2H), 3.16 (t, 2H), 2.5 (s, 3H), 2.1 (m, 2H), 1.95 (m, 2H).

Step C: Preparation of 2-(4-fluorophenyl)-4,5,6,7-tetrahydro-3-[2-(methylsulfonyl)-4-pyrimidinyl]pyrazolo[1,5-a]pyridine A mixture of 2-(4-fluorophenyl)-4,5,6,7-tetrahydro-3-[2-(methylthio)-4-pyrimidinyl]pyrazolo[1,5-c]pyridine (i.e. the product of Step B) (6.0 g, 17.6 mmol) and 3-chloroperbenzoic acid (70%, 7.77 g, 35.2 mmol) dissolved in chloroform (125 mL) was stirred at 25° C. for 18 h. The reaction mixture was diluted with dichloromethane (50 mL) and treated with silica gel (20.0 g). The reaction mixture was concentrated under reduced pressure to leave a mixture of silica gel and crude product, which was purified by silica gel chromatography using a gradient of ethyl acetate/hexanes (1:9 to 2:3) as eluant to give 6.0 g of the title product, a compound of the present invention, as a yellow solid.

$^1$H NMR (CDCl$_3$) δ 8.5 (d, 1H), 7.4 (m, 2H), 7.09 (m, 3H), 4.24 (t, 2H), 3.3 (s, 3H), 3.24 (t, 2H), 2.13 (m, 2H), 1.97 (m, 2H).

Step D: Preparation of N-(cyclopropylmethyl)-4-[2-(4-fluorophenyl)-4,5,6,7-tetrahydropyrazolo[1,5-c]pyridin-3-yl]-2-pyrimidinamine A mixture of 2-(4-fluorophenyl)-4,5,6,7-tetrahydro-3-[2-(methylsulfonyl)-4-pyrimidinyl]pyrazolo[1,5-a]pyridine (i.e. the product of Step C) (200 mg, 0.54 mmol) and cyclopropylmethylamine (2.46 g, 34.6 mmol) was stirred at 85° C. for 18 h. The reaction mixture was diluted with dichloromethane (50 mL) and treated with silica gel (20.0 g). The silica gel suspension was then concentrated under reduced pressure to leave a mixture of silica gel and crude product, which was purified by silica gel chromatography using a gradient of ethyl acetate/hexanes (1:9 to 2:3) as eluant to give 97 mg of the title product, a compound of the present invention, as an off-white solid.

$^1$H NMR (CDCl$_3$) δ 8.05 (d, 1H), 7.47 (m, 2H), 7.04 (t, 2H), 6.24 (d, 1H), 5.31 (m, 1H), 4.22 (t, 2H), 3.23 (t, 2H), 3.11 (t, 2H), 2.09 (m, 2H), 1.91 (m, 2H), 1.06 (m, 1H), 0.51 (m, 2H), 0.23 (m, 2H).

EXAMPLE 2

Preparation of 3-(2-chloro-4-pyrimidinyl)-2-(4-fluorophenyl)-4,5,6,7-tetrahydropyrazolo[1,5-a]pyridine (Compound 150), N-cyclobutyl-4-[2-(4-fluorophenyl)-4,5,6,7-tetrahydropyrazolo[1,5-a]pyridin-3-yl]-2-pyrimidinamine (Compound 51), 4-[2-(4-fluorophenyl)-4,5,6,7-tetrahydropyrazolo[1,5-a]pyridin-3-yl]-N-(1-methylethyl)-2-pyrimidinamine (Compound 8) and N-[4-[2-(4-fluorophenyl)-4,5,6,7-tetrahydropyrazolo[1,5-a]pyridin-3-yl]-2-pyrimidinyl]acetamide (Compound 52)

Step A: Preparation of 2-chloro-4-[2-(4-fluorophenyl)ethynyl]pyrimidine 2,4-Dichloropyrimidine (50.0 g, 333 mmol) and 1-ethynyl-4-fluorobenzene (40.0 g, 333 mmol) were added to triethylamine (200 mL) at 25° C. To the reaction mixture were added dichlorobis(triphenylphosphine)palladium(II) (1.0 g, 1.4 mmol) and copper iodide (1.0 g, 5.2 mmol). The reaction mixture was stirred under a nitrogen atmosphere at room temperature for 18 h. The residue was partitioned between water (400 mL) and dichloromethane (400 mL). The organic layer was washed with water (2×400 mL), dried (MgSO$_4$) and evaporated under reduced pressure to give an oil. Flash chromatographic purification on silica gel with 0 to 50% ethyl acetate/hexanes as eluant gave 69.5 g of the title compound as a light brown solid.

$^1$H NMR (CDCl$_3$) δ 8.63 (d, 1H), 7.62 (m, 2H), 7.4 (d, 1H), 7.11 (t, 2H).

Step B: Preparation of 3-(2-chloro-4-pyrimidinyl)-2-(4-fluorophenyl)-4,5,6,7-tetrahydropyrazolo[1,5-a]pyridine A suspension of tetrahydropyrido[c]sydnone (18.6 g, 129 mmol) (prepared according to the procedure of *Heterocycles* 1990, 31(3), 481-4) and 2-chloro-4-[2-(4-fluorophenyl)ethynyl]pyrimidine (i.e. the product of Step A) (30.0 g, 129 mmol) in 300 mL of mesitylene was stirred at 165° C. for 18 h. The reaction mixture was evaporated under reduced pressure to leave an oil. This residue was purified by silica gel chromatography using a gradient of ethyl acetate/hexanes (0:1 to 2:4) to give 28.0 g of the title compound, a compound of the present invention, as a beige solid.

¹H NMR (CDCl₃) δ 8.26 (d, 1H), 7.43 (m, 2H), 7.10 (m, 2H), 6.82 (d, 1H), 4.23 (t, 2H), 3.20 (t, 2H), 2.12 (m, 2H), 1.96 (m, 2H).

Step C: Preparation of N-cyclobutyl-4-[2-(4-fluorophenyl)-4,5,6,7-tetrahydropyrazolo[1,5-a]pyridin-3-yl]-2-pyrimidinamine A mixture of 3-(2-chloro-4-pyrimidinyl)-2-(4-fluorophenyl)-4,5,6,7-tetrahydropyrazolo[1,5-a]pyridine (i.e. the product of Step B) (200 mg, 0.54 mmol), triethylamine (55 mg, 0.54 mmol) and cyclobutylamine (5.0 mL) was stirred at 65° C. for 18 h. The reaction mixture was diluted with dichloromethane (50 mL) and treated with silica gel (20.0 g). The silica gel suspension was concentrated under reduced pressure to leave a mixture of silica gel and crude product, which was purified by silica gel chromatography using a gradient of ethyl acetate/hexanes (1:9 to 1:0) as eluant to give 70 mg of the title product, a compound of the present invention, as a white solid.

¹H NMR (CDCl₃) δ 8.26 (d, 1H), 7.43 (m, 2H), 7.10 (t, 2H), 6.82 (d, 1H), 5.27 (d, 1H), 4.41 (m, 1H), 4.21 (t, 2H), 3.11 (t, 2H), 2.36 (m, 2H), 2.09 (m, 2H), 1.92 (m, 4H), 1.72 (m, 2H).

Step D: Preparation of 4-[2-(4-fluorophenyl)-4,5,6,7-tetrahydropyrazolo[1,5-a]pyridin-3-yl]-N-(1-methylethyl)-2-pyrimidinamine A mixture of 3-(2-chloro-4-pyrimidinyl)-2-(4-fluorophenyl)-4,5,6,7-tetrahydropyrazolo[1,5-a]pyridine (i.e. the product of Step B) (200 mg, 0.54 mmol) and isopropylamine (5.0 mL) was stirred at 34° C. for 18 h. The reaction mixture was diluted with dichloromethane (50 mL) and treated with silica gel (20.0 g). The silica gel suspension was concentrated under reduced pressure to leave a mixture of silica gel and crude product, which was purified by silica gel chromatography using a gradient of ethyl acetate/hexanes (1:9 to 1:0) as eluant to give 115 mg of the title product, a compound of the present invention, as an off-white solid.

¹H NMR (CDCl₃) δ 8.05 (d, 1H), 7.43 (m, 2H), 7.10 (t, 2H), 6.21 (d, 1H), 4.99 (d, 1H), 4.21 (t, 2H), 4.05 (m, 1H), 3.11 (t, 2H), 2.10 (m, 2H), 1.95 (m, 2H), 1.23 (d, 6H).

Step E: Preparation of N-[4-[2-(4-fluorophenyl)-4,5,6,7-tetrahydropyrazolo[1,5-a]pyridin-3-yl]-2-pyrimidinyl]acetamide A mixture of 3-(2-chloro-4-pyrimidinyl)-2-(4-fluorophenyl)-4,5,6,7-tetrahydropyrazolo[1,5-a]pyridine (i.e. the product of Step B) (0.10 g, 0.27 mmol), acetamide (0.08 g, 1.3 mmol), molecular sieves (4 Å, 3.0 g) in 4 mL of N,N-dimethylformamide was stirred at room temperature for 15 minutes. Sodium hydride (55% dispersion, 0.06 g, 1.3 mmol) was added, and the reaction mixture was heated at 100° C. overnight. The reaction mixture was then filtered though a pad of Celite® diatomaceous filter aid, and then concentrated under reduced pressure. The crude oil was purified by medium-pressure liquid chromatography on silica gel using 0-100% of ethyl acetate in hexanes as eluant to give 55 mg of the title compound, a compound of the present invention, as an oil.

¹H NMR (CDCl₃) δ 8.31 (d, 1H), 8.04 (br s, 1H), 7.46 (m, 2H), 7.09 (m, 2H), 6.67 (d, 1H), 4.26 (m, 2H), 3.17 (m, 2H), 2.44 (s, 3H), 2.14 (m, 2H), 1.97 (m, 2H).

EXAMPLE 3

Preparation of 4-[2-(4-fluorophenyl)-4,5,6,7-tetrahydropyrazolo[1,5-a]pyrazin-3-yl]-N-(1-methylethyl)-2-pyrimidinamine (Compound 141) and methyl 2-(4-fluorophenyl)-6,7-dihydro-3-[2-[(1-methylethyl)amino]-4-pyrimidinyl]pyrazolo[1,5-a]pyrazine-5 (4H)-carboxylate (Compound 138)

Step A: Preparation of 1-(phenylmethyl)hydrogen 4-nitroso-1,3-piperazinedicarboxylate To a solution of 1-(phenylmethyl)hydrogen 1,3-piperazinedicarboxylate (5.0 g, 18.9 mmol) in 1 N hydrochloric acid (50 mL) at 0° C. was added sodium nitrite (2.5 g, 36.2 mmol). The reaction mixture was stirred at 0° C. for 3 h, and then allowed to warm to 25° C. The reaction mixture was partitioned between water (400 mL) and dichloromethane (400 mL). The organic layer was washed with water (2×400 mL), dried (MgSO₄), and evaporated under reduced pressure to give 5.7 g of the title compound as a viscous oil. This compound was carried on without further purification or characterization.

Step B: Preparation of 4,5,6,7-tetrahydro-3-hydroxy-5-[(phenylmethoxy)carbonyl][1,2,3]oxadiazolo[3,4-a]pyrazin-8-ium inner salt A solution of 1-(phenylmethyl)hydrogen 4-nitroso-1,3-piperazinedicarboxylate (i.e. the product of Step A) (5.7 g, 19 mmol) was treated with trifluoroacetic acid anhydride (4.89 g, 23.3 mmol) at 0° C. The reaction mixture was stirred at 0° C. for 2 h and then allowed to warm to 25° C. while stirring was continued for 1 h. The reaction mixture was concentrated under reduced pressure, and the residue was diluted with dichloromethane (50 mL) and treated with silica gel (5.0 g). The silica gel suspension was concentrated under reduced pressure to leave a mixture of silica gel and crude product, which was purified by silica gel chromatography using a gradient of ethyl acetate/hexanes (1:1 to 1:0) as eluant to give 3.0 g of the title compound as a yellow oil.

¹H NMR (CDCl₃) δ 7.37 (m, 5H), 5.20 (s, 2H), 4.59 (s, 2H), 4.32 (m, 2H), 4.03 (m, 2H).

Step C: Preparation of phenylmethyl 3-(2-chloro-4-pyrimidinyl)-2-(4-fluorophenyl)-6,7-dihydropyrazolo[1,5-a]pyrazine-5(4H)-carboxylate A mixture of 2-chloro-4-[2-(4-fluorophenyl)ethynyl]pyrimidine (i.e. the product of Example 2, Step A) (2.51 g, 10.8 mmol) and 4,5,6,7-tetrahydro-3-hydroxy-5-[(phenylmethoxy)carbonyl][1,2,3]oxadiazolo[3,4-a]pyrazin-8-ium inner salt (i.e. the product of Step B) (3.00 g, 10.8 mmol) in mesitylene (100 mL) was stirred at 165° C. for 18 h. The reaction mixture was cooled and concentrated under reduced pressure. The residue was diluted with dichloromethane (50 mL) and treated with silica gel (10.0 g). The silica gel suspension was concentrated under reduced pressure to leave a mixture of silica gel and crude product, which was purified by silica gel chromatography using a gradient of ethyl acetate/hexanes (0:1 to 1:1) as eluant to give 1.5 g of the title compound as a white solid.

¹H NMR (CDCl₃) δ 8.26 (d, 1H), 7.4 (m, 7H), 7.14 (t, 2H), 6.85 (d, 1H), 5.24 (br s, 2H), 5.17 (m, 2H), 4.29 (m, 2H), 4.05 (t, 2H).

Step D: Preparation of phenylmethyl 2-(4-fluorophenyl)-6,7-dihydro-3-[2-[(1-methylethyl)amino]-4-pyrimidinyl]pyrazolo[1,5-a]pyrazine-5 (4H)-carboxylate A solution of isopropylamine (2.0 mL) and phenylmethyl 3-(2-chloro-4-pyrimidinyl)-2-(4-fluorophenyl)-6,7-dihydropyrazolo[1,5-a]pyrazine-5(4H)-carboxylate (i.e. the product of Step C) (1.00 g, 2.05 mmol) was heated in a sealed tube at 80° C. in a microwave reactor for 8 h. The reaction mixture was concentrated under reduced pressure to remove the excess amine. The residue was diluted with dichloromethane (50 mL) and treated with silica gel (10.0 g). The silica gel suspension was concentrated to leave a mixture of silica gel and crude product, which was purified by silica gel chromatography using a gradient of ethyl acetate/hexanes (0:1 to 7:1) as eluant to give 0.5 g of the title compound as a white solid.

$^1$H NMR (DMSO-d$_6$) δ 7.99 (br s, 1H), 7.47 (dd, 2H), 7.37 (m, 5H), 7.09 (t, 2H), 6.18 (d, 1H), 5.13 (s, 2H), 5.21 (s, 2H), 4.9 (m, 1H), 4.27 (m, 2H), 4.04 (m, 2H), 1.21 (m, 6H).

Step E: Preparation of 4-[2-(4-fluorophenyl)-4,5,6,7-tetrahydropyrazolo[1,5-a]pyrazin-3-yl]-N-(1-methylethyl)-2-pyrimidinamine Palladium (10% on activated carbon, 25 mg) and 2 M hydrogen chloride in methanol (20 mL) were added to a solution of phenylmethyl 2-(4-fluorophenyl)-6,7-dihydro-3-[2-[(1-methylethyl)amino]-4-pyrimidinyl]pyrazolo[1,5-a]pyrazine-5(4H)-carboxylate (i.e. the product of Step D) (0.50 g, 0.14 mmol) in methanol (30 mL). The resulting suspension was shaken on a Parr apparatus under hydrogen gas (68.9 kPa) for 18 h. The resulting suspension was filtered and concentrated to dryness to give 0.42 g of the title product, a compound of the present invention, as a white solid.

$^1$H NMR (CDCl$_3$) δ 9.35 (s, 1H), 8.15 (s, 1H), 7.65 (dd, 2H), 7.27 (t, 2H), 5.02 (s, 1H), 4.72 (s, 1H), 4.49 (s, 2H), 4.43 (t, 2H), 4.01 (s, 2H), 3.44 (m, 1H), 1.22 (d, 3H), 1.07 (d, 3H).

Step F: Preparation of methyl 2-(4-fluorophenyl)-6,7-dihydro-3-[2-[(1-methylethyl)amino]-4-pyrimidinyl]pyrazolo[1,5-a]pyrazine-5(4H)-carboxylate Triethylamine (96 mg, 0.948 mmol) was added to a solution of 4-[2-(4-fluorophenyl)-4,5,6,7-tetrahydropyrazolo[1,5-a]pyrazin-3-yl]-N-(1-methylethyl)-2-pyrimidinamine (i.e. the product of Step E) (0.150 g, 0.426 mmol) and methyl chloroformate (41.1 μL, 0.178 mmol) in tetrahydrofuran (40 mL). The reaction mixture was stirred at 25° C. for 24 h. The resulting mixture was concentrated under reduced pressure. The residue was diluted with dichloromethane (50 mL) and treated with silica gel (10.0 g). The silica gel suspension was concentrated under reduced pressure to leave a mixture of silica gel and crude product, which was purified by silica gel chromatography using a gradient of ethyl acetate/hexanes (0:1 to 1:4) as eluant to give 25 mg of the title product, a compound of the present invention, as an off-white solid.

$^1$H NMR (CDCl$_3$) δ 8.00 (d, 1H), 7.48 (m, 2H), 7.10 (t, 2H), 6.19 (d, 1H), 5.10 (s, 2H), 4.98 (d, 1H), 4.27 (m, 2H), 4.19 (m, 1H), 4.02 (m, 2H), 3.79 (s, 3H), 1.28 (d, 6H).

EXAMPLE 4

Preparation of N-cyclopropyl-4-[2-(4-fluorophenyl)-4,5,6,7-tetrahydropyrazolo[1,5-b]pyridazin-3-yl]-2-pyrimidinamine (Compound 131) and 1-[3-[2-(cyclopropylamino)-4-pyrimidinyl]-2-(4-fluorophenyl)-5,6-dihydropyrazolo[1,5-b]pyridazin-7(4H)-yl] ethanone (Compound 134)

Step A: Preparation of 1-(phenylmethyl)hydrogen tetrahydro-2-nitrosopyridazine-1,(3S)(2H)-dicarboxylate A solution of sodium nitrite (1.03 g, 15.0 mmol) in 8 mL of water was added dropwise over 10 minutes to a suspension of 1-(phenylmethyl)hydrogen tetrahydropyridazine-1,(3S)(2H)-dicarboxylate (2.64 g, 10.0 mmol; prepared as described in Coats et al. *J. Org. Chem.* 2004, 69, 1734) in 1 N hydrochloric acid (30 mL) at 4° C. After 3.5 h the reaction mixture was diluted with ethyl acetate (40 mL), and the layers were separated. The aqueous layer was extracted with ethyl acetate (2×20 mL), and the combined organic layers were dried over sodium sulfate, filtered and concentrated under reduced pressure to give 3.14 g of the title compound as a yellow oil. This compound was carried on without further purification or characterization.

Step B: Preparation of 4,5,6,7-tetrahydro-3-hydroxy-7-[(phenylmethoxy)carbonyl][1,2,3]oxadiazolo[3,4-b]pyridazin-8-ium inner salt A solution of the crude 1-(phenylmethyl)hydrogen tetrahydro-2-nitrosopyridazine-1,(3S)(2H)-dicarboxylate (i.e. the product of Step A) (3.14 g, 10.0 mmol) in diethyl ether (80 mL) at 2° C. was treated with trifluoroacetic acid anhydride (2.52 g, 12.0 mmol). A precipitate was observed after 30 minutes. The reaction mixture was stirred at 0° C. for 3 h and then filtered. The precipitate was rinsed with hexanes to give 2.23 g of the title compound as a white solid.

$^1$H NMR (CDCl$_3$) δ 7.37 (m, 5H), 5.32 (s, 2H), 3.99 (m, 2H), 2.79 (m, 2H), 1.97 (m, 2H).

Step C: Preparation of phenylmethyl 3-(2-chloro-4-pyrimidinyl)-2-(4-fluorophenyl)-5,6-dihydropyrazolo[1,5-b]pyridazine-7(4H)-carboxylate A mixture of the sydnone 4,5,6,7-tetrahydro-3-hydroxy-7-[(phenylmethoxy)carbonyl][1,2,3]oxadiazolo[3,4-b]pyridazin-8-ium inner salt (i.e. the product of Step B) (1.54 g, 5.59 mmol) and 4-[2-(4-fluorophenyl)ethynyl]-2-(methylthio)pyrimidine (i.e. the product of Example 1, Step A) (1.0 g, 4.30 mmol) in mesitylene (10 mL) was stirred at 140° C. for 4 h. The reaction mixture was cooled and concentrated under reduced pressure. The residue was purified by medium pressure liquid chromatography using 5-40% ethyl acetate in hexanes as eluant to give 0.9 g of the title compound as a yellow solid.

$^1$H NMR (CDCl$_3$) δ 8.29 (d, 1H), 7.46 (m, 2H), 7.34 (m, 5H), 7.11 (m, 2H), 6.86 (d, 1H), 5.28 (s, 2H), 4.01 (m, 2H), 3.34 (m, 2H), 2.05 (m, 2H).

Step D: Preparation of phenylmethyl 3-[2-(cyclopropylamino)-4-pyrimidinyl]-2-(4-fluorophenyl)-5,6-dihydropyrazolo[1,5-b]pyridazine-7(4H)-carboxylate A solution of the phenylmethyl 3-(2-chloro-4-pyrimidinyl)-2-(4-fluorophenyl)-5,6-dihydropyrazolo[1,5-b]pyridazine-7(4H)-carboxylate (i.e. the product of Step C) (464 mg, 1.0 mmol) and cyclopropylamine (1.3 mL, 18.5 mmol) in chloroform (3 mL) was heated at 120° C. in a sealed tube under microwave irradiation for 1 h and then at 160° C. for 5 minutes. The reaction mixture was diluted with water and extracted with dichloromethane. The combined organic layers were dried over sodium sulfate, filtered and concentrated under reduced pressure. The crude residue was purified by medium pressure liquid chromatography using 20-100% ethyl acetate in hexanes as eluant to give 240 mg of the title compound as a solid.

$^1$H NMR (CDCl$_3$) δ 8.09 (d, 1H), 7.50 (m, 2H), 7.33 (m, 5H), 7.07 (m, 2H), 6.30 (d, 1H), 5.28 (m, 2H), 5.25 (s, 1H), 3.99 (m, 2H), 3.31 (m, 2H), 2.76 (m, 1H), 2.00 (m, 2H), 0.78 (m, 2H), 0.56 (m, 2H).

Step E: Preparation of N-cyclopropyl-4-[2-(4-fluorophenyl)-4,5,6,7-tetrahydropyrazolo[1,5-b]pyridazin-3-yl]-2-pyrimidinamine Nitrogen gas was bubbled through a solution of phenylmethyl 3-[2-(cyclopropylamino)-4-pyrimidinyl]-2-(4-fluorophenyl)-5,6-dihydropyrazolo[1,5-b]pyridazine-7(4H)-carboxylate (i.e. the product of Step D) (150 mg, 0.31 mmol) in methanol (5 mL) for 5 minutes. To the reaction mixture was added 10% palladium on activated carbon (150 mg, 100 wt %), and the resulting mixture was stirred under hydrogen (100 kPa) at room temperature for 2 h. The reaction mixture was then filtered through a pad of Celite® diatomaceous filter aid, and the catalyst was rinsed with methanol and filtered. The combined filtrates were concentrated, and the crude residue was purified by medium pressure liquid chromatography using 0-25% isopropanol in dichloromethane as eluant to give 92 mg of the title product, a compound of the present invention, as an off-white solid.
$^1$H NMR (CDCl$_3$) δ 8.08 (d, 1H), 7.49 (m, 2H), 7.05 (m, 2H), 6.30 (d, 1H), 5.29 (m, 2H), 3.49 (m, 2H), 3.28 (m, 2H), 2.77 (m, 1H), 1.98 (m, 2H), 0.79 (m, 2H), 0.56 (m, 2H).

Step F: Preparation of 1-[3-[2-(cyclopropylamino)-4-pyrimidinyl]-2-(4-fluorophenyl)-5,6-dihydropyrazolo[1,5-b]pyridazin-7(4H)-yl]ethanone A catalytic amount of 4-dimethylaminopyridine (ca. 5 mg) was added to a solution of N-cyclopropyl-4-[2-(4-fluorophenyl)-4,5,6,7-tetrahydropyrazolo[1,5-b]pyridazin-3-yl]-2-pyrimidinamine (i.e. the product of Step E) (42.1 mg, 0.12 mmol) and acetic anhydride (0.023 mL, 0.24 mmol) in 2 mL of pyridine at room temperature. After 3 h the reaction mixture was diluted with water and extracted with ethyl acetate (3×10 mL). The combined organic phase was dried over magnesium sulfate, filtered and concentrated under reduced pressure. The crude residue was purified by medium pressure liquid chromatography using 20-100% ethyl acetate in hexanes as eluant to give 25 mg of the title product, a compound of the present invention, as a white solid.
$^1$H NMR (CDCl$_3$) δ 8.13 (d, 1H), 7.51 (m, 2H), 7.09 (m, 2H), 6.31 (d, 1H), 5.30 (s, 1H), 4.02 (m, 2H), 3.29 (s, 2H), 2.78 (m, 1H), 2.27 (s, 3H), 2.07 (m, 2H), 0.81 (m, 2H), 0.58 (m, 2H).

EXAMPLE 5

Preparation of 2-[[4-[2-(4-fluorophenyl)-4,5,6,7-tetrahydropyrazolo[1,5-b]pyridazin-3-yl]-2-pyrimidinyl]amino]-1-propanol (Compound 132)

Step A: Preparation of phenylmethyl 2-(4-fluorophenyl)-5,6-dihydro-3-[2-[(2-hydroxy-1-methylethyl)amino]-4-pyrimidinyl]pyrazolo[1,5-b]pyridazine-7(4H)-carboxylate A solution of phenylmethyl 3-(2-chloro-4-pyrimidinyl)-2-(4-fluorophenyl)-5,6-dihydropyrazolo[1,5-b]pyridazine-7(4H)-carboxylate (i.e. the product of Example 4, Step C) (390 mg, 0.84 mmol) and DL-2-amino-1-propanol (2.62 mL, 3.36 mmol) in chloroform (3 mL) was heated at 120° C. in a sealed tube under microwave irradiation for 1 h. The reaction mixture was concentrated under reduced pressure, and the crude residue was purified by medium pressure liquid chromatography using 10-80% ethyl acetate in hexanes as eluant to give 150 mg of the title compound as an orange solid.
$^1$H NMR (CDCl$_3$) δ 8.03 (d, 1H), 7.48 (m, 2H), 7.33 (m, 5H), 7.06 (m, 2H), 6.27 (d, 1H), 5.27 (s, 2H), 5.13 (m, 1H), 3.99 (m, 2H), 3.75 (m, 1H), 3.63 (m, 2H), 3.24 (m, 2H), 2.03 (m, 2H), 1.25 (d, 3H).

Step B: Preparation of 2-[[4-[2-(4-fluorophenyl)-4,5,6,7-tetrahydropyrazolo[1,5-b]pyridazin-3-yl]-2-pyrimidinyl]amino]-1-propanol Nitrogen gas was bubbled through a solution of phenylmethyl 2-(4-fluorophenyl)-5,6-dihydro-3-[2-[(2-hydroxy-1-methylethyl)amino]-4-pyrimidinyl]pyrazolo[1,5-b]pyridazine-7(4H)-carboxylate (i.e. the product of Step A) (107 mg, 0.21 mmol) in methanol (5 mL) for 5 minutes. To the reaction mixture was added 10% palladium on activated carbon (227 mg), and the resulting mixture was stirred under hydrogen (100 kPa) for 2 h at room temperature. The reaction mixture was filtered through a pad of Celite® diatomaceous filter aid, and the palladium catalyst was rinsed with methanol and filtered. The combined filtrates were concentrated, and the crude residue was purified by medium pressure liquid chromatography using 10-50% isopropanol in dichloromethane as eluant to give 47 mg of the title product, a compound of the present invention, as a white solid.
$^1$H NMR (CDCl$_3$) δ 8.01 (d, 1H), 7.47 (m, 2H), 7.05 (m, 2H), 6.28 (d, 1H), 5.27 (s, 1H), 5.08 (m, 1H), 4.10 (m, 1H), 3.75 (m, 1H), 3.62 (m, 1H), 3.49 (m, 2H), 3.20 (m, 2H), 2.00 (m, 2H), 1.26 (m, 3H).

EXAMPLE 6

Preparation of 3-(2-chloro-4-pyrimidinyl)-2-(4-fluorophenyl)-4,5,6,7-tetrahydropyrazolo[1,5-b]pyridazine (Compound 145) and N-cyclopropyl-4-[2-(4-fluorophenyl)-4,5,6,7-tetrahydro-7-methylpyrazolo[1,5-b]pyridazin-3-yl]-2-pyrimidinamine (Compound 135)

Step A: Preparation of 3-(2-chloro-4-pyrimidinyl)-2-(4-fluorophenyl)-4,5,6,7-tetrahydropyrazolo[1,5-b]pyridazine Nitrogen gas was bubbled through a solution of phenylmethyl 3-(2-chloro-4-pyrimidinyl)-2-(4-fluorophenyl)-5,6-dihydropyrazolo[1,5-b]pyridazine-7(4H)-carboxylate (i.e. the product of Example 4, Step C) (1.0 g, 2.16 mmol) in methanol (10 mL) for 5 minutes. To the reaction mixture was added 10% palladium on activated carbon (229 mg, 23 wt %), and the resulting mixture was stirred at room temperature under hydrogen (100 kPa) for 1 h. The reaction mixture was filtered through a pad of Celite® diatomaceous filter aid, and the palladium catalyst was rinsed with methanol and filtered. The combined filtrates were concentrated, and the crude residue was purified by medium pressure liquid chromatography using 20-100% ethyl acetate in hexanes as eluant to give 180 mg of the title compound as a solid.
$^1$H NMR (CDCl$_3$) δ 8.26 (d, 1H), 7.45 (m, 2H), 7.10 (m, 2H), 6.85 (d, 1H), 5.30 (s, 1H), 3.51 (m, 2H), 3.31 (m, 2H), 2.03 (m, 2H).

Step B: Preparation of 3-(2-chloro-4-pyrimidinyl)-2-(4-fluorophenyl)-4,5,6,7-tetrahydro-7-methylpyrazolo[1,5-b]pyridazine A mixture of 3-(2-chloro-4-pyrimidinyl)-2-(4-fluorophenyl)-4,5,6,7-tetrahydropyrazolo[1,5-b]pyridazine (i.e. the product of Step A) (50.0 mg, 0.15 mmol), iodomethane (0.019 mL, 0.31 mmol) and potassium carbonate (63 mg, 0.46 mmol) in N,N-dimethylformamide (3 mL) was stirred at room temperature for 2 h, followed by at 50° C. for 1 h and then at 100° C. for 2 h. The reaction mixture was diluted with water and extracted with ethyl acetate (3×10 mL). The combined organic phase was dried over magnesium sulfate, filtered and concentrated under reduced pressure. The crude residue was purified by medium pressure liquid chromatography using 20-80% ethyl acetate in hexanes as eluant to give 37.4 mg of the title product, a compound of the present invention, as a white solid.

$^1$H NMR (CDCl$_3$) δ 8.25 (d, 1H), 7.45 (m, 2H), 7.10 (m, 2H), 6.83 (d, 1H), 3.39 (m, 2H), 3.26 (m, 2H), 3.10 (s, 3H), 2.05 (m, 2H).

Step C: Preparation of N-cyclopropyl-4-[2-(4-fluorophenyl)-4,5,6,7-tetrahydro-7-methylpyrazolo[1,5-b]pyridazin-3-yl]-2-pyrimidinamine A solution of 3-(2-chloro-4-pyrimidinyl)-2-(4-fluorophenyl)-4,5,6,7-tetrahydro-7-methylpyrazolo[1,5-b]pyridazine (i.e. the product of Step B) (30.0 mg, 0.087 mmol) and cyclopropylamine (0.31 mL, 4.36 mmol) in 1-methyl-2-pyrrolidinone (2 mL) was heated under microwave irradiation at 150° C. for 30 minutes. The reaction mixture was diluted with water and extracted with ethyl acetate (3×10 mL). The combined organic layers were washed with brine, dried over magnesium sulfate, filtered and concentrated under reduced pressure. The crude residue was purified by medium pressure liquid chromatography using 20-80% ethyl acetate in hexanes as eluant to give 27 mg of the title product, a compound of the present invention, as a white solid.

$^1$H NMR (CDCl$_3$) δ 8.07 (d, 1H), 7.50 (m, 2H), 7.05 (m, 2H), 6.28 (d, 1H), 5.23 (s, 1H), 3.38 (m, 2H), 3.23 (m, 2H), 3.09 (s, 3H), 2.77 (m, 1H), 2.01 (m, 1H), 0.80 (m, 2H), 0.56 (m, 2H).

EXAMPLE 7

Preparation of 2-(4-fluorophenyl)-4,5-dihydro-3-[2-(methylsulfonyl)-4-pyrimidinyl]-7H-pyrazolo[1,5-c][1,3]oxazine (Compound 178) and 4-[2-(4-fluorophenyl)-4,5-dihydro-7H-pyrazolo[1,5-c][1,3]oxazin-3-yl]-N-(1-methylethyl)-2-pyrimidinamine (Compound 112)

Step A: Preparation of tetrahydro-2H-1,3-oxazine-4-carboxylic acid

Homoserine lactone hydrobromide (5.92 g, 32.5 mmol) was dissolved in a mixture of formaldehyde (37% in water, 16 mL), 1 N hydrochloric acid (3 mL) and water (75 mL).

The reaction mixture was stirred for 4 days. The solvent was then evaporated under reduced pressure to yield a white solid, which was then suspended in ethanol (100 mL). After 15 minutes, the undissolved solids were filtered off, and the filtrate was concentrated to give approximately 25 mL of crude residue. After the addition of 25 mL ethyl acetate, the crude mixture was stored a freezer at –10° C. overnight. The solid was then collected by filtration to give 4.1 g of the title compound as a white solid.

$^1$H NMR (DMSO-d$_6$) δ 4.93 (d, 1H), 4.48 (d, 1H), 4.31 (m, 1H), 4.04 (m, 1H), 3.76 (m, 1H), 2.09 (m, 1H), 1.90 (m, 1H).

Step B: Preparation of tetrahydro-3-nitroso-2H-1,3-oxazine-4-carboxylic acid

Tetrahydro-2H-1,3-oxazine-4-carboxylic acid (i.e. the product of Step A) (2.00 g, 15.3 mmol) was dissolved in 1 N hydrochloric acid (12.4 mL), and the solution was cooled to 0° C. Sodium nitrite (1.42 g, 20.6 mmol) was then added portionwise, and the reaction mixture was stirred for 1 h. The reaction mixture was then extracted twice with dichloromethane and once with ethyl acetate. The combined organic layers were washed with brine, dried over magnesium sulfate, filtered and concentrated under reduced pressure to give 1.29 g of the title compound as a solid. This compound was of sufficient purity to use in subsequent reactions.

$^1$H NMR (DMSO-d$_6$) δ 13.51 (br s., 1H), 6.01 (d, 1H), 5.52 (d, 1H), 5.27 (d, 1H), 3.99 (m, 1H), 3.70 (m, 1H), 2.07 (m, 1H), 1.95 (m, 1H).

Step C: Preparation of 3-hydroxy-7H-[1,2,3]oxadiazolo[3,4-c][1,3]oxazin-8-ium inner salt Tetrahydro-3-nitroso-2H-1,3-oxazine-4-carboxylic acid (i.e. the product of Step B) (1.29 g, 8.0 mmol) was dissolved in diethyl ether (10 mL) and cooled to 0° C. Trifluoroacetic anhydride (2.0 g, 9.6 mmol) was then added in three portions over 5 minutes. The reaction mixture was stirred at 0° C. for 1 h and then placed in a freezer at –10° C. overnight. The solid formed was isolated by filtration to give 0.99 g of the title compound as a white solid. This compound was of sufficient purity to use in subsequent reactions.

$^1$H NMR (DMSO-d$_6$) δ 5.86 (s, 2H), 4.14 (m, 2H), 2.69 (m, 2H).

Step D: Preparation of 2-(4-fluorophenyl)-4,5-dihydro-3-[2-(methylthio)-4-pyrimidinyl]-7H-pyrazolo[1,5-c][1,3]oxazine A mixture of 4-[2-(4-fluorophenyl)ethynyl]-2-(methylthio)pyrimidine (i.e. the product of Example 1, Step A) (1.26 g, 5.16 mmol) and 3-hydroxy-7H-[1,2,3]oxadiazolo[3,4-c][1,3]oxazin-8-ium inner salt (i.e. the product of Step C) (0.99 g, 6.96 mmol) in mesitylene (20 mL) was heated at 160° C. for 24 h. The reaction mixture was concentrated under reduced pressure, and the residual oil was purified by medium pressure liquid chromatography using 0-100% ethyl acetate in hexanes as eluant to give 290 mg of the title compound as a white solid.

$^1$H NMR (CDCl$_3$) δ 8.24 (d, 1H), 7.45 (m, 2H), 7.09 (m, 2H), 6.62 (d, 1H), 5.60 (s, 2H), 4.14 (m, 2H), 3.34 (m, 2H), 2.51 (s, 3H).

Step E: Preparation of 2-(4-fluorophenyl)-4,5-dihydro-3-[2-(methylsulfonyl)-4-pyrimidinyl]-7H-pyrazolo[1,5-c][1,3]oxazine 3-Chloroperbenzoic acid (70%, 0.290 g, 1.87 mmol) was added to a solution of 2-(4-fluorophenyl)-4,5-dihydro-3-[2-(methylthio)-4-pyrimidinyl]-7H-pyrazolo[1,5-c][1,3]oxazine (i.e. the product of Step D) (0.29 g, 0.85 mmol) in chloroform (20 mL). The reaction mixture was stirred at room temperature for 24 h and then washed three times with saturated aqueous Na$_2$CO$_3$ solution. The organic layer was dried and concentrated to give 0.30 g of the title product, a compound of the present invention, as a solid. This compound was of sufficient purity to use in subsequent reactions.

$^1$H NMR (CDCl$_3$) δ 8.53 (d, 1H), 7.46 (m, 2H), 7.15 (m, 2H), 7.10 (d, 1H), 5.62 (s, 2H), 4.18 (m, 2H), 3.47 (m, 2H), 3.33 (s, 3H).

Step F: Preparation of 4-[2-(4-fluorophenyl)-4,5-dihydro-7H-pyrazolo[1,5-c][1,3]oxazin-3-yl]-N-(1-methylethyl)-2-pyrimidinamine A solution of 2-(4-fluorophenyl)-4,5-dihydro-3-[2-(methylsulfonyl)-4-pyrimidinyl]-7H-pyrazolo[1,5-c][1,3]oxazine (i.e. the product of Step E) (0.15 g, 0.4 mmol) and isopropylamine (0.95 g, 16 mmol) in 2.5 mL of chloroform in a sealed tube was heated in a microwave reactor for 1 h at 120° C. The reaction mixture was then concentrated under reduced pressure and purified by medium pressure liquid chromatography using 0-100% ethyl acetate in hexanes as eluant to give 100 mg of the title product, a compound of the present invention, as a white solid.

$^1$H NMR (CDCl$_3$) δ 8.04 (d, 1H), 7.48 (m, 2H), 7.07 (m, 2H), 6.22 (d, 1H), 5.60 (s, 2H), 4.92 (d, 1H), 4.14 (m, 3H), 3.32 (m, 2H), 1.24 (d, 6H).

EXAMPLE 8

Preparation of 4-[2-(2,4-difluorophenyl)-4H,6H-pyrazolo[1,5-c]thiazol-3-yl]-N-(2-methoxy-1-methylethyl)-2-pyrimidinamine (Compound 83)

Step A: Preparation of 3-(2-chloro-4-pyrimidinyl)-2-(2,4-difluorophenyl)-4H,6H-pyrazolo[1,5-c]thiazole A solution of 3-hydroxy-4H,6H-thiazolo[3,4-c][1,2,3]oxadiazol-7-ium, inner salt (0.63 g, 4.3 mmol) (prepared from thiazolidine-4-carboxylic acid by nitrosation and treatment with trifluoroacetic anhydride as described in Sutcliffe et al. *Tetrahedron* 2000, 24, 10011-10021) and 4-[2-(2,4-difluorophenyl)ethynyl]-2-chloropyrimidine (1.0 g, 4.0 mmol) in mesitylene (15 mL) was heated at 155-160° C. under nitrogen for 48 h. The reaction mixture was concentrated under reduced pressure. The crude residue was purified by medium pressure liquid chromatography using 0 to 50% ethyl acetate in hexanes as eluant to give 0.09 g of the title compound as a white solid.

$^1$H NMR (CDCl$_3$) δ 8.33 (d, 1H), 7.50 (m, 1H), 7.00 (m, 2H), 6.77 (m, 1H), 5.30 (t, 2H), 4.56 (t, 2H).

Step B: Preparation of 4-[2-(2,4-difluorophenyl)-4H,6H-pyrazolo[1,5-c]thiazol-3-yl]-N-(2-methoxy-1-methylethyl)-2-pyrimidinamine A mixture of 3-(2-chloro-4-pyrimidinyl)-2-(2,4-difluorophenyl)-4H,6H-pyrazolo[1,5-c]thiazole (i.e. the product of Step A) (0.090 g, 0.27 mmol) and isopropylamine (1.00 mL, 11.8 mmol) in chloroform (2 mL) was heated in a sealed tube in a microwave reactor at 150° C. for 1 h. The reaction mixture was concentrated under reduced pressure and purified by column chromatography on silica gel using 10 to 100% ethyl acetate in hexanes as eluant to give 50 mg of the title product, a compound of the present invention, as a pale yellow oil.

$^1$H NMR (CDCl$_3$) δ 8.03 (d, 1H), 7.47 (m, 1H), 6.99 (m, 1H), 6.91 (m, 1H), 6.12 (dd, 1H), 5.28 (t, 2H), 4.84 (s, 1H), 4.50 (t, 2H), 4.05 (m, 1H), 1.23 (d, 6H).

EXAMPLE 9

Preparation of 4-[2-(4-fluorophenyl)-6,7-dihydro-5,5-dioxido-4H-pyrazolo[5,1-c][1,4]thiazin-3-yl]-N-(1-methylethyl)-2-pyrimidinamine (Compound 114)

3-Chloroperbenzoic acid (70%, 0.10 g, 0.68 mmol) was added to a solution of 4-[2-(4-fluorophenyl)-6,7-dihydro-4H-pyrazolo[5,1-c][1,4]thiazin-3-yl]-N-(1-methylethyl)-2-pyrimidinamine (prepared using a procedure analogous to Example 8) in chloroform (10 mL). The reaction mixture was stirred at room temperature for 24 h and then washed three times with saturated aqueous Na$_2$CO$_3$ solution. The organic layer was dried, concentrated and purified by medium pressure liquid chromatography using 0-100% ethyl acetate in hexanes as eluant to give 14 mg of the title product, a compound of the present invention, as a white solid.

$^1$H NMR (CDCl$_3$) δ 8.04 (d, 1H), 7.45 (m, 2H), 7.10 (m, 2H), 6.16 (d, 1H), 5.02 (d, 1H), 4.89 (s, 2H), 4.86 (m, 2H), 4.11 (m, 1H), 3.59 (m, 2H), 1.28 (d, 6H).

By the procedures described herein together with methods known in the art, the following compounds of Tables 1A to 6 can be prepared. The following abbreviations are used in the Tables which follow: t means tertiary, s means secondary, n means normal, means iso, c means cyclo, Me means methyl, Et means ethyl, Pr means propyl, i-Pr means isopropyl, Bu means butyl, Hex means hexyl, OMe means methoxy, SMe means methylthio, —CN means cyano, Ph means phenyl, —NO$_2$ means nitro, SO$_2$ means S(O)$_2$, S(O)Me means methylsulfinyl, and S(O)$_2$Me means methylsulfonyl. Substituents R$^{9b}$ and R$^{12}$ are numbered starting at the position where they attach to the remainder of Formula 1.

TABLE 1A

| R$^{9a}$ | R$^{9a}$ | R$^{9a}$ | R$^{9a}$ |
|---|---|---|---|
| R$^{9b}$ is H. | | | |
| Me | CH$_2$-2-cyclohexenyl | 2-chloro-2-propenyl | CH$_2$OPh |
| Et | 4-tetrahydropyranyl | 3,3-dichloro-2-propenyl | CH$_2$Ph |
| i-Pr | 3-tetrahydropyranyl | CH$_2$-2-tetrahydrofuranyl | CH$_2$CH$_2$Ph |
| n-Pr | 3-tetrahydrofuranyl | CH$_2$-2-tetrahydropyranyl | CH(Me)Ph |
| i-Bu | Ph | CH$_2$CN | CH$_2$-2-Cl—Ph |
| n-Bu | 2-Cl-phenyl | CH$_2$NO$_2$ | CH$_2$-3-Cl—Ph |
| s-Bu | 3-Cl-phenyl | CH$_2$CH$_2$OH | CH$_2$-4-Cl—Ph |
| 3-Me—Bu | 4-Cl-phenyl | CH$_2$CH$_2$OMe | CH$_2$-2-thienyl |
| n-pentyl | 2-pyridinyl | CH$_2$CH(Me)OMe | CH$_2$-2-pyridinyl |

TABLE 1A-continued

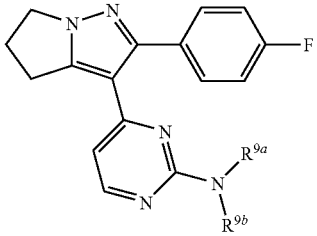

| $R^{9a}$ | $R^{9a}$ | $R^{9a}$ | $R^{9a}$ |
|---|---|---|---|
| n-Hex | 2-pyrimidinyl | CH(Me)CH₂OMe | CH₂-3-pyridinyl |
| 2-propenyl | 2-pyrazinyl | CH(Me)CH(OMe)₂ | CH(Et)₂ |
| 2-Me-2-propenyl | 2-thiazolyl | CH₂-2-dioxolanyl | CH₂CH(Et)₂ |
| 3-butenyl | 2-oxazolyl | CH₂CH₂OCF₃ | CH₂CH(n-Pr)Me |
| 3-pentenyl | CF₃ | CH₂CH₂SMe | CH(Me)Et |
| 2-propynyl | CF₂CF₃ | CH₂CH(Me)SMe | CH(Me)—n-Pr |
| 3-butynyl | CH₂CF₃ | CH₂CH₂S(O)Me | CH(CF₃)Et |
| 2-butynyl | CH(Me)CF₃ | CH₂CH₂S(O)₂Me | CH(Et)—n-Pr |
| c-Pr | CH₂CH₂F | CH₂CO₂Me | CH(Me)—n-Bu |
| c-pentyl | CH₂CH₂CH₂F | CH₂CO₂—i-Pr | 2,2-dimethylpropyl |
| c-Hex | CH₂CF₂CF₃ | CH(Me)CO₂Me | CH₂CH₂CH(Me)₂ |
| 2-cyclohexenyl | CH₂CH₂CF₃ | CH₂C(O)Me | |
| 3-cyclohexenyl | CH₂CH(Me)CF₃ | CH₂CH₂C(O)Me | |
| CH₂—c-Pr | (S)-CH₂CH(Me)CF₃ | CH₂SiMe₃ | |
| CH₂—c-Hex | CH₂CH₂CH₂CH₂F | CH₂CH₂SiMe₃ | |
| $R^{9b}$ is CH₃. | | | |
| Me | CH₂-2-cyclohexenyl | 2-chloro-2-propenyl | CH₂OPh |
| Et | 4-tetrahydropyranyl | 3,3-dichloro-2-propenyl | CH₂Ph |
| i-Pr | 3-tetrahydropyranyl | CH₂-2-tetrahydrofuranyl | CH₂CH₂Ph |
| n-Pr | 3-tetrahydrofuranyl | CH₂-2-tetrahydropyranyl | CH(Me)Ph |
| i-Bu | Ph | CH₂CN | CH₂-2-Cl—Ph |
| n-Bu | 2-Cl-phenyl | CH₂NO₂ | CH₂-3-Cl—Ph |
| s-Bu | 3-Cl-phenyl | CH₂CH₂OH | CH₂-4-Cl—Ph |
| 3-Me—Bu | 4-Cl-phenyl | CH₂CH₂OMe | CH₂-2-thienyl |
| n-pentyl | 2-pyridinyl | CH₂CH(Me)OMe | CH₂-2-pyridinyl |
| n-Hex | 2-pyrimidinyl | CH(Me)CH₂OMe | CH₂-3-pyridinyl |
| 2-propenyl | 2-pyrazinyl | CH(Me)CH(OMe)₂ | CH(Et)₂ |
| 2-Me-2-propenyl | 2-thiazolyl | CH₂-2-dioxolanyl | CH₂CH(Et)₂ |
| 3-butenyl | 2-oxazolyl | CH₂CH₂OCF₃ | CH₂CH(n-Pr)Me |
| 3-pentenyl | CF₃ | CH₂CH₂SMe | CH(Me)Et |
| 2-propynyl | CF₂CF₃ | CH₂CH(Me)SMe | CH(Me)—n-Pr |
| 3-butynyl | CH₂CF₃ | CH₂CH₂S(O)Me | CH(CF₃)Et |
| 2-butynyl | CH(Me)CF₃ | CH₂CH₂S(O)₂Me | CH(Et)—n-Pr |
| c-Pr | CH₂CH₂F | CH₂CO₂Me | CH(Me)—n-Bu |
| c-pentyl | CH₂CH₂CH₂F | CH₂CO₂—i-Pr | 2,2-dimethylpropyl |
| c-Hex | CH₂CF₂CF₃ | CH(Me)CO₂Me | CH₂CH₂CH(Me)₂ |
| 2-cyclohexenyl | CH₂CH₂CF₃ | CH₂C(O)Me | |
| 3-cyclohexenyl | CH₂CH(Me)CF₃ | CH₂CH₂C(O)Me | |
| CH₂—c-Pr | (S)-CH₂CH(Me)CF₃ | CH₂SiMe₃ | |
| CH₂—c-Hex | CH₂CH₂CH₂CH₂F | CH₂CH₂SiMe₃ | |

TABLE 1B

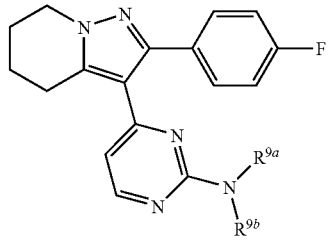

| $R^{9a}$ | $R^{9a}$ | $R^{9a}$ | $R^{9a}$ |
|---|---|---|---|
| $R^{9b}$ is H. | | | |
| Me | CH₂-2-cyclohexenyl | 2-chloro-2-propenyl | CH₂OPh |
| Et | 4-tetrahydropyranyl | 3,3-dichloro-2-propenyl | CH₂Ph |
| i-Pr | 3-tetrahydropyranyl | CH₂-2-tetrahydrofuranyl | CH₂CH₂Ph |

TABLE 1B-continued

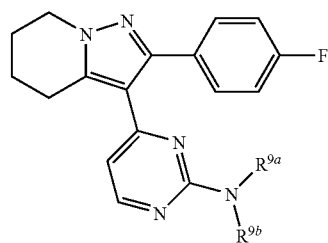

| $R^{9a}$ | $R^{9a}$ | $R^{9a}$ | $R^{9a}$ |
|---|---|---|---|
| n-Pr | 3-tetrahydrofuranyl | $CH_2$-2-tetrahydropyranyl | CH(Me)Ph |
| i-Bu | Ph | $CH_2CN$ | $CH_2$-2-Cl—Ph |
| n-Bu | 2-Cl-phenyl | $CH_2NO_2$ | $CH_2$-3-Cl—Ph |
| s-Bu | 3-Cl-phenyl | $CH_2CH_2OH$ | $CH_2$-4-Cl—Ph |
| 3-Me—Bu | 4-Cl-phenyl | $CH_2CH_2OMe$ | $CH_2$-2-thienyl |
| n-pentyl | 2-pyridinyl | $CH_2CH(Me)OMe$ | $CH_2$-2-pyridinyl |
| n-Hex | 2-pyrimidinyl | $CH(Me)CH_2OMe$ | $CH_2$-3-pyridinyl |
| 2-propenyl | 2-pyrazinyl | $CH(Me)CH(OMe)_2$ | $CH(Et)_2$ |
| 2-Me-2-propenyl | 2-thiazolyl | $CH_2$-2-dioxolanyl | $CH_2CH(Et)_2$ |
| 3-butenyl | 2-oxazolyl | $CH_2CH_2OCF_3$ | $CH_2CH(n-Pr)Me$ |
| 3-pentenyl | $CF_3$ | $CH_2CH_2SMe$ | CH(Me)Et |
| 2-propynyl | $CF_2CF_3$ | $CH_2CH(Me)SMe$ | CH(Me)—n-Pr |
| 3-butynyl | $CH_2CF_3$ | $CH_2CH_2S(O)Me$ | $CH(CF_3)Et$ |
| 2-butynyl | $CH(Me)CF_3$ | $CH_2CH_2S(O)_2Me$ | CH(Et)—n-Pr |
| c-Pr | $CH_2CH_2F$ | $CH_2CO_2Me$ | CH(Me)—n-Bu |
| c-pentyl | $CH_2CH_2CH_2F$ | $CH_2CO_2$—i-Pr | 2,2-dimethylpropyl |
| c-Hex | $CH_2CF_2CF_3$ | $CH(Me)CO_2Me$ | $CH_2CH_2CH(Me)_2$ |
| 2-cyclohexenyl | $CH_2CH_2CF_3$ | $CH_2C(O)Me$ | |
| 3-cyclohexenyl | $CH_2CH(Me)CF_3$ | $CH_2CH_2C(O)Me$ | |
| $CH_2$—c-Pr | (S)-$CH_2CH(Me)CF_3$ | $CH_2SiMe_3$ | |
| $CH_2$—c-Hex | $CH_2CH_2CH_2F$ | $CH_2CH_2SiMe_3$ | |

$R^{9b}$ is $CH_3$.

| Me | $CH_2$-2-cyclohexenyl | 2-chloro-2-propenyl | $CH_2OPh$ |
| Et | 4-tetrahydropyranyl | 3,3-dichloro-2-propenyl | $CH_2Ph$ |
| i-Pr | 3-tetrahydropyranyl | $CH_2$-2-tetrahydrofuranyl | $CH_2CH_2Ph$ |
| n-Pr | 3-tetrahydrofuranyl | $CH_2$-2-tetrahydropyranyl | CH(Me)Ph |
| i-Bu | Ph | $CH_2CN$ | $CH_2$-2-Cl—Ph |
| n-Bu | 2-Cl-phenyl | $CH_2NO_2$ | $CH_2$-3-Cl—Ph |
| s-Bu | 3-Cl-phenyl | $CH_2CH_2OH$ | $CH_2$-4-Cl—Ph |
| 3-Me—Bu | 4-Cl-phenyl | $CH_2CH_2OMe$ | $CH_2$-2-thienyl |
| n-pentyl | 2-pyridinyl | $CH_2CH(Me)OMe$ | $CH_2$-2-pyridinyl |
| n-Hex | 2-pyrimidinyl | $CH(Me)CH_2OMe$ | $CH_2$-3-pyridinyl |
| 2-propenyl | 2-pyrazinyl | $CH(Me)CH(OMe)_2$ | $CH(Et)_2$ |
| 2-Me-2-propenyl | 2-thiazolyl | $CH_2$-2-dioxolanyl | $CH_2CH(Et)_2$ |
| 3-butenyl | 2-oxazolyl | $CH_2CH_2OCF_3$ | $CH_2CH(n-Pr)Me$ |
| 3-pentenyl | $CF_3$ | $CH_2CH_2SMe$ | CH(Me)Et |
| 2-propynyl | $CF_2CF_3$ | $CH_2CH(Me)SMe$ | CH(Me)—n-Pr |
| 3-butynyl | $CH_2CF_3$ | $CH_2CH_2S(O)Me$ | $CH(CF_3)Et$ |
| 2-butynyl | $CH(Me)CF_3$ | $CH_2CH_2S(O)_2Me$ | CH(Et)—n-Pr |
| c-Pr | $CH_2CH_2F$ | $CH_2CO_2Me$ | CH(Me)—n-Bu |
| c-pentyl | $CH_2CH_2CH_2F$ | $CH_2CO_2$—i-Pr | 2,2-dimethylpropyl |
| c-Hex | $CH_2CF_2CF_3$ | $CH(Me)CO_2Me$ | $CH_2CH_2CH(Me)_2$ |
| 2-cyclohexenyl | $CH_2CH_2CF_3$ | $CH_2C(O)Me$ | |
| 3-cyclohexenyl | $CH_2CH(Me)CF_3$ | $CH_2CH_2C(O)Me$ | |
| $CH_2$—c-Pr | (S)-$CH_2CH(Me)CF_3$ | $CH_2SiMe_3$ | |
| $CH_2$—c-Hex | $CH_2CH_2CH_2F$ | $CH_2CH_2SiMe_3$ | |

TABLE 1C

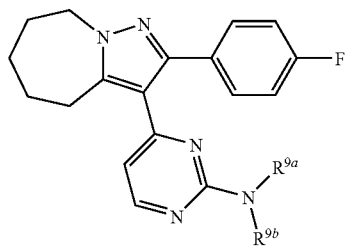

| $R^{9a}$ | $R^{9a}$ | $R^{9a}$ | $R^{9a}$ |
|---|---|---|---|
| \multicolumn{4}{c}{$R^{9b}$ is H.} | | | |

| $R^{9a}$ | $R^{9a}$ | $R^{9a}$ | $R^{9a}$ |
|---|---|---|---|
| Me | CH$_2$-2-cyclohexenyl | 2-chloro-2-propenyl | CH$_2$OPh |
| Et | 4-tetrahydropyranyl | 3,3-dichloro-2-propenyl | CH$_2$Ph |
| i-Pr | 3-tetrahydropyranyl | CH$_2$-2-tetrahydrofuranyl | CH$_2$CH$_2$Ph |
| n-Pr | 3-tetrahydrofuranyl | CH$_2$-2-tetrahydropyranyl | CH(Me)Ph |
| i-Bu | Ph | CH$_2$CN | CH$_2$-2-Cl—Ph |
| n-Bu | 2-Cl-phenyl | CH$_2$NO$_2$ | CH$_2$-3-Cl—Ph |
| s-Bu | 3-Cl-phenyl | CH$_2$CH$_2$OH | CH$_2$-4-Cl—Ph |
| 3-Me—Bu | 4-Cl-phenyl | CH$_2$CH$_2$OMe | CH$_2$-2-thienyl |
| n-pentyl | 2-pyridinyl | CH$_2$CH(Me)OMe | CH$_2$-2-pyridinyl |
| n-Hex | 2-pyrimidinyl | CH(Me)CH$_2$OMe | CH$_2$-3-pyridinyl |
| 2-propenyl | 2-pyrazinyl | CH(Me)CH(OMe)$_2$ | CH(Et)$_2$ |
| 2-Me-2-propenyl | 2-thiazolyl | CH$_2$-2-dioxolanyl | CH$_2$CH(Et)$_2$ |
| 3-butenyl | 2-oxazolyl | CH$_2$CH$_2$OCF$_3$ | CH$_2$CH(n-Pr)Me |
| 3-pentenyl | CF$_3$ | CH$_2$CH$_2$SMe | CH(Me)Et |
| 2-propynyl | CF$_2$CF$_3$ | CH$_2$CH(Me)SMe | CH(Me)—n-Pr |
| 3-butynyl | CH$_2$CF$_3$ | CH$_2$CH$_2$S(O)Me | CH(CF$_3$)Et |
| 2-butynyl | CH(Me)CF$_3$ | CH$_2$CH$_2$S(O)$_2$Me | CH(Et)—n-Pr |
| c-Pr | CH$_2$CH$_2$F | CH$_2$CO$_2$Me | CH(Me)—n-Bu |
| c-pentyl | CH$_2$CH$_2$CH$_2$F | CH$_2$CO$_2$—i-Pr | 2,2-dimethylpropyl |
| c-Hex | CH$_2$CF$_2$CF$_3$ | CH(Me)CO$_2$Me | CH$_2$CH$_2$CH(Me)$_2$ |
| 2-cyclohexenyl | CH$_2$CH$_2$CF$_3$ | CH$_2$C(O)Me | |
| 3-cyclohexenyl | CH$_2$CH(Me)CF$_3$ | CH$_2$CH$_2$C(O)Me | |
| CH$_2$—c-Pr | (S)-CH$_2$CH(Me)CF$_3$ | CH$_2$SiMe$_3$ | |
| CH$_2$—c-Hex | CH$_2$CH$_2$CH$_2$CH$_2$F | CH$_2$CH$_2$SiMe$_3$ | |
| \multicolumn{4}{c}{$R^{9b}$ is CH$_3$.} | | | |
| Me | CH$_2$-2-cyclohexenyl | 2-chloro-2-propenyl | CH$_2$OPh |
| Et | 4-tetrahydropyranyl | 3,3-dichloro-2-propenyl | CH$_2$Ph |
| i-Pr | 3-tetrahydropyranyl | CH$_2$-2-tetrahydrofuranyl | CH$_2$CH$_2$Ph |
| n-Pr | 3-tetrahydrofuranyl | CH$_2$-2-tetrahydropyranyl | CH(Me)Ph |
| i-Bu | Ph | CH$_2$CN | CH$_2$-2-Cl—Ph |
| n-Bu | 2-Cl-phenyl | CH$_2$NO$_2$ | CH$_2$-3-Cl—Ph |
| s-Bu | 3-Cl-phenyl | CH$_2$CH$_2$OH | CH$_2$-4-Cl—Ph |
| 3-Me—Bu | 4-Cl-phenyl | CH$_2$CH$_2$OMe | CH$_2$-2-thienyl |
| n-pentyl | 2-pyridinyl | CH$_2$CH(Me)OMe | CH$_2$-2-pyridinyl |
| n-Hex | 2-pyrimidinyl | CH(Me)CH$_2$OMe | CH$_2$-3-pyridinyl |
| 2-propenyl | 2-pyrazinyl | CH(Me)CH(OMe)$_2$ | CH(Et)$_2$ |
| 2-Me-2-propenyl | 2-thiazolyl | CH$_2$-2-dioxolanyl | CH$_2$CH(Et)$_2$ |
| 3-butenyl | 2-oxazolyl | CH$_2$CH$_2$OCF$_3$ | CH$_2$CH(n-Pr)Me |
| 3-pentenyl | CF$_3$ | CH$_2$CH$_2$SMe | CH(Me)Et |
| 2-propynyl | CF$_2$CF$_3$ | CH$_2$CH(Me)SMe | CH(Me)—n-Pr |
| 3-butynyl | CH$_2$CF$_3$ | CH$_2$CH$_2$S(O)Me | CH(CF$_3$)Et |
| 2-butynyl | CH(Me)CF$_3$ | CH$_2$CH$_2$S(O)$_2$Me | CH(Et)—n-Pr |
| c-Pr | CH$_2$CH$_2$F | CH$_2$CO$_2$Me | CH(Me)—n-Bu |
| c-pentyl | CH$_2$CH$_2$CH$_2$F | CH$_2$CO$_2$—i-Pr | 2,2-dimethylpropyl |
| c-Hex | CH$_2$CF$_2$CF$_3$ | CH(Me)CO$_2$Me | CH$_2$CH$_2$CH(Me)$_2$ |
| 2-cyclohexenyl | CH$_2$CH$_2$CF$_3$ | CH$_2$C(O)Me | |
| 3-cyclohexenyl | CH$_2$CH(Me)CF$_3$ | CH$_2$CH$_2$C(O)Me | |
| CH$_2$—c-Pr | (S)-CH$_2$CH(Me)CF$_3$ | CH$_2$SiMe$_3$ | |
| CH$_2$—c-Hex | CH$_2$CH$_2$CH$_2$CH$_2$F | CH$_2$CH$_2$SiMe$_3$ | |

TABLE 2

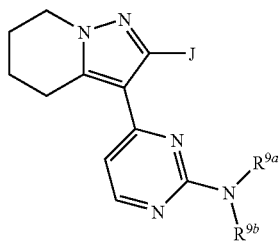

| $R^{9a}$ | $R^{9a}$ | $R^{9a}$ | $R^{9a}$ |
|---|---|---|---|
| \multicolumn{4}{c}{J is Ph and $R^{9b}$ is H.} | | | |
| Me | CH$_2$-2-cyclohexenyl | 2-chloro-2-propenyl | CH$_2$OPh |
| Et | 4-tetrahydropyranyl | 3,3-dichloro-2-propenyl | CH$_2$Ph |
| i-Pr | 3-tetrahydropyranyl | CH$_2$-2-tetrahydrofuranyl | CH$_2$CH$_2$Ph |
| n-Pr | 3-tetrahydrofuranyl | CH$_2$-2-tetrahydropyranyl | CH(Me)Ph |
| i-Bu | Ph | CH$_2$CN | CH$_2$-2-Cl—Ph |
| n-Bu | 2-Cl-phenyl | CH$_2$NO$_2$ | CH$_2$-3-Cl—Ph |
| s-Bu | 3-Cl-phenyl | CH$_2$CH$_2$OH | CH$_2$-4-Cl—Ph |
| 3-Me—Bu | 4-Cl-phenyl | CH$_2$CH$_2$OMe | CH$_2$-2-thienyl |
| n-pentyl | 2-pyridinyl | CH$_2$CH(Me)OMe | CH$_2$-2-pyridinyl |
| n-Hex | 2-pyrimidinyl | CH(Me)CH$_2$OMe | CH$_2$-3-pyridinyl |
| 2-propenyl | 2-pyrazinyl | CH(Me)CH(OMe)$_2$ | CH(Et)$_2$ |
| 2-Me-2-propenyl | 2-thiazolyl | CH$_2$-2-dioxolanyl | CH$_2$CH(Et)$_2$ |
| 3-butenyl | 2-oxazolyl | CH$_2$CH$_2$OCF$_3$ | CH$_2$CH(n-Pr)Me |
| 3-pentenyl | CF$_3$ | CH$_2$CH$_2$SMe | CH(Me)Et |
| 2-propynyl | CF$_2$CF$_3$ | CH$_2$CH(Me)SMe | CH(Me)—n-Pr |
| 3-butynyl | CH$_2$CF$_3$ | CH$_2$CH$_2$S(O)Me | CH(CF$_3$)Et |
| 2-butynyl | CH(Me)CF$_3$ | CH$_2$CH$_2$S(O)$_2$Me | CH(Et)—n-Pr |
| c-Pr | CH$_2$CH$_2$F | CH$_2$CO$_2$Me | CH(Me)—n-Bu |
| c-pentyl | CH$_2$CH$_2$CH$_2$F | CH$_2$CO$_2$—i-Pr | 2,2-dimethylpropyl |
| c-Hex | CH$_2$CF$_2$CF$_3$ | CH(Me)CO$_2$Me | CH$_2$CH$_2$CH(Me)$_2$ |
| 2-cyclohexenyl | CH$_2$CH$_2$CF$_3$ | CH$_2$C(O)Me | |
| 3-cyclohexenyl | CH$_2$CH(Me)CF$_3$ | CH$_2$CH$_2$C(O)Me | |
| CH$_2$—c-Pr | (S)-CH$_2$CH(Me)CF$_3$ | CH$_2$SiMe$_3$ | |
| CH$_2$—c-Hex | CH$_2$CH$_2$CH$_2$F | CH$_2$CH$_2$SiMe$_3$ | |
| \multicolumn{4}{c}{J is 2-F—Ph and $R^{9b}$ is H.} | | | |
| Me | CH$_2$-2-cyclohexenyl | 2-chloro-2-propenyl | CH$_2$OPh |
| Et | 4-tetrahydropyranyl | 3,3-dichloro-2-propenyl | CH$_2$Ph |
| i-Pr | 3-tetrahydropyranyl | CH$_2$-2-tetrahydrofuranyl | CH$_2$CH$_2$Ph |
| n-Pr | 3-tetrahydrofuranyl | CH$_2$-2-tetrahydropyranyl | CH(Me)Ph |
| i-Bu | Ph | CH$_2$CN | CH$_2$-2-Cl—Ph |
| n-Bu | 2-Cl-phenyl | CH$_2$NO$_2$ | CH$_2$-3-Cl—Ph |
| s-Bu | 3-Cl-phenyl | CH$_2$CH$_2$OH | CH$_2$-4-Cl—Ph |
| 3-Me—Bu | 4-Cl-phenyl | CH$_2$CH$_2$OMe | CH$_2$-2-thienyl |
| n-pentyl | 2-pyridinyl | CH$_2$CH(Me)OMe | CH$_2$-2-pyridinyl |
| n-Hex | 2-pyrimidinyl | CH(Me)CH$_2$OMe | CH$_2$-3-pyridinyl |
| 2-propenyl | 2-pyrazinyl | CH(Me)CH(OMe)$_2$ | CH(Et)$_2$ |
| 2-Me-2-propenyl | 2-thiazolyl | CH$_2$-2-dioxolanyl | CH$_2$CH(Et)$_2$ |
| 3-butenyl | 2-oxazolyl | CH$_2$CH$_2$OCF$_3$ | CH$_2$CH(n-Pr)Me |
| 3-pentenyl | CF$_3$ | CH$_2$CH$_2$SMe | CH(Me)Et |
| 2-propynyl | CF$_2$CF$_3$ | CH$_2$CH(Me)SMe | CH(Me)—n-Pr |
| 3-butynyl | CH$_2$CF$_3$ | CH$_2$CH$_2$S(O)Me | CH(CF$_3$)Et |
| 2-butynyl | CH(Me)CF$_3$ | CH$_2$CH$_2$S(O)$_2$Me | CH(Et)—n-Pr |
| c-Pr | CH$_2$CH$_2$F | CH$_2$CO$_2$Me | CH(Me)—n-Bu |
| c-pentyl | CH$_2$CH$_2$CH$_2$F | CH$_2$CO$_2$—i-Pr | 2,2-dimethylpropyl |
| c-Hex | CH$_2$CF$_2$CF$_3$ | CH(Me)CO$_2$Me | CH$_2$CH$_2$CH(Me)$_2$ |
| 2-cyclohexenyl | CH$_2$CH$_2$CF$_3$ | CH$_2$C(O)Me | |
| 3-cyclohexenyl | CH$_2$CH(Me)CF$_3$ | CH$_2$CH$_2$C(O)Me | |
| CH$_2$—c-Pr | (S)-CH$_2$CH(Me)CF$_3$ | CH$_2$SiMe$_3$ | |
| CH$_2$—c-Hex | CH$_2$CH$_2$CH$_2$F | CH$_2$CH$_2$SiMe$_3$ | |
| \multicolumn{4}{c}{J is 2-Cl—Ph and $R^{9b}$ is H.} | | | |
| Me | CH$_2$-2-cyclohexenyl | 2-chloro-2-propenyl | CH$_2$OPh |
| Et | 4-tetrahydropyranyl | 3,3-dichloro-2-propenyl | CH$_2$Ph |
| i-Pr | 3-tetrahydropyranyl | CH$_2$-2-tetrahydrofuranyl | CH$_2$CH$_2$Ph |
| n-Pr | 3-tetrahydrofuranyl | CH$_2$-2-tetrahydropyranyl | CH(Me)Ph |
| i-Bu | Ph | CH$_2$CN | CH$_2$-2-Cl—Ph |
| n-Bu | 2-Cl-phenyl | CH$_2$NO$_2$ | CH$_2$-3-Cl—Ph |
| s-Bu | 3-Cl-phenyl | CH$_2$CH$_2$OH | CH$_2$-4-Cl—Ph |
| 3-Me—Bu | 4-Cl-phenyl | CH$_2$CH$_2$OMe | CH$_2$-2-thienyl |
| n-pentyl | 2-pyridinyl | CH$_2$CH(Me)OMe | CH$_2$-2-pyridinyl |
| n-Hex | 2-pyrimidinyl | CH(Me)CH$_2$OMe | CH$_2$-3-pyridinyl |
| 2-propenyl | 2-pyrazinyl | CH(Me)CH(OMe)$_2$ | CH(Et)$_2$ |

TABLE 2-continued

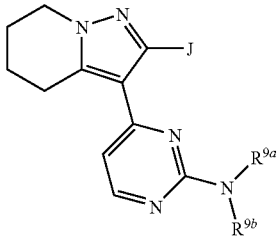

| R$^{9a}$ | R$^{9a}$ | R$^{9a}$ | R$^{9a}$ |
|---|---|---|---|
| 2-Me-2-propenyl | 2-thiazolyl | CH$_2$-2-dioxolanyl | CH$_2$CH(Et)$_2$ |
| 3-butenyl | 2-oxazolyl | CH$_2$CH$_2$OCF$_3$ | CH$_2$CH(n-Pr)Me |
| 3-pentenyl | CF$_3$ | CH$_2$CH$_2$SMe | CH(Me)Et |
| 2-propynyl | CF$_2$CF$_3$ | CH$_2$CH(Me)SMe | CH(Me)—n-Pr |
| 3-butynyl | CH$_2$CF$_3$ | CH$_2$CH$_2$S(O)Me | CH(CF$_3$)Et |
| 2-butynyl | CH(Me)CF$_3$ | CH$_2$CH$_2$S(O)$_2$Me | CH(Et)—n-Pr |
| c-Pr | CH$_2$CH$_2$F | CH$_2$CO$_2$Me | CH(Me)—n-Bu |
| c-pentyl | CH$_2$CH$_2$CH$_2$F | CH$_2$CO$_2$—i-Pr | 2,2-dimethylpropyl |
| c-Hex | CH$_2$CF$_2$CF$_3$ | CH(Me)CO$_2$Me | CH$_2$CH$_2$CH(Me)$_2$ |
| 2-cyclohexenyl | CH$_2$CH$_2$CF$_3$ | CH$_2$C(O)Me | |
| 3-cyclohexenyl | CH$_2$CH(Me)CF$_3$ | CH$_2$CH$_2$C(O)Me | |
| CH$_2$—c-Pr | (S)-CH$_2$CH(Me)CF$_3$ | CH$_2$SiMe$_3$ | |
| CH$_2$—c-Hex | CH$_2$CH$_2$CH$_2$F | CH$_2$CH$_2$SiMe$_3$ | |

J is 4-Cl—Ph and R$^{9b}$ is H.

| | | | |
|---|---|---|---|
| Me | CH$_2$-2-cyclohexenyl | 2-chloro-2-propenyl | CH$_2$OPh |
| Et | 4-tetrahydropyranyl | 3,3-dichloro-2-propenyl | CH$_2$Ph |
| i-Pr | 3-tetrahydropyranyl | CH$_2$-2-tetrahydrofuranyl | CH$_2$CH$_2$Ph |
| n-Pr | 3-tetrahydrofuranyl | CH$_2$-2-tetrahydropyranyl | CH(Me)Ph |
| i-Bu | Ph | CH$_2$CN | CH$_2$-2-Cl—Ph |
| n-Bu | 2-Cl-phenyl | CH$_2$NO$_2$ | CH$_2$-3-Cl—Ph |
| s-Bu | 3-Cl-phenyl | CH$_2$CH$_2$OH | CH$_2$-4-Cl—Ph |
| 3-Me—Bu | 4-Cl-phenyl | CH$_2$CH$_2$OMe | CH$_2$-2-thienyl |
| n-pentyl | 2-pyridinyl | CH$_2$CH(Me)OMe | CH$_2$-2-pyridinyl |
| n-Hex | 2-pyrimidinyl | CH(Me)CH$_2$OMe | CH$_2$-3-pyridinyl |
| 2-propenyl | 2-pyrazinyl | CH(Me)CH(OMe)$_2$ | CH(Et)$_2$ |
| 2-Me-2-propenyl | 2-thiazolyl | CH$_2$-2-dioxolanyl | CH$_2$CH(Et)$_2$ |
| 3-butenyl | 2-oxazolyl | CH$_2$CH$_2$OCF$_3$ | CH$_2$CH(n-Pr)Me |
| 3-pentenyl | CF$_3$ | CH$_2$CH$_2$SMe | CH(Me)Et |
| 2-propynyl | CF$_2$CF$_3$ | CH$_2$CH(Me)SMe | CH(Me)—n-Pr |
| 3-butynyl | CH$_2$CF$_3$ | CH$_2$CH$_2$S(O)Me | CH(CF$_3$)Et |
| 2-butynyl | CH(Me)CF$_3$ | CH$_2$CH$_2$S(O)$_2$Me | CH(Et)—n-Pr |
| c-Pr | CH$_2$CH$_2$F | CH$_2$CO$_2$Me | CH(Me)—n-Bu |
| c-pentyl | CH$_2$CH$_2$CH$_2$F | CH$_2$CO$_2$—i-Pr | 2,2-dimethylpropyl |
| c-Hex | CH$_2$CF$_2$CF$_3$ | CH(Me)CO$_2$Me | CH$_2$CH$_2$CH(Me)$_2$ |
| 2-cyclohexenyl | CH$_2$CH$_2$CF$_3$ | CH$_2$C(O)Me | |
| 3-cyclohexenyl | CH$_2$CH(Me)CF$_3$ | CH$_2$CH$_2$C(O)Me | |
| CH$_2$—c-Pr | (S)-CH$_2$CH(Me)CF$_3$ | CH$_2$SiMe$_3$ | |
| CH$_2$—c-Hex | CH$_2$CH$_2$CH$_2$F | CH$_2$CH$_2$SiMe$_3$ | |

J is 3-Me—Ph and R$^{9b}$ is H.

| | | | |
|---|---|---|---|
| Me | CH$_2$-2-cyclohexenyl | 2-chloro-2-propenyl | CH$_2$OPh |
| Et | 4-tetrahydropyranyl | 3,3-dichloro-2-propenyl | CH$_2$Ph |
| i-Pr | 3-tetrahydropyranyl | CH$_2$-2-tetrahydrofuranyl | CH$_2$CH$_2$Ph |
| n-Pr | 3-tetrahydrofuranyl | CH$_2$-2-tetrahydropyranyl | CH(Me)Ph |
| i-Bu | Ph | CH$_2$CN | CH$_2$-2-Cl—Ph |
| n-Bu | 2-Cl-phenyl | CH$_2$NO$_2$ | CH$_2$-3-Cl—Ph |
| s-Bu | 3-Cl-phenyl | CH$_2$CH$_2$OH | CH$_2$-4-Cl—Ph |
| 3-Me—Bu | 4-Cl-phenyl | CH$_2$CH$_2$OMe | CH$_2$-2-thienyl |
| n-pentyl | 2-pyridinyl | CH$_2$CH(Me)OMe | CH$_2$-2-pyridinyl |
| n-Hex | 2-pyrimidinyl | CH(Me)CH$_2$OMe | CH$_2$-3-pyridinyl |
| 2-propenyl | 2-pyrazinyl | CH(Me)CH(OMe)$_2$ | CH(Et)$_2$ |
| 2-Me-2-propenyl | 2-thiazolyl | CH$_2$-2-dioxolanyl | CH$_2$CH(Et)$_2$ |
| 3-butenyl | 2-oxazolyl | CH$_2$CH$_2$OCF$_3$ | CH$_2$CH(n-Pr)Me |
| 3-pentenyl | CF$_3$ | CH$_2$CH$_2$SMe | CH(Me)Et |
| 2-propynyl | CF$_2$CF$_3$ | CH$_2$CH(Me)SMe | CH(Me)—n-Pr |
| 3-butynyl | CH$_2$CF$_3$ | CH$_2$CH$_2$S(O)Me | CH(CF$_3$)Et |
| 2-butynyl | CH(Me)CF$_3$ | CH$_2$CH$_2$S(O)$_2$Me | CH(Et)—n-Pr |
| c-Pr | CH$_2$CH$_2$F | CH$_2$CO$_2$Me | CH(Me)—n-Bu |
| c-pentyl | CH$_2$CH$_2$CH$_2$F | CH$_2$CO$_2$—i-Pr | 2,2-dimethylpropyl |
| c-Hex | CH$_2$CF$_2$CF$_3$ | CH(Me)CO$_2$Me | CH$_2$CH$_2$CH(Me)$_2$ |
| 2-cyclohexenyl | CH$_2$CH$_2$CF$_3$ | CH$_2$C(O)Me | |
| 3-cyclohexenyl | CH$_2$CH(Me)CF$_3$ | CH$_2$CH$_2$C(O)Me | |
| CH$_2$—c-Pr | (S)-CH$_2$CH(Me)CF$_3$ | CH$_2$SiMe$_3$ | |
| CH$_2$—c-Hex | CH$_2$CH$_2$CH$_2$F | CH$_2$CH$_2$SiMe$_3$ | |

TABLE 2-continued

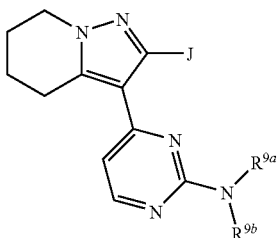

| $R^{9a}$ | $R^{9a}$ | $R^{9a}$ | $R^{9a}$ |
|---|---|---|---|
| J is Ph and $R^{9b}$ is $CH_3$. | | | |
| Me | $CH_2$-2-cyclohexenyl | 2-chloro-2-propenyl | $CH_2OPh$ |
| Et | 4-tetrahydropyranyl | 3,3-dichloro-2-propenyl | $CH_2Ph$ |
| i-Pr | 3-tetrahydropyranyl | $CH_2$-2-tetrahydrofuranyl | $CH_2CH_2Ph$ |
| n-Pr | 3-tetrahydrofuranyl | $CH_2$-2-tetrahydropyranyl | $CH(Me)Ph$ |
| i-Bu | Ph | $CH_2CN$ | $CH_2$-2-Cl—Ph |
| n-Bu | 2-Cl-phenyl | $CH_2NO_2$ | $CH_2$-3-Cl—Ph |
| s-Bu | 3-Cl-phenyl | $CH_2CH_2OH$ | $CH_2$-4-Cl—Ph |
| 3-Me—Bu | 4-Cl-phenyl | $CH_2CH_2OMe$ | $CH_2$-2-thienyl |
| n-pentyl | 2-pyridinyl | $CH_2CH(Me)OMe$ | $CH_2$-2-pyridinyl |
| n-Hex | 2-pyrimidinyl | $CH(Me)CH_2OMe$ | $CH_2$-3-pyridinyl |
| 2-propenyl | 2-pyrazinyl | $CH(Me)CH(OMe)_2$ | $CH(Et)_2$ |
| 2-Me-2-propenyl | 2-thiazolyl | $CH_2$-2-dioxolanyl | $CH_2CH(Et)_2$ |
| 3-butenyl | 2-oxazolyl | $CH_2CH_2OCF_3$ | $CH_2CH(n-Pr)Me$ |
| 3-pentenyl | $CF_3$ | $CH_2CH_2SMe$ | $CH(Me)Et$ |
| 2-propynyl | $CF_2CF_3$ | $CH_2CH(Me)SMe$ | $CH(Me)$—n-Pr |
| 3-butynyl | $CH_2CF_3$ | $CH_2CH_2S(O)Me$ | $CH(CF_3)Et$ |
| 2-butynyl | $CH(Me)CF_3$ | $CH_2CH_2S(O)_2Me$ | $CH(Et)$—n-Pr |
| c-Pr | $CH_2CH_2F$ | $CH_2CO_2Me$ | $CH(Me)$—n-Bu |
| c-pentyl | $CH_2CH_2CH_2F$ | $CH_2CO_2$—i-Pr | 2,2-dimethylpropyl |
| c-Hex | $CH_2CF_2CF_3$ | $CH(Me)CO_2Me$ | $CH_2CH_2CH(Me)_2$ |
| 2-cyclohexenyl | $CH_2CH_2CF_3$ | $CH_2C(O)Me$ | |
| 3-cyclohexenyl | $CH_2CH(Me)CF_3$ | $CH_2CH_2C(O)Me$ | |
| $CH_2$—c-Pr | (S)-$CH_2CH(Me)CF_3$ | $CH_2SiMe_3$ | |
| $CH_2$—c-Hex | $CH_2CH_2CH_2F$ | $CH_2CH_2SiMe_3$ | |
| J is 2-F—Ph and $R^{9b}$ is $CH_3$. | | | |
| Me | $CH_2$-2-cyclohexenyl | 2-chloro-2-propenyl | $CH_2OPh$ |
| Et | 4-tetrahydropyranyl | 3,3-dichloro-2-propenyl | $CH_2Ph$ |
| i-Pr | 3-tetrahydropyranyl | $CH_2$-2-tetrahydrofuranyl | $CH_2CH_2Ph$ |
| n-Pr | 3-tetrahydrofuranyl | $CH_2$-2-tetrahydropyranyl | $CH(Me)Ph$ |
| i-Bu | Ph | $CH_2CN$ | $CH_2$-2-Cl—Ph |
| n-Bu | 2-Cl-phenyl | $CH_2NO_2$ | $CH_2$-3-Cl—Ph |
| s-Bu | 3-Cl-phenyl | $CH_2CH_2OH$ | $CH_2$-4-Cl—Ph |
| 3-Me—Bu | 4-Cl-phenyl | $CH_2CH_2OMe$ | $CH_2$-2-thienyl |
| n-pentyl | 2-pyridinyl | $CH_2CH(Me)OMe$ | $CH_2$-2-pyridinyl |
| n-Hex | 2-pyrimidinyl | $CH(Me)CH_2OMe$ | $CH_2$-3-pyridinyl |
| 2-propenyl | 2-pyrazinyl | $CH(Me)CH(OMe)_2$ | $CH(Et)_2$ |
| 2-Me-2-propenyl | 2-thiazolyl | $CH_2$-2-dioxolanyl | $CH_2CH(Et)_2$ |
| 3-butenyl | 2-oxazolyl | $CH_2CH_2OCF_3$ | $CH_2CH(n-Pr)Me$ |
| 3-pentenyl | $CF_3$ | $CH_2CH_2SMe$ | $CH(Me)Et$ |
| 2-propynyl | $CF_2CF_3$ | $CH_2CH(Me)SMe$ | $CH(Me)$—n-Pr |
| 3-butynyl | $CH_2CF_3$ | $CH_2CH_2S(O)Me$ | $CH(CF_3)Et$ |
| 2-butynyl | $CH(Me)CF_3$ | $CH_2CH_2S(O)_2Me$ | $CH(Et)$—n-Pr |
| c-Pr | $CH_2CH_2F$ | $CH_2CO_2Me$ | $CH(Me)$—n-Bu |
| c-pentyl | $CH_2CH_2CH_2F$ | $CH_2CO_2$—i-Pr | 2,2-dimethylpropyl |
| c-Hex | $CH_2CF_2CF_3$ | $CH(Me)CO_2Me$ | $CH_2CH_2CH(Me)_2$ |
| 2-cyclohexenyl | $CH_2CH_2CF_3$ | $CH_2C(O)Me$ | |
| 3-cyclohexenyl | $CH_2CH(Me)CF_3$ | $CH_2CH_2C(O)Me$ | |
| $CH_2$—c-Pr | (S)-$CH_2CH(Me)CF_3$ | $CH_2SiMe_3$ | |
| $CH_2$—c-Hex | $CH_2CH_2CH_2F$ | $CH_2CH_2SiMe_3$ | |
| J is 2-Cl—Ph and $R^{9b}$ is $CH_3$. | | | |
| Me | $CH_2$-2-cyclohexenyl | 2-chloro-2-propenyl | $CH_2OPh$ |
| Et | 4-tetrahydropyranyl | 3,3-dichloro-2-propenyl | $CH_2Ph$ |
| i-Pr | 3-tetrahydropyranyl | $CH_2$-2-tetrahydrofuranyl | $CH_2CH_2Ph$ |
| n-Pr | 3-tetrahydrofuranyl | $CH_2$-2-tetrahydropyranyl | $CH(Me)Ph$ |
| i-Bu | Ph | $CH_2CN$ | $CH_2$-2-Cl—Ph |
| n-Bu | 2-Cl-phenyl | $CH_2NO_2$ | $CH_2$-3-Cl—Ph |
| s-Bu | 3-Cl-phenyl | $CH_2CH_2OH$ | $CH_2$-4-Cl—Ph |
| 3-Me—Bu | 4-Cl-phenyl | $CH_2CH_2OMe$ | $CH_2$-2-thienyl |
| n-pentyl | 2-pyridinyl | $CH_2CH(Me)OMe$ | $CH_2$-2-pyridinyl |
| n-Hex | 2-pyrimidinyl | $CH(Me)CH_2OMe$ | $CH_2$-3-pyridinyl |
| 2-propenyl | 2-pyrazinyl | $CH(Me)CH(OMe)_2$ | $CH(Et)_2$ |

TABLE 2-continued

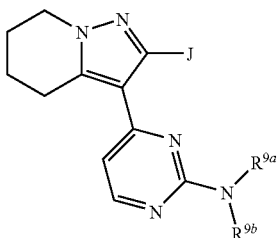

| R9a | R9a | R9a | R9a |
|---|---|---|---|
| 2-Me-2-propenyl | 2-thiazolyl | CH$_2$-2-dioxolanyl | CH$_2$CH(Et)$_2$ |
| 3-butenyl | 2-oxazolyl | CH$_2$CH$_2$OCF$_3$ | CH$_2$CH(n-Pr)Me |
| 3-pentenyl | CF$_3$ | CH$_2$CH$_2$SMe | CH(Me)Et |
| 2-propynyl | CF$_2$CF$_3$ | CH$_2$CH(Me)SMe | CH(Me)—n-Pr |
| 3-butynyl | CH$_2$CF$_3$ | CH$_2$CH$_2$S(O)Me | CH(CF$_3$)Et |
| 2-butynyl | CH(Me)CF$_3$ | CH$_2$CH$_2$S(O)$_2$Me | CH(Et)—n-Pr |
| c-Pr | CH$_2$CH$_2$F | CH$_2$CO$_2$Me | CH(Me)—n-Bu |
| c-pentyl | CH$_2$CH$_2$CH$_2$F | CH$_2$CO$_2$—i-Pr | 2,2-dimethylpropyl |
| c-Hex | CH$_2$CF$_2$CF$_3$ | CH(Me)CO$_2$Me | CH$_2$CH$_2$CH(Me)$_2$ |
| 2-cyclohexenyl | CH$_2$CH$_2$CF$_3$ | CH$_2$C(O)Me | |
| 3-cyclohexenyl | CH$_2$CH(Me)CF$_3$ | CH$_2$CH$_2$C(O)Me | |
| CH$_2$—c-Pr | (S)-CH$_2$CH(Me)CF$_3$ | CH$_2$SiMe$_3$ | |
| CH$_2$—c-Hex | CH$_2$CH$_2$CH$_2$F | CH$_2$CH$_2$SiMe$_3$ | |

J is 4-Cl—Ph and R$^{9b}$ is CH$_3$.

| | | | |
|---|---|---|---|
| Me | CH$_2$-2-cyclohexenyl | 2-chloro-2-propenyl | CH$_2$OPh |
| Et | 4-tetrahydropyranyl | 3,3-dichloro-2-propenyl | CH$_2$Ph |
| i-Pr | 3-tetrahydropyranyl | CH$_2$-2-tetrahydrofuranyl | CH$_2$CH$_2$Ph |
| n-Pr | 3-tetrahydrofuranyl | CH$_2$-2-tetrahydropyranyl | CH(Me)Ph |
| i-Bu | Ph | CH$_2$CN | CH$_2$-2-Cl—Ph |
| n-Bu | 2-Cl-phenyl | CH$_2$NO$_2$ | CH$_2$-3-Cl—Ph |
| s-Bu | 3-Cl-phenyl | CH$_2$CH$_2$OH | CH$_2$-4-Cl—Ph |
| 3-Me—Bu | 4-Cl-phenyl | CH$_2$CH$_2$OMe | CH$_2$-2-thienyl |
| n-pentyl | 2-pyridinyl | CH$_2$CH(Me)OMe | CH$_2$-2-pyridinyl |
| n-Hex | 2-pyrimidinyl | CH(Me)CH$_2$OMe | CH$_2$-3-pyridinyl |
| 2-propenyl | 2-pyrazinyl | CH(Me)CH(OMe)$_2$ | CH(Et)$_2$ |
| 2-Me-2-propenyl | 2-thiazolyl | CH$_2$-2-dioxolanyl | CH$_2$CH(Et)$_2$ |
| 3-butenyl | 2-oxazolyl | CH$_2$CH$_2$OCF$_3$ | CH$_2$CH(n-Pr)Me |
| 3-pentenyl | CF$_3$ | CH$_2$CH$_2$SMe | CH(Me)Et |
| 2-propynyl | CF$_2$CF$_3$ | CH$_2$CH(Me)SMe | CH(Me)—n-Pr |
| 3-butynyl | CH$_2$CF$_3$ | CH$_2$CH$_2$S(O)Me | CH(CF$_3$)Et |
| 2-butynyl | CH(Me)CF$_3$ | CH$_2$CH$_2$S(O)$_2$Me | CH(Et)—n-Pr |
| c-Pr | CH$_2$CH$_2$F | CH$_2$CO$_2$Me | CH(Me)—n-Bu |
| c-pentyl | CH$_2$CH$_2$CH$_2$F | CH$_2$CO$_2$—i-Pr | 2,2-dimethylpropyl |
| c-Hex | CH$_2$CF$_2$CF$_3$ | CH(Me)CO$_2$Me | CH$_2$CH$_2$CH(Me)$_2$ |
| 2-cyclohexenyl | CH$_2$CH$_2$CF$_3$ | CH$_2$C(O)Me | |
| 3-cyclohexenyl | CH$_2$CH(Me)CF$_3$ | CH$_2$CH$_2$C(O)Me | |
| CH$_2$—c-Pr | (S)-CH$_2$CH(Me)CF$_3$ | CH$_2$SiMe$_3$ | |
| CH$_2$—c-Hex | CH$_2$CH$_2$CH$_2$F | CH$_2$CH$_2$SiMe$_3$ | |

J is 3-Me—Ph and R$^{9b}$ is CH$_3$.

| | | | |
|---|---|---|---|
| Me | CH$_2$-2-cyclohexenyl | 2-chloro-2-propenyl | CH$_2$OPh |
| Et | 4-tetrahydropyranyl | 3,3-dichloro-2-propenyl | CH$_2$Ph |
| i-Pr | 3-tetrahydropyranyl | CH$_2$-2-tetrahydrofuranyl | CH$_2$CH$_2$Ph |
| n-Pr | 3-tetrahydrofuranyl | CH$_2$-2-tetrahydropyranyl | CH(Me)Ph |
| i-Bu | Ph | CH$_2$CN | CH$_2$-2-Cl—Ph |
| n-Bu | 2-Cl-phenyl | CH$_2$NO$_2$ | CH$_2$-3-Cl—Ph |
| s-Bu | 3-Cl-phenyl | CH$_2$CH$_2$OH | CH$_2$-4-Cl—Ph |
| 3-Me—Bu | 4-Cl-phenyl | CH$_2$CH$_2$OMe | CH$_2$-2-thienyl |
| n-pentyl | 2-pyridinyl | CH$_2$CH(Me)OMe | CH$_2$-2-pyridinyl |
| n-Hex | 2-pyrimidinyl | CH(Me)CH$_2$OMe | CH$_2$-3-pyridinyl |
| 2-propenyl | 2-pyrazinyl | CH(Me)CH(OMe)$_2$ | CH(Et)$_2$ |
| 2-Me-2-propenyl | 2-thiazolyl | CH$_2$-2-dioxolanyl | CH$_2$CH(Et)$_2$ |
| 3-butenyl | 2-oxazolyl | CH$_2$CH$_2$OCF$_3$ | CH$_2$CH(n-Pr)Me |
| 3-pentenyl | CF$_3$ | CH$_2$CH$_2$SMe | CH(Me)Et |
| 2-propynyl | CF$_2$CF$_3$ | CH$_2$CH(Me)SMe | CH(Me)—n-Pr |
| 3-butynyl | CH$_2$CF$_3$ | CH$_2$CH$_2$S(O)Me | CH(CF$_3$)Et |
| 2-butynyl | CH(Me)CF$_3$ | CH$_2$CH$_2$S(O)$_2$Me | CH(Et)—n-Pr |
| c-Pr | CH$_2$CH$_2$F | CH$_2$CO$_2$Me | CH(Me)—n-Bu |
| c-pentyl | CH$_2$CH$_2$CH$_2$F | CH$_2$CO$_2$—i-Pr | 2,2-dimethylpropyl |
| c-Hex | CH$_2$CF$_2$CF$_3$ | CH(Me)CO$_2$Me | CH$_2$CH$_2$CH(Me)$_2$ |
| 2-cyclohexenyl | CH$_2$CH$_2$CF$_3$ | CH$_2$C(O)Me | |
| 3-cyclohexenyl | CH$_2$CH(Me)CF$_3$ | CH$_2$CH$_2$C(O)Me | |

TABLE 2-continued

[Structure: tetrahydropyrazolo[1,5-a]pyridine fused with pyrimidine bearing N(R^9a)(R^9b), with J substituent]

| R^9a | R^9a | R^9a | R^9a |
|---|---|---|---|
| CH₂—c-Pr | (S)-CH₂CH(Me)CF₃ | CH₂SiMe₃ | |
| CH₂—c-Hex | CH₂CH₂CH₂F | CH₂CH₂SiMe₃ | |

TABLE 3

[Structure: pyrazole fused ring with Y^a, Y^b substituents, pyrimidine with NH-R^9b, and J substituent]

| R^9a | R^9a | R^9a | R^9a |
|---|---|---|---|
| \multicolumn{4}{|c|}{Y^a is CH₂, Y^b is O and J is Ph.} | | | |
| Me | CH₂-2-cyclohexenyl | 2-chloro-2-propenyl | CH₂OPh |
| Et | 4-tetrahydropyranyl | 3,3-dichloro-2-propenyl | CH₂Ph |
| i-Pr | 3-tetrahydropyranyl | CH₂-2-tetrahydrofuranyl | CH₂CH₂Ph |
| n-Pr | 3-tetrahydrofuranyl | CH₂-2-tetrahydropyranyl | CH(Me)Ph |
| i-Bu | Ph | CH₂CN | CH₂-2-Cl—Ph |
| n-Bu | 2-Cl-phenyl | CH₂NO₂ | CH₂-3-Cl—Ph |
| s-Bu | 3-Cl-phenyl | CH₂CH₂OH | CH₂-4-Cl—Ph |
| 3-MeBu | 4-Cl-phenyl | CH₂CH₂OMe | CH₂-2-thienyl |
| n-pentyl | 2-pyridinyl | CH₂CH(Me)OMe | CH₂-2-pyridinyl |
| n-Hex | 2-pyrimidinyl | CH(Me)CH₂OMe | CH₂-3-pyridinyl |
| 2-propenyl | 2-pyrazinyl | CH(Me)CH(OMe)₂ | CH(Et)₂ |
| 2-Me-2-propenyl | 2-thiazolyl | CH₂-2-dioxolanyl | CH₂CH(Et)₂ |
| 3-butenyl | 2-oxazolyl | CH₂CH₂OCF₃ | CH₂CH(n-Pr)Me |
| 3-pentenyl | CF₃ | CH₂CH₂SMe | CH(Me)Et |
| 2-propynyl | CF₂CF₃ | CH₂CH(Me)SMe | CH(Me)—n-Pr |
| 3-butynyl | CH₂CF₃ | CH₂CH₂S(O)Me | CH(CF₃)Et |
| 2-butynyl | CH(Me)CF₃ | CH₂CH₂S(O)₂Me | CH(Et)—n-Pr |
| c-Pr | CH₂CH₂F | CH₂CO₂Me | CH(Me)—n-Bu |
| c-pentyl | CH₂CH₂CH₂F | CH₂CO₂—i-Pr | 2,2-dimethylpropyl |
| c-Hex | CH₂CF₂CF₃ | CH(Me)CO₂Me | CH₂CH₂CH(Me)₂ |
| 2-cyclohexenyl | CH₂CH₂CF₃ | CH₂C(O)Me | |
| 3-cyclohexenyl | CH₂CH(Me)CF₃ | CH₂CH₂C(O)Me | |
| CH₂—c-Pr | (S)-CH₂CH(Me)CF₃ | CH₂SiMe₃ | |
| CH₂—c-Hex | CH₂CH₂CH₂F | CH₂CH₂SiMe₃ | |
| \multicolumn{4}{|c|}{Y^a is CH₂, Y^b is O and J is 4-F—Ph.} | | | |
| Me | CH₂-2-cyclohexenyl | 2-chloro-2-propenyl | CH₂OPh |
| Et | 4-tetrahydropyranyl | 3,3-dichloro-2-propenyl | CH₂Ph |
| i-Pr | 3-tetrahydropyranyl | CH₂-2-tetrahydrofuranyl | CH₂CH₂Ph |
| n-Pr | 3-tetrahydrofuranylyl | CH₂-2-tetrahydropyran | CH(Me)Ph |
| i-Bu | Ph | CH₂CN | CH₂-2-Cl—Ph |
| n-Bu | 2-Cl-phenyl | CH₂NO₂ | CH₂-3-Cl—Ph |
| s-Bu | 3-Cl-phenyl | CH₂CH₂OH | CH₂-4-Cl—Ph |
| 3-Me—Bu | 4-Cl-phenyl | CH₂CH₂OMe | CH₂-2-thienyl |
| n-pentyl | 2-pyridinyl | CH₂CH(Me)OMe | CH₂-2-pyridinyl |
| n-Hex | 2-pyrimidinyl | CH(Me)CH₂OMe | CH₂-3-pyridinyl |
| 2-propenyl | 2-pyrazinyl | CH(Me)CH(OMe)₂ | CH(Et)₂ |
| 2-Me-2-propenyl | 2-thiazolyl | CH₂-2-dioxolanyl | CH₂CH(Et)₂ |
| 3-butenyl | 2-oxazolyl | CH₂CH₂OCF₃ | CH₂CH(n-Pr)Me |
| 3-pentenyl | CF₃ | CH₂CH₂SMe | CH(Me)Et |
| 2-propynyl | CF₂CF₃ | CH₂CH(Me)SMe | CH(Me)—n-Pr |
| 3-butynyl | CH₂CF₃ | CH₂CH₂S(O)Me | CH(CF₃)Et |

TABLE 3-continued

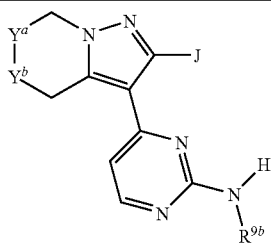

| $R^{9a}$ | $R^{9a}$ | $R^{9a}$ | $R^{9a}$ |
|---|---|---|---|
| 2-butynyl | CH(Me)CF₃ | CH₂CH₂S(O)₂Me | CH(Et)—n-Pr |
| c-Pr | CH₂CH₂F | CH₂CO₂Me | CH(Me)—n-Bu |
| c-pentyl | CH₂CH₂CH₂F | CH₂CO₂—i-Pr | 2,2-dimethylpropyl |
| c-Hex | CH₂CF₂CF₃ | CH(Me)CO₂Me | CH₂CH₂CH(Me)₂ |
| 2-cyclohexenyl | CH₂CH₂CF₃ | CH₂C(O)Me | |
| 3-cyclohexenyl | CH₂CH(Me)CF₃ | CH₂CH₂C(O)Me | |
| CH₂—c-Pr | (S)-CH₂CH(Me)CF₃ | CH₂SiMe₃ | |
| CH₂—c-Hex | CH₂CH₂CH₂F | CH₂CH₂SiMe₃ | |

$Y^a$ is CH₂, $Y^b$ is O and J is 2-F—Ph.

| Me | CH₂-2-cyclohexenyl | 2-chloro-2-propenyl | CH₂OPh |
| Et | 4-tetrahydropyranyl | 3,3-dichloro-2-propenyl | CH₂Ph |
| i-Pr | 3-tetrahydropyranyl | CH₂-2-tetrahydrofuranyl | CH₂CH₂Ph |
| n-Pr | 3-tetrahydrofuranyl | CH₂-2-tetrahydropyranyl | CH(Me)Ph |
| i-Bu | Ph | CH₂CN | CH₂-2-Cl—Ph |
| n-Bu | 2-Cl-phenyl | CH₂NO₂ | CH₂-3-Cl—Ph |
| s-Bu | 3-Cl-phenyl | CH₂CH₂OH | CH₂-4-Cl—Ph |
| 3-Me—Bu | 4-Cl-phenyl | CH₂CH₂OMe | CH₂-2-thienyl |
| n-pentyl | 2-pyridinyl | CH₂CH(Me)OMe | CH₂-2-pyridinyl |
| n-Hex | 2-pyrimidinyl | CH(Me)CH₂OMe | CH₂-3-pyridinyl |
| 2-propenyl | 2-pyrazinyl | CH(Me)CH(OMe)₂ | CH(Et)₂ |
| 2-Me-2-propenyl | 2-thiazolyl | CH₂-2-dioxolanyl | CH₂CH(Et)₂ |
| 3-butenyl | 2-oxazolyl | CH₂CH₂OCF₃ | CH₂CH(n-Pr)Me |
| 3-pentenyl | CF₃ | CH₂CH₂SMe | CH(Me)Et |
| 2-propynyl | CF₂CF₃ | CH₂CH(Me)SMe | CH(Me)—n-Pr |
| 3-butynyl | CH₂CF₃ | CH₂CH₂S(O)Me | CH(CF₃)Et |
| 2-butynyl | CH(Me)CF₃ | CH₂CH₂S(O)₂Me | CH(Et)—n-Pr |
| c-Pr | CH₂CH₂F | CH₂CO₂Me | CH(Me)—n-Bu |
| c-pentyl | CH₂CH₂CH₂F | CH₂CO₂—i-Pr | 2,2-dimethylpropyl |
| c-Hex | CH₂CF₂CF₃ | CH(Me)CO₂Me | CH₂CH₂CH(Me)₂ |
| 2-cyclohexenyl | CH₂CH₂CF₃ | CH₂C(O)Me | |
| 3-cyclohexenyl | CH₂CH(Me)CF₃ | CH₂CH₂C(O)Me | |
| CH₂—c-Pr | (S)-CH₂CH(Me)CF₃ | CH₂SiMe₃ | |
| CH₂—c-Hex | CH₂CH₂CH₂F | CH₂CH₂SiMe₃ | |

$Y^a$ is CH₂, $Y^b$ is O and J is 2-Cl—Ph.

| Me | CH₂-2-cyclohexenyl | 2-chloro-2-propenyl | CH₂OPh |
| Et | 4-tetrahydropyranyl | 3,3-dichloro-2-propenyl | CH₂Ph |
| i-Pr | 3-tetrahydropyranyl | CH₂-2-tetrahydrofuranyl | CH₂CH₂Ph |
| n-Pr | 3-tetrahydrofuranyl | CH₂-2-tetrahydropyranyl | CH(Me)Ph |
| i-Bu | Ph | CH₂CN | CH₂-2-Cl—Ph |
| n-Bu | 2-Cl-phenyl | CH₂NO₂ | CH₂-3-Cl—Ph |
| s-Bu | 3-Cl-phenyl | CH₂CH₂OH | CH₂-4-Cl—Ph |
| 3-Me—Bu | 4-Cl-phenyl | CH₂CH₂OMe | CH₂-2-thienyl |
| n-pentyl | 2-pyridinyl | CH₂CH(Me)OMe | CH₂-2-pyridinyl |
| n-Hex | 2-pyrimidinyl | CH(Me)CH₂OMe | CH₂-3-pyridinyl |
| 2-propenyl | 2-pyrazinyl | CH(Me)CH(OMe)₂ | CH(Et)₂ |
| 2-Me-2-propenyl | 2-thiazolyl | CH₂-2-dioxolanyl | CH₂CH(Et)₂ |
| 3-butenyl | 2-oxazolyl | CH₂CH₂OCF₃ | CH₂CH(n-Pr)Me |
| 3-pentenyl | CF₃ | CH₂CH₂SMe | CH(Me)Et |
| 2-propynyl | CF₂CF₃ | CH₂CH(Me)SMe | CH(Me)—n-Pr |
| 3-butynyl | CH₂CF₃ | CH₂CH₂S(O)Me | CH(CF₃)Et |
| 2-butynyl | CH(Me)CF₃ | CH₂CH₂S(O)₂Me | CH(Et)—n-Pr |
| c-Pr | CH₂CH₂F | CH₂CO₂Me | CH(Me)—n-Bu |
| c-pentyl | CH₂CH₂CH₂F | CH₂CO₂—i-Pr | 2,2-dimethylpropyl |
| c-Hex | CH₂CF₂CF₃ | CH(Me)CO₂Me | CH₂CH₂CH(Me)₂ |
| 2-cyclohexenyl | CH₂CH₂CF₃ | CH₂C(O)Me | |
| 3-cyclohexenyl | CH₂CH(Me)CF₃ | CH₂CH₂C(O)Me | |
| CH₂—c-Pr | (S)-CH₂CH(Me)CF₃ | CH₂SiMe₃ | |
| CH₂—c-Hex | CH₂CH₂CH₂F | CH₂CH₂SiMe₃ | |

$Y^a$ is CH₂, $Y^b$ is O and J is 4-Cl—Ph.

| Me | CH₂-2-cyclohexenyl | 2-chloro-2-propenyl | CH₂OPh |
| Et | 4-tetrahydropyranyl | 3,3-dichloro-2-propenyl | CH₂Ph |
| i-Pr | 3-tetrahydropyranyl | CH₂-2-tetrahydrofuranyl | CH₂CH₂Ph |

TABLE 3-continued

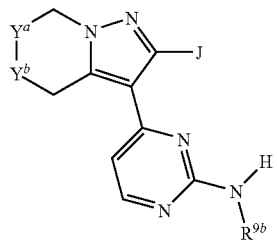

| R9a | R9a | R9a | R9a |
|---|---|---|---|
| n-Pr | 3-tetrahydrofuranyl | $CH_2$-2-tetrahydropyranyl | CH(Me)Ph |
| i-Bu | Ph | $CH_2CN$ | $CH_2$-2-Cl—Ph |
| n-Bu | 2-Cl-phenyl | $CH_2NO_2$ | $CH_2$-3-Cl—Ph |
| s-Bu | 3-Cl-phenyl | $CH_2CH_2OH$ | $CH_2$-4-Cl—Ph |
| 3-Me—Bu | 4-Cl-phenyl | $CH_2CH_2OMe$ | $CH_2$-2-thienyl |
| n-pentyl | 2-pyridinyl | $CH_2CH(Me)OMe$ | $CH_2$-2-pyridinyl |
| n-Hex | 2-pyrimidinyl | $CH(Me)CH_2OMe$ | $CH_2$-3-pyridinyl |
| 2-propenyl | 2-pyrazinyl | $CH(Me)CH(OMe)_2$ | $CH(Et)_2$ |
| 2-Me-2-propenyl | 2-thiazolyl | $CH_2$-2-dioxolanyl | $CH_2CH(Et)_2$ |
| 3-butenyl | 2-oxazolyl | $CH_2CH_2OCF_3$ | $CH_2CH$(n-Pr)Me |
| 3-pentenyl | $CF_3$ | $CH_2CH_2SMe$ | CH(Me)Et |
| 2-propynyl | $CF_2CF_3$ | $CH_2CH(Me)SMe$ | CH(Me)—n-Pr |
| 3-butynyl | $CH_2CF_3$ | $CH_2CH_2S(O)Me$ | $CH(CF_3)Et$ |
| 2-butynyl | $CH(Me)CF_3$ | $CH_2CH_2S(O)_2Me$ | CH(Et)—n-Pr |
| c-Pr | $CH_2CH_2F$ | $CH_2CO_2Me$ | CH(Me)—n-Bu |
| c-pentyl | $CH_2CH_2CH_2F$ | $CH_2CO_2$—i-Pr | 2,2-dimethylpropyl |
| c-Hex | $CH_2CF_2CF_3$ | $CH(Me)CO_2Me$ | $CH_2CH_2CH(Me)_2$ |
| 2-cyclohexenyl | $CH_2CH_2CF_3$ | $CH_2C(O)Me$ | |
| 3-cyclohexenyl | $CH_2CH(Me)CF_3$ | $CH_2CH_2C(O)Me$ | |
| $CH_2$—c-Pr | (S)-$CH_2CH(Me)CF_3$ | $CH_2SiMe_3$ | |
| $CH_2$—c-Hex | $CH_2CH_2CH_2F$ | $CH_2CH_2SiMe_3$ | |
| | $Y^a$ is $CH_2$, $Y^b$ is O and J is 3-Me—Ph. | | |
| Me | $CH_2$-2-cyclohexenyl | 2-chloro-2-propenyl | $CH_2OPh$ |
| Et | 4-tetrahydropyranyl | 3,3-dichloro-2-propenyl | $CH_2Ph$ |
| i-Pr | 3-tetrahydropyranyl | $CH_2$-2-tetrahydrofuranyl | $CH_2CH_2Ph$ |
| n-Pr | 3-tetrahydrofuranyl | $CH_2$-2-tetrahydropyranyl | CH(Me)Ph |
| i-Bu | Ph | $CH_2CN$ | $CH_2$-2-Cl—Ph |
| n-Bu | 2-Cl-phenyl | $CH_2NO_2$ | $CH_2$-3-Cl—Ph |
| s-Bu | 3-Cl-phenyl | $CH_2CH_2OH$ | $CH_2$-4-Cl—Ph |
| 3-Me—Bu | 4-Cl-phenyl | $CH_2CH_2OMe$ | $CH_2$-2-thienyl |
| n-pentyl | 2-pyridinyl | $CH_2CH(Me)OMe$ | $CH_2$-2-pyridinyl |
| n-Hex | 2-pyrimidinyl | $CH(Me)CH_2OMe$ | $CH_2$-3-pyridinyl |
| 2-propenyl | 2-pyrazinyl | $CH(Me)CH(OMe)_2$ | $CH(Et)_2$ |
| 2-Me-2-propenyl | 2-thiazolyl | $CH_2$-2-dioxolanyl | $CH_2CH(Et)_2$ |
| 3-butenyl | 2-oxazolyl | $CH_2CH_2OCF_3$ | $CH_2CH$(n-Pr)Me |
| 3-pentenyl | $CF_3$ | $CH_2CH_2SMe$ | CH(Me)Et |
| 2-propynyl | $CF_2CF_3$ | $CH_2CH(Me)SMe$ | CH(Me)—n-Pr |
| 3-butynyl | $CH_2CF_3$ | $CH_2CH_2S(O)Me$ | $CH(CF_3)Et$ |
| 2-butynyl | $CH(Me)CF_3$ | $CH_2CH_2S(O)_2Me$ | CH(Et)—n-Pr |
| c-Pr | $CH_2CH_2F$ | $CH_2CO_2Me$ | CH(Me)—n-Bu |
| c-pentyl | $CH_2CH_2CH_2F$ | $CH_2CO_2$—i-Pr | 2,2-dimethylpropyl |
| c-Hex | $CH_2CF_2CF_3$ | $CH(Me)CO_2Me$ | $CH_2CH_2CH(Me)_2$ |
| 2-cyclohexenyl | $CH_2CH_2CF_3$ | $CH_2C(O)Me$ | |
| 3-cyclohexenyl | $CH_2CH(Me)CF_3$ | $CH_2CH_2C(O)Me$ | |
| $CH_2$—c-Pr | (S)-$CH_2CH(Me)CF_3$ | $CH_2SiMe_3$ | |
| $CH_2$—c-Hex | $CH_2CH_2CH_2F$ | $CH_2CH_2SiMe_3$ | |
| | $Y^a$ is $CH_2$, $Y^b$ is $SO_2$ and J is Ph. | | |
| Me | $CH_2$-2-cyclohexenyl | 2-chloro-2-propenyl | $CH_2OPh$ |
| Et | 4-tetrahydropyranyl | 3,3-dichloro-2-propenyl | $CH_2Ph$ |
| i-Pr | 3-tetrahydropyranyl | $CH_2$-2-tetrahydrofuranyl | $CH_2CH_2Ph$ |
| n-Pr | 3-tetrahydrofuranyl | $CH_2$-2-tetrahydropyranyl | CH(Me)Ph |
| i-Bu | Ph | $CH_2CN$ | $CH_2$-2-Cl—Ph |
| n-Bu | 2-Cl-phenyl | $CH_2NO_2$ | $CH_2$-3-Cl—Ph |
| s-Bu | 3-Cl-phenyl | $CH_2CH_2OH$ | $CH_2$-4-Cl—Ph |
| 3-Me—Bu | 4-Cl-phenyl | $CH_2CH_2OMe$ | $CH_2$-2-thienyl |
| n-pentyl | 2-pyridinyl | $CH_2CH(Me)OMe$ | $CH_2$-2-pyridinyl |
| n-Hex | 2-pyrimidinyl | $CH(Me)CH_2OMe$ | $CH_2$-3-pyridinyl |
| 2-propenyl | 2-pyrazinyl | $CH(Me)CH(OMe)_2$ | $CH(Et)_2$ |
| 2-Me-2-propenyl | 2-thiazolyl | $CH_2$-2-dioxolanyl | $CH_2CH(Et)_2$ |
| 3-butenyl | 2-oxazolyl | $CH_2CH_2OCF_3$ | $CH_2CH$(n-Pr)Me |
| 3-pentenyl | $CF_3$ | $CH_2CH_2SMe$ | CH(Me)Et |
| 2-propynyl | $CF_2CF_3$ | $CH_2CH(Me)SMe$ | CH(Me)—n-Pr |
| 3-butynyl | $CH_2CF_3$ | $CH_2CH_2S(O)Me$ | $CH(CF_3)Et$ |

TABLE 3-continued

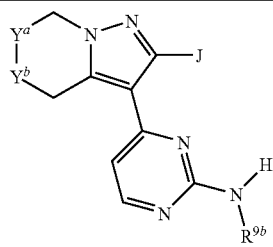

| R⁹ᵃ | R⁹ᵃ | R⁹ᵃ | R⁹ᵃ |
|---|---|---|---|
| 2-butynyl | CH(Me)CF₃ | CH₂CH₂S(O)₂Me | CH(Et)—n-Pr |
| c-Pr | CH₂CH₂F | CH₂CO₂Me | CH(Me)—n-Bu |
| c-pentyl | CH₂CH₂CH₂F | CH₂CO₂—i-Pr | 2,2-dimethylpropyl |
| c-Hex | CH₂CF₂CF₃ | CH(Me)CO₂Me | CH₂CH₂CH(Me)₂ |
| 2-cyclohexenyl | CH₂CH₂CF₃ | CH₂C(O)Me | |
| 3-cyclohexenyl | CH₂CH(Me)CF₃ | CH₂CH₂C(O)Me | |
| CH₂—c-Pr | (S)-CH₂CH(Me)CF₃ | CH₂SiMe₃ | |
| CH₂—c-Hex | CH₂CH₂CH₂CH₂F | CH₂CH₂SiMe₃ | |
| | Yᵃ is CH₂, Yᵇ is SO₂ and J is 4-F—Ph. | | |
| Me | CH₂-2-cyclohexenyl | 2-chloro-2-propenyl | CH₂OPh |
| Et | 4-tetrahydropyranyl | 3,3-dichloro-2-propenyl | CH₂Ph |
| i-Pr | 3-tetrahydropyranyl | CH₂-2-tetrahydrofuranyl | CH₂CH₂Ph |
| n-Pr | 3-tetrahydrofuranyl | CH₂-2-tetrahydropyranyl | CH(Me)Ph |
| i-Bu | Ph | CH₂CN | CH₂-2-Cl—Ph |
| n-Bu | 2-Cl-phenyl | CH₂NO₂ | CH₂-3-Cl—Ph |
| s-Bu | 3-Cl-phenyl | CH₂CH₂OH | CH₂-4-Cl—Ph |
| 3-Me—Bu | 4-Cl-phenyl | CH₂CH₂OMe | CH₂-2-thienyl |
| n-pentyl | 2-pyridinyl | CH₂CH(Me)OMe | CH₂-2-pyridinyl |
| n-Hex | 2-pyrimidinyl | CH(Me)CH₂OMe | CH₂-3-pyridinyl |
| 2-propenyl | 2-pyrazinyl | CH(Me)CH(OMe)₂ | CH(Et)₂ |
| 2-Me-2-propenyl | 2-thiazolyl | CH₂-2-dioxolanyl | CH₂CH(Et)₂ |
| 3-butenyl | 2-oxazolyl | CH₂CH₂OCF₃ | CH₂CH(n-Pr)Me |
| 3-pentenyl | CF₃ | CH₂CH₂SMe | CH(Me)Et |
| 2-propynyl | CF₂CF₃ | CH₂CH(Me)SMe | CH(Me)—n-Pr |
| 3-butynyl | CH₂CF₃ | CH₂CH₂S(O)Me | CH(CF₃)Et |
| 2-butynyl | CH(Me)CF₃ | CH₂CH₂S(O)₂Me | CH(Et)—n-Pr |
| c-Pr | CH₂CH₂F | CH₂CO₂Me | CH(Me)—n-Bu |
| c-pentyl | CH₂CH₂CH₂F | CH₂CO₂—i-Pr | 2,2-dimethylpropyl |
| c-Hex | CH₂CF₂CF₃ | CH(Me)CO₂Me | CH₂CH₂CH(Me)₂ |
| 2-cyclohexenyl | CH₂CH₂CF₃ | CH₂C(O)Me | |
| 3-cyclohexenyl | CH₂CH(Me)CF₃ | CH₂CH₂C(O)Me | |
| CH₂—c-Pr | (S)-CH₂CH(Me)CF₃ | CH₂SiMe₃ | |
| CH₂—c-Hex | CH₂CH₂CH₂CH₂F | CH₂CH₂SiMe₃ | |
| | Yᵃ is CH₂, Yᵇ is SO₂ and J is 2-F—Ph. | | |
| Me | CH₂-2-cyclohexenyl | 2-chloro-2-propenyl | CH₂OPh |
| Et | 4-tetrahydropyranyl | 3,3-dichloro-2-propenyl | CH₂Ph |
| i-Pr | 3-tetrahydropyranyl | CH₂-2-tetrahydrofuranyl | CH₂CH₂Ph |
| n-Pr | 3-tetrahydrofuranyl | CH₂-2-tetrahydropyranyl | CH(Me)Ph |
| i-Bu | Ph | CH₂CN | CH₂-2-Cl—Ph |
| n-Bu | 2-Cl-phenyl | CH₂NO₂ | CH₂-3-Cl—Ph |
| s-Bu | 3-Cl-phenyl | CH₂CH₂OH | CH₂-4-Cl—Ph |
| 3-Me—Bu | 4-Cl-phenyl | CH₂CH₂OMe | CH₂-2-thienyl |
| n-pentyl | 2-pyridinyl | CH₂CH(Me)OMe | CH₂-2-pyridinyl |
| n-Hex | 2-pyrimidinyl | CH(Me)CH₂OMe | CH₂-3-pyridinyl |
| 2-propenyl | 2-pyrazinyl | CH(Me)CH(OMe)₂ | CH(Et)₂ |
| 2-Me-2-propenyl | 2-thiazolyl | CH₂-2-dioxolanyl | CH₂CH(Et)₂ |
| 3-butenyl | 2-oxazolyl | CH₂CH₂OCF₃ | CH₂CH(n-Pr)Me |
| 3-pentenyl | CF₃ | CH₂CH₂SMe | CH(Me)Et |
| 2-propynyl | CF₂CF₃ | CH₂CH(Me)SMe | CH(Me)—n-Pr |
| 3-butynyl | CH₂CF₃ | CH₂CH₂S(O)Me | CH(CF₃)Et |
| 2-butynyl | CH(Me)CF₃ | CH₂CH₂S(O)₂Me | CH(Et)—n-Pr |
| c-Pr | CH₂CH₂F | CH₂CO₂Me | CH(Me)—n-Bu |
| c-pentyl | CH₂CH₂CH₂F | CH₂CO₂—i-Pr | 2,2-dimethylpropyl |
| c-Hex | CH₂CF₂CF₃ | CH(Me)CO₂Me | CH₂CH₂CH(Me)₂ |
| 2-cyclohexenyl | CH₂CH₂CF₃ | CH₂C(O)Me | |
| 3-cyclohexenyl | CH₂CH(Me)CF₃ | CH₂CH₂C(O)Me | |
| CH₂—c-Pr | (S)-CH₂CH(Me)CF₃ | CH₂SiMe₃ | |
| CH₂—c-Hex | CH₂CH₂CH₂CH₂F | CH₂CH₂SiMe₃ | |
| | Yᵃ is CH₂, Yᵇ is SO₂ and J is 2-Cl—Ph. | | |
| Me | CH₂-2-cyclohexenyl | 2-chloro-2-propenyl | CH₂OPh |
| Et | 4-tetrahydropyranyl | 3,3-dichloro-2-propenyl | CH₂Ph |
| i-Pr | 3-tetrahydropyranyl | CH₂-2-tetrahydrofuranyl | CH₂CH₂Ph |

TABLE 3-continued

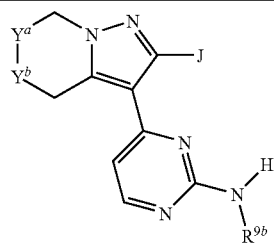

| $R^{9a}$ | $R^{9a}$ | $R^{9a}$ | $R^{9a}$ |
|---|---|---|---|
| n-Pr | 3-tetrahydrofuranyl | CH$_2$-2-tetrahydropyranyl | CH(Me)Ph |
| i-Bu | Ph | CH$_2$CN | CH$_2$-2-Cl—Ph |
| n-Bu | 2-Cl-phenyl | CH$_2$NO$_2$ | CH$_2$-3-Cl—Ph |
| s-Bu | 3-Cl-phenyl | CH$_2$CH$_2$OH | CH$_2$-4-Cl—Ph |
| 3-Me—Bu | 4-Cl-phenyl | CH$_2$CH$_2$OMe | CH$_2$-2-thienyl |
| n-pentyl | 2-pyridinyl | CH$_2$CH(Me)OMe | CH$_2$-2-pyridinyl |
| n-Hex | 2-pyrimidinyl | CH(Me)CH$_2$OMe | CH$_2$-3-pyridinyl |
| 2-propenyl | 2-pyrazinyl | CH(Me)CH(OMe)$_2$ | CH(Et)$_2$ |
| 2-Me-2-propenyl | 2-thiazolyl | CH$_2$-2-dioxolanyl | CH$_2$CH(Et)$_2$ |
| 3-butenyl | 2-oxazolyl | CH$_2$CH$_2$OCF$_3$ | CH$_2$CH(n-Pr)Me |
| 3-pentenyl | CF$_3$ | CH$_2$CH$_2$SMe | CH(Me)Et |
| 2-propynyl | CF$_2$CF$_3$ | CH$_2$CH(Me)SMe | CH(Me)—n-Pr |
| 3-butynyl | CH$_2$CF$_3$ | CH$_2$CH$_2$S(O)Me | CH(CF$_3$)Et |
| 2-butynyl | CH(Me)CF$_3$ | CH$_2$CH$_2$S(O)$_2$Me | CH(Et)—n-Pr |
| c-Pr | CH$_2$CH$_2$F | CH$_2$CO$_2$Me | CH(Me)—n-Bu |
| c-pentyl | CH$_2$CH$_2$CH$_2$F | CH$_2$CO$_2$-i-Pr | 2,2-dimethylpropyl |
| c-Hex | CH$_2$CF$_2$CF$_3$ | CH(Me)CO$_2$Me | CH$_2$CH$_2$CH(Me)$_2$ |
| 2-cyclohexenyl | CH$_2$CH$_2$CF$_3$ | CH$_2$C(O)Me | |
| 3-cyclohexenyl | CH$_2$CH(Me)CF$_3$ | CH$_2$CH$_2$C(O)Me | |
| CH$_2$—c-Pr | (S)-CH$_2$CH(Me)CF$_3$ | CH$_2$SiMe$_3$ | |
| CH$_2$—c-Hex | CH$_2$CH$_2$CH$_2$CH$_2$F | CH$_2$CH$_2$SiMe$_3$ | |
| | $Y^a$ is CH$_2$, $Y^b$ is SO$_2$ and J is 4-Cl—Ph. | | |
| Me | CH$_2$-2-cyclohexenyl | 2-chloro-2-propenyl | CH$_2$OPh |
| Et | 4-tetrahydropyranyl | 3,3-dichloro-2-propenyl | CH$_2$Ph |
| i-Pr | 3-tetrahydropyranyl | CH$_2$-2-tetrahydrofuranyl | CH$_2$CH$_2$Ph |
| n-Pr | 3-tetrahydrofuranyl | CH$_2$-2-tetrahydropyranyl | CH(Me)Ph |
| i-Bu | Ph | CH$_2$CN | CH$_2$-2-Cl—Ph |
| n-Bu | 2-Cl-phenyl | CH$_2$NO$_2$ | CH$_2$-3-Cl—Ph |
| s-Bu | 3-Cl-phenyl | CH$_2$CH$_2$OH | CH$_2$-4-Cl—Ph |
| 3-Me—Bu | 4-Cl-phenyl | CH$_2$CH$_2$OMe | CH$_2$-2-thienyl |
| n-pentyl | 2-pyridinyl | CH$_2$CH(Me)OMe | CH$_2$-2-pyridinyl |
| n-Hex | 2-pyrimidinyl | CH(Me)CH$_2$OMe | CH$_2$-3-pyridinyl |
| 2-propenyl | 2-pyrazinyl | CH(Me)CH(OMe)$_2$ | CH(Et)$_2$ |
| 2-Me-2-propenyl | 2-thiazolyl | CH$_2$-2-dioxolanyl | CH$_2$CH(Et)$_2$ |
| 3-butenyl | 2-oxazolyl | CH$_2$CH$_2$OCF$_3$ | CH$_2$CH(n-Pr)Me |
| 3-pentenyl | CF$_3$ | CH$_2$CH$_2$SMe | CH(Me)Et |
| 2-propynyl | CF$_2$CF$_3$ | CH$_2$CH(Me)SMe | CH(Me)—n-Pr |
| 3-butynyl | CH$_2$CF$_3$ | CH$_2$CH$_2$S(O)Me | CH(CF$_3$)Et |
| 2-butynyl | CH(Me)CF$_3$ | CH$_2$CH$_2$S(O)$_2$Me | CH(Et)—n-Pr |
| c-Pr | CH$_2$CH$_2$F | CH$_2$CO$_2$Me | CH(Me)—n-Bu |
| c-pentyl | CH$_2$CH$_2$CH$_2$F | CH$_2$CO$_2$-i-Pr | 2,2-dimethylpropyl |
| c-Hex | CH$_2$CF$_2$CF$_3$ | CH(Me)CO$_2$Me | CH$_2$CH$_2$CH(Me)$_2$ |
| 2-cyclohexenyl | CH$_2$CH$_2$CF$_3$ | CH$_2$C(O)Me | |
| 3-cyclohexenyl | CH$_2$CH(Me)CF$_3$ | CH$_2$CH$_2$C(O)Me | |
| CH$_2$—c-Pr | (S)-CH$_2$CH(Me)CF$_3$ | CH$_2$SiMe$_3$ | |
| CH$_2$—c-Hex | CH$_2$CH$_2$CH$_2$CH$_2$F | CH$_2$CH$_2$SiMe$_3$ | |
| | $Y^a$ is CH$_2$, $Y^b$ is SO$_2$ and J is 3-Me—Ph. | | |
| Me | CH$_2$-2-cyclohexenyl | 2-chloro-2-propenyl | CH$_2$OPh |
| Et | 4-tetrahydropyranyl | 3,3-dichloro-2-propenyl | CH$_2$Ph |
| i-Pr | 3-tetrahydropyranyl | CH$_2$-2-tetrahydrofuranyl | CH$_2$CH$_2$Ph |
| n-Pr | 3-tetrahydrofuranyl | CH$_2$-2-tetrahydropyranyl | CH(Me)Ph |
| i-Bu | Ph | CH$_2$CN | CH$_2$-2-Cl—Ph |
| n-Bu | 2-Cl-phenyl | CH$_2$NO$_2$ | CH$_2$-3-Cl—Ph |
| s-Bu | 3-Cl-phenyl | CH$_2$CH$_2$OH | CH$_2$-4-Cl—Ph |
| 3-Me—Bu | 4-Cl-phenyl | CH$_2$CH$_2$OMe | CH$_2$-2-thienyl |
| n-pentyl | 2-pyridinyl | CH$_2$CH(Me)OMe | CH$_2$-2-pyridinyl |
| n-Hex | 2-pyrimidinyl | CH(Me)CH$_2$OMe | CH$_2$-3-pyridinyl |
| 2-propenyl | 2-pyrazinyl | CH(Me)CH(OMe)$_2$ | CH(Et)$_2$ |
| 2-Me-2-propenyl | 2-thiazolyl | CH$_2$-2-dioxolanyl | CH$_2$CH(Et)$_2$ |
| 3-butenyl | 2-oxazolyl | CH$_2$CH$_2$OCF$_3$ | CH$_2$CH(n-Pr)Me |
| 3-pentenyl | CF$_3$ | CH$_2$CH$_2$SMe | CH(Me)Et |
| 2-propynyl | CF$_2$CF$_3$ | CH$_2$CH(Me)SMe | CH(Me)—n-Pr |
| 3-butynyl | CH$_2$CF$_3$ | CH$_2$CH$_2$S(O)Me | CH(CF$_3$)Et |

TABLE 3-continued

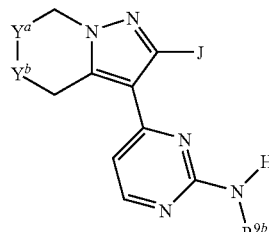

| $R^{9a}$ | $R^{9a}$ | $R^{9a}$ | $R^{9a}$ |
|---|---|---|---|
| 2-butynyl | CH(Me)CF₃ | CH₂CH₂S(O)₂Me | CH(Et)—n-Pr |
| c-Pr | CH₂CH₂F | CH₂CO₂Me | CH(Me)—n-Bu |
| c-pentyl | CH₂CH₂CH₂F | CH₂CO₂—i-Pr | 2,2-dimethylpropyl |
| c-Hex | CH₂CF₂CF₃ | CH(Me)CO₂Me | CH₂CH₂CH(Me)₂ |
| 2-cyclohexenyl | CH₂CH₂CF₃ | CH₂C(O)Me | |
| 3-cyclohexenyl | CH₂CH(Me)CF₃ | CH₂CH₂C(O)Me | |
| CH₂—c-Pr | (S)-CH₂CH(Me)CF₃ | CH₂SiMe₃ | |
| CH₂—c-Hex | CH₂CH₂CH₂CH₂F | CH₂CH₂SiMe₃ | |
| | $Y^a$ is O, $Y^b$ is CH₂ and J is Ph. | | |
| Me | CH₂-2-cyclohexenyl | 2-chloro-2-propenyl | CH₂OPh |
| Et | 4-tetrahydropyranyl | 3,3-dichloro-2-propenyl | CH₂Ph |
| i-Pr | 3-tetrahydropyranyl | CH₂-2-tetrahydrofuranyl | CH₂CH₂Ph |
| n-Pr | 3-tetrahydrofuranyl | CH₂-2-tetrahydropyranyl | CH(Me)Ph |
| i-Bu | Ph | CH₂CN | CH₂-2-Cl—Ph |
| n-Bu | 2-Cl-phenyl | CH₂NO₂ | CH₂-3-Cl—Ph |
| s-Bu | 3-Cl-phenyl | CH₂CH₂OH | CH₂-4-Cl—Ph |
| 3-Me—Bu | 4-Cl-phenyl | CH₂CH₂OMe | CH₂-2-thienyl |
| n-pentyl | 2-pyridinyl | CH₂CH(Me)OMe | CH₂-2-pyridinyl |
| n-Hex | 2-pyrimidinyl | CH(Me)CH₂OMe | CH₂-3-pyridinyl |
| 2-propenyl | 2-pyrazinyl | CH(Me)CH(OMe)₂ | CH(Et)₂ |
| 2-Me-2-propenyl | 2-thiazolyl | CH₂-2-dioxolanyl | CH₂CH(Et)₂ |
| 3-butenyl | 2-oxazolyl | CH₂CH₂OCF₃ | CH₂CH(n-Pr)Me |
| 3-pentenyl | CF₃ | CH₂CH₂SMe | CH(Me)Et |
| 2-propynyl | CF₂CF₃ | CH₂CH(Me)SMe | CH(Me)—n-Pr |
| 3-butynyl | CH₂CF₃ | CH₂CH₂S(O)Me | CH(CF₃)Et |
| 2-butynyl | CH(Me)CF₃ | CH₂CH₂S(O)₂Me | CH(Et)—n-Pr |
| c-Pr | CH₂CH₂F | CH₂CO₂Me | CH(Me)—n-Bu |
| c-pentyl | CH₂CH₂CH₂F | CH₂CO₂—i-Pr | 2,2-dimethylpropyl |
| c-Hex | CH₂CF₂CF₃ | CH(Me)CO₂Me | CH₂CH₂CH(Me)₂ |
| 2-cyclohexenyl | CH₂CH₂CF₃ | CH₂C(O)Me | |
| 3-cyclohexenyl | CH₂CH(Me)CF₃ | CH₂CH₂C(O)Me | |
| CH₂—c-Pr | (S)-CH₂CH(Me)CF₃ | CH₂SiMe₃ | |
| CH₂—c-Hex | CH₂CH₂CH₂CH₂F | CH₂CH₂SiMe₃ | |
| | $Y^a$ is O, $Y^b$ is CH₂ and J is 4-F—Ph. | | |
| Me | CH₂-2-cyclohexenyl | 2-chloro-2-propenyl | CH₂OPh |
| Et | 4-tetrahydropyranyl | 3,3-dichloro-2-propenyl | CH₂Ph |
| i-Pr | 3-tetrahydropyranyl | CH₂-2-tetrahydrofuranyl | CH₂CH₂Ph |
| n-Pr | 3-tetrahydrofuranyl | CH₂-2-tetrahydropyranyl | CH(Me)Ph |
| i-Bu | Ph | CH₂CN | CH₂-2-Cl—Ph |
| n-Bu | 2-Cl-phenyl | CH₂NO₂ | CH₂-3-Cl—Ph |
| s-Bu | 3-Cl-phenyl | CH₂CH₂OH | CH₂-4-Cl—Ph |
| 3-Me—Bu | 4-Cl-phenyl | CH₂CH₂OMe | CH₂-2-thienyl |
| n-pentyl | 2-pyridinyl | CH₂CH(Me)OMe | CH₂-2-pyridinyl |
| n-Hex | 2-pyrimidinyl | CH(Me)CH₂OMe | CH₂-3-pyridinyl |
| 2-propenyl | 2-pyrazinyl | CH(Me)CH(OMe)₂ | CH(Et)₂ |
| 2-Me-2-propenyl | 2-thiazolyl | CH₂-2-dioxolanyl | CH₂CH(Et)₂ |
| 3-butenyl | 2-oxazolyl | CH₂CH₂OCF₃ | CH₂CH(n-Pr)Me |
| 3-pentenyl | CF₃ | CH₂CH₂SMe | CH(Me)Et |
| 2-propynyl | CF₂CF₃ | CH₂CH(Me)SMe | CH(Me)—n-Pr |
| 3-butynyl | CH₂CF₃ | CH₂CH₂S(O)Me | CH(CF₃)Et |
| 2-butynyl | CH(Me)CF₃ | CH₂CH₂S(O)₂Me | CH(Et)—n-Pr |
| c-Pr | CH₂CH₂F | CH₂CO₂Me | CH(Me)—n-Bu |
| c-pentyl | CH₂CH₂CH₂F | CH₂CO₂—i-Pr | 2,2-dimethylpropyl |
| c-Hex | CH₂CF₂CF₃ | CH(Me)CO₂Me | CH₂CH₂CH(Me)₂ |
| 2-cyclohexenyl | CH₂CH₂CF₃ | CH₂C(O)Me | |
| 3-cyclohexenyl | CH₂CH(Me)CF₃ | CH₂CH₂C(O)Me | |
| CH₂—c-Pr | (S)-CH₂CH(Me)CF₃ | CH₂SiMe₃ | |
| CH₂—c-Hex | CH₂CH₂CH₂CH₂F | CH₂CH₂SiMe₃ | |
| | $Y^a$ is O, $Y^b$ is CH₂ and J is 2-F—Ph. | | |
| Me | CH₂-2-cyclohexenyl | 2-chloro-2-propenyl | CH₂OPh |
| Et | 4-tetrahydropyranyl | 3,3-dichloro-2-propenyl | CH₂Ph |
| i-Pr | 3-tetrahydropyranyl | CH₂-2-tetrahydrofuranyl | CH₂CH₂Ph |

TABLE 3-continued

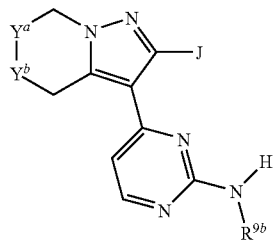

| $R^{9a}$ | $R^{9a}$ | $R^{9a}$ | $R^{9a}$ |
|---|---|---|---|
| n-Pr | 3-tetrahydrofuranyl | CH₂-2-tetrahydropyranyl | CH(Me)Ph |
| i-Bu | Ph | CH₂CN | CH₂-2-Cl—Ph |
| n-Bu | 2-Cl-phenyl | CH₂NO₂ | CH₂-3-Cl—Ph |
| s-Bu | 3-Cl-phenyl | CH₂CH₂OH | CH₂-4-Cl—Ph |
| 3-Me—Bu | 4-Cl-phenyl | CH₂CH₂OMe | CH₂-2-thienyl |
| n-pentyl | 2-pyridinyl | CH₂CH(Me)OMe | CH₂-2-pyridinyl |
| n-Hex | 2-pyrimidinyl | CH(Me)CH₂OMe | CH₂-3-pyridinyl |
| 2-propenyl | 2-pyrazinyl | CH(Me)CH(OMe)₂ | CH(Et)₂ |
| 2-Me-2-propenyl | 2-thiazolyl | CH₂-2-dioxolanyl | CH₂CH(Et)₂ |
| 3-butenyl | 2-oxazolyl | CH₂CH₂OCF₃ | CH₂CH(n-Pr)Me |
| 3-pentenyl | CF₃ | CH₂CH₂SMe | CH(Me)Et |
| 2-propynyl | CF₂CF₃ | CH₂CH(Me)SMe | CH(Me)—n-Pr |
| 3-butynyl | CH₂CF₃ | CH₂CH₂S(O)Me | CH(CF₃)Et |
| 2-butynyl | CH(Me)CF₃ | CH₂CH₂S(O)₂Me | CH(Et)—n-Pr |
| c-Pr | CH₂CH₂F | CH₂CO₂Me | CH(Me)—n-Bu |
| c-pentyl | CH₂CH₂CH₂F | CH₂CO₂—i-Pr | 2,2-dimethylpropyl |
| c-Hex | CH₂CF₂CF₃ | CH(Me)CO₂Me | CH₂CH₂CH(Me)₂ |
| 2-cyclohexenyl | CH₂CH₂CF₃ | CH₂C(O)Me | |
| 3-cyclohexenyl | CH₂CH(Me)CF₃ | CH₂CH₂C(O)Me | |
| CH₂—c-Pr | (S)-CH₂CH(Me)CF₃ | CH₂SiMe₃ | |
| CH₂—c-Hex | CH₂CH₂CH₂CH₂F | CH₂CH₂SiMe₃ | |

$Y^a$ is O, $Y^b$ is CH₂ and J is 2-Cl—Ph.

| Me | CH₂-2-cyclohexenyl | 2-chloro-2-propenyl | CH₂OPh |
| Et | 4-tetrahydropyranyl | 3,3-dichloro-2-propenyl | CH₂Ph |
| i-Pr | 3-tetrahydropyranyl | CH₂-2-tetrahydrofuranyl | CH₂CH₂Ph |
| n-Pr | 3-tetrahydrofuranyl | CH₂-2-tetrahydropyranyl | CH(Me)Ph |
| i-Bu | Ph | CH₂CN | CH₂-2-Cl—Ph |
| n-Bu | 2-Cl-phenyl | CH₂NO₂ | CH₂-3-Cl—Ph |
| s-Bu | 3-Cl-phenyl | CH₂CH₂OH | CH₂-4-Cl—Ph |
| 3-Me—Bu | 4-Cl-phenyl | CH₂CH₂OMe | CH₂-2-thienyl |
| n-pentyl | 2-pyridinyl | CH₂CH(Me)OMe | CH₂-2-pyridinyl |
| n-Hex | 2-pyrimidinyl | CH(Me)CH₂OMe | CH₂-3-pyridinyl |
| 2-propenyl | 2-pyrazinyl | CH(Me)CH(OMe)₂ | CH(Et)₂ |
| 2-Me-2-propenyl | 2-thiazolyl | CH₂-2-dioxolanyl | CH₂CH(Et)₂ |
| 3-butenyl | 2-oxazolyl | CH₂CH₂OCF₃ | CH₂CH(n-Pr)Me |
| 3-pentenyl | CF₃ | CH₂CH₂SMe | CH(Me)Et |
| 2-propynyl | CF₂CF₃ | CH₂CH(Me)SMe | CH(Me)—n-Pr |
| 3-butynyl | CH₂CF₃ | CH₂CH₂S(O)Me | CH(CF₃)Et |
| 2-butynyl | CH(Me)CF₃ | CH₂CH₂S(O)₂Me | CH(Et)—n-Pr |
| c-Pr | CH₂CH₂F | CH₂CO₂Me | CH(Me)—n-Bu |
| c-pentyl | CH₂CH₂CH₂F | CH₂CO₂—i-Pr | 2,2-dimethylpropyl |
| c-Hex | CH₂CF₂CF₃ | CH(Me)CO₂Me | CH₂CH₂CH(Me)₂ |
| 2-cyclohexenyl | CH₂CH₂CF₃ | CH₂C(O)Me | |
| 3-cyclohexenyl | CH₂CH(Me)CF₃ | CH₂CH₂C(O)Me | |
| CH₂—c-Pr | (S)-CH₂CH(Me)CF₃ | CH₂SiMe₃ | |
| CH₂—c-Hex | CH₂CH₂CH₂CH₂F | CH₂CH₂SiMe₃ | |

$Y^a$ is O, $Y^b$ is CH₂ and J is 4-Cl—Ph.

| Me | CH₂-2-cyclohexenyl | 2-chloro-2-propenyl | CH₂OPh |
| Et | 4-tetrahydropyranyl | 3,3-dichloro-2-propenyl | CH₂Ph |
| i-Pr | 3-tetrahydropyranyl | CH₂-2-tetrahydrofuranyl | CH₂CH₂Ph |
| n-Pr | 3-tetrahydrofuranyl | CH₂-2-tetrahydropyranyl | CH(Me)Ph |
| i-Bu | Ph | CH₂CN | CH₂-2-Cl—Ph |
| n-Bu | 2-Cl-phenyl | CH₂NO₂ | CH₂-3-Cl—Ph |
| s-Bu | 3-Cl-phenyl | CH₂CH₂OH | CH₂-4-Cl—Ph |
| 3-Me—Bu | 4-Cl-phenyl | CH₂CH₂OMe | CH₂-2-thienyl |
| n-pentyl | 2-pyridinyl | CH₂CH(Me)OMe | CH₂-2-pyridinyl |
| n-Hex | 2-pyrimidinyl | CH(Me)CH₂OMe | CH₂-3-pyridinyl |
| 2-propenyl | 2-pyrazinyl | CH(Me)CH(OMe)₂ | CH(Et)₂ |
| 2-Me-2-propenyl | 2-thiazolyl | CH₂-2-dioxolanyl | CH₂CH(Et)₂ |
| 3-butenyl | 2-oxazolyl | CH₂CH₂OCF₃ | CH₂CH(n-Pr)Me |
| 3-pentenyl | CF₃ | CH₂CH₂SMe | CH(Me)Et |
| 2-propynyl | CF₂CF₃ | CH₂CH(Me)SMe | CH(Me)—n-Pr |
| 3-butynyl | CH₂CF₃ | CH₂CH₂S(O)Me | CH(CF₃)Et |

TABLE 3-continued

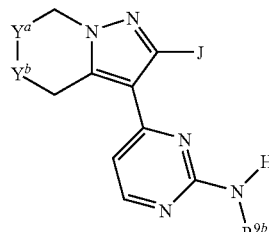

| $R^{9a}$ | $R^{9a}$ | $R^{9a}$ | $R^{9a}$ |
|---|---|---|---|
| 2-butynyl | CH(Me)CF$_3$ | CH$_2$CH$_2$S(O)$_2$Me | CH(Et)—n-Pr |
| c-Pr | CH$_2$CH$_2$F | CH$_2$CO$_2$Me | CH(Me)—n-Bu |
| c-pentyl | CH$_2$CH$_2$CH$_2$F | CH$_2$CO$_2$—i-Pr | 2,2-dimethylpropyl |
| c-Hex | CH$_2$CF$_2$CF$_3$ | CH(Me)CO$_2$Me | CH$_2$CH$_2$CH(Me)$_2$ |
| 2-cyclohexenyl | CH$_2$CH$_2$CF$_3$ | CH$_2$C(O)Me | |
| 3-cyclohexenyl | CH$_2$CH(Me)CF$_3$ | CH$_2$CH$_2$C(O)Me | |
| CH$_2$—c-Pr | (S)-CH$_2$CH(Me)CF$_3$ | CH$_2$SiMe$_3$ | |
| CH$_2$—c-Hex | CH$_2$CH$_2$CH$_2$F | CH$_2$CH$_2$SiMe$_3$ | |
| | $Y^a$ is O, $Y^b$ is CH$_2$ and J is 3-Me—Ph. | | |
| Me | CH$_2$-2-cyclohexenyl | 2-chloro-2-propenyl | CH$_2$OPh |
| Et | 4-tetrahydropyranyl | 3,3-dichloro-2-propenyl | CH$_2$Ph |
| i-Pr | 3-tetrahydropyranyl | CH$_2$-2-tetrahydrofuranyl | CH$_2$CH$_2$Ph |
| n-Pr | 3-tetrahydrofuranyl | CH$_2$-2-tetrahydropyranyl | CH(Me)Ph |
| i-Bu | Ph | CH$_2$CN | CH$_2$-2-Cl—Ph |
| n-Bu | 2-Cl-phenyl | CH$_2$NO$_2$ | CH$_2$-3-Cl—Ph |
| s-Bu | 3-Cl-phenyl | CH$_2$CH$_2$OH | CH$_2$-4-Cl—Ph |
| 3-Me—Bu | 4-Cl-phenyl | CH$_2$CH$_2$OMe | CH$_2$-2-thienyl |
| n-pentyl | 2-pyridinyl | CH$_2$CH(Me)OMe | CH$_2$-2-pyridinyl |
| n-Hex | 2-pyrimidinyl | CH(Me)CH$_2$OMe | CH$_2$-3-pyridinyl |
| 2-propenyl | 2-pyrazinyl | CH(Me)CH(OMe)$_2$ | CH(Et)$_2$ |
| 2-Me-2-propenyl | 2-thiazolyl | CH$_2$-2-dioxolanyl | CH$_2$CH(Et)$_2$ |
| 3-butenyl | 2-oxazolyl | CH$_2$CH$_2$OCF$_3$ | CH$_2$CH(n-Pr)Me |
| 3-pentenyl | CF$_3$ | CH$_2$CH$_2$SMe | CH(Me)Et |
| 2-propynyl | CF$_2$CF$_3$ | CH$_2$CH(Me)SMe | CH(Me)—n-Pr |
| 3-butynyl | CH$_2$CF$_3$ | CH$_2$CH$_2$S(O)Me | CH(CF$_3$)Et |
| 2-butynyl | CH(Me)CF$_3$ | CH$_2$CH$_2$S(O)$_2$Me | CH(Et)—n-Pr |
| c-Pr | CH$_2$CH$_2$F | CH$_2$CO$_2$Me | CH(Me)—n-Bu |
| c-pentyl | CH$_2$CH$_2$CH$_2$F | CH$_2$CO$_2$—i-Pr | 2,2-dimethylpropyl |
| c-Hex | CH$_2$CF$_2$CF$_3$ | CH(Me)CO$_2$Me | CH$_2$CH$_2$CH(Me)$_2$ |
| 2-cyclohexenyl | CH$_2$CH$_2$CF$_3$ | CH$_2$C(O)Me | |
| 3-cyclohexenyl | CH$_2$CH(Me)CF$_3$ | CH$_2$CH$_2$C(O)Me | |
| CH$_2$—c-Pr | (S)-CH$_2$CH(Me)CF$_3$ | CH$_2$SiMe$_3$ | |
| CH$_2$—c-Hex | CH$_2$CH$_2$CH$_2$F | CH$_2$CH$_2$SiMe$_3$ | |
| | $Y^a$ is CH$_2$, $Y^b$ is S and J is Ph. | | |
| Me | CH$_2$-2-cyclohexenyl | 2-chloro-2-propenyl | CH$_2$OPh |
| Et | 4-tetrahydropyranyl | 3,3-dichloro-2-propenyl | CH$_2$Ph |
| i-Pr | 3-tetrahydropyranyl | CH$_2$-2-tetrahydrofuranyl | CH$_2$CH$_2$Ph |
| n-Pr | 3-tetrahydrofuranyl | CH$_2$-2-tetrahydropyranyl | CH(Me)Ph |
| i-Bu | Ph | CH$_2$CN | CH$_2$-2-Cl—Ph |
| n-Bu | 2-Cl-phenyl | CH$_2$NO$_2$ | CH$_2$-3-Cl—Ph |
| s-Bu | 3-Cl-phenyl | CH$_2$CH$_2$OH | CH$_2$-4-Cl—Ph |
| 3-Me—Bu | 4-Cl-phenyl | CH$_2$CH$_2$OMe | CH$_2$-2-thienyl |
| n-pentyl | 2-pyridinyl | CH$_2$CH(Me)OMe | CH$_2$-2-pyridinyl |
| n-Hex | 2-pyrimidinyl | CH(Me)CH$_2$OMe | CH$_2$-3-pyridinyl |
| 2-propenyl | 2-pyrazinyl | CH(Me)CH(OMe)$_2$ | CH(Et)$_2$ |
| 2-Me-2-propenyl | 2-thiazolyl | CH$_2$-2-dioxolanyl | CH$_2$CH(Et)$_2$ |
| 3-butenyl | 2-oxazolyl | CH$_2$CH$_2$OCF$_3$ | CH$_2$CH(n-Pr)Me |
| 3-pentenyl | CF$_3$ | CH$_2$CH$_2$SMe | CH(Me)Et |
| 2-propynyl | CF$_2$CF$_3$ | CH$_2$CH(Me)SMe | CH(Me)—n-Pr |
| 3-butynyl | CH$_2$CF$_3$ | CH$_2$CH$_2$S(O)Me | CH(CF$_3$)Et |
| 2-butynyl | CH(Me)CF$_3$ | CH$_2$CH$_2$S(O)$_2$Me | CH(Et)—n-Pr |
| c-Pr | CH$_2$CH$_2$F | CH$_2$CO$_2$Me | CH(Me)—n-Bu |
| c-pentyl | CH$_2$CH$_2$CH$_2$F | CH$_2$CO$_2$—i-Pr | 2,2-dimethylpropyl |
| c-Hex | CH$_2$CF$_2$CF$_3$ | CH(Me)CO$_2$Me | CH$_2$CH$_2$CH(Me)$_2$ |
| 2-cyclohexenyl | CH$_2$CH$_2$CF$_3$ | CH$_2$C(O)Me | |
| 3-cyclohexenyl | CH$_2$CH(Me)CF$_3$ | CH$_2$CH$_2$C(O)Me | |
| CH$_2$—c-Pr | (S)-CH$_2$CH(Me)CF$_3$ | CH$_2$SiMe$_3$ | |
| CH$_2$—c-Hex | CH$_2$CH$_2$CH$_2$F | CH$_2$CH$_2$SiMe$_3$ | |
| | $Y^a$ is CH$_2$, $Y^b$ is S and J is 4-F—Ph. | | |
| Me | CH$_2$-2-cyclohexenyl | 2-chloro-2-propenyl | CH$_2$OPh |
| Et | 4-tetrahydropyranyl | 3,3-dichloro-2-propenyl | CH$_2$Ph |
| i-Pr | 3-tetrahydropyranyl | CH$_2$-2-tetrahydrofuranyl | CH$_2$CH$_2$Ph |

TABLE 3-continued

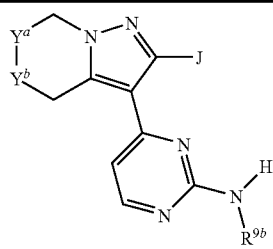

| $R^{9a}$ | $R^{9a}$ | $R^{9a}$ | $R^{9a}$ |
|---|---|---|---|
| n-Pr | 3-tetrahydrofuranyl | CH$_2$-2-tetrahydropyranyl | CH(Me)Ph |
| i-Bu | Ph | CH$_2$CN | CH$_2$-2-Cl—Ph |
| n-Bu | 2-Cl-phenyl | CH$_2$NO$_2$ | CH$_2$-3-Cl—Ph |
| s-Bu | 3-Cl-phenyl | CH$_2$CH$_2$OH | CH$_2$-4-Cl—Ph |
| 3-Me—Bu | 4-Cl-phenyl | CH$_2$CH$_2$OMe | CH$_2$-2-thienyl |
| n-pentyl | 2-pyridinyl | CH$_2$CH(Me)OMe | CH$_2$-2-pyridinyl |
| n-Hex | 2-pyrimidinyl | CH(Me)CH$_2$OMe | CH$_2$-3-pyridinyl |
| 2-propenyl | 2-pyrazinyl | CH(Me)CH(OMe)$_2$ | CH(Et)$_2$ |
| 2-Me-2-propenyl | 2-thiazolyl | CH$_2$-2-dioxolanyl | CH$_2$CH(Et)$_2$ |
| 3-butenyl | 2-oxazolyl | CH$_2$CH$_2$OCF$_3$ | CH$_2$CH(n-Pr)Me |
| 3-pentenyl | CF$_3$ | CH$_2$CH$_2$SMe | CH(Me)Et |
| 2-propynyl | CF$_2$CF$_3$ | CH$_2$CH(Me)SMe | CH(Me)—n-Pr |
| 3-butynyl | CH$_2$CF$_3$ | CH$_2$CH$_2$S(O)Me | CH(CF$_3$)Et |
| 2-butynyl | CH(Me)CF$_3$ | CH$_2$CH$_2$S(O)$_2$Me | CH(Et)—n-Pr |
| c-Pr | CH$_2$CH$_2$F | CH$_2$CO$_2$Me | CH(Me)—n-Bu |
| c-pentyl | CH$_2$CH$_2$CH$_2$F | CH$_2$CO$_2$—i-Pr | 2,2-dimethylpropyl |
| c-Hex | CH$_2$CF$_2$CF$_3$ | CH(Me)CO$_2$Me | CH$_2$CH$_2$CH(Me)$_2$ |
| 2-cyclohexenyl | CH$_2$CH$_2$CF$_3$ | CH$_2$C(O)Me | |
| 3-cyclohexenyl | CH$_2$CH(Me)CF$_3$ | CH$_2$CH$_2$C(O)Me | |
| CH$_2$—c-Pr | (S)-CH$_2$CH(Me)CF$_3$ | CH$_2$SiMe$_3$ | |
| CH$_2$—c-Hex | CH$_2$CH$_2$CH$_2$CH$_2$F | CH$_2$CH$_2$SiMe$_3$ | |
| | $Y^a$ is CH$_2$, $Y^b$ is S and J is 2-F—Ph. | | |
| Me | CH$_2$-2-cyclohexenyl | 2-chloro-2-propenyl | CH$_2$OPh |
| Et | 4-tetrahydropyranyl | 3,3-dichloro-2-propenyl | CH$_2$Ph |
| i-Pr | 3-tetrahydropyranyl | CH$_2$-2-tetrahydrofuranyl | CH$_2$CH$_2$Ph |
| n-Pr | 3-tetrahydrofuranyl | CH$_2$-2-tetrahydropyranyl | CH(Me)Ph |
| i-Bu | Ph | CH$_2$CN | CH$_2$-2-Cl—Ph |
| n-Bu | 2-Cl-phenyl | CH$_2$NO$_2$ | CH$_2$-3-Cl—Ph |
| s-Bu | 3-Cl-phenyl | CH$_2$CH$_2$OH | CH$_2$-4-Cl—Ph |
| 3-Me—Bu | 4-Cl-phenyl | CH$_2$CH$_2$OMe | CH$_2$-2-thienyl |
| n-pentyl | 2-pyridinyl | CH$_2$CH(Me)OMe | CH$_2$-2-pyridinyl |
| n-Hex | 2-pyrimidinyl | CH(Me)CH$_2$OMe | CH$_2$-3-pyridinyl |
| 2-propenyl | 2-pyrazinyl | CH(Me)CH(OMe)$_2$ | CH(Et)$_2$ |
| 2-Me-2-propenyl | 2-thiazolyl | CH$_2$-2-dioxolanyl | CH$_2$CH(Et)$_2$ |
| 3-butenyl | 2-oxazolyl | CH$_2$CH$_2$OCF$_3$ | CH$_2$CH(n-Pr)Me |
| 3-pentenyl | CF$_3$ | CH$_2$CH$_2$SMe | CH(Me)Et |
| 2-propynyl | CF$_2$CF$_3$ | CH$_2$CH(Me)SMe | CH(Me)—n-Pr |
| 3-butynyl | CH$_2$CF$_3$ | CH$_2$CH$_2$S(O)Me | CH(CF$_3$)Et |
| 2-butynyl | CH(Me)CF$_3$ | CH$_2$CH$_2$S(O)$_2$Me | CH(Et)—n-Pr |
| c-Pr | CH$_2$CH$_2$F | CH$_2$CO$_2$Me | CH(Me)—n-Bu |
| c-pentyl | CH$_2$CH$_2$CH$_2$F | CH$_2$CO$_2$—i-Pr | 2,2-dimethylpropyl |
| c-Hex | CH$_2$CF$_2$CF$_3$ | CH(Me)CO$_2$Me | CH$_2$CH$_2$CH(Me)$_2$ |
| 2-cyclohexenyl | CH$_2$CH$_2$CF$_3$ | CH$_2$C(O)Me | |
| 3-cyclohexenyl | CH$_2$CH(Me)CF$_3$ | CH$_2$CH$_2$C(O)Me | |
| CH$_2$—c-Pr | (S)-CH$_2$CH(Me)CF$_3$ | CH$_2$SiMe$_3$ | |
| CH$_2$—c-Hex | CH$_2$CH$_2$CH$_2$CH$_2$F | CH$_2$CH$_2$SiMe$_3$ | |
| | $Y^a$ is CH$_2$, $Y^b$ is S and J is 2-Cl—Ph. | | |
| Me | CH$_2$-2-cyclohexenyl | 2-chloro-2-propenyl | CH$_2$OPh |
| Et | 4-tetrahydropyranyl | 3,3-dichloro-2-propenyl | CH$_2$Ph |
| i-Pr | 3-tetrahydropyranyl | CH$_2$-2-tetrahydrofuranyl | CH$_2$CH$_2$Ph |
| n-Pr | 3-tetrahydrofuranyl | CH$_2$-2-tetrahydropyranyl | CH(Me)Ph |
| i-Bu | Ph | CH$_2$CN | CH$_2$-2-Cl—Ph |
| n-Bu | 2-Cl-phenyl | CH$_2$NO$_2$ | CH$_2$-3-Cl—Ph |
| s-Bu | 3-Cl-phenyl | CH$_2$CH$_2$OH | CH$_2$-4-Cl—Ph |
| 3-Me—Bu | 4-Cl-phenyl | CH$_2$CH$_2$OMe | CH$_2$-2-thienyl |
| n-pentyl | 2-pyridinyl | CH$_2$CH(Me)OMe | CH$_2$-2-pyridinyl |
| n-Hex | 2-pyrimidinyl | CH(Me)CH$_2$OMe | CH$_2$-3-pyridinyl |
| 2-propenyl | 2-pyrazinyl | CH(Me)CH(OMe)$_2$ | CH(Et)$_2$ |
| 2-Me-2-propenyl | 2-thiazolyl | CH$_2$-2-dioxolanyl | CH$_2$CH(Et)$_2$ |
| 3-butenyl | 2-oxazolyl | CH$_2$CH$_2$OCF$_3$ | CH$_2$CH(n-Pr)Me |
| 3-pentenyl | CF$_3$ | CH$_2$CH$_2$SMe | CH(Me)Et |
| 2-propynyl | CF$_2$CF$_3$ | CH$_2$CH(Me)SMe | CH(Me)—n-Pr |
| 3-butynyl | CH$_2$CF$_3$ | CH$_2$CH$_2$S(O)Me | CH(CF$_3$)Et |

TABLE 3-continued

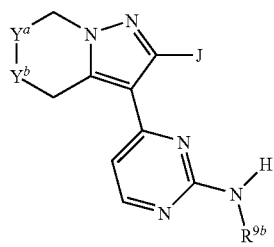

| $R^{9a}$ | $R^{9a}$ | $R^{9a}$ | $R^{9a}$ |
|---|---|---|---|
| 2-butynyl | CH(Me)CF$_3$ | CH$_2$CH$_2$S(O)$_2$Me | CH(Et)—n-Pr |
| c-Pr | CH$_2$CH$_2$F | CH$_2$CO$_2$Me | CH(Me)—n-Bu |
| c-pentyl | CH$_2$CH$_2$CH$_2$F | CH$_2$CO$_2$—i-Pr | 2,2-dimethylpropyl |
| c-Hex | CH$_2$CF$_2$CF$_3$ | CH(Me)CO$_2$Me | CH$_2$CH$_2$CH(Me)$_2$ |
| 2-cyclohexenyl | CH$_2$CH$_2$CF$_3$ | CH$_2$C(O)Me | |
| 3-cyclohexenyl | CH$_2$CH(Me)CF$_3$ | CH$_2$CH$_2$C(O)Me | |
| CH$_2$—c-Pr | (S)-CH$_2$CH(Me)CF$_3$ | CH$_2$SiMe$_3$ | |
| CH$_2$—c-Hex | CH$_2$CH$_2$CH$_2$CH$_2$F | CH$_2$CH$_2$SiMe$_3$ | |
| | $Y^a$ is CH$_2$, $Y^b$ is S and J is 4-Cl—Ph. | | |
| Me | CH$_2$-2-cyclohexenyl | 2-chloro-2-propenyl | CH$_2$OPh |
| Et | 4-tetrahydropyranyl | 3,3-dichloro-2-propenyl | CH$_2$Ph |
| i-Pr | 3-tetrahydropyranyl | CH$_2$-2-tetrahydrofuranyl | CH$_2$CH$_2$Ph |
| n-Pr | 3-tetrahydrofuranyl | CH$_2$-2-tetrahydropyranyl | CH(Me)Ph |
| i-Bu | Ph | CH$_2$CN | CH$_2$-2-Cl—Ph |
| n-Bu | 2-Cl-phenyl | CH$_2$NO$_2$ | CH$_2$-3-Cl—Ph |
| s-Bu | 3-Cl-phenyl | CH$_2$CH$_2$OH | CH$_2$-4-Cl—Ph |
| 3-Me—Bu | 4-Cl-phenyl | CH$_2$CH$_2$OMe | CH$_2$-2-thienyl |
| n-pentyl | 2-pyridinyl | CH$_2$CH(Me)OMe | CH$_2$-2-pyridinyl |
| n-Hex | 2-pyrimidinyl | CH(Me)CH$_2$OMe | CH$_2$-3-pyridinyl |
| 2-propenyl | 2-pyrazinyl | CH(Me)CH(OMe)$_2$ | CH(Et)$_2$ |
| 2-Me-2-propenyl | 2-thiazolyl | CH$_2$-2-dioxolanyl | CH$_2$CH(Et)$_2$ |
| 3-butenyl | 2-oxazolyl | CH$_2$CH$_2$OCF$_3$ | CH$_2$CH(n-Pr)Me |
| 3-pentenyl | CF$_3$ | CH$_2$CH$_2$SMe | CH(Me)Et |
| 2-propynyl | CF$_2$CF$_3$ | CH$_2$CH(Me)SMe | CH(Me)—n-Pr |
| 3-butynyl | CH$_2$CF$_3$ | CH$_2$CH$_2$S(O)Me | CH(CF$_3$)Et |
| 2-butynyl | CH(Me)CF$_3$ | CH$_2$CH$_2$S(O)$_2$Me | CH(Et)—n-Pr |
| c-Pr | CH$_2$CH$_2$F | CH$_2$CO$_2$Me | CH(Me)—n-Bu |
| c-pentyl | CH$_2$CH$_2$CH$_2$F | CH$_2$CO$_2$—i-Pr | 2,2-dimethylpropyl |
| c-Hex | CH$_2$CF$_2$CF$_3$ | CH(Me)CO$_2$Me | CH$_2$CH$_2$CH(Me)$_2$ |
| 2-cyclohexenyl | CH$_2$CH$_2$CF$_3$ | CH$_2$C(O)Me | |
| 3-cyclohexenyl | CH$_2$CH(Me)CF$_3$ | CH$_2$CH$_2$C(O)Me | |
| CH$_2$—c-Pr | (S)-CH$_2$CH(Me)CF$_3$ | CH$_2$SiMe$_3$ | |
| CH$_2$—c-Hex | CH$_2$CH$_2$CH$_2$CH$_2$F | CH$_2$CH$_2$SiMe$_3$ | |
| | $Y^a$ is CH$_2$, $Y^b$ is S and J is 3-Me—Ph. | | |
| Me | CH$_2$-2-cyclohexenyl | 2-chloro-2-propenyl | CH$_2$OPh |
| Et | 4-tetrahydropyranyl | 3,3-dichloro-2-propenyl | CH$_2$Ph |
| i-Pr | 3-tetrahydropyranyl | CH$_2$-2-tetrahydrofuranyl | CH$_2$CH$_2$Ph |
| n-Pr | 3-tetrahydrofuranyl | CH$_2$-2-tetrahydropyranyl | CH(Me)Ph |
| i-Bu | Ph | CH$_2$CN | CH$_2$-2-Cl—Ph |
| n-Bu | 2-Cl-phenyl | CH$_2$NO$_2$ | CH$_2$-3-Cl—Ph |
| s-Bu | 3-Cl-phenyl | CH$_2$CH$_2$OH | CH$_2$-4-Cl—Ph |
| 3-Me—Bu | 4-Cl-phenyl | CH$_2$CH$_2$OMe | CH$_2$-2-thienyl |
| n-pentyl | 2-pyridinyl | CH$_2$CH(Me)OMe | CH$_2$-2-pyridinyl |
| n-Hex | 2-pyrimidinyl | CH(Me)CH$_2$OMe | CH$_2$-3-pyridinyl |
| 2-propenyl | 2-pyrazinyl | CH(Me)CH(OMe)$_2$ | CH(Et)$_2$ |
| 2-Me-2-propenyl | 2-thiazolyl | CH$_2$-2-dioxolanyl | CH$_2$CH(Et)$_2$ |
| 3-butenyl | 2-oxazolyl | CH$_2$CH$_2$OCF$_3$ | CH$_2$CH(n-Pr)Me |
| 3-pentenyl | CF$_3$ | CH$_2$CH$_2$SMe | CH(Me)Et |
| 2-propynyl | CF$_2$CF$_3$ | CH$_2$CH(Me)SMe | CH(Me)—n-Pr |
| 3-butynyl | CH$_2$CF$_3$ | CH$_2$CH$_2$S(O)Me | CH(CF$_3$)Et |
| 2-butynyl | CH(Me)CF$_3$ | CH$_2$CH$_2$S(O)$_2$Me | CH(Et)—n-Pr |
| c-Pr | CH$_2$CH$_2$F | CH$_2$CO$_2$Me | CH(Me)—n-Bu |
| c-pentyl | CH$_2$CH$_2$CH$_2$F | CH$_2$CO$_2$—i-Pr | 2,2-dimethylpropyl |
| c-Hex | CH$_2$CF$_2$CF$_3$ | CH(Me)CO$_2$Me | CH$_2$CH$_2$CH(Me)$_2$ |
| 2-cyclohexenyl | CH$_2$CH$_2$CF$_3$ | CH$_2$C(O)Me | |
| 3-cyclohexenyl | CH$_2$CH(Me)CF$_3$ | CH$_2$CH$_2$C(O)Me | |
| CH$_2$—c-Pr | (S)-CH$_2$CH(Me)CF$_3$ | CH$_2$SiMe$_3$ | |
| CH$_2$—c-Hex | CH$_2$CH$_2$CH$_2$CH$_2$F | CH$_2$CH$_2$SiMe$_3$ | |

TABLE 4A

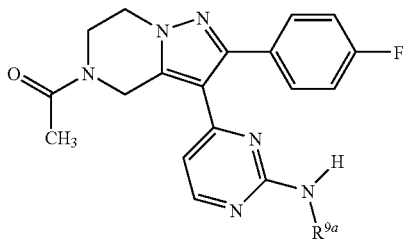

| $R^{9a}$ | $R^{9a}$ | $R^{9a}$ | $R^{9a}$ |
| --- | --- | --- | --- |
| Me | $CH_2$-2-cyclohexenyl | 2-chloro-2-propenyl | $CH_2OPh$ |
| Et | 4-tetrahydropyranyl | 3,3-dichloro-2-propenyl | $CH_2Ph$ |
| i-Pr | 3-tetrahydropyranyl | $CH_2$-2-tetrahydrofuranyl | $CH_2CH_2Ph$ |
| n-Pr | 3-tetrahydrofuranyl | $CH_2$-2-tetrahydropyranyl | $CH(Me)Ph$ |
| i-Bu | Ph | $CH_2CN$ | $CH_2$-2-Cl—Ph |
| n-Bu | 2-Cl-phenyl | $CH_2NO_2$ | $CH_2$-3-Cl—Ph |
| s-Bu | 3-Cl-phenyl | $CH_2CH_2OH$ | $CH_2$-4-Cl—Ph |
| 3-Me—Bu | 4-Cl-phenyl | $CH_2CH_2OMe$ | $CH_2$-2-thienyl |
| n-pentyl | 2-pyridinyl | $CH_2CH(Me)OMe$ | $CH_2$-2-pyridinyl |
| n-Hex | 2-pyrimidinyl | $CH(Me)CH_2OMe$ | $CH_2$-3-pyridinyl |
| 2-propenyl | 2-pyrazinyl | $CH(Me)CH(OMe)_2$ | $CH(Et)_2$ |
| 2-Me-2-propenyl | 2-thiazolyl | $CH_2$-2-dioxolanyl | $CH_2CH(Et)_2$ |
| 3-butenyl | 2-oxazolyl | $CH_2CH_2OCF_3$ | $CH_2CH(n-Pr)Me$ |
| 3-pentenyl | $CF_3$ | $CH_2CH_2SMe$ | $CH(Me)Et$ |
| 2-propynyl | $CF_2CF_3$ | $CH_2CH(Me)SMe$ | $CH(Me)$—n-Pr |
| 3-butynyl | $CH_2CF_3$ | $CH_2CH_2S(O)Me$ | $CH(CF_3)Et$ |
| 2-butynyl | $CH(Me)CF_3$ | $CH_2CH_2S(O)_2Me$ | $CH(Et)$—n-Pr |
| c-Pr | $CH_2CH_2F$ | $CH_2CO_2Me$ | $CH(Me)$—n-Bu |
| c-pentyl | $CH_2CH_2CH_2F$ | $CH_2CO_2$—i-Pr | 2,2-dimethylpropyl |
| c-Hex | $CH_2CF_2CF_3$ | $CH(Me)CO_2Me$ | $CH_2CH_2CH(Me)_2$ |
| 2-cyclohexenyl | $CH_2CH_2CF_3$ | $CH_2C(O)Me$ | |
| 3-cyclohexenyl | $CH_2CH(Me)CF_3$ | $CH_2CH_2C(O)Me$ | |
| $CH_2$—c-Pr | (S)-$CH_2CH(Me)CF_3$ | $CH_2SiMe_3$ | |
| $CH_2$—c-Hex | $CH_2CH_2CH_2CH_2F$ | $CH_2CH_2SiMe_3$ | |

TABLE 4B

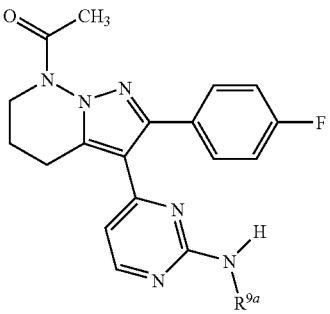

| $R^{9a}$ | $R^{9a}$ | $R^{9a}$ | $R^{9a}$ |
| --- | --- | --- | --- |
| Me | $CH_2$-2-cyclohexenyl | 2-chloro-2-propenyl | $CH_2OPh$ |
| Et | 4-tetrahydropyranyl | 3,3-dichloro-2-propenyl | $CH_2Ph$ |
| i-Pr | 3-tetrahydropyranyl | $CH_2$-2-tetrahydrofuranyl | $CH_2CH_2Ph$ |
| n-Pr | 3-tetrahydrofuranyl | $CH_2$-2-tetrahydropyranyl | $CH(Me)Ph$ |
| i-Bu | Ph | $CH_2CN$ | $CH_2$-2-Cl—Ph |
| n-Bu | 2-Cl-phenyl | $CH_2NO_2$ | $CH_2$-3-Cl—Ph |
| s-Bu | 3-Cl-phenyl | $CH_2CH_2OH$ | $CH_2$-4-Cl—Ph |
| 3-Me—Bu | 4-Cl-phenyl | $CH_2CH_2OMe$ | $CH_2$-2-thienyl |
| n-pentyl | 2-pyridinyl | $CH_2CH(Me)OMe$ | $CH_2$-2-pyridinyl |
| n-Hex | 2-pyrimidinyl | $CH(Me)CH_2OMe$ | $CH_2$-3-pyridinyl |
| 2-propenyl | 2-pyrazinyl | $CH(Me)CH(OMe)_2$ | $CH(Et)_2$ |
| 2-Me-2-propenyl | 2-thiazolyl | $CH_2$-2-dioxolanyl | $CH_2CH(Et)_2$ |
| 3-butenyl | 2-oxazolyl | $CH_2CH_2OCF_3$ | $CH_2CH(n-Pr)Me$ |
| 3-pentenyl | $CF_3$ | $CH_2CH_2SMe$ | $CH(Me)Et$ |
| 2-propynyl | $CF_2CF_3$ | $CH_2CH(Me)SMe$ | $CH(Me)$—n-Pr |
| 3-butynyl | $CH_2CF_3$ | $CH_2CH_2S(O)Me$ | $CH(CF_3)Et$ |
| 2-butynyl | $CH(Me)CF_3$ | $CH_2CH_2S(O)_2Me$ | $CH(Et)$—n-Pr |
| c-Pr | $CH_2CH_2F$ | $CH_2CO_2Me$ | $CH(Me)$—n-Bu |
| c-pentyl | $CH_2CH_2CH_2F$ | $CH_2CO_2$—i-Pr | 2,2-dimethylpropyl |

TABLE 4B-continued

[Structure: 7-acetyl-2-(4-fluorophenyl)-4,5-dihydropyrazolo[1,5-a]pyridazine with 4-pyrimidinyl substituent bearing NHR$^{9a}$]

| R$^{9a}$ | R$^{9a}$ | R$^{9a}$ | R$^{9a}$ |
| --- | --- | --- | --- |
| c-Hex | CH$_2$CF$_2$CF$_3$ | CH(Me)CO$_2$Me | CH$_2$CH$_2$CH(Me)$_2$ |
| 2-cyclohexenyl | CH$_2$CH$_2$CF$_3$ | CH$_2$C(O)Me | |
| 3-cyclohexenyl | CH$_2$CH(Me)CF$_3$ | CH$_2$CH$_2$C(O)Me | |
| CH$_2$—c-Pr | (S)-CH$_2$CH(Me)CF$_3$ | CH$_2$SiMe$_3$ | |
| CH$_2$—c-Hex | CH$_2$CH$_2$CH$_2$CH$_2$F | CH$_2$CH$_2$SiMe$_3$ | |

TABLE 5

[Structure: 2-(4-fluorophenyl)-4,5,6,7-tetrahydropyrazolo[1,5-a]pyridine with 4-pyrimidinyl substituent bearing OR$^{12}$]

| R$^{12}$ | R$^{12}$ | R$^{12}$ | R$^{12}$ |
| --- | --- | --- | --- |
| Me | CH$_2$-2-cyclohexenyl | 2-chloro-2-propenyl | CH$_2$OPh |
| Et | 4-tetrahydropyranyl | 3,3-dichloro-2-propenyl | CH$_2$Ph |
| i-Pr | 3-tetrahydropyranyl | CH$_2$-2-tetrahydrofuranyl | CH$_2$CH$_2$Ph |
| n-Pr | 3-tetrahydrofuranyl | CH$_2$-2-tetrahydropyranyl | CH(Me)Ph |
| i-Bu | Ph | CH$_2$CN | CH$_2$-2-Cl—Ph |
| n-Bu | 2-Cl-phenyl | CH$_2$NO$_2$ | CH$_2$-3-Cl—Ph |
| s-Bu | 3-Cl-phenyl | CH$_2$CH$_2$OH | CH$_2$-4-Cl—Ph |
| 3-Me—Bu | 4-Cl-phenyl | CH$_2$CH$_2$OMe | CH$_2$-2-thienyl |
| n-pentyl | 2-pyridinyl | CH$_2$CH(Me)OMe | CH$_2$-2-pyridinyl |
| n-Hex | 2-pyrimidinyl | CH(Me)CH$_2$OMe | CH$_2$-3-pyridinyl |
| 2-propenyl | 2-pyrazinyl | CH(Me)CH(OMe)$_2$ | CH(Et)$_2$ |
| 2-Me-2-propenyl | 2-thiazolyl | CH$_2$-2-dioxolanyl | CH$_2$CH(Et)$_2$ |
| 3-butenyl | 2-oxazolyl | CH$_2$CH$_2$OCF$_3$ | CH$_2$CH(n-Pr)Me |
| 3-pentenyl | CF$_3$ | CH$_2$CH$_2$SMe | CH(Me)Et |
| 2-propynyl | CF$_2$CF$_3$ | CH$_2$CH(Me)SMe | CH(Me)—n-Pr |
| 3-butynyl | CH$_2$CF$_3$ | CH$_2$CH$_2$S(O)Me | CH(CF$_3$)Et |
| 2-butynyl | CH(Me)CF$_3$ | CH$_2$CH$_2$S(O)$_2$Me | CH(Et)—n-Pr |
| c-Pr | CH$_2$CH$_2$F | CH$_2$CO$_2$Me | CH(Me)—n-Bu |
| c-pentyl | CH$_2$CH$_2$CH$_2$F | CH$_2$CO$_2$—i-Pr | 2,2-dimethylpropyl |
| c-Hex | CH$_2$CF$_2$CF$_3$ | CH(Me)CO$_2$Me | CH$_2$CH$_2$CH(Me)$_2$ |
| 2-cyclohexenyl | CH$_2$CH$_2$CF$_3$ | CH$_2$C(O)Me | |
| 3-cyclohexenyl | CH$_2$CH(Me)CF$_3$ | CH$_2$CH$_2$C(O)Me | |
| CH$_2$—c-Pr | (S)-CH$_2$CH(Me)CF$_3$ | CH$_2$SiMe$_3$ | |
| CH$_2$—c-Hex | CH$_2$CH$_2$CH$_2$CH$_2$F | CH$_2$CH$_2$SiMe$_3$ | |

TABLE 6

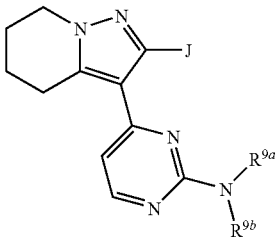

| J | J | J |
|---|---|---|
| $R^{9a}$ is i-Pr and $R^{9b}$ is H. | | |
| 1-naphthalenyl | 2-pyridinyl | 2-thiazolyl |
| 2-naphthalenyl | 3-pyridinyl | 4-thiazolyl |
| 2-thienyl | 4-pyridinyl | 3-isoxazolinyl |
| 3-thienyl | 2-pyrimidinyl | 1-Me-imidazol-2-yl |
| 2-oxazolyl | 4-pyrimidinyl | 1-Me-imidazol-5-yl |
| 4-oxazolyl | 2-pyrazinyl | cyclohexyl |
| $R^{9a}$ is cyclopropyl and $R^{9b}$ is H. | | |
| 1-naphthalenyl | 2-pyridinyl | 2-thiazolyl |
| 2-naphthalenyl | 3-pyridinyl | 4-thiazolyl |
| 2-thienyl | 4-pyridinyl | 3-isoxazolinyl |
| $R^{9a}$ is cyclopropyl and $R^{9b}$ is H. | | |
| 3-thienyl | 2-pyrimidinyl | 1-Me-imidazol-2-yl |
| 2-oxazolyl | 4-pyrimidinyl | 1-Me-imidazol-5-yl |
| 4-oxazolyl | 2-pyrazinyl | cyclohexyl |
| $R^{9a}$ is CH(Me)CH$_2$OMe and $R^{9b}$ is H. | | |
| 1-naphthalenyl | 2-pyridinyl | 2-thiazolyl |
| 2-naphthalenyl | 3-pyridinyl | 4-thiazolyl |
| 2-thienyl | 4-pyridinyl | 3-isoxazolinyl |
| 3-thienyl | 2-pyrimidinyl | 1-Me-imidazol-2-yl |
| 2-oxazolyl | 4-pyrimidinyl | 1-Me-imidazol-5-yl |
| 4-oxazolyl | 2-pyrazinyl | cyclohexyl |
| $R^{9a}$ is CH(Me)CH$_2$OH and $R^{9b}$ is H. | | |
| 1-naphthalenyl | 2-pyridinyl | 2-thiazolyl |
| 2-naphthalenyl | 3-pyridinyl | 4-thiazolyl |
| 2-thienyl | 4-pyridinyl | 3-isoxazolinyl |
| 3-thienyl | 2-pyrimidinyl | 1-Me-imidazol-2-yl |
| 2-oxazolyl | 4-pyrimidinyl | 1-Me-imidazol-5-yl |
| 4-oxazolyl | 2-pyrazinyl | cyclohexyl |

Formulation/Utility

A compound of this invention will generally be used as a fungicidal active ingredient in a composition, i.e. formulation, with at least one additional component selected from the group consisting of surfactants, solid diluents and liquid diluents, which serve as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions and/or suspoemulsions) and the like, which optionally can be thickened into gels. The general types of aqueous liquid compositions are soluble concentrate, suspension concentrate, capsule suspension, concentrated emulsion, microemulsion and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, pills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water. Spray volumes can range from about from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting. Liquid and solid formulations can be applied onto seeds of crops and other desirable vegetation as seed treatments before planting to protect developing roots and other subterranean plant parts and/or foliage through systemic uptake.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-99 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers*, 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, triacetin, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide*, 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents, Seventh Edition*, John Wiley and Sons, New York, 1987.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The compound of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 μm can be wet milled using media mills to obtain particles with average diameters below 3 μm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 μm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. Nos. 4,144,050, 3,920,442 and DE 3,246,493. Tablets can be prepared as taught in U.S. Pat. No. 5,180,587, 5,232,701 and 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, UK, 2000.

In the following Examples, all percentages are by weight and all formulations are prepared in conventional ways. Compound numbers refer to compounds in Index Tables A-F. Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except where otherwise indicated.

EXAMPLE A

| High Strength Concentrate | |
|---|---|
| Compound 1 | 98.5% |
| silica aerogel | 0.5% |
| synthetic amorphous fine silica | 1.0% |

EXAMPLE B

| Wettable Powder | |
|---|---|
| Compound 2 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

EXAMPLE C

| Granule | |
|---|---|
| Compound 3 | 10.0% |
| attapulgite granules (low volatile matter, 0.71/ 0.30 mm; U.S.S. No. 25-50 sieves) | 90.0% |

EXAMPLE D

| Extruded Pellet | |
|---|---|
| Compound 2 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

EXAMPLE E

| Emulsifiable Concentrate | |
|---|---|
| Compound 3 | 10.0% |
| polyoxyethylene sorbitol hexoleate | 20.0% |
| $C_6$-$C_{10}$ fatty acid methyl ester | 70.0% |

EXAMPLE F

| Microemulsion | |
|---|---|
| Compound 4 | 5.0% |
| polyvinylpyrrolidone-vinyl acetate copolymer | 30.0% |
| alkylpolyglycoside | 30.0% |
| glyceryl monooleate | 15.0% |
| water | 20.0% |

EXAMPLE G

| Seed Treatment | |
|---|---|
| Compound 1 | 20.00% |
| polyvinylpyrrolidone-vinyl acetate copolymer | 5.00% |
| montan acid wax | 5.00% |
| calcium ligninsulfonate | 1.00% |
| polyoxyethylene/polyoxypropylene block copolymers | 1.00% |
| stearyl alcohol (POE 20) | 2.00% |
| polyorganosilane | 0.20% |
| colorant red dye | 0.05% |
| water | 65.75% |

The compounds of this invention are useful as plant disease control agents. The present invention therefore further comprises a method for controlling plant diseases caused by fungal plant pathogens comprising applying to the plant or portion thereof to be protected, or to the plant seed to be protected, an effective amount of a compound of the invention or a fungicidal composition containing said compound. The compounds and/or compositions of this invention provide control of diseases caused by a broad spectrum of fungal plant pathogens in the Basidiomycete, Ascomycete, Oomycete and Deuteromycete classes. They are effective in controlling a broad spectrum of plant diseases, particularly foliar pathogens of ornamental, turf, vegetable, field, cereal, and fruit crops. These pathogens include: Oomycetes, including *Phytophthora* diseases such as *Phytophthora infestans, Phytophthora megasperma, Phytophthora parasitica, Phytophthora cinnamomi* and *Phytophthora capsici, Pythium* diseases such as *Pythium aphanidermatum*, and diseases in the Peronosporaceae family such as *Plasmopara viticola, Peronospora* spp. (including *Peronospora tabacina* and *Peronospora parasitica*), *Pseudoperonospora* spp. (including *Pseudoperonospora cubensis*) and *Bremia lactucae*; Ascomycetes, including *Alternaria* diseases such as *Alternaria solani* and *Alternaria brassicae, Guignardia* diseases such as *Guignardia bidwell, Venturia* diseases such as *Venturia inaequalis, Septoria* diseases such as *Septoria nodorum* and *Septoria tritici*, powdery mildew diseases such as *Erysiphe* spp. (including *Erysiphe graminis* and *Erysiphe polygoni*), *Uncinula necatur, Sphaerotheca fuligena* and *Podosphaera leucotricha, Pseudocercosporella herpotrichoides, Botrytis* diseases such as *Botrytis cinerea, Monilinia fructicola, Sclerotinia* diseases such as *Sclerotinia sclerotiorum, Magnaporthe grisea, Phomopsis viticola, Helminthosporium* diseases such as *Helminthosporium tritici repentis, Pyrenophora teres*, anthracnose diseases such as *Glomerella* or *Colletotrichum* spp. (such as *Colletotrichum graminicola* and *Colletotrichum orbiculare*), and *Gaeumannomyces graminis*; Basidiomycetes, including rust diseases caused by *Puccinia* spp. (such as *Puccinia recondite, Puccinia striiformis, Puccinia horde, Puccinia graminis* and *Puccinia arachidis*), *Hemileia vastatrix* and *Phakopsora pachyrhizi*; other pathogens including *Rhizoctonia* spp. (such as *Rhizoctonia solani*); *Fusarium* diseases such as *Fusarium roseum, Fusarium graminearum* and *Fusarium oxysporum; Verticillium dahliae; Sclerotium rolfsii; Rynchosporium secalis; Cercosporidium personatum, Cercospora arachidicola* and *Cercospora beticola*; and other genera and species closely related to these pathogens. In addition to their fungicidal activity, the compositions or combinations also have activity against bacteria such as *Erwinia amylovora, Xanthomonas campestris, Pseudomonas syringae*, and other related species.

Plant disease control is ordinarily accomplished by applying an effective amount of a compound of this invention either pre- or post-infection, to the portion of the plant to be protected such as the roots, stems, foliage, fruit, seeds, tubers or bulbs, or to the media (soil or sand) in which the plants to be protected are growing. The compounds can also be applied to seeds to protect the seeds and seedlings developing from the seeds. The compounds can also be applied through irrigation water to treat plants.

Rates of application for these compounds can be influenced by many factors of the environment and should be determined under actual use conditions. Foliage can normally be protected when treated at a rate of from less than about 1 g/ha to about 5,000 g/ha of active ingredient. Seed and seedlings can normally be protected when seed is treated at a rate of from about 0.1 to about 10 g per kilogram of seed.

Compounds of this invention can also be mixed with one or more other biologically active compounds or agents including fungicides, insecticides, nematocides, bactericides, acaricides, herbicides, herbicide safeners, growth regulators such as insect molting inhibitors and rooting stimulants, chemosterilants, semiochemicals, repellents, attractants, pheromones, feeding stimulants, plant nutrients, other biologically active compounds or entomopathogenic bacteria, virus or fungi to form a multi-component pesticide giving an even broader spectrum of agricultural protection. Thus the present invention also pertains to a composition comprising a fungicidally effective amount of a compound of Formula 1 and a biologically effective amount of at least one additional biologically active compound or agent and can further comprise at least one of a surfactant, a solid diluent or a liquid diluent. The other biologically active compounds or agents can be formulated in compositions comprising at least one of a surfactant, solid or liquid diluent. For mixtures of the present invention, one or more other biologically active compounds or agents can be formulated together with a compound of Formula 1, to form a premix, or one or more other biologically active compounds or agents can be formulated separately from the compound of Formula 1, and the formulations combined together before application (e.g., in a spray tank) or, alternatively, applied in succession.

Examples of such biologically active compounds or agents with which compounds of this invention can be formulated are: insecticides such as abamectin, acephate, acetamiprid, amidoflumet (S-1955), avermectin, azadirachtin, azinphosmethyl, bifenthrin, bifenazate, buprofezin, carbofuran, cartap, chlorantraniliprole (DPX-E2Y45), chlorfenapyr, chlorfluazuron, chlorpyrifos, chlorpyrifos-methyl, chromafenozide, clothianidin, cyflumetofen, cyfluthrin, beta-cyfluthrin, cyhalothrin, lambda-cyhalothrin, cypermethrin, cyromazine, deltamethrin, diafenthiuron, diazinon, dieldrin, diflubenzuron, dimefluthrin, dimethoate, dinotefuran, diofenolan, emamectin, endosulfan, esfenvalerate, ethiprole, fenothiocarb, fenoxycarb, fenpropathrin, fenvalerate, fipronil, flonicamid, flubendiamide, flucythrinate, tau-fluvalinate, flufenerim (UR-50701), flufenoxuron, fonophos, halofenozide, hexaflumuron, hydramethylnon, imidacloprid, indoxacarb, isofenphos, lufenuron, malathion, metaflumizone, metaldehyde, methamidophos, methidathion, methomyl, methoprene, methoxychlor, metofluthrin, monocrotophos, methoxyfenozide, nitenpyram, nithiazine, novaluron, noviflumuron (XDE-007), oxamyl, parathion, parathion-methyl, permethrin, phorate, phosalone, phosmet, phosphamidon, pirimicarb, profenofos, profluthrin, pymetrozine, pyrafluprole, pyrethrin, pyridalyl, pyrifluquinazon, pyriprole, pyriproxyfen, rotenone, ryanodine, spinetoram, spinosad, spirodiclofen, spiromesifen (BSN 2060), spirotetramat, sulprofos, tebufenozide, teflubenzuron, tefluthrin, terbufos, tetrachlorvinphos, thiacloprid, thiamethoxam, thiodicarb, thiosultap-sodium, tralomethrin, triazamate, trichlorfon and triflumuron; fungicides such as acibenzolar-S-methyl, aldimorph, amisulbrom, anilazine, azaconazole, azoxystrobin, benalaxyl, benalaxyl-M, benodanil, benomyl, benthiavalicarb, benthiavalicarb-isopropyl, bethoxazin, binapacryl, biphenyl, bitertanol, bixafen, blasticidin-S, Bordeaux mixture (tribasic copper sulfate), boscalid, bromuconazole, bupirimate, captafol, captan, carbendazim, carboxin, carpropamid, chloroneb, chlorothalonil, chlozolinate, clotrimazole, copper oxychloride, copper salts such as copper sulfate and copper hydroxide, cyazofamid, cyflufenamid, cymoxanil, cyproconazole, cyprodinil, dichlofluanid, diclocymet, diclomezine, dicloran, diethofencarb, difenoconazole, diflumetorim, dimethirimol, dimethomorph, dimoxystrobin, diniconazole, diniconazole-M, dinocap, dithianon, dodemorph, dodine, edifenphos, enestroburin, epoxiconazole, ethaboxam, ethirimol, etridiazole, famoxadone, fenamidone, fenarimol, fenbuconazole, fenfuram, fenhexamid, fenoxanil, fenpiclonil, fenpropidin, fenpropimorph, fentin acetate, fentin chloride, fentin hydroxide, ferbam, ferimzone, fluazinam, fludioxonil, flumorph, fluopicolide, fluopyram, fluoroimide, fluoxastrobin, fluquinconazole, flusilazole, flusulfamide, flutolanil, flutriafol, folpet, fosetyl-aluminum, fuberidazole, furalaxyl, furametpyr, guazatine, hexaconazole, hymexazol, imazalil, imibenconazole, iminoctadine albesilate, iminoctadine triacetate, iodocarb, ipconazole, iprobenfos, iprodione, iprovalicarb, isoprothiolane, isotianil, kasugamycin, kresoxim-methyl, mancozeb, mandipropamid, maneb, mepanipyrim, mepronil, meptyldinocap, metalaxyl, metalaxyl-M, metconazole, methasulfocarb, metiram, metominostrobin, metrafenone, myclobutanil, naftifine, neo-asozin (ferric methanearsonate), nuarimol, octhilinone, ofurace, orysastrobin, oxadixyl, oxolinic acid, oxpoconazole, oxycarboxin, oxytetracycline, pefurazoate, penconazole, pencycuron, penthiopyrad, phosphorous acid and salts, phthalide, picoxystrobin, piperalin, polyoxin, probenazole, prochloraz, procymidone, propamocarb, propamocarb-hydrochloride, propiconazole, propineb, proquinazid, prothiocarb, prothioconazole, pyrazophos, pyraclostrobin, pyribencarb, pyributicarb, pyrifenox, pyrimethanil, pyrrolnitrin, pyroquilon, quinomethionate, quinoxyfen, quintozene, silthiofam, simeconazole, spiroxamine, streptomycin, sulfur, tebuconazole, tecloftalam, tecnazene, terbinafine, tetraconazole, thiabendazole, thifluzamide, thiophanate, thiophanate-methyl, thiram, tiadinil, tolclofos-methyl, tolyfluanid, triadimefon, triadimenol, triazoxide, tricyclazole, tridemorph, trifloxystrobin, triflumizole, triforine, triticonazole, uniconazole, validamycin, valiphenal, vinclozolin, zineb, ziram, zoxamide, N-[2-(1,3-dimethylbutyl)phenyl]-5-fluoro-1,3-dimethyl-1H-pyrazol-4-carboxamide, N-[2-(1S,2R)-[1,1'-bicyclopropyl]-2-ylphenyl]-3-(difluoromethyl)-1-methyl-1H-pyrazole-4-carboxamide, α-[methoxyimino]-N-methyl-2-[[[1-[3-(trifluoromethyl)-phenyl]-ethoxy]imino]methyl] benzeneacetamide, 2-[[[3-(2,6-dichlorophenyl)-1-methyl-2-propen-1-ylidene]amino]oxy]methyl]-α-(methoxyimino)-N-methylbenzeneacetamide, N-[2-[4-[[3-(4-chlorophenyl)-2-propyn-1-yl]oxy]-3-methoxy phenyl]ethyl]-3-methyl-2-[(methylsulfonyl)amino]butanamide, N-[2-[4-[[3-(4-chlorophenyl)-2-propyn-1-yl]oxy]-3-methoxyphenyl] ethyl]-3-methyl-2-[(ethylsulfonyl)amino]butanamide, 2-[[2-fluoro-5-(trifluoromethyl)phenyl]thio]-2-[3-(2-methoxyphenyl)-2-thiazolidinylidene]acetonitrile, 2-butoxy-6-iodo-3-propyl-4H-1-benzopyran-4-one, 3-[5-(4-chlorophenyl)-2,3-dimethyl-3-isoxazolidinyl]pyridine, 4-fluorophenyl N-[1-[[[1-(4-cyanophenyl)ethyl]sulfonyl]-methyl]propyl]carbamate, 5-chloro-6-(2,4,6-trifluorophenyl)-7-(4-methylpiperidin-1-yl) [1,2,4]triazolo[1,5-a]pyrimidine, N-(4-chloro-2-nitrophenyl)-N-ethyl-4-methylbenzenesulfonamide, N-[[(cyclopropylmethoxy) amino][6-(difluoromethoxy)-2,3-difluorophenyl] methylene]-benzeneacetamide, N'-[4-[4-chloro-3-(trifluoromethyl)phenoxy]-2,5-dimethylphenyl]-N-ethyl-N-methylmethanimidamide, and 1-[(2-propenylthio)carbonyl]-2-(1-methylethyl)-4-(2-methylphenyl)-5-amino-1H-pyrazol-3-one; nematocides such as aldicarb, aldoxycarb, fenamiphos, imicyafos and oxamyl; bactericides such as streptomycin; acaricides such as amitraz, chinomethionat, chlorobenzilate, cyenopyrafen, cyhexatin, dicofol, dienochlor, etoxazole, fenazaquin, fenbutatin oxide, fenpropathrin, fenpyroximate, hexythiazox, propargite, pyridaben and tebufenpyrad; and biological agents including entomopathogenic bacteria, such as *Bacillus thuringiensis* subsp. *aizawai, Bacillus thuringiensis* subsp. *kurstaki*, and the encapsulated delta-endotoxins of *Bacillus thuringiensis* (e.g., Cellcap, MPV, MPVII); entomopathogenic fungi, such as green muscardine fungus; and entomopathogenic virus including baculovirus, nucleopolyhedro virus (NPV) such as HzNPV, AfNPV; and granulosis virus (GV) such as CpGV.

Compounds of this invention and compositions thereof can be applied to plants genetically transformed to express proteins toxic to invertebrate pests (such as *Bacillus thuringiensis* delta-endotoxins). The effect of the exogenously applied fungicidal compounds of this invention may be synergistic with the expressed toxin proteins.

General references for agricultural protectants (i.e. insecticides, fungicides, nematocides, acaricides, herbicides and biological agents) include *The Pesticide Manual,* 13th Edition, C. D. S. Tomlin, Ed., British Crop Protection Council, Farnham, Surrey, U.K., 2003 and *The BioPesticide Manual,* 2nd Edition, L. G. Copping, Ed., British Crop Protection Council, Farnham, Surrey, U.K., 2001.

For embodiments where one or more of these various mixing partners are used, the weight ratio of these various mixing partners (in total) to the compound of Formula 1 is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components may expand the spectrum of diseases controlled beyond the spectrum controlled by the compound of Formula 1 alone.

In certain instances, combinations of a compound of this invention with other biologically active (particularly fungicidal) compounds or agents (i.e. active ingredients) can result in a greater-than-additive (i.e. synergistic) effect. Reducing the quantity of active ingredients released in the environment while ensuring effective pest control is always desirable. When synergism of fungicidal active ingredients occurs at application rates giving agronomically satisfactory levels of fungal control, such combinations can be advantageous for reducing crop production cost and decreasing environmental load.

Of note is a combination of a compound of Formula 1 with at least one other fungicidal active ingredient. Of particular note is such a combination where the other fungicidal active ingredient has different site of action from the compound of Formula 1. In certain instances, a combination with at least one other fungicidal active ingredient having a similar spectrum of control but a different site of action will be particularly advantageous for resistance management. Thus, a composition of the present invention can further comprise a biologically effective amount of at least one additional fungicidal active ingredient having a similar spectrum of control but a different site of action.

Of particular note are compositions which in addition to compound of Formula 1 include at least one compound selected from the group consisting of (1) alkylenebis(dithiocarbamate) fungicides; (2) cymoxanil; (3) phenylamide fungicides; (4) pyrimidinone fungicides; (5) chlorothalonil; (6) carboxamides acting at complex II of the fungal mitochondrial respiratory electron transfer site; (7) quinoxyfen; (8) metrafenone; (9) cyflufenamid; (10) cyprodinil; (11) copper compounds; (12) phthalimide fungicides; (13) fosetyl-aluminum; (14) benzimidazole fungicides; (15) cyazofamid; (16) fluazinam; (17) iprovalicarb; (18) propamocarb; (19) validomycin; (20) dichlorophenyl dicarboximide fungicides; (21) zoxamide; (22) fluopicolide; (23) mandipropamid; (24) carboxylic acid amides acting on phospholipid biosynthesis and cell wall deposition; (25) dimethomorph; (26) non-DMI sterol biosynthesis inhibitors; (27) inhibitors of demethylase in sterol biosynthesis; (28) bc$_1$ complex fungicides; and salts of compounds of (1) through (28).

Further descriptions of classes of fungicidal compounds are provided below.

Pyrimidinone fungicides (group (4)) include compounds of Formula A1

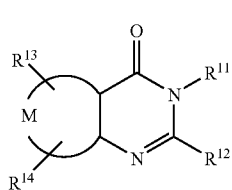

A1 wherein M forms a fused phenyl, thiophene or pyridine ring; $R^{11}$ is $C_1$-$C_6$ alkyl; $R^{12}$ is $C_1$-$C_6$ alkyl or $C_1$-$C_6$ alkoxy; $R^{13}$ is halogen; and $R^{14}$ is hydrogen or halogen.

Pyrimidinone fungicides are described in PCT Patent Application Publication WO 94/26722 and U.S. Pat. Nos. 6,066,638, 6,245,770, 6,262,058 and 6,277,858. Of note are pyrimidinone fungicides selected from the group: 6-bromo-3-propyl-2-propyloxy-4(3H)-quinazolinone, 6,8-diiodo-3-propyl-2-propyloxy-4(3H)-quinazolinone, 6-iodo-3-propyl-2-propyloxy-4(3H)-quinazolinone (proquinazid), 6-chloro-2-propoxy-3-propyl-thieno[2,3-d]pyrimidin-4(3H)-one, 6-bromo-2-propoxy-3-propylthieno[2,3-d]pyrimidin-4(3H)-one, 7-bromo-2-propoxy-3-propylthieno[3,2-d]pyrimidin-4(3H)-one, 6-bromo-2-propoxy-3-propylpyrido[2,3-d]pyrimidin-4(3H)-one, 6,7-dibromo-2-propoxy-3-propyl-thieno[3,2-d]pyrimidin-4(3H)-one, and 3-(cyclopropylmethyl)-6-iodo-2-(propylthio)pyrido-[2,3-d]pyrimidin-4(3H)-one.

Sterol biosynthesis inhibitors (group (27)) control fungi by inhibiting enzymes in the sterol biosynthesis pathway. Demethylase-inhibiting fungicides have a common site of action within the fungal sterol biosynthesis pathway, involving inhibition of demethylation at position 14 of lanosterol or 24-methylene dihydrolanosterol, which are precursors to sterols in fungi. Compounds acting at this site are often referred to as demethylase inhibitors, DMI fungicides, or DMIs. The demethylase enzyme is sometimes referred to by other names in the biochemical literature, including cytochrome P-450 (14DM). The demethylase enzyme is described in, for example, *J. Biol. Chem.* 1992, 267, 13175-79 and references cited therein. DMI fungicides are divided between several chemical classes: azoles (including triazoles and imidazoles), pyrimidines, piperazines and pyridines. The triazoles include azaconazole, bromuconazole, cyproconazole, difenoconazole, diniconazole (including diniconazole-M), epoxiconazole, etaconazole, fenbuconazole, fluquinconazole, flusilazole, flutriafol, hexaconazole, imibenconazole, ipconazole, metconazole, myclobutanil, penconazole, propiconazole, prothioconazole, quinconazole, simeconazole, tebuconazole, tetraconazole, triadimefon, triadimenol, triticonazole and uniconazole. The imidazoles include clotrimazole, econazole, imazalil, isoconazole, miconazole, oxpoconazole, prochloraz and triflumizole. The pyrimidines include fenarimol, nuarimol and triarimol. The piperazines include triforine. The pyridines include buthiobate and pyrifenox. Biochemical investigations have shown that all of the above mentioned fungicides are DMI fungicides as described by K. H. Kuck et al. in *Modern Selective Fungicides—Properties, Applications and Mechanisms of Action*, H. Lyr (Ed.), Gustav Fischer Verlag: New York, 1995, 205-258.

bc$_1$ Complex Fungicides (group 28) have a fungicidal mode of action which inhibits the bc$_1$ complex in the mitochondrial respiration chain. The bc$_1$ complex is sometimes referred to by other names in the biochemical literature, including complex III of the electron transfer chain, and ubihydroquinone:cytochrome c oxidoreductase. This complex is uniquely identified by Enzyme Commission number EC1.10.2.2. The bc$_1$ complex is described in, for example, *J. Biol. Chem.* 1989, 264, 14543-48; *Methods Enzymol.* 1986, 126, 253-71; and references cited therein. Strobilurin fungicides such as azoxystrobin, dimoxystrobin, enestroburin (SYP-Z071), fluoxastrobin, kresoxim-methyl, metominostrobin, orysastrobin, picoxystrobin, pyraclostrobin and trifloxystrobin are known to have this mode of action (H. Sauter et al., *Angew. Chem. Int. Ed.* 1999, 38, 1328-1349). Other fungicidal compounds that inhibit the bc$_1$ complex in the mitochondrial respiration chain include famoxadone and fenamidone.

Alkylenebis(dithiocarbamate)s (group (1)) include compounds such as mancozeb, maneb, propineb and zineb. Phenylamides (group (3)) include compounds such as metalaxyl, benalaxyl, furalaxyl and oxadixyl. Carboxamides (group (6)) include compounds such as boscalid, carboxin, fenfuram, flutolanil, furametpyr, mepronil, oxycarboxin, thifluzamide, penthiopyrad and N-[2-(1,3-dimethylbutyl)phenyl]-5-fluoro-1,3-dimethyl-1H-pyrazole-4-carboxamide (PCT Patent Publication WO 2003/010149), and are known to inhibit mitochondrial function by disrupting complex II (succinate dehydrogenase) in the respiratory electron transport chain. Copper compounds (group (11)) include compounds such as copper oxychloride, copper sulfate and copper hydroxide, including compositions such as Bordeaux mixture (tribasic copper sulfate). Phthalimides (group (12)) include compounds such as folpet and captan. Benzimidazole fungicides (group (14)) include benomyl and carbendazim. Dichlorophenyl dicarboximide fungicides (group (20)) include chlozolinate, dichlozoline, iprodione, isovaledione, myclozolin, procymidone and vinclozolin.

Non-DMI sterol biosynthesis inhibitors (group (26)) include morpholine and piperidine fungicides. The morpholines and piperidines are sterol biosynthesis inhibitors that have been shown to inhibit steps in the sterol biosynthesis pathway at a point later than the inhibitions achieved by the DMI sterol biosynthesis (group (27)). The morpholines include aldimorph, dodemorph, fenpropimorph, tridemorph and trimorphamide. The piperidines include fenpropidin.

Preferred for better control of plant diseases caused by fungal plant pathogens (e.g., lower use rate or broader spectrum of plant pathogens controlled) or resistance management are mixtures of a compound of this invention with a fungicide selected from the group selected from cyproconazole, azoxystrobin, boscalid, chlorothalonil, epoxiconazole, fluoxastrobin, penthiopyrad, quinoxyfen, prothioconazole, picoxystrobin, metrafenone, tebuconazole, pyraclostrobin, proquinazid, cyprodinil, fenpropimorph, famoxadone and 5-chloro-6-(2,4,6-trifluorophenyl)-7-(4-methylpiperidin-1-yl)[1,2,4]triazolo[1,5-c]pyrimidine.

Specifically preferred mixtures (compound numbers refer to compounds in Index Tables A-F) are selected from the group: compound 8 and cyproconazole; compound 109 and cyproconazole; compound 107 and cyproconazole; compound 108 and cyproconazole; compound 5 and cyproconazole; compound 12 and cyproconazole; compound 26 and cyproconazole; compound 27 and cyproconazole; compound 54 and cyproconazole; compound 116 and cyproconazole; compound 117 and cyproconazole; compound 121 and cyproconazole; compound 8 and azoxystrobin; compound 109 and azoxystrobin; compound 107 and azoxystrobin; compound 108 and azoxystrobin; compound 5 and azoxystrobin; compound 12 and azoxystrobin; compound 26 and azoxystrobin; compound 27 and azoxystrobin; compound 54 and azoxystrobin; compound 116 and azoxystrobin; compound 117 and azoxystrobin; compound 121 and azoxystrobin; compound 8 and boscalid; compound 109 and boscalid; compound 107 and boscalid; compound 108 and boscalid; compound 5 and boscalid; compound 12 and boscalid; compound 26 and boscalid; compound 27 and boscalid; compound 54 and boscalid; compound 116 and boscalid; compound 117 and boscalid; compound 121 and boscalid; compound 8 and chlorothalonil; compound 109 and chlorothalonil; compound 107 and chlorothalonil; compound 108 and chlorothalonil; compound 5 and chlorothalonil; compound 12 and chlorothalonil; compound 26 and chlorothalonil; compound 27 and chlorothalonil; compound 54 and chlorothalonil; compound 116 and chlorothalonil; compound 117 and chlorothalonil; compound 121 and chlorothalonil; compound 8 and epoxiconazole; compound 109 and epoxiconazole; compound 107 and epoxiconazole; compound 108 and epoxiconazole; compound 5 and epoxiconazole; compound 12 and epoxiconazole; compound 26 and epoxiconazole; compound 27 and epoxiconazole; compound 54 and epoxiconazole; compound 116 and epoxiconazole; compound 117 and epoxiconazole; compound 121 and epoxiconazole; compound 8 and fluoxastrobin; compound 109 and fluoxastrobin; compound 107 and fluoxastrobin; compound 108 and fluoxastrobin; compound 5 and fluoxastrobin; compound 12 and fluoxastrobin; compound 26 and fluoxastrobin; compound 27 and fluoxastrobin; compound 54 and fluoxastrobin; compound 116 and fluoxastrobin; compound 117 and fluoxastrobin; compound 121 and fluoxastrobin; compound 8 and penthiopyrad; compound 109 and penthiopyrad; compound 107 and penthiopyrad; compound 108 and penthiopyrad; compound 5 and penthiopyrad; compound 12 and penthiopyrad; compound 26 and penthiopyrad; compound 27 and penthiopyrad; compound 54 and penthiopyrad; compound 116 and penthiopyrad; compound 117 and penthiopyrad; compound 121 and penthiopyrad; compound 8 and quinoxyfen; compound 109 and quinoxyfen; compound 107 and quinoxyfen; compound 108 and quinoxyfen; compound 5 and quinoxyfen; compound 12 and quinoxyfen; compound 26 and quinoxyfen; compound 27 and quinoxyfen; compound 54 and quinoxyfen; compound 116 and quinoxyfen; compound 117 and quinoxyfen; compound 121 and quinoxyfen; compound 8 and prothioconazole; compound 109 and prothioconazole; compound 107 and prothioconazole; compound 108 and prothioconazole; compound 5 and prothioconazole; compound 12 and prothioconazole; compound 26 and prothioconazole; compound 27 and prothioconazole; compound 54 and prothioconazole; compound 116 and prothioconazole; compound 117 and prothioconazole; compound 121 and prothioconazole; compound 8 and picoxystrobin; compound 109 and picoxystrobin; compound 107 and picoxystrobin; compound 108 and picoxystrobin; compound 5 and picoxystrobin; compound 12 and picoxystrobin; compound 26 and picoxystrobin; compound 27 and picoxystrobin; compound 54 and picoxystrobin; compound 116 and picoxystrobin; compound 117 and picoxystrobin; compound 121 and picoxystrobin; compound 8 and metrafenone; compound 109 and metrafenone; compound 107 and metrafenone; compound 108 and metrafenone; compound 5 and metrafenone; compound 12 and metrafenone; compound 26 and metrafenone; compound 27 and metrafenone; compound 54 and metrafenone; compound 116 and metrafenone; compound 117 and metrafenone; compound 121 and metrafenone; compound 8 and tebuconazole; compound 109 and tebuconazole; compound 107 and tebuconazole; compound 108 and tebuconazole; compound 5 and tebuconazole; compound 12 and tebuconazole; compound 26 and tebuconazole; compound 27 and tebuconazole; compound 54 and tebuconazole; compound 116 and tebuconazole; compound 117 and tebuconazole; compound 121 and tebuconazole; compound 8 and pyraclostrobin; compound 109 and pyraclostrobin; compound 107 and pyraclostrobin; compound 108 and pyraclostrobin; compound 5 and pyraclostrobin; compound 12 and pyraclostrobin; compound 26 and pyraclostrobin; compound 27 and pyraclostrobin; compound 54 and pyraclostrobin; compound 116 and pyraclostrobin; compound 117 and pyraclostrobin; compound 121 and pyraclostrobin; compound 8 and proquinazid; compound 109 and proquinazid; compound 107 and proquinazid; compound 108 and proquinazid; compound 5 and proquinazid; compound 12 and proquinazid; compound 26 and proquinazid; compound 27 and proquinazid; compound 54 and proquinazid; compound 116 and proquinazid; compound 117 and proquinazid; compound 121 and proquinazid; compound 8 and cyprodinil; compound 109 and cyprodinil; compound 107 and cyprodinil; compound 108 and cyprodinil; compound 5 and cyprodinil; compound 12 and cyprodinil; compound 26 and cyprodinil; compound 27 and cyprodinil; compound 54 and cyprodinil; compound 116 and cyprodinil; compound 117 and cyprodinil; compound 121 and cyprodinil; compound 8 and fenpropimorph; compound 109 and fenpropimorph; compound 107 and fenpropimorph; compound 108 and fenpropimorph; compound 5 and fenpropimorph; compound 12 and fenpropimorph; compound 26 and fenpropimorph; compound 27 and fenpropimorph; compound 54 and fenpropimorph; compound 116 and fenpropimorph; compound 117 and fenpropimorph; compound 121 and fenpropimorph; compound 8 and famoxadone; compound 109 and famoxadone; compound 107 and famoxadone; compound 108 and famoxadone; compound 5 and famoxadone; compound 12 and famoxadone; compound 26 and famoxadone; compound 27 and famoxadone; compound 54 and famoxadone; compound 116 and famoxadone; compound 117 and famoxadone; compound 121 and famoxadone; compound 8 and 5-chloro-6-(2,4,6-trifluorophenyl)-7-(4-methylpiperidin-1-yl) [1,2,4]-triazolo[1,5-a]pyrimidine; compound 109 and 5-chloro-6-(2,4,6-trifluorophenyl)-7-(4-methylpiperidin-1-yl)[1,2,4]triazolo[1,5-a]pyrimidine; compound 107 and 5-chloro-6-(2,4,6-trifluorophenyl)-7-(4-methylpiperidin-1-yl) [1,2,4]triazolo[1,5-a]pyrimidine; compound 108 and 5-chloro-6-(2,4,6-trifluorophenyl)-7-(4-methylpiperidin-1-yl)[1,2,4]triazolo[1,5-a]-pyrimidine; compound 5 and 5-chloro-6-(2,4,6-trifluorophenyl)-7-(4-methylpiperidin-1-yl)[1,2,4]triazolo[1,5-a]pyrimidine; compound 12 and 5-chloro-6-(2,4,6-trifluorophenyl)-7-(4-methylpiperidin-1-yl)[1,2,4]triazolo[1,5-a]pyrimidine; compound 26 and 5-chloro-6-(2,4,6-trifluorophenyl)-7-(4-methylpiperidin-1-yl)[1,2,4]triazolo[1,5-a]pyrimidine; compound 27 and 5-chloro-6-(2,4,6-trifluorophenyl)-7-(4-methylpiperidin-1-yl)[1,2,4]-triazolo[1,5-a]pyrimidine; compound 54 and 5-chloro-6-(2,4,6-trifluorophenyl)-7-(4-methylpiperidin-1-yl)[1,2,4]triazolo[1,5-a]pyrimidine; compound 116 and 5-chloro-6-(2,4,6-trifluorophenyl)-7-(4-methylpiperidin-1-yl)[1,2,4]triazolo[1,5-c]pyrimidine; compound 117 and 5-chloro-6-(2,4,6-trifluorophenyl)-7-(4-methylpiperidin-1-yl)[1,2,4]triazolo[1,5-a]-pyrimidine; compound 121 and 5-chloro-6-(2,4,6-trifluorophenyl)-7-(4-methylpiperidin-1-yl)[1,2,4]triazolo[1,5-a]pyrimidine.

The following Tests demonstrate the control efficacy of compounds of this invention on specific pathogens. The pathogen control protection afforded by the compounds is not limited, however, to these species. See Index Tables A-F for compound descriptions of Formula 1 and Index Table G for compound descriptions of Formula 1a. The following abbreviations are used in the Index Tables which follow: t is tertiary, s is secondary, n is normal, i is iso, c is cyclo, Me is methyl, Et is ethyl, Pr is propyl, i-Pr is isopropyl, Bu is butyl, c-Pr is cyclopropyl, c-Bu is cyclobutyl, t-Bu is tent-butyl, Ph is phenyl, OMe is methoxy and $SO_2$ is sulfonyl. "(HCl)" in the $R^{9b}$ column means hydrogen chloride salt. (R) or (S) denotes the absolute chirality of the asymmetric carbon center. The abbreviation "Ex." stands for "Example" and is followed by a number indicating in which example the compound is prepared.

INDEX TABLE A

| Cmpd No. | J | $R^{9a}$ | $R^{9b}$ | M.P. (° C.) |
|---|---|---|---|---|
| 1 | 4-F—Ph | $CH(CH_3)CH_2OCH_3$ | H | * |
| 2 | 4-F—Ph | s-Bu | H | 144-145 |
| 3 | 4-F—Ph | $CH_2C(CH_3)_3$ | H | 173-174 |
| 4 | 4-F—Ph | $CH(CH_3)(CH_2)_2CH_3$ | H | * |
| 5 | 4-F—Ph | $CH(CH_3)CH_2OH$ | H | 191-192 |
| 6 | 4-F—Ph | $CH_2CH(CH_3)CH_2CH_3$ | H | 140-141 |
| 7 | 4-F—Ph | cyclopentyl | H | 161-163 |
| 8 (Ex. 2) | 4-F—Ph | i-Pr | H | 178-180 |
| 9[a] | 4-F—Ph | 4-(s-Bu)—Ph | H | 110-112 |
| 10 | 4-F—Ph | H | H | 232-235 |
| 11 | 4-F—Ph | n-Pr | H | 128-129 |
| 12 | 4-F—Ph | cyclopropyl | H | 164-165 |
| 13 | 4-F—Ph | $CH_3$ | H | 156-158 |
| 14 | 4-F—Ph | $CH_3$ | $CH_3$ | 157-158 |
| 15 | 4-F—Ph | $CH_2CH=CH_2$ | H | 133-134 |
| 16 | 4-F—Ph | $CH_2CH_2NH_2$ | H | 175-176 |
| 17 | 4-F—Ph | $CH_2C≡CH$ | H | 165-166 |
| 18 | 4-F—Ph | $CH_2CH_3$ | H | 158-159 |
| 19 | 4-F—Ph | (R)-s-Bu | H | 137-140 |
| 20 | 4-F—Ph | (S)-s-Bu | H | * |
| 21 | 4-Cl—Ph | i-Pr | H | * |
| 22 | 4-Cl—Ph | cyclopropyl | H | 169-170 |
| 23 | 4-F—Ph | $N(CH_3)_2$ | H | 158-159 |
| 24 (Ex. 1) | 4-F—Ph | $CH_2$-cyclopropyl | H | 124-125 |
| 25 | 4-F—Ph | $CH_2CH_2OH$ | H | 181-182 |
| 26 | Ph | i-Pr | H | * |
| 27 | Ph | cyclopropyl | H | * |
| 28 | 2,4-di-F—Ph | cyclopropyl | H | * |
| 29 | 4-F—Ph | $CH_2CH(CH_3)_2$ | H | 140-141 |
| 30 | 4-F—Ph | $C(CH_3)_2CH_2OH$ | | 155-157 |
| 31 | 4-F—Ph | $CH(CH_2CH_3)CH_2OH$ | H | 168-170 |
| 32 | 3-Me-4-F—Ph | $CH(CH_3)CH_2OH$ | H | * |
| 33 | 3-Me-4-F—Ph | i-Pr | H | * |
| 34[a] | 4-F—Ph | #-CH2-(tetrahydrofuran-2-yl) | H | 129-131 |
| 35 | 4-F—Ph | $CH_2Si(CH_3)_3$ | | 124-125 |
| 36 | 2-F—Ph | i-Pr | | * |
| 37 | 4-F—Ph | $CH_2CH_2CH_2OH$ | H | * |
| 38 | 2-F—Ph | $CH(CH_3)CH_2OH$ | H | * |
| 39 | 4-F—Ph | $CH_2$-2-thienyl | H | 153-155 |
| 40 | 4-F—Ph | 4-F—Ph | H | 177-178 |
| 41[a] | 4-F—Ph | #-CH2CH2-(1-ethylpyrrolidin-2-yl) | H | * |

INDEX TABLE A-continued

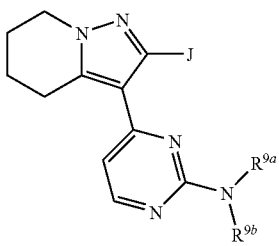

| Cmpd No. | J | $R^{9a}$ | $R^{9b}$ | M.P. (° C.) |
|---|---|---|---|---|
| 42 | 3-thienyl | $CH(CH_3)CH_2OH$ | H | * |
| 43 | 3-thienyl | i-Pr | H | * |
| 44[a] | 4-F—Ph | 1-(hydroxymethyl)cyclopropyl-CH2- | H | 157-159 |
| 45 | 2-Me—Ph | i-Pr | H | * |
| 46 | 2-Me—Ph | $CH(CH_3)CH_2OH$ | H | * |
| 47 | 4-F—Ph | (R)-$CH(CH_3)CH_2OH$ | H | 155-156 |
| 48 | 4-F—Ph | (S)-$CH(CH_3)CH_2OH$ | H | 159-160 |
| 49[a] | 4-F—Ph | tetrahydropyran-4-yl | H | 200-202 |
| 50 | 3-Me-4-F—Ph | $CH_2Si(CH_3)_3$ | H | 133-136 |
| 51 (Ex. 2) | 4-F—Ph | cyclobutyl | H | 155-157 |
| 52 (Ex. 2) | 4-F—Ph | $C(O)CH_3$ | H | * |
| 53 | Ph | $CH(CH_3)CH_2OCH_3$ | H | * |
| 54[a] | Ph | (S)-CH(CH3)CH2OH variant | H | 151-154 |
| 55 | Ph | $CH_2Si(CH_3)_3$ | H | * |
| 56 | 3-Me-4-F—Ph | cyclopropyl | H | 143-144 |
| 57 | 4-F—Ph | (R)-$CH(CH_3)CH_2OH$ | H | 162-163 |
| 58 | 4-F—Ph | $CH_2C{\equiv}CH$ | H | 145-150 |
| 59 | Ph | $CH_2C{\equiv}CH$ | H | 168-169 |
| 60 | 4-F—Ph | 4-$OCF_3$—Ph | H | * |
| 61 | 3-thienyl | cyclopropyl | H | * |
| 62 | 3-Me-4-F—Ph | $CH(CH_3)CH_2OCH_3$ | H | * |
| 63 | 4-F—Ph | $CH(CH_2OH)_2$ | H | 174-177 |
| 64 | 4-F—Ph | $CH(CH_3)CH_2SO_3^-Na^+$ | H | 176-179 |
| 65 | 4-F—Ph | OMe | H | * |
| 66[a] | 4-F—Ph | -CH(CH3)CH2-O-C(O)-(CH2)2CO2H | H | 194-196 |
| 67[a] | 4-F—Ph | -CH(CH3)CH2-O-C(O)CH3 | H | 164-165 |

INDEX TABLE A-continued
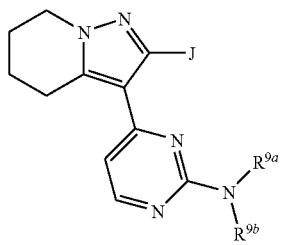
| Cmpd No. | J | R⁹ᵃ | R⁹ᵇ | M.P. (° C.) |
|---|---|---|---|---|
| 68ᵃ | 4-F—Ph | (isobutyl nicotinate group) | H | 131-133 |
| 69 | 4-F—Ph | i-Pr | H(HCl) | 149-150 |
| 70 | 4-F—Ph | CH₃ | NH₂ | * |
| 71ᵃ | 4-F—Ph | (isobutyl phthalimide group) | H | * |
| 72 | 4-F—Ph | CH(CH₃)CH₂OH | H(HCl) | 128-130 |
| 73ᵃ | 4-F—Ph | (CH(n-Pr)CH₂OH) | H | 137-139 |
| 74ᵃ | 4-F—Ph | (CH(i-Pr)CH₂OH) | H | 139-140 |
| 75 | 4-F—Ph | O—CH₂—c-Bu | H | * |
| 77 | 4-F—Ph | CH(CH₃)CH₂N(CH₃)₂ | H | * |
| 78ᵃ | 4-F—Ph | (2-furyl ethyl) | H | 160-162 |
| 79ᵃ | 4-F—Ph | (5-methyl-2-furyl ethyl) | H | 155-156 |
| 80ᵃ | 4-F—Ph | (tetrahydropyran-4-yl ethyl) | H | 148-150 |

INDEX TABLE A-continued

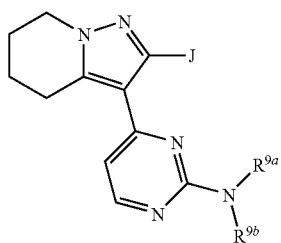

| Cmpd No. | J | $R^{9a}$ | $R^{9b}$ | M.P. (° C.) |
|---|---|---|---|---|
| 81 | 4-F—Ph | —CH$_2$CH(CH$_3$)— | | * |
| 82 | 4-F—Ph | —CH$_2$CH$_2$CH$_2$— | | 128-130 |
| 142 | Ph | CH$_3$ | H | * |
| 143 | Ph | CH$_2$CH$_3$ | H | * |
| 179 | Ph | n-Pr | H | * |
| 180 | 3-thienyl | cyclopropyl | H | 157-158 |
| 181 | 3-Me—Ph | cyclopropyl | H | 162-164 |
| 182 | Ph | 4-fluoro-3-methoxyphenyl | H | * |
| 185 | 3-Me—Ph | n-Pr | H | 112-115 |
| 186 | 3-Me—Ph | CH$_2$CH$_3$ | H | 145-149 |
| 187 | 3-Me—Ph | CH$_3$ | H | * |

[a] The bond which is identified with "#" connected to the nitrogen atom attached to $R^{9a}$.
*See Index Table H for $^1$H NMR data.

INDEX TABLE B

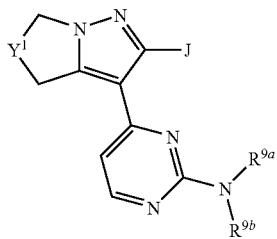

| Cmpd No | $Y^1$ | J | $R^{9a}$ | $R^{9b}$ | M.P. (° C.) |
|---|---|---|---|---|---|
| 83 (Ex. 8) | S | 2,4-di-F—Ph | i-Pr | H | * |
| 84 | CH$_2$ | 4-F—Ph | CH(CH$_3$)CH$_2$OCH$_3$ | H | * |
| 85 | CH$_2$ | 4-F—Ph | CH(CH$_3$)CH$_2$CH$_3$ | H | * |
| 86 | CH$_2$ | 4-OMe—Ph | CH(CH$_3$)CH$_2$OCH$_3$ | H | * |
| 87 | CH$_2$ | 2,4-di-F—Ph | CH(CH$_3$)CH$_2$CH$_3$ | H | * |
| 88 | CH$_2$ | 2,4-di-F—Ph | CH(CH$_3$)CH$_2$OCH$_3$ | H | * |
| 89 | CH$_2$ | 4-Me—Ph | CH(CH$_3$)CH$_2$OCH$_3$ | H | * |
| 90 | CH$_2$ | 4-F—Ph | CH$_3$ | H | * |
| 91 | CH$_2$ | 4-F—Ph | i-Pr | H | * |
| 92 | CH$_2$ | 4-F—Ph | cyclopropyl | H | * |
| 93 | CH$_2$ | 4-OMe—Ph | cyclopropyl | H | * |
| 94 | CH$_2$ | 2,4-di-F—Ph | cyclopropyl | H | * |
| 95 | CH$_2$ | 4-F—Ph | CH$_2$CH=CH$_2$ | H | * |
| 96 | CH$_2$ | 2-F—Ph | CH(CH$_3$)CH$_2$OCH$_3$ | H | * |
| 97 | CH$_2$ | 2-F—Ph | i-Pr | H | * |
| 98 | CH$_2$ | 2-F—Ph | CH$_2$CH(CH$_3$)$_2$ | H | * |
| 99 | CH$_2$ | 2-F—Ph | cyclopropyl | H | * |
| 100 | CH$_2$ | 3-F—Ph | CH(CH$_3$)CH$_2$OCH$_3$ | H | * |
| 101 | CH$_2$ | 3-F—Ph | CH(CH$_3$)CH$_2$CH$_3$ | H | * |
| 102 | CH$_2$ | 3-F—Ph | i-Pr | H | * |
| 103 | CH$_2$ | 3-F—Ph | cyclopropyl | H | * |
| 104 | CH$_2$ | 3,5-di-F—Ph | cyclopropyl | H | * |

*See Index Table H for $^1$H NMR data.

INDEX TABLE C

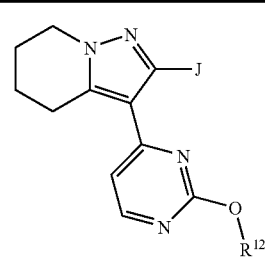

| Cmpd No. | J | $R^{12}$ | M.P. (° C.) |
|---|---|---|---|
| 105 | 4-F—Ph | CH$_3$ | 103-104 |
| 106[b] | 4-F—Ph | 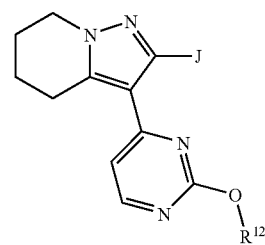 | 179-180 |

[b] The bond which is identified with "#" is connected to the oxygen atom attached to $R^{12}$.

INDEX TABLE D

| Cmpd No. | Y² | Y³ | J | R⁹ᵃ | R⁹ᵇ | M.P. (° C.) |
|---|---|---|---|---|---|---|
| 107 | O | $CH_2$ | 4-F—Ph | i-Pr | H | 144-146 |
| 108 | O | $CH_2$ | 4-F—Ph | $CH(CH_3)CH_2OH$ | H | 124-126 |
| 109 | O | $CH_2$ | 4-F—Ph | cyclopropyl | H | * |
| 110 | S | $CH_2$ | 4-F—Ph | i-Pr | H | 172-175 |
| 111 | S | $CH_2$ | 4-F—Ph | $CH(CH_3)CH_2OH$ | H | 182-184 |
| 112 (Ex. 7) | $CH_2$ | O | 4-F—Ph | i-Pr | H | 167-169 |
| 113 | $CH_2$ | O | 4-F—Ph | (R)-$CH(CH_3)CH_2OH$ | H | * |
| 114 (Ex. 9) | $S(O)_2$ | $CH_2$ | 4-F—Ph | i-Pr | H | * |
| 115 | $S(O)_2$ | $CH_2$ | 4-F—Ph | i-Pr | OH | * |
| 116 | O | $CH_2$ | Ph | i-Pr | H | 185-187 |
| 117 | O | $CH_2$ | Ph | cyclopropyl | H | 186-189 |
| 118 | O | $CH_2$ | 3-thienyl | i-Pr | H | 177-179 |
| 119 | O | $CH_2$ | 3-Me-4-F—Ph | cyclopropyl | H | 191-193 |
| 120 | O | $CH_2$ | 3-Me-4-F—Ph | i-Pr | H | 119-122 |
| 121 | O | $CH_2$ | 3-thienyl | cyclopropyl | H | 182-184 |
| 122 | O | $CH_2$ | Ph | $CH(CH_3)CH_2OH$ | H | 196-199 |
| 123 | O | $CH_2$ | 3-Me-4-F—Ph | $CH(CH_3)CH_2OH$ | H | 194-197 |
| 124 | O | $CH_2$ | 3-thienyl | $CH(CH_3)CH_2OH$ | H | 193-194 |
| 125 | O | $CH_2$ | 2,4-di-F—Ph | i-Pr | H | 151-153 |
| 126 | O | $CH_2$ | 2,4-di-F—Ph | cyclopropyl | H | 229-230 |
| 127 | O | $CH_2$ | 2,4-di-F—Ph | $CH(CH_3)CH_2OH$ | H | 157-160 |
| 128ᶜ | O | $CH_2$ | 4-F—Ph | i-Pr | H(HCl) | * |
| 129ᵈ | O | $CH_2$ | 4-F—Ph | #-tetrahydropyran-4-yl | H | * |
| 183 | O | $CH_2$ | Ph | $CH_2CH_3$ | H | 174-176 |
| 184 | O | $CH_2$ | Ph | n-Pr | H | 186-188 |

ᶜCompound 128 is a hydrogen chloride salt.
ᵈThe bond which is identified with "#" is connected to the nitrogen atom attached to R⁹ᵃ.
*See Index Table H for ¹H NMR data.

INDEX TABLE E

| Cmpd No. | Y⁴ | Y⁵ | R⁹ᵃ | R²ᵃ | R²ᵇ | M.P. (° C.) |
|---|---|---|---|---|---|---|
| 130 | C | N | i-Pr | $H_2$ | $C(O)CH_3$ | * |
| 131 (Ex. 4) | N | C | cyclopropyl | H | $H_2$ | 184-187 |
| 132 (Ex. 5) | N | C | $CH(CH_3)CH_2OH$ | H | $H_2$ | 165-167 |
| 133 | C | N | i-Pr | $H_2$ | $H_2^+Cl^-$ | * |
| 134 (Ex. 4) | N | C | cyclopropyl | $C(O)CH_3$ | $H_2$ | * |
| 135 (Ex. 6) | N | C | cyclopropyl | $CH_3$ | $H_2$ | * |
| 136 | N | C | i-Pr | H | $H_2$ | 145-147 |
| 137 | N | N | cyclopropyl | $CH_2CH=CH_2$ | H | 133-134 |

INDEX TABLE E-continued

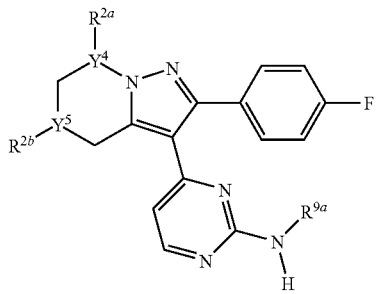

| Cmpd No. | $Y^4$ | $Y^5$ | $R^{9a}$ | $R^{2a}$ | $R^{2b}$ | M.P. (°C.) |
|---|---|---|---|---|---|---|
| 138 (Ex. 3) | C | N | H | $H_2$ | $C(O)OCH_3$ | 88-89 |
| 139[e] | N | C | #  | $C(O)CH_3$ | $H_2$ | 133-135 |
| 141 (Ex. 3) | C | N | i-Pr | $H_2$ | H | * |

[e]The bond which is identified with "#" is connected to the nitrogen atom attached to $R^{9a}$.
*See Index Table H for $^1H$ NMR data.

INDEX TABLE F

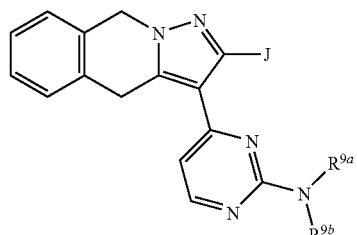

| Cmpd No. | J | $R^{9a}$ | M.P. (°C.) |
|---|---|---|---|
| 140 | 4-F—Ph | (S)-$CH(CH_3)CH_2OH$ | 210-214 |

INDEX TABLE G

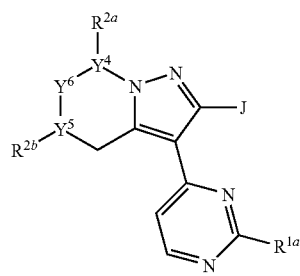

| Cmpd No. | $Y^4$ | $Y^5$ | $Y^6$ | $R^{2b}$ | $R^{2a}$ | J | $R^{1a}$ | M.P. (°C) |
|---|---|---|---|---|---|---|---|---|
| 144 | N | C | $CH_2$ | $H_2$ | $C(O)OCH_2$—Ph | 4-F—Ph | Cl | 115-120 |
| 145 (Ex. 6) | N | C | $CH_2$ | $H_2$ | H | 4-F—Ph | Cl | 206-207 |
| 146 | N | C | $CH_2$ | $H_2$ | —$CH_2CH$=$CH_2$ | 4-F—Ph | Cl | 97-99 |
| 147 | C | C | $CH_2$ | $H_2$ | $H_2$ | t-butyl | Cl | * |
| 148 | N | C | $CH_2$ | $H_2$ | $C(O)CF_3$ | 4-F—Ph | Cl | * |
| 149 | N | C | $CH_2$ | $H_2$ | $C(O)OCH_2$—Ph | Ph | Cl | 64-67 |
| 150 (Ex. 2) | C | C | $CH_2$ | $H_2$ | $H_2$ | 4-F—Ph | Cl | * |
| 151 | C | C | $CH_2$ | $H_2$ | $H_2$ | 2,4-di-F—Ph | Cl | * |
| 152 | C | C | $CH_2$ | $H_2$ | $H_2$ | 2-Cl—Ph | Cl | * |
| 153 | C | C | $CH_2$ | $H_2$ | $H_2$ | Ph | Cl | * |
| 154 | C | S | $CH_2$ | — | $H_2$ | 4-F—Ph | Cl | * |
| 155 | C | N | $CH_2$ | $C(O)OCH_2Ph$ | $H_2$ | 4-F—Ph | Cl | * |
| 156 | C | C | $CH_2$ | $H_2$ | $H_2$ | 4-$Me_2N$—Ph | Cl | * |
| 157 | N | C | $CH_2$ | $H_2$ | $C(O)NHCH_3$ | 4-F—Ph | Cl | 74-77 |
| 158 | N | C | $CH_2$ | $H_2$ | $C(O)NH_2$ | 4-F—Ph | Cl | 90-93 |
| 159 | N | C | $CH_2$ | $H_2$ | $C(O)N(CH_3)_2$ | 4-F—Ph | Cl | 190-194 |
| 160 | C | C | $CH_2$ | $H_2$ | $H_2$ | 4-$OCH_3$—Ph | $SO_2CH_3$ | * |
| 161 | C | C | $CH_2$ | $H_2$ | $H_2$ | 4-Cl—Ph | $SO_2CH_3$ | * |
| 162 | C | C | $CH_2$ | $H_2$ | $H_2$ | 4-F-3-$CH_3$—Ph | $SO_2CH_3$ | * |
| 163 | C | O | $CH_2$ | — | $H_2$ | 4-F—Ph | $SO_2CH_3$ | * |
| 164 | C | C | $CH_2$ | $H_2$ | $H_2$ | 2-F—Ph | $SO_2CH_3$ | * |
| 165 | C | C | $CH_2$ | $H_2$ | $H_2$ | 1-naphthalenyl | $SO_2CH_3$ | * |
| 166 | C | C | $CH_2$ | $H_2$ | $H_2$ | 2-$CF_3$—Ph | $SO_2CH_3$ | * |
| 168 | C | C | $CH_2$ | $H_2$ | $H_2$ | 3-thienyl | $SO_2CH_3$ | * |
| 169 | C | C | $CH_2$ | $H_2$ | $H_2$ | 2-$CH_3$—Ph | $SO_2CH_3$ | * |

INDEX TABLE G-continued

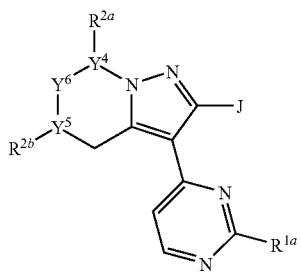

| Cmpd No. | Y⁴ | Y⁵ | Y⁶ | R²ᵇ | R²ᵃ | J | R¹ᵃ | M.P. (° C) |
|---|---|---|---|---|---|---|---|---|
| 170 | C | C | CH₂ | H₂ | H₂ | 2-CF₃—Ph | SO₂CH₃ | * |
| 171 | C | C | CH₂ | H₂ | H₂ | 1-CH₃-imidazol-5-yl | SO₂CH₃ | * |
| 172 | C | C | CH₂ | H₂ | H₂ | 3-F—Ph | SO₂CH₃ | * |
| 173 | C | C | CH₂ | H₂ | H₂ | 3,5-di-F—Ph | SO₂CH₃ | * |
| 174 (Ex. 1) | C | C | CH₂ | H₂ | H₂ | 4-F—Ph | SO₂CH₃ | * |
| 175 | C | C | CH₂ | H₂ | H₂ | 3-Cl—Ph | SO₂CH₃ | * |
| 176 | C | C | CH₂ | H₂ | H₂ | 2-thienyl | SO₂CH₃ | * |
| 177 | C | C | CH₂ | H₂ | H₂ | 3-CH₃—Ph | SO₂CH₃ | * |
| 178 (Ex. 7) | C | C | O | H₂ | H₂ | 4-F—Ph | SO₂CH₃ | * |

*See Index Table H for ¹H NMR data.

INDEX TABLE H

| Cmpd No. | ¹H NMR Data (CDCl₃ solution unless indicated otherwise)ᵃ |
|---|---|
| 1 | δ 8.15 (m, 1H), 7.46 (m, 2H), 7.05 (m, 2H), 6.23 (m, 1H), 5.15 (d, 1H), 4.22 (m, 3H), 3.40 (m, 2H), 3.38 (s, 3H), 3.12 (m, 2H), 2.10 (m, 2H), 1.93 (m, 2H), 1.25 (d, 3H). |
| 4 | δ 8.03 (d, 1H), 7.48 (m, 2H), 7.04 (t, 2H), 6.21 (d, 1H), 4.99 (d, 1H), 4.21 (t, 2H), 4.02 (m, 2H), 3.12 (t, 1H), 2.09 (m, 2H), 1.91 (m, 2H), 1.45 (m, 4H), 1.18 (d, 3H), 0.91 (t, 3H). |
| 20 | δ 8.02 (d, 1H), 7.48 (m, 2H), 7.04, (t, 2H), 6.21 (d, 1H), 5.13 (m, 1H), 4.22 (t, 2H), 3.95 (m, 1H), 3.11 (t, 2H), 2.09 (m, 2H), 1.91 (m, 2H), 1.54 (m, 2H), 1.18 (d, 3H), 0.91 (t, 3H). |
| 21 | δ 8.04 (d, 1H), 7.44 (m, 2H), 7.32 (m, 2H), 6.23 (d, 1H), 4.94 (d, 1H), 4.22 (m, 2H), 4.11 (m, 1H), 3.10 (m, 2H), 2.09 (m, 2H), 1.92 (m, 2H), 1.22 (d, 6H). |
| 24 | δ 8.05 (d, 1H), 7.47 (m, 2H), 7.04 (t, 2H), 6.24 (d, 1H), 5.31 (m, 1H), 4.22 (t, 2H), 3.23 (t, 2H), 3.11 (t, 2H), 2.09 (m, 2H), 1.91 (m, 2H), 1.06 (m, 1H), 0.51 (m, 2H), 0.23 (m, 2H). |
| 26 | δ 8.00 (d, 1H), 7.49 (m, 2H), 7.34 (m, 3H), 6.23 (d, 1H), 4.83 (d, 1H), 4.23 (m, 2H), 4.13 (m, 1H), 3.13 (m, 2H), 2.10 (m, 2H), 1.92 (m, 2H), 1.23 (m, 6H). |
| 27 | δ 8.06 (d, 1H), 7.50 (m, 2H), 7.35 (m, 3H), 6.31 (d, 1H), 5.22 (br s, 1H), 4.23 (m, 2H), 3.18 (m, 2H), 2.77 (m, 1H), 2.09 (m, 2H), 1.92 (m, 2H), 0.79 (m, 2H), 0.56 (m, 2H). |
| 28 | δ 8.09 (d, 1H), 7.49 (m, 2H), 6.94 (m, 1H), 6.82 (m, 1H), 6.23 (d, 1H), 5.16 (br s, 1H), 4.24 (m, 2H), 3.20 (m, 2H), 2.70 (m, 1H), 2.11 (m, 2H), 1.93 (m, 2H), 0.73 (m, 2H), 0.52 (m, 2H). |
| 32 | δ 7.99 (d, 1H), 7.36 (m, 1H), 7.22 (m, 1H), 6.96 (m, 1H), 6.25 (d, 1H), 5.48 (d, 1H), 4.20 (m, 2H), 4.09 (m, 1H), 3.70 (m, 1H), 3.60 (m, 1H), 3.10 (m, 2H), 2.27 (m, 3H), 2.08 (m, 2H), 1.89 (m, 2H), 1.24 (d, 3H). |
| 33 | δ 8.01 (d, 1H), 7.36 (m, 1H), 7.23 (m, 1H), 6.97 (m, 1H), 6.23 (d, 1H), 5.11 (d, 1H), 4.21 (m, 2H), 4.12 (m, 1H), 3.13 (m, 2H), 2.27 (m, 3H), 2.08 (m, 2H), 1.91 (m, 2H), 1.22 (d, 6H). |
| 36 | δ 8.00 (d, 1H), 7.49 (m, 1H), 7.35 (m, 1H), 7.19 (m, 1H), 7.08 (m, 1H), 6.17 (m, 1H), 4.97 (d, 1H), 4.24 (m, 2H), 4.01 (m, 1H), 3.18 (m, 2H), 2.10 (m, 2H), 1.93 (m, 2H), 1.17 (d, 6H). |
| 38 | δ 7.99 (d, 1H), 7.49 (m, 1H), 7.36 (m, 1H), 7.19 (m, 1H), 7.07 (m, 1H), 6.22 (d, 1H), 5.22 (d, 1H), 4.23 (m, 2H), 3.95 (m, 1H), 3.64 (m, 1H), 3.52 (m, 1H), 3.14 (m, 2H), 2.09 (m, 2H), 1.92 (m, 2H), 1.17 (d, 3H). |
| 41 | δ 8.04 (d, 1H), 7.47 (m, 2H), 7.04 (t, 2H), 6.22 (d, 1H), 5.6 (m, 1H), 4.21 (t, 2H), 3.6 (b, 2H), 3.25 (br s, 2H), 3.11 (t, 2H), 2.87 (m, 1H), 2.64 (m, 1H), 2.33 (b, 2H), 2.10 (m, 2H), 1.91 (m, 2H), 1.74 (m, 2H), 1.12 (t, 3H). |
| 42 | δ 8.04 (d, 1H), 7.44 (m, 1H), 7.30 (m, 1H), 7.19 (m, 1H), 6.39 (d, 1H), 5.33 (d, 1H), 4.19 (m, 2H), 4.11 (m, 1H), 3.72 (m, 1H), 3.59 (m, 1H), 3.06 (m, 2H), 2.07 (m, 2H), 1.88 (m, 2H), 1.25 (m, 3H). |
| 43 | δ 8.06 (d, 1H), 7.46 (m, 1H), 7.30 (m, 1H), 7.21 (m, 1H), 6.35 (d, 1H), 5.16 (s, 1H), 4.20 (m, 2H), 4.14 (m, 1H), 3.10 (m, 2H), 2.08 (m, 2H), 1.90 (m, 2H), 1.24 (d, 6H). |
| 45 | δ 7.86 (d, 1H), 7.25 (m, 2H), 7.18 (m, 2H), 5.94 (d, 1H), 4.98 (d, 1H), 4.19 (m, 2H), 4.04 (m, 1H), 3.23 (m, 2H), 2.09 (m, 3H), 2.05 (m, 2H), 1.91 (m, 2H), 1.17 (d, 6H). |
| 46 | δ 7.88 (d, 1H), 7.29 (m, 2H), 7.22 (m, 2H), 6.03 (d, 1H), 5.13 (d, 1H), 4.22 (m, 2H), 4.01 (m, 1H), 3.67 (m, 1H), 3.54 (m, 1H), 3.22 (m, 2H), 2.11 (m, 5H), 1.94 (m, 2H), 1.20 (m, 3H). |
| 51 | δ 8.26 (d, 1H), 7.43 (m, 2H), 7.10 (t, 2H), 6.82 (d, 1H), 5.27 (d, 1H), 4.41 (m, 1H), 4.21 (t, 2H), 3.11 (t, 2H), 2.36 (m, 2H), 2.09 (m, 2H), 1.92 (m, 4H), 1.72 (m, 2H). |
| 52 | δ 8.31 (d, 1H), 8.04 (br s, 1H), 7.46 (m, 2H), 7.09 (m, 2H), 6.67 (d, 1H), 4.26 (m, 2H), 3.17 (m, 2H), 2.44 (s, 3H), 2.14 (m, 2H), 1.97 (m, 2H). |
| 53 | δ 8.00 (d, 1H), 7.50 (m, 2H), 7.34 (m, 3H), 6.24 (d, 1H), 5.48 (d, 1H), 4.22 (m, 3H), 3.45 (m, 1H), 3.37 (m, 4H), 3.13 (m, 2H), 2.06 (m, 2H), 1.89 (m, 2H), 1.24 (m, 3H). |

INDEX TABLE H-continued

| Cmpd No. | ¹H NMR Data (CDCl$_3$ solution unless indicated otherwise)$^a$ |
|---|---|
| 55 | δ 7.91 (d, 1H), 7.39 (m, 2H), 7.21 (m, 3H), 6.12 (d, 1H), 4.86 (m, 1H), 4.10 (m, 2H), 3.01 (m, 2H), 2.74 (m, 2H), 1.96 (m, 2H), 1.79 (m, 2H), 0.00 (s, 9H). |
| 61 | δ 8.13 (d, 1H), 7.50 (m, 1H), 7.30 (m, 1H), 7.23 (m, 1H), 6.43 (m, 1H), 5.64 (br s, 1H), 4.20 (m, 2H), 3.14 (m, 2H), 2.78 (m, 1H), 2.07 (m, 2H), 1.89 (m, 2H), 0.77 (m, 2H), 0.55 (m, 2H). |
| 62 | δ 8.03 (d, 1H), 7.38 (m, 1H), 7.25 (m, 1H), 6.97 (m, 1H), 6.25 (d, 1H), 5.67 (br s, 1H), 4.21 (m, 3H), 3.46 (m, 1H), 3.36 (m, 4H), 3.13 (m, 2H), 2.27 (m, 3H), 2.07 (m, 2H), 1.89 (m, 2H), 1.24 (m, 3H). |
| 70 | δ 8.12 (d, 1H), 7.43 (dd, 2H), 7.05 (t, 2H), 6.22 (d, 1H), 4.38 (br s, 2H), 4.22 (t, 2H), 3.34 (s, 3H), 3.13 (t, 2H), 2.11 (m, 2H), 1.92 (m, 2H). |
| 71 | δ 7.88 (d, 1H), 7.69 (m, 2H), 7.58 (d, 2H), 7.25 (m, 2H), 6.98 (m, 2H), 6.07 (d, 1H), 5.25 (d, 1H), 4.55 (m, 1H), 4.21 (m, 2H), 3.83 (m, 2H), 3.19 (m, 1H), 2.98 (m, 1H), 2.12 (m, 2H), 1.93 (m, 2H), 1.31 (d, 3H). |
| 77 | δ 8.04 (d, 1H), 7.47 (m, 2H), 7.03 (t, 2H), 6.23 (d, 1H), 5.33 (m, H), 4.21 (t, 2H), 4.02 (m, 1H), 3.11 (t, 2H), 2.44 (dd, 1H), 2.25 (m, 7H) 2.09 (m, 2H), 1.91 (m, 2H), 1.21 (d, 3H). |
| 81 | δ 8.23 (d, 2H), 7.44 (dd, 2H), 7.06 (t, 2H), 6.53 (d, 1H), 4.22 (t, 2H), 3.17 (t, 2H), 2.6 (m, 1H), 2.47 (d, 1H), 2.2 (d, 1H), 2.11 (m, 1H), 1.94 (m, 2H), 1.41 (d, 3H). |
| 83 | δ 8.03 (d, 1H), 7.47 (m, 1H), 6.99 (m, 1H), 6.91 (m, 1H), 6.12 (dd, 1H), 5.28 (t, 2H), 4.84 (s, 1H), 4.50 (t, 2H), 4.05 (d, 1H), 1.23 (d, 6H). |
| 86 | δ 8.00 (d, 1H), 7.46 (m, 2H), 6.96 (m, 2H), 6.33 (d, 1H), 5.19 (d, 1H), 4.21 (m, 3H), 3.84 (s, 3H), 3.49 (m, 1H), 3.37 (m, 4H), 3.22 (m, 2H), 2.65 (m, 2H), 1.25 (m, 3H). |
| 87 | δ 8.03 (d, 1H), 7.48 (s, 1H), 6.95 (d, 1H), 6.88 (t, 1H), 6.20 (d, 1H), 4.72 (d, 1H), 4.24 (t, 2H), 3.25 (d, 2H), 2.69 (d, 2H), 1.50 (m, 2H), 1.12 (d, 3H), 0.91 (t, 3H). |
| 88 | δ 8.04 (d, 1H), 7.46 (m, 1H), 6.95 (d, 1H), 6.87 (d, 1H), 6.22 (d, 1H), 5.06 (d, 1H), 4.24 (t, 2H), 3.41 (m, 1H), 3.33 (m, 5H), 3.26 (t, 2H), 2.68 (m, 2H), 1.19 (d, 3H). |
| 89 | δ 7.98 (d, 1H), 7.43 (d, 2H), 7.19 (d, 2H), 6.31 (d, 1H), 4.90 (d, 1H), 4.21 (t, 2H), 3.96 (dd, 1H), 3.23 (t, 2H), 2.65 (m, 2H), 2.39 (s, 3H), 1.52 (m, 2H), 1.19 (d, 3H), 0.95 (t, 3H). |
| 90 | δ 8.05 (d, 1H) 7.50 (m, 2H) 7.03 (m, 2H) 6.31 (d, 1H) 5.04 (s, 1H) 4.22 (m, 1H) 3.24 (t, 1H) 2.96 (d, 3H) 2.65 (m, 1H) 2.04 (s, 3H). |
| 91 | δ 8.02 (d, 1H), 7.52 (m, 2H), 7.08 (m, 2H), 6.27 (d, 1H), 5.01 (d, 1H), 4.24 (m, 2H), 4.09 (dd, 1H), 3.22 (t, 2H), 2.67 (m, 2H), 1.22 (d, 6H). |
| 92 | δ 8.07 (d, 1H), 7.54 (m, 2H), 7.09 (m, 2H), 6.35 (d, 1H), 5.58 (s, 1H), 4.21 (m, 2H), 3.25 (t, 2H), 2.74 (dd, 1H), 2.66 (m, 2H), 0.76 (m, 2H), 0.53 (m, 2H). |
| 93 | δ 8.05 (d, 1H), 7.47 (m, 2H), 6.92 (m, 2H), 6.39 (d, 1H), 5.36 (s, 1H), 4.21 (m, 2H), 3.85 (s, 3H), 3.25 (t, 2H), 2.77 (m, 1H), 2.65 (t, 2H), 0.78 (dd, 2H), 0.55 (dd, 2H). |
| 94 | δ 8.08 (d, 1H), 7.49 (m, 1H), 6.95 (m, 1H), 6.87 (m, 1H), 6.26 (d, 1H), 5.27 (s, 1H), 4.24 (m, 2H), 3.28 (t, 2H), 2.67 (m, 3H), 0.72 (m, 2H), 0.49 (m, 2H). |
| 95 | δ 8.05 (d, 1H), 7.50 (m, 2H), 7.07 (m, 2H), 6.32 (d, 1H), 5.96 (m, 1H), 5.25 (m, 2H), 5.12 (m, 1H), 4.22 (m, 2H), 4.01 (m, 2H), 3.22 (m, 2H), 2.65 (m, 2H). |
| 96 | δ 8.18 (d, 1H), 7.27 (m, 2H), 7.09 (m, 2H), 5.16 (s, 1H), 4.26 (m, 3H), 3.38 (m, 2H), 3.29 (m, 3H), 3.25 (m, 1H), 2.92 (m, 2H), 2.66 (m, 2H), 1.27 (d, 3H). |
| 97 | δ 8.01 (d, 1H), 7.49 (m, 1H), 7.21 (m, 1H), 7.11 (m, 2H), 6.20 (d, 1H), 4.74 (s, 1H), 4.26 (m, 2H), 3.27 (m, 2H), 2.91 (d, 1H), 2.67 (m, 2H), 1.17 (d, 6H). |
| 98 | δ 8.01 (d, 1H), 7.50 (m, 1H), 7.38 (m, 1H), 7.21 (m, 1H), 7.11 (t, 1H), 6.22 (d, 1H), 4.98 (s, 1H), 4.25 (m, 2H), 3.26 (m, 2H), 3.09 (s, 2H), 2.70 (m, 2H), 1.82 (m, 1H), 0.92 (d, 6H). |
| 99 | δ 8.06 (d, 1H), 7.50 (m, 1H), 7.39 (dd, 1H), 7.21 (m, 1H), 7.12 (m, 1H), 6.27 (dd, 1H), 5.13 (s, 1H), 4.25 (m, 2H), 3.30 (t, 2H), 2.70 (m, 3H), 0.72 (m, 2H), 0.51 (m, 2H). |
| 100 | δ 8.01 (d, 1H), 7.31 (m, 3H), 7.06 (m, 1H), 6.33 (d, 1H), 5.63 (s, 1H), 4.18 (m, 3H), 3.46 (m, 1H), 3.37 (m, 4H), 3.22 (m, 2H), 2.67 (m, 2H), 1.24 (d, 3H). |
| 101 | δ 8.04 (d, 1H), 7.31 (m, 3H), 7.06 (m, 1H), 6.31 (d, 1H), 4.81 (s, 1H), 4.23 (m, 2H), 3.91 (s, 1H), 3.22 (m, 2H), 2.69 (m, 2H), 1.54 (m, 2H), 1.18 (d, 3H), 0.94 (t, 3H). |
| 102 | δ 8.04 (d, 1H), 7.31 (m, 3H), 7.05 (m, 1H), 6.31 (d, 1H), 5.21 (s, 1H), 4.20 (m, 2H), 4.09 (m, 1H), 3.21 (t, 2H), 2.66 (m, 2H), 1.20 (d, 6H). |
| 103 | δ 8.09 (d, 1H), 7.32 (m, 3H), 7.06 (m, 1H), 6.39 (d, 1H), 5.68 (s, 1H), 4.21 (m, 2H), 3.24 (t, 1H), 2.73 (m, 2H), 2.66 (m, 2H), 0.75 (m, 2H), 0.52 (m, 2H). |
| 109 | δ 8.03 (d, 1H), 7.50 (m, 2H), 7.11 (m, 2H), 6.29 (d, 1H), 5.36 (s, 1H), 5.26 (s, 2H), 4.27 (m, 2H), 4.16 (m, 2H), 2.77 (m, 1H), 0.83 (m, 2H), 0.58 (m, 2H). |
| 113 | δ 8.02 (d, 1H), 7.46 (m, 2H), 7.07 (m, 2H), 6.25 (d, 1H), 5.59 (s, 2H), 5.34 (d, 1H), 4.10 (m, 4H), 3.71 (m, 1H), 3.58 (m, 1H), 3.28 (m, 2H), 1.25 (m, 3H). |
| 114 | δ 8.04 (d, 1H), 7.45 (m, 2H), 7.10 (m, 2H), 6.16 (d, 1H), 5.02 (d, 1H), 4.89 (s, 2H), 4.86 (m, 2H), 4.11 (m, 1H), 3.59 (m, 2H), 1.28 (d, 6H). |
| 115 | δ 7.67 (d, 1H), 7.39 (m, 2H), 7.05 (m, 2H), 6.19 (d, 1H), 4.88 (m, 2H), 4.69 (s, 2H), 4.21 (m, 1H), 3.60 (d, 2H), 1.37 (d, 6H). |
| 128 | δ 8.60 (br s, 1H), 7.78 (br s, 1H), 7.39 (br s, 2H), 7.19 (br s, 2H), 6.35 (br s, 1H), 5.20 (br s, 2H), 4.28 (m, 5H), 1.39 (br s, 6H). |
| 130 | δ 8.02 (m, 1H), 7.47 (m, 2H), 7.10 (m, 2H), 6.20 (m, 1H), 5.16 (m, 2H), 4.97 (d, 1H), 4.32 (m, 1H), 4.26 (m, 1H), 4.17 (m, 2H), 3.99 (m, 1H), 2.24 (m, 3H), 1.30 (d, 6H). |
| 131 | δ 8.08 (d, 1H), 7.49 (m, 2H), 7.05 (m, 2H), 6.30 (d, 1H), 5.29 (m, 2H), 3.49 (m, 2H), 3.28 (m, 2H), 2.77 (m, 1H), 1.98 (m, 2H), 0.79 (m, 2H), 0.56 (m, 2H). |
| 132 | δ 8.01 (d, 1H), 7.47 (m, 2H), 7.05 (m, 2H), 6.28 (d, 1H), 5.27 (s, 1H), 5.08 (m, 1H), 4.10 (m, 1H), 3.75 (m, 1H), 3.62 (m, 1H), 3.49 (m, 2H), 3.20 (m, 2H), 2.00 (m, 2H), 1.26 (m, 3H). |
| 134 | δ 8.13 (d, 1H), 7.51 (m, 2H), 7.09 (m, 2H), 6.31 (d, 1H), 5.30 (s, 1H), 4.02 (m, 2H), 3.29 (s, 2H), 2.78 (m, 1H), 2.27 (s, 3H), 2.07 (m, 2H), 0.81 (m, 2H), 0.58 (m, 2H). |
| 135 | δ 8.13 (d, 1H), 7.51 (m, 2H), 7.09 (m, 2H), 6.31 (d, 1H), 5.30 (s, 1H), 4.02 (m, 2H), 3.29 (s, 2H), 2.78 (m, 1H), 2.27 (s, 3H), 2.07 (m, 2H), 0.81 (m, 2H), 0.58 (m, 2H). |
| 136 | δ 8.02 (d, 1H), 7.48 (m, 2H), 7.04 (m, 2H), 6.22 (d, 1H), 5.25 (s, 2H), 4.86 (m, 1H), 3.49 (m, 2H), 3.23 (m, 2H), 1.99 (m, 2H), 1.24 (d, 6H). |
| 137 | δ 8.07 (d, 1H), 7.49 (m, 2H), 7.05 (m, 2H), 6.28 (d, 1H), 6.03 (m, 1H), 5.29 (m, 3H), 4.01 (d, 2H), 3.39 (m, 2H), 3.24 (m, 2H), 2.78 (m, 1H), 1.95 (m, 2H), 0.80 (m, 2H), 0.56 (m, 2H). |

INDEX TABLE H-continued

| Cmpd No. | $^1$H NMR Data (CDCl$_3$ solution unless indicated otherwise)$^a$ |
|---|---|
| 138 | δ 8.00 (d, 1H), 7.48 (m, 2H), 7.10 (t, 2H), 6.19 (d, 1H), 5.10 (s, 2H), 4.98 (d, 1H), 4.27 (m, 2H), 4.19 (m, 1H), 4.02 (br s, 2H), 3.79 (s, 3H), 1.28 (d, 6H). |
| 139 | δ 8.11 (d, 1H), 7.49 (m, 2H), 7.09 (m, 2H), 6.30 (d, 1H), 4.99 (s, 1H), 4.01 (m, 4H), 3.48 (m, 2H), 3.20 (m, 2H), 2.27 (s, 3H), 2.09 (m, 2H), 1.98 (m, 2H), 1.53 (m, 2H). |
| 141 | δ 9.35 (s, 1H), 8.15 (s, 1H), 7.65 (dd, 2H), 7.27 (t, 2H), 5.02 (s, 1H), 4.72 (s, 1H), 4.49 (s, 2H), 4.43 (t, 2H), 4.01 (s, 2H), 3.44 (m, 1H), 1.22 (d, 3H), 1.07 (d, 3H). |
| 142 | δ 8.03 (d, 1H), 7.49 (m, 2H), 7.35 (m, 3H), 6.26 (d, 1H), 4.99 (s, 1H), 4.23 (t, 2H), 3.15 (t, 2H), 2.99 (d, 3H), 2.10 (m, 2H), 1.91 (m, 2H). |
| 143 | δ 8.00 (d, 1H), 7.49 (m, 2H), 7.34 (m, 3H), 6.24 (d, 1H), 4.97 (s, 1H), 4.23 (t, 2H), 3.44 (m, 2H), 3.14 (t, 2H), 2.10 (m, 2H), 1.92 (m, 2H), 1.23 (t, 3H). |
| 147 | δ 8.53 (d, 1H), 7.18 (d, 1H), 4.13 (m, 2H), 2.72 (m, 2H), 2.05 (m, 2H), 1.85 (m, 2H), 1.35 (s, 9H). |
| 148 | δ 8.35 (d, 1H) 7.47 (m, 2H) 7.13 (m, 2H) 6.90 (d, 1H) 4.13 (m, 2H) 3.42 (m, 2H) 2.25 (m, 2H). |
| 150 | δ 8.27 (d, 1H), 7.43 (m, 2H), 7.10 (t, 2H), 6.83 (d, 1H), 4.23 (m, 2H), 3.2 (m, 2H), 2.12 (m, 2H), 1.96 (m, 2H). |
| 151 | 8.29 (d, 1H), 7.49 (m, 1H), 7.00 (m, 1H), 6.88 (m, 1H), 6.78 (d, 1H), 4.25 (t, 2H), 3.24 (t, 2H), 2.13 (m, 2H), 1.97 (m, 2H). |
| 152 | 8.20 (d, 1H), 7.42 (m, 4H), 6.60 (d, 1H), 4.26 (m, 2H), 3.30 (m, 2H), 2.14 (m, 2H), 1.99 (m, 2H). |
| 153 | δ 8.22 (d, 1H), 7.43 (m, 5H), 6.84 (d, 1H), 4.24 (m, 2H), 3.22 (m, 2H), 2.12 (m, 2H), 1.96 (m, 2H). |
| 154 | δ 8.29 (d, 1H), 7.42 (m, 2H), 7.12 (m, 2H), 6.84 (d, 1H), 4.49 (m, 2H), 4.32 (s, 2H), 3.15 (m, 2H). |
| 155 | δ 8.28 (d, 1H), 7.42 (m, 7H), 7.14 (m, 2H), 6.85 (d, 1H), 5.24 (s, 2H), 5.17 (br s, 2H), 4.29 (br s, 2H), 4.05 (m, 2H). |
| 156 | δ 8.22 (d, 1H), 7.30 (d, 2H), 6.97 (d, 1H), 6.73 (d, 2H), 4.22 (m, 2H), 3.20 (m, 2H), 3.00 (s, 6H), 2.10 (m, 2H), 1.94 (m, 2H). |
| 160 | δ 8.48 (d, 1H), 7.37 (d, 2H), 7.12 (d, 1H), 6.96 (d, 2H), 4.23 (m, 2H), 3.86 (s, 3H), 3.32 (s, 3H), 3.25 (m, 2H), 2.12 (m, 2H), 1.96 (m, 2H). |
| 161 | δ 8.53 (d, 1H), 7.40 (s, 4H), 7.09 (d, 1H), 4.24 (m, 2H), 3.31 (s, 3H), 3.25 (m, 2H), 2.12 (m, 2H), 1.97 (m, 2H). |
| 162 | δ 8.50 (d, 1H), 7.32 (d, 1H), 7.20 (m, 1H), 7.07 (m, 2H), 4.24 (m, 2H), 3.32 (s, 3H), 3.26 (m, 2H), 2.30 (m, 3H), 2.12 (m, 2H), 1.97 (m, 2H). |
| 163 | δ 8.52 (d, 1H), 7.47 (m, 2H), 7.18 (m, 2H), 7.11 (d, 1H), 5.27 (s, 2H), 4.29 (m, 2H), 4.19 (m, 2H), 3.34 (s, 3H). |
| 164 | δ 8.55 (d, 1H), 7.52 (m, 1H), 7.44 (m, 1H), 7.27 (m, 1H), 7.14 (m, 1H), 7.06 (d, 1H), 4.27 (m, 2H), 3.29 (m, 2H), 3.23 (s, 3H), 2.14 (m, 2H), 1.99 (m, 2H). |
| 165 | δ 8.20 (d, 1H), 7.95 (m, 2H), 7.68 (d, 1H), 7.52 (m, 3H), 7.38 (m, 1H), 6.59 (d, 1H), 4.31 (m, 2H), 3.42 (m, 2H), 3.21 (s, 3H), 2.18 (m, 2H), 2.05 (m, 2H). |
| 166 | δ 8.42 (d, 1H), 7.84 (m, 1H), 7.62 (m, 2H), 7.40 (m, 1H), 6.67 (d, 1H), 4.26 (m, 2H), 3.34 (m, 2H), 3.21 (s, 3H), 2.15 (m, 2H), 2.02 (m, 2H). |
| 168 | δ 8.55 (d, 1H), 7.47 (m, 1H), 7.42 (m, 1H), 7.21 (d, 1H), 7.14 (m, 1H), 4.23 (m, 2H), 3.33 (s, 3H), 3.25 (m, 2H), 2.12 (m, 2H), 1.96 (m, 2H). |
| 169 | δ 8.40 (m, 1H), 7.36 (m, 1H), 7.29 (m, 3H), 6.79 (d, 1H), 4.25 (m, 2H), 3.36 (m, 2H), 3.28 (s, 3H), 2.15 (m, 2H), 2.12 (m, 3H), 2.01 (m, 2H). |
| 170 | δ 8.56 (d, 1H), 7.69 (d, 2H), 7.60 (d, 2H), 7.08 (d, 1H), 4.26 (t, 2H), 3.29 (s, 3H), 3.25 (t, 2H), 2.14 (m, 2H), 1.98 (m, 2H). |
| 171 | δ 8.55 (d, 1H), 7.63 (br s, 1H), 7.19 (br s, 1H), 7.12 (d, 1H), 4.25 (t, 2H), 3.54 (s, 3H), 3.31 (m, 5H), 2.14 (m, 2H), 2.00 (m, 2H). |
| 172 | δ 8.53 (d, 1H), 7.39 (m, 1H), 7.21 (m, 2H), 7.12 (m, 2H), 4.25 (t, 2H), 3.31 (s, 3H), 3.25 (t, 2H), 2.13 (m, 2H), 1.98 (m, 2H). |
| 173 | δ 8.60 (d, 1H), 7.13 (d, 1H), 7.01 (m, 2H), 6.87 (m, 1H), 4.24 (t, 2H), 3.33 (s, 3H), 3.24 (t, 2H), 2.13 (m, 2H), 1.97 (m, 2H). |
| 174 | δ 8.53 (d, 1H), 7.44 (m, 2H), 7.13 (t, 2H), 7.08 (d, 1H), 4.24 (t, 2H), 3.31 (s, 3H), 3.25 (t, 2H), 2.13 (m, 2H), 1.97 (m, 2H). |
| 175 | δ 8.55 (d, 1H), 7.50 (s, 1H), 7.35 (m, 3H), 7.11 (d, 1H), 4.25 (t, 2H), 3.31 (s, 3H), 3.25 (t, 2H), 2.13 (m, 2H), 1.99 (m, 2H). |
| 176 | δ 8.58 (d, 1H), 7.41 (d, 1H), 7.35 (d, 1H), 7.15 (m, 1H), 7.09 (d, 1H), 4.24 (t, 2H), 3.34 (s, 3H), 3.23 (t, 2H), 2.11 (m, 2H), 1.95 (m, 2H). |
| 177 | δ 8.48 (d, 1H), 7.24 (m, 4H), 7.11 (d, 1H), 4.25 (t, 2H), 3.31 (s, 3H), 3.26 (t, 2H), 2.38 (s, 3H), 2.12 (m, 2H), 1.97 (m, 2H). |
| 178 | δ 8.53 (d, 1H), 7.46 (m, 2H), 7.16 (t, 2H), 7.10 (d, 1H), 5.61 (t, 2H), 4.17 (m, 2H), 3.46 (m, 2H), 3.33 (s, 3H). |
| 179 | δ 8.00 (d, 1H), 7.50 (m, 2H), 7.34 (m, 3H), 6.24 (d, 1H), 5.08 (s, 1H), 4.23 (t, 2H), 3.35 (m, 2H), 3.14 (t, 2H), 2.10 (m, 2H), 2.91 (m, 2H), 1.62 (m, 2H), 0.97 (t, 3H). |
| 182 | δ 8.16 (d, 1H), 7.50 (m, 2H), 7.34 (m, 4H), 6.96 (m, 3H), 6.46 (d, 1H), 4.24 (t, 2H), 3.86 (s, 3H), 3.07 (t, 2H), 2.11 (m, 2H), 2.90 (m, 2H). |
| 187 | δ 8.02 (d, 1H) 7.36 (s, 1H) 7.24 (m, 2H) 7.15 (d, 1H) 6.27 (d, 1H) 5.17 (m, 1H) 4.22 (t, 2H) 3.16 (t, 2H) 2.99 (d, 3H) 2.35 (s, 3H) 2.09 (m, 2H) 1.91 (m, 2H). |

$^a$$^1$H NMR data are in ppm downfield from tetramethylsilane.
Couplings are designated by (s)—singlet, (d)—doublet, (t)—triplet, (m)—multiplet, (dd)—doublet of doublets, (br s)—broad singlet.

BIOLOGICAL EXAMPLES OF THE INVENTION

General protocol for preparing test suspensions for Tests A-M: The test compounds were first dissolved in acetone in an amount equal to 3% of the final volume and then suspended at the desired concentration (in ppm) in acetone and purified water (50/50 mix) containing 250 ppm of the surfactant Trem® 014 (polyhydric alcohol esters). The resulting test suspensions were then used in Tests A-M. Spraying a 200 ppm test suspension to the point of run-off on the test plants was the equivalent of an application rate of 500 g/ha.

Test A

The test suspension was sprayed to the point of run-off on wheat seedlings. The following day the seedlings were inoculated with a spore dust of *Erysiphe graminis* f. sp. *tritici* (the causal agent of wheat powdery mildew) and incubated in a growth chamber at 20° C. for 8 days, after which time disease ratings were made.

Test B

The test suspension was sprayed to the point of run-off on wheat seedlings. The following day the seedlings were inoculated with a spore suspension of *Puccinia recondite* f sp. *tritici* (the causal agent of wheat leaf rust) and incubated in a saturated atmosphere at 20° C. for 24 h, and then moved to a growth chamber at 20° C. for 7 days, after which time disease ratings were made.

Test C

The test suspension was sprayed to the point of run-off on wheat seedlings. The following day the seedlings were inoculated with a spore suspension of *Fusarium graminearum* (the causal agent of wheat head scab) and incubated in a saturated atmosphere at 20° C. for 72 h, and then moved to a growth chamber at 20° C. for 5 days, after which time disease ratings were made.

Test D

The test suspension was sprayed to the point of run-off on wheat seedlings. The following day the seedlings were inoculated with a spore suspension of *Septoria nodorum* (the causal agent of wheat glume blotch) and incubated in a saturated atmosphere at 20° C. for 48 h, and then moved to a growth chamber at 20° C. for 7 days, after which time disease ratings were made.

Test E

The test suspension was sprayed to the point of run-off on wheat seedlings. The following day the seedlings were inoculated with a spore suspension of *Septoria tritici* (the causal agent of wheat leaf blotch) and incubated in saturated atmosphere at 20° C. for 48 h, and moved to a growth chamber at 20° C. for 19 additional days, after which time disease ratings were made.

Test F

The test suspension was sprayed to the point of run-off on cucumber seedlings. The following day the seedlings were inoculated with a spore suspension of *Colletotrichum orbiculare* (the causal agent of cucumber *Colletotrichum anthracnose*) and incubated in saturated atmosphere at 20° C. for 24 h, and moved to a growth chamber at 24° C. for 5 additional days, after which time disease ratings were made.

Test G

The test suspension was sprayed to the point of run-off on wheat seedlings. The following day the seedlings were inoculated with a spore suspension of *Alternaria solani* (the causal agent of tomato early blight) and incubated in a saturated atmosphere at 27° C. for 48 h, and then moved to a growth chamber at 20° C. for 5 days, after which time disease ratings were made.

Test H

The test suspension was sprayed to the point of run-off on tomato seedlings. The following day the seedlings were inoculated with a spore suspension of *Botrytis cinerea* (the causal agent of tomato *Botrytis*) and incubated in saturated atmosphere at 20° C. for 48 h, and then moved to a growth chamber at 24° C. for 3 additional days, after which time disease ratings were made.

Test I

The test suspension was sprayed to the point of run-off on creeping bent grass seedlings. The following day the seedlings were inoculated with a spore suspension of *Rhizoctonia oryzae* (the causal agent of turf brown patch) and incubated in a saturated atmosphere at 27° C. for 48 h, and then moved to a growth chamber at 27° C. for 3 days, after which time disease ratings were made.

Test J

The test suspension was sprayed to the point of run-off on tomato seedlings. The following day the seedlings were inoculated with a spore suspension of *Phytophthora infestans* (the causal agent of tomato late blight) and incubated in a saturated atmosphere at 20° C. for 24 h, and then moved to a growth chamber at 20° C. for 4 days, after which time disease ratings were made.

Test K

Grape seedlings were inoculated with a spore suspension of *Plasmopara viticola* (the causal agent of grape downy mildew) and incubated in a saturated atmosphere at 20° C. for 24 h. After a short drying period, the test suspension was sprayed to the point of run-off on the grape seedlings and then moved to a growth chamber at 20° C. for 6 days, after which time the test units were placed back into a saturated atmosphere at 20° C. for 24 h. Upon removal, disease ratings were made.

Test L

The test suspension was sprayed to the point of run-off on bluegrass seedlings. The following day the seedlings were inoculated with a spore suspension of *Pythium aphanidermatum* (the causal agent of bluegrass *pythium* blight) and incubated in a covered containers to provide saturated atmosphere at 27° C. for 48 h, and then the covers were removed and the plants left at 27° C. for 3 additional days, after which time disease ratings were made.

Test M

The test suspension was sprayed to the point of run-off on cucumber seedlings. The following day the seedlings were inoculated with a spore suspension of *Sclerotinia sclerotiorum* (the causal agent of cucumber white mold) and incubated in saturated atmosphere at 24° C. for 72 h, and then moved to a growth chamber at 24° C. for 3 additional days, after which time disease ratings were made.

Results for Tests A-M are given in Table A. In the table, a rating of 100 indicates 100% disease control and a rating of 0 indicates no disease control (relative to the controls). A dash (-) indicates no test results. All results are for 200 ppm test suspension except where followed by "*" which indicates 40 ppm or by "**" which indicates 10 ppm.

TABLE A

| Cmpd No. | Test A | Test B | Test C | Test D | Test E | Test F | Test G | Test H | Test I | Test J | Test K | Test L | Test M |
|---|---|---|---|---|---|---|---|---|---|---|---|---|---|
| 1 | 94 | 100 | 100 | 98 | 98 | 96 | — | 91 | 41 | 100 | 0 | 100 | 99 |
| 2 | 0 | 98 | — | 98 | 97 | 85 | — | 92 | 31 | 47 | 0 | 100 | 0 |
| 3 | 47 | 91 | 99 | 0 | 72 | 0 | — | 0 | 0 | 0 | 0 | 0 | — |
| 4 | 0 | 92 | 100 | 60 | 90 | 8 | — | 55 | 0 | 0 | 21 | 0 | — |
| 5 | 96 | 100 | 100 | 97 | 97 | 99 | 98* | 99 | 0 | 99 | — | 100 | — |
| 6 | 0 | 73 | 100 | 0 | — | 0 | — | 0 | 0 | 0 | 0 | 0 | — |
| 7 | 82 | 99 | 100 | 98 | 99 | 90 | — | 82 | 0 | 93 | 0 | 0 | — |
| 8 | 81 | 99 | 100 | 100 | 100 | 99 | 99* | 97 | 62 | 100 | — | 100 | — |
| 9 | 52 | 97 | 99 | 92 | 0 | 79 | — | 81 | 0 | 0 | 0 | 0 | — |
| 10 | 90 | 99 | 99 | 87 | — | 0 | — | 63 | 0 | 64 | 0 | 42 | — |
| 11 | 93 | 99 | 100 | 99 | 98 | 83 | — | 97 | 44 | 100 | 0 | 100 | — |
| 12 | 97 | 99 | 100 | 99 | 100 | 94 | — | 98 | 64 | 100 | 0 | 100 | — |
| 13 | 98 | 99 | 100 | 97 | — | 31 | — | 29 | 77 | 97 | 0 | 100 | — |
| 14 | 95 | 91 | 100 | 73 | 99 | 0 | — | 0 | 0 | 60 | 0 | 0 | — |
| 15 | 86 | 99 | 100 | 98 | — | 17 | — | 92 | 0 | 97 | 0 | 100 | — |
| 16 | 20 | 99 | 99 | 0 | — | 0 | — | 19 | 0 | 91 | 0 | 70 | — |
| 17 | 64 | 99 | 100 | 98 | — | 77 | — | 97 | 0 | 100 | 86 | 100 | — |
| 18 | 96 | 100 | 100 | 97 | — | 98 | — | 74 | 0 | 99 | 0 | 100 | — |
| 19 | 26 | 99 | 100 | 98 | — | 66 | — | 74 | 0 | 31 | 0 | 93 | — |
| 20 | 78 | 99 | 100 | 99 | — | 88 | — | 96 | 0 | 99 | 0 | 100 | — |
| 21 | 96 | — | — | 82 | 100 | — | — | — | — | 52 | — | 76 | — |
| 22 | 50 | — | — | 87 | 94 | — | — | — | — | 83 | — | 77 | — |
| 23 | 99 | — | — | 94 | 98 | — | — | — | — | 71 | — | 0 | — |
| 24 | 97 | — | — | 98 | 98 | — | — | — | — | 72 | — | 0 | — |
| 25 | 96 | — | — | 87 | 97 | — | — | — | — | 83 | — | 100 | — |
| 26 | 91 | — | — | 99 | 96 | — | — | — | — | 91 | — | 100 | — |
| 27 | 96 | 95* | 99* | 98 | 97 | 66** | 95** | — | — | 97 | — | 98 | — |
| 28 | 94 | — | — | 92 | 96 | — | — | — | — | 95 | — | 98 | — |
| 29 | 0 | 95 | 100 | 98 | 85 | — | — | — | — | 47 | — | 0 | — |
| 30 | 0 | 91 | 92 | 69 | 93 | — | — | — | — | 47 | — | 0 | — |
| 31 | 0 | 95 | 94 | 78 | 98 | — | — | — | — | 80 | — | 99 | — |
| 32 | 0* | 74* | 0* | 0* | — | — | — | — | — | 98* | — | 99* | — |
| 33 | 0* | 77* | 98* | 94* | — | — | — | — | — | 95* | — | 97* | — |
| 34 | 96 | 100 | 98 | 100 | 94 | — | — | — | — | 91 | — | 100 | — |
| 35 | 0 | 99 | 99 | 99 | 100 | — | — | — | — | 67 | — | 0 | — |
| 36 | 0 | 91 | 99 | 96 | 96 | — | — | — | — | 90 | — | 99 | — |
| 37 | 70 | 86 | 96 | 0 | 68 | — | — | — | — | 95 | — | 93 | — |
| 38 | 0 | 94 | 96 | 64 | 92 | — | — | — | — | 95 | — | 99 | — |
| 39 | 0 | 67 | 60 | 60 | 88 | — | — | — | — | 0 | — | 0 | — |
| 40 | 0 | 85 | 84 | 99 | 98 | — | — | — | — | 0 | — | 0 | — |
| 41 | 0 | 79 | 0 | 0 | 50 | — | — | — | — | 0 | — | 91 | — |
| 42 | 0 | 85 | 66 | 0 | 59 | — | — | — | — | 99 | — | 100 | — |
| 43 | 0 | 92 | 98 | 90 | 96 | — | — | — | — | 97 | — | 100 | — |
| 44 | 91 | 85 | 99 | 89 | 100 | — | — | — | — | 65 | — | 0 | — |
| 45 | 41 | 89 | 0 | 60 | 97 | — | — | — | — | 76 | — | 85 | — |
| 46 | 0 | 74 | 0 | 0 | 50 | — | — | — | — | 97 | — | 100 | — |
| 47 | 0 | 91 | 69 | 0 | 94 | — | — | — | — | 99 | — | 100 | — |
| 48 | 0 | 99 | 99 | 0 | 99 | — | — | — | — | 99 | — | 100 | — |
| 49 | 76 | 99 | 100 | 100 | 90 | — | — | — | — | 100 | — | 99 | — |
| 50 | 0* | 0* | 92* | 0* | — | — | — | — | — | 31* | — | 68* | — |
| 51 | 81 | 98 | 100 | 100 | 100 | — | — | — | — | 93 | — | 100 | — |
| 52 | 0 | 100 | 99 | 97 | 98 | — | — | — | — | 95 | — | 100 | — |
| 53 | 0* | 98* | 99* | 84* | — | — | — | — | — | 99* | — | 100* | — |
| 54 | 0* | 98* | 95* | 60* | — | — | — | — | — | 99* | — | 100* | — |
| 55 | 0* | 91* | 99* | 44* | — | — | — | — | — | 17* | — | 0* | — |
| 56 | 86* | 0* | 100* | 99* | — | — | — | — | — | 93* | — | 100* | — |
| 57 | 0* | 86* | 0* | 0* | — | — | — | — | — | 99* | — | 100* | — |
| 58 | 0* | 0* | 100* | 82* | — | — | — | — | — | 26* | — | 62* | — |
| 59 | 0* | 92* | 99* | 94* | — | — | — | — | — | 71* | — | 67** | — |
| 60 | 0 | 74 | 91 | 64 | 71 | — | — | — | — | 9 | — | 0 | — |
| 61 | 79 | 94 | 98 | 99 | 98 | — | — | — | — | 97 | — | 99 | — |
| 62 | 78* | 80* | 98* | 60* | — | — | — | — | — | 96* | — | 99* | — |
| 63 | 81 | 91 | 0 | 0 | 82 | — | — | — | — | 9 | — | 100 | — |
| 64 | 0 | 0 | 0 | 0 | 0 | — | — | — | — | 0 | — | 0 | — |
| 65 | 28 | 65 | 87 | 31 | 98 | — | — | — | — | 43 | — | 99 | — |
| 66 | 0 | 88 | 83 | 0 | 72 | — | — | — | — | 97 | — | 100 | — |

TABLE A-continued

| Cmpd No. | Test A | Test B | Test C | Test D | Test E | Test F | Test G | Test H | Test I | Test J | Test K | Test L | Test M |
|---|---|---|---|---|---|---|---|---|---|---|---|---|---|
| 67 | 0 | 100 | 100 | 78 | 93 | — | — | — | — | 99 | — | 100 | — |
| 68 | 0 | 98 | 99 | 95 | 93 | — | — | — | — | 95 | — | 100 | — |
| 69 | 59 | 97 | 100 | 99 | 100 | — | — | — | — | 97 | — | 100 | — |
| 70 | 83 | 0* | 0* | 90 | 84* | 91 | 46* | 29 | 9 | 53* | — | 98* | — |
| 71 | 0 | 0* | 0* | 64 | 33* | 0 | 0* | 0 | — | 9* | — | 97* | — |
| 72 | 0 | 94* | 0* | 82 | 47* | 0 | 98* | 77 | 0 | 99* | — | 100* | — |
| 73 | 0 | 85* | 0* | 78 | 84* | 0 | 0* | 0 | 0 | 17* | — | 98* | — |
| 74 | 20 | 91* | 10* | 60 | 86* | 0 | 0* | 0 | 0 | 0* | — | 93* | — |
| 75 | 31 | 0* | 0* | 0 | 92* | 0 | 0* | 0 | 0 | 0* | — | 0* | — |
| 77 | 82 | — | 92* | 49 | 0* | 0 | 0* | 29 | 0 | 40* | — | 0* | — |
| 78 | 58 | — | 99* | 69 | 60* | 0 | 0* | 0 | 0 | 17* | — | 0* | — |
| 79 | 76 | — | 99* | 69 | 93* | 0 | 0* | 0 | 0 | 0* | — | 0* | — |
| 80 | 82 | — | 98* | 82 | 93* | 0 | 68* | 44 | 0 | 33* | — | 0* | — |
| 81 | 0 | 98 | 98 | 87 | 100 | — | — | — | — | 99 | — | 95 | — |
| 82 | 81 | 91 | 96 | 60 | 97 | — | — | — | — | 99 | — | 0 | — |
| 83 | 0 | 0 | 0 | 60 | 67 | — | — | — | — | 93 | — | 99 | — |
| 84 | 60 | 99 | 100 | 99 | — | 98 | — | 52 | 16 | 93 | 0 | 100 | — |
| 85 | 0 | 99 | 100 | 82 | — | 88 | — | 52 | 16 | 67 | 0 | 100 | — |
| 86 | 0 | — | 0 | 51 | — | 0 | — | 0 | 0 | 94 | 0 | 99 | — |
| 87 | 0 | — | 99 | 78 | — | 0 | — | 0 | 0 | 94 | 0 | 99 | — |
| 88 | 0 | — | 100 | 60 | — | 0 | — | 21 | 0 | 100 | 0 | 99 | — |
| 89 | 21 | — | 100 | 60 | — | 0 | — | 8 | 0 | 0 | 0 | 99 | — |
| 90 | 96 | 99 | 100 | 100 | — | 17 | — | 0 | 0 | 99 | 0 | 97 | — |
| 91 | 74 | 99 | 100 | 98 | — | 16 | — | 99 | 0 | 0 | 0 | 88 | — |
| 92 | 94 | 99 | 100 | 99 | — | 80 | — | 90 | 0 | 99 | 0 | 99 | — |
| 93 | 0 | 0 | 99 | 0 | — | 0 | — | 0 | 0 | 95 | 0 | 90 | — |
| 94 | 82 | 97 | 100 | 98 | — | 24 | — | 96 | 16 | 99 | 0 | 99 | — |
| 95 | 68 | 100 | 100 | 99 | — | 21 | — | 87 | 0 | 99 | 0 | 95 | — |
| 96 | 0 | 19 | 96 | 0 | 62 | — | — | — | — | 98 | — | 83 | — |
| 97 | 0 | 55 | 100 | 82 | 61 | — | — | — | — | 96 | — | 100 | — |
| 98 | 0 | 74 | 97 | 82 | 95 | — | — | — | — | 88 | — | 99 | — |
| 99 | 0 | 94 | 99 | 89 | 98 | — | — | — | — | 99 | — | 100 | — |
| 100 | 0 | 89 | 99 | 90 | 92 | — | — | — | — | 98 | — | 100 | — |
| 101 | 0 | 89 | 99 | 92 | 94 | — | — | — | — | 57 | — | 91 | — |
| 102 | 73 | 92 | 100 | 97 | 100 | — | — | — | — | 96 | — | 99 | — |
| 103 | 85 | 95 | 99 | 99 | 100 | — | — | — | — | 99 | — | 100 | — |
| 104 | 0 | 0 | 55 | 0 | 88 | — | — | — | — | 88 | — | 91 | — |
| 105 | 0 | 94 | 94 | 78 | 100 | — | — | — | — | 73 | — | 0 | — |
| 106 | 0 | 94 | 92 | 69 | 72 | — | — | — | — | 9 | — | 0 | — |
| 107 | 92 | 99 | 99 | 99 | 100 | 99 | 99* | 90 | 80 | 100 | — | 100 | — |
| 108 | 43 | 99 | 98 | 87 | 99 | — | — | — | — | 77 | — | 100 | — |
| 109 | 92 | — | 100 | 0 | 100 | — | — | — | — | 99 | — | 100 | — |
| 110 | 0 | 95 | 92 | 60 | 17 | — | — | — | — | 99 | — | 100 | — |
| 111 | 21 | 95 | 95 | 64 | 31 | — | — | — | — | 80 | — | 100 | — |
| 112 | 0 | 95 | 100 | 93 | 99 | — | — | — | — | 99 | — | 99 | — |
| 113 | 0 | 97 | 99 | 78 | 91 | — | — | — | — | 96 | — | 100 | — |
| 114 | 57 | 100 | 94 | 73 | 86 | — | — | — | — | 100 | — | 100 | — |
| 115 | 0* | 63* | 0* | 69* | — | — | — | — | — | 73* | — | — | — |
| 116 | 90 | 93 | 100 | 92 | 91 | — | — | — | — | 95 | — | 100 | — |
| 117 | 86 | 97 | 99 | 98 | 98 | — | — | — | — | 95 | — | 100 | — |
| 118 | 0 | 86 | 98 | 78 | 82 | — | — | — | — | 80 | — | 99 | — |
| 119 | 61 | 76 | 100 | 99 | 87 | — | — | — | — | 93 | — | 92 | — |
| 120 | 86 | 90 | 100 | 100 | 95 | — | — | — | — | 88 | — | 98 | — |
| 121 | 0 | 94 | 99 | 84 | 93 | 15 | 89 | 66 | — | 97 | — | 99 | — |
| 122 | 0 | 96 | 99 | 73 | 80 | — | — | — | — | 99 | — | 100 | — |
| 123 | 0 | 90 | 99 | 0 | 31 | — | — | — | — | 91 | — | 100 | — |
| 124 | 0 | 86 | 98 | 60 | 54 | — | — | — | — | 66 | — | 99 | — |
| 125 | 20 | 86 | 100 | 89 | 88 | — | — | — | — | 100 | — | 100 | — |
| 126 | 0 | 86 | 99 | 82 | 70 | — | — | — | — | 87 | — | 99 | — |
| 127 | 0 | 97 | 96 | 60 | 86 | — | — | — | — | 100 | — | 99 | — |
| 128 | 0 | 96* | 99* | 99 | 94* | 99 | 99* | 89 | — | 100* | — | 100* | — |
| 129 | 0 | 98* | 100* | 99 | 81* | — | 95* | 84 | 53 | 95* | — | 100* | — |
| 130 | 86 | 92* | 0* | 97 | 97* | 0 | 58* | 34 | 0 | 100* | — | 100* | — |
| 131 | 96 | 100 | 100 | 87 | — | 58 | 81 | 9 | 57 | 97 | 0 | 100 | — |
| 132 | 66 | 88* | 0* | 0 | 0* | 0 | 0* | 0 | 0 | 65* | — | 100* | — |
| 133 | 0 | 19* | 42* | 0 | 0* | 98 | 0* | 0 | 0 | 73* | — | 99* | — |
| 134 | 91 | 85* | 84* | 96 | 77** | 99* | 98** | 53 | 24 | 90** | — | 100* | — |
| 135 | 95 | 61* | 84* | 89 | 90* | 99 | 99* | 70 | 0 | 70* | — | — | — |
| 136 | 0 | 92* | 77* | 97 | 28* | 0 | 99* | 41 | 0 | 57* | — | 100* | — |
| 137 | 86 | 0* | 69* | 92 | 73* | 0 | 99* | 0 | 0 | 53* | — | 99* | — |
| 138 | 0 | 98* | 86* | 99 | 83* | — | 99* | 68 | 0 | 88* | — | 99* | — |
| 139 | 73 | 90* | 95* | 99 | 29* | — | 99* | 0 | 40 | 93* | — | 100* | — |
| 140 | 0 | 90 | 98 | 0 | 49 | — | — | — | — | 26 | — | 99 | — |
| 142 | 95 | 100 | 97 | 98 | 100 | — | 0 | 53 | — | — | — | — | — |
| 143 | 96 | 100 | 99 | 100 | 100 | — | — | — | 86 | — | — | — | — |
| 179 | 75 | 100 | 100 | 99 | 100 | — | — | — | 89 | — | — | — | — |
| 180 | 79 | 99 | 96 | 98 | 100 | — | — | — | 96 | — | — | — | — |
| 181 | 97 | 100 | 100 | 100 | 100 | — | 99 | 94 | — | — | — | — | — |

TABLE A-continued

| Cmpd No. | Test A | Test B | Test C | Test D | Test E | Test F | Test G | Test H | Test I | Test J | Test K | Test L | Test M |
|---|---|---|---|---|---|---|---|---|---|---|---|---|---|
| 182 | 92 | 77 | — | 97 | 100 | — | — | 81 | — | — | — | — | — |
| 183 | — | 100 | 99 | 97 | 100 | — | — | 81 | — | — | — | — | — |
| 184 | 61 | 99 | 99 | 90 | 100 | — | 98 | 80 | — | — | — | — | — |
| 185 | 74 | 97 | — | 99 | 97 | — | 95 | 99 | — | — | — | — | — |
| 186 | 79 | 99 | — | 99 | 95 | — | 99 | 99 | — | — | — | — | — |
| 187 | 79 | 99 | — | 92 | 99 | — | — | 92 | — | — | — | — | — |

What is claimed is:

1. A compound selected from Formula 1, N-oxides and salts thereof,

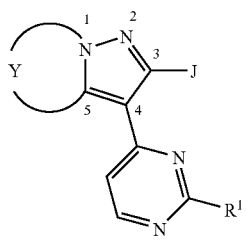

1 wherein

Y is

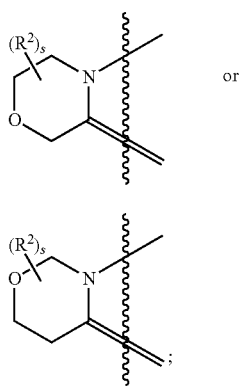

s is an integer from 0 to 4;

each $R^2$ is independently H, halogen, cyano, hydroxy, —CHO, —NHCHO, —$N_3$, —N=C=O, —N=C=S, —SH, —C(=O)$NH_2$, —C(=O)NHCN, —C(=O)OR$^6$, —C(=O)NHOR$^{6a}$, $C_1$-$C_5$ alkyl, $C_2$-$C_5$ alkenyl, $C_2$-$C_5$ alkynyl, $C_3$-$C_6$ cycloalkyl, $C_3$-$C_6$ halocycloalkyl, $C_3$-$C_6$ cycloalkenyl, $C_1$-$C_5$ haloalkyl, $C_1$-$C_5$ alkoxy, $C_1$-$C_5$ haloalkoxy, $C_3$-$C_6$ cycloalkoxy, $C_2$-$C_5$ alkenyloxy, $C_3$-$C_5$ haloalkenyloxy, $C_2$-$C_5$ alkynyloxy, $C_2$-$C_5$ alkylcarbonyl, $C_2$-$C_5$ alkylcarbonyloxy, $C_2$-$C_5$ haloalkylcarbonyloxy, $C_3$-$C_5$ alkoxycarbonylalkoxy, $C_1$-$C_5$ alkylthio, $C_1$-$C_5$ haloalkylthio, $C_3$-$C_6$ cycloalkylthio, $C_2$-$C_5$ alkyl(thiocarbonyl), $C_2$-$C_5$ alkylthio(thiocarbonyl), $C_1$-$C_5$ alkylsulfinyl, $C_1$-$C_5$ haloalkylsulfinyl, $C_3$-$C_6$ cycloalkylsulfinyl, $C_1$-$C_5$ alkylsulfonyl, $C_1$-$C_5$ haloalkylsulfonyl, $C_3$-$C_6$ cycloalkylsulfonyl, $C_3$-$C_5$ trialkylsilyl, $C_3$-$C_5$ halotrialkylsilyl, $C_1$-$C_5$ alkylamino, $C_2$-$C_5$ haloalkylamino, $C_3$-$C_6$ cycloalkylamino, $C_2$-$C_5$ dialkylamino or $C_3$-$C_5$ halodialkylamino;

each $R^3$ is independently H, —CN, —C(=O)$NH_2$, —C(=O)NHCN, —CHO, —NHCHO, —C(=O)OR$^6$, —C(=O)NHOR$^{6a}$, hydroxy, $C_1$-$C_5$ alkyl, $C_2$-$C_5$ alkenyl, $C_2$-$C_5$ alkynyl, $C_3$-$C_6$ cycloalkyl, $C_3$-$C_6$ halocycloalkyl, $C_3$-$C_6$ cycloalkenyl, $C_4$-$C_{10}$ cycloalkylalkyl, $C_4$-$C_7$ alkylcycloalkyl, $C_5$-$C_7$ alkylcycloalkylalkyl, $C_1$-$C_5$ haloalkyl, $C_2$-$C_5$ alkylcarbonyl, $C_2$-$C_5$ haloalkylcarbonyl, $C_4$-$C_7$ cycloalkylcarbonyl, $C_2$-$C_6$ alkoxycarbonyl, $C_2$-$C_6$ haloalkoxycarbonyl, $C_4$-$C_7$ cycloalkoxycarbonyl, $C_3$-$C_6$ alkoxyalkylcarbonyl, $C_3$-$C_6$ alkoxyalkoxycarbonyl, $C_2$-$C_6$ (alkylthio)carbonyl, $C_2$-$C_6$ alkoxy(thiocarbonyl), $C_2$-$C_6$ alkyl(thiocarbonyl), $C_2$-$C_6$ alkylthio(thiocarbonyl), $C_2$-$C_6$ alkylaminocarbonyl, $C_4$-$C_7$ cycloalkylaminocarbonyl, $C_3$-$C_6$ dialkylaminocarbonyl, $C_2$-$C_6$ alkylamino(thiocarbonyl), $C_3$-$C_6$ dialkylamino(thiocarbonyl), $C_3$-$C_6$ alkoxy(alkyl)aminocarbonyl, $C_1$-$C_5$ alkoxy, $C_1$-$C_5$ haloalkoxy, $C_1$-$C_5$ alkylthio, $C_1$-$C_5$ haloalkylthio, $C_3$-$C_6$ cycloalkylthio, $C_1$-$C_5$ alkylaminosulfonyl, $C_3$-$C_5$ trialkylsilyl or $C_3$-$C_5$ halotrialkylsilyl;

each $R^4$ is independently H, cyano, amino, hydroxy, $C_1$-$C_6$ alkyl, $C_3$-$C_{10}$ cycloalkyl, $C_2$-$C_6$ alkylcarbonyl, $C_2$-$C_6$ haloalkylcarbonyl, $C_1$-$C_6$ alkoxy, phenyl or benzoyl;

each $R^{5a}$ and $R^{5b}$ is independently $C_1$-$C_5$ alkyl, $C_2$-$C_5$ alkenyl, $C_2$-$C_5$ alkynyl, $C_3$-$C_5$ cycloalkyl, $C_3$-$C_6$ halocycloalkyl, $C_4$-$C_{10}$ cycloalkylalkyl, $C_4$-$C_7$ alkylcycloalkyl, $C_5$-$C_7$ alkylcycloalkylalkyl, $C_1$-$C_5$ haloalkyl, $C_1$-$C_5$ alkoxy or $C_1$-$C_5$ haloalkoxy;

each $R^6$ is independently H, $C_1$-$C_6$ alkyl, $C_1$-$C_6$ haloalkyl, $C_3$-$C_6$ cycloalkyl, $C_4$-$C_7$ cycloalkylalkyl, $C_4$-$C_7$ alkylcycloalkyl or benzyl;

each $R^{6a}$ is independently $C_1$-$C_6$ alkyl, $C_1$-$C_6$ haloalkyl, $C_3$-$C_6$ cycloalkyl, $C_4$-$C_7$ cycloalkylalkyl or $C_4$-$C_7$ alkylcycloalkyl;

J is a phenyl or 5-or 6-membered heteroaromatic ring or a naphthalenyl or 8-to 10-membered heteroaromatic bicyclic ring system, each ring or ring system optionally substituted with up to 5 substituents independently selected from $R^7$ on carbon atom ring members and $R^8$ on nitrogen atom ring members; or J is a 5-or 6-membered nonaromatic carbocyclic or heterocyclic ring, optionally including ring members selected from the group consisting of C(=O), C(=S), C(=NR$^4$), SiR$^{5a}$R$^{5b}$ and S(=O)$_p$(=NR$^4$)$_q$, each ring optionally substituted with 1 to 5 substituents independently selected from $R^7$ on carbon atom ring members and $R^8$ on nitrogen atom ring members;

each $R^7$ is independently halogen, $C_1$-$C_6$ alkyl, $C_2$-$C_6$ alkenyl, $C_2$-$C_6$ alkynyl, $C_3$-$C_6$ cycloalkyl, $C_3$-$C_6$ halocycloalkyl, $C_4$-$C_7$ alkylcycloalkyl, $C_1$-$C_6$ haloalkyl, $C_2$-$C_6$ haloalkenyl, cyano, nitro, $C_1$-$C_6$ alkoxy, $C_1$-$C_6$ haloalkoxy, $C_1$-$C_6$ alkylthio, $C_1$-$C_6$ alkylsulfinyl, $C_1$-$C_6$ alkylsulfonyl, $C_1$-$C_6$ haloalkylthio, $C_1$-$C_6$ haloalkylsulfinyl, $C_1$-$C_6$ haloalkylsulfonyl, $C_1$-$C_6$ alkylamino, $C_2$-$C_6$ dialkylamino, $C_2$-$C_6$ alkylcarbonyl, $C_2$-$C_6$ alkoxycarbonyl, $C_2$-$C_6$ alkylaminocarbonyl, $C_3$-$C_6$ dialkylaminocarbonyl or $C_3$-$C_6$ trialkylsilyl;

$R^8$ is $C_1$-$C_3$ alkyl;

$R^1$ is H, —$NR^{9a}R^{9b}$, —$NR^{10}$—$NR^{11a}R^{11b}$, —$OR^{12}$, —N=$CR^{13a}R^{13b}$ or —$NR^{10}$N=$CR^{14a}R^{14b}$;

each $R^{9a}$ and $R^{11a}$ is independently H, $C_1$-$C_{10}$ alkyl, $C_2$-$C_{10}$ alkenyl, $C_2$-$C_{10}$ alkynyl, $C_1$-$C_{10}$ haloalkyl, $C_2$-$C_{10}$ haloalkenyl, $C_2$-$C_{10}$ haloalkynyl, $C_2$-$C_{10}$ alkoxyalkyl, $C_3$-$C_{10}$ alkoxyalkoxyalkyl, $C_3$-$C_{10}$ alkoxyalkenyl, $C_3$-$C_{10}$ alkoxyalkynyl, $C_3$-$C_{10}$ dialkoxyalkyl, $C_4$-$C_{10}$ trialkoxyalkyl, $C_2$-$C_{10}$ haloalkoxyalkyl, $C_2$-$C_{10}$ alkoxyhaloalkyl, $C_2$-$C_{10}$ haloalkoxyhaloalkyl, $C_1$-$C_{10}$ hydroxyalkyl, $C_2$-$C_{10}$ cyanoalkyl, $C_2$-$C_{10}$ alkylthioalkyl, $C_2$-$C_{10}$ alkylsulfinylalkyl, $C_3$-$C_{10}$ alkylaminoalkyl, $C_3$-$C_{10}$ haloalkylaminoalkyl, $C_5$-$C_{10}$ cycloalkylaminoalkyl, $C_4$-$C_{10}$ dialkylaminoalkyl, $C_4$-$C_{10}$ halodialkylaminoalkyl, $C_6$-$C_{10}$ cycloalkyl(alkyl)aminoalkyl, $C_2$-$C_{10}$ alkylcarbonyl, $C_2$-$C_{10}$ haloalkylcarbonyl, $C_4$-$C_{10}$ cycloalkylcarbonyl, $C_2$-$C_{10}$ alkoxycarbonyl, $C_2$-$C_{10}$ haloalkoxycarbonyl, $C_4$-$C_{10}$ cycloalkoxycarbonyl, $C_3$-$C_{10}$ alkoxyalkylcarbonyl, $C_3$-$C_{10}$ alkoxyalkoxycarbonyl, $C_2$-$C_{10}$ (alkylthio)carbonyl, $C_2$-$C_{10}$ alkoxy(thiocarbonyl), $C_2$-$C_{10}$ alkyl(thiocarbonyl), $C_2$-$C_{10}$ alkylthio(thiocarbonyl), $C_2$-$C_{10}$ alkylaminocarbonyl, $C_4$-$C_{10}$ cycloalkylaminocarbonyl, $C_3$-$C_{10}$ dialkylaminocarbonyl, $C_2$-$C_{10}$ alkylamino(thiocarbonyl), $C_3$-$C_{10}$ dialkylamino(thiocarbonyl), $C_2$-$C_{10}$ alkylsulfonylaminocarbonyl, $C_2$-$C_{10}$ haloalkylsulfonylaminocarbonyl, $C_3$-$C_{10}$ alkoxy(alkyl)aminocarbonyl, $C_1$-$C_{10}$ alkoxy, $C_1$-$C_{10}$ haloalkoxy, $C_3$-$C_{10}$ cycloalkoxy, $C_1$-$C_{10}$ alkylsulfonyl, $C_1$-$C_{10}$ haloalkylsulfonyl, $C_3$-$C_{10}$ cycloalkylsulfonyl, $C_1$-$C_{10}$ alkylaminosulfonyl, $C_2$-$C_{10}$ dialkylaminosulfonyl or —$(CR^{15a}R^{15b})_mR^{16}$;

each $R^{9b}$ and $R^{11b}$ is independently H, $C_1$-$C_{10}$ alkyl, $C_2$-$C_{10}$ alkenyl, $C_2$-$C_{10}$ alkynyl, $C_1$-$C_{10}$ haloalkyl, $C_2$-$C_{10}$ haloalkenyl, $C_2$-$C_{10}$ haloalkynyl, $C_2$-$C_{10}$ alkoxyalkyl, $C_3$-$C_{10}$ alkoxyalkoxyalkyl, $C_3$-$C_{10}$ alkoxyalkenyl, $C_3$-$C_{10}$ alkoxyalkynyl, $C_3$-$C_{10}$ dialkoxyalkyl, $C_4$-$C_{10}$ trialkoxyalkyl, $C_2$-$C_{10}$ haloalkoxyalkyl, $C_2$-$C_{10}$ alkoxyhaloalkyl, $C_2$-$C_{10}$ haloalkoxyhaloalkyl, $C_1$-$C_{10}$ hydroxyalkyl, $C_2$-$C_{10}$ cyanoalkyl, $C_2$-$C_{10}$ alkylthioalkyl, $C_2$-$C_{10}$ alkylsulfinylalkyl, $C_3$-$C_{10}$ alkylaminoalkyl, $C_3$-$C_{10}$ haloalkylaminoalkyl, $C_5$-$C_{10}$ cycloalkylaminoalkyl, $C_4$-$C_{10}$ dialkylaminoalkyl, $C_4$-$C_{10}$ halodialkylaminoalkyl, $C_6$-$C_{10}$ cycloalkyl(alkyl)aminoalkyl, $C_2$-$C_{10}$ alkylcarbonyl, $C_2$-$C_{10}$ haloalkylcarbonyl, $C_4$-$C_{10}$ cycloalkylcarbonyl, $C_2$-$C_{10}$ alkoxycarbonyl, $C_2$-$C_{10}$ haloalkoxycarbonyl, $C_4$-$C_{10}$ cycloalkoxycarbonyl, $C_3$-$C_{10}$ alkoxyalkylcarbonyl, $C_3$-$C_{10}$ alkoxyalkoxycarbonyl, $C_2$-$C_{10}$ (alkylthio)carbonyl, $C_2$-$C_{10}$ alkoxy(thiocarbonyl), $C_2$-$C_{10}$ alkyl(thiocarbonyl), $C_2$-$C_{10}$ alkylthio(thiocarbonyl), $C_2$-$C_{10}$ alkylaminocarbonyl, $C_4$-$C_{10}$ cycloalkylaminocarbonyl, $C_3$-$C_{10}$ dialkylaminocarbonyl, $C_2$-$C_{10}$ alkylamino(thiocarbonyl), $C_3$-$C_{10}$ dialkylamino(thiocarbonyl), $C_2$-$C_{10}$ alkylsulfonylaminocarbonyl, $C_2$-$C_{10}$ haloalkylsulfonylaminocarbonyl, $C_3$-$C_{10}$ alkoxy(alkyl)aminocarbonyl, $C_1$-$C_{10}$ alkylsulfonyl, $C_1$-$C_{10}$ haloalkylsulfonyl, $C_3$-$C_{10}$ cycloalkylsulfonyl, $C_1$-$C_{10}$ alkylaminosulfonyl, $C_2$-$C_{10}$ dialkylaminosulfonyl or —$(CR^{15a}R^{15b})_mR^{16}$; or each $R^{9a}$ and $R^{9b}$ pair, or $R^{11a}$ and $R^{11b}$ pair is independently taken together with the nitrogen to which it is attached to form a 3- to 6-membered ring containing ring members selected from carbon and heteroatoms, said ring optionally including ring members selected from the group consisting of $NR^3$, C(=O), C(=S), C(=$NR^4$), $SiR^{5a}R^{5b}$ and $S(=O)_p(=NR^4)_q$, and optionally substituted on carbon ring members with 1 to 4 substituents selected from the group consisting of halogen, —CN, $C_1$-$C_2$ alkyl and $C_1$-$C_2$ alkoxy;

$R^{12}$ is H, $C_1$-$C_{10}$ alkyl, $C_2$-$C_{10}$ alkenyl, $C_2$-$C_{10}$ alkynyl, $C_1$-$C_{10}$ haloalkyl, $C_2$-$C_{10}$ haloalkenyl, $C_2$-$C_{10}$ haloalkynyl, $C_2$-$C_{10}$ alkoxyalkyl, $C_3$-$C_{10}$ alkoxyalkoxyalkyl, $C_3$-$C_{10}$ alkoxyalkenyl, $C_3$-$C_{10}$ alkoxyalkynyl, $C_3$-$C_{10}$ dialkoxyalkyl, $C_4$-$C_{10}$ trialkoxyalkyl, $C_2$-$C_{10}$ haloalkoxyalkyl, $C_2$-$C_{10}$ alkoxyhaloalkyl, $C_2$-$C_{10}$ haloalkoxyhaloalkyl, $C_2$-$C_{10}$ hydroxyalkyl, $C_2$-$C_{10}$ cyanoalkyl, $C_2$-$C_{10}$ alkylthioalkyl, $C_2$-$C_{10}$ alkylsulfinylalkyl, $C_3$-$C_{10}$ alkylaminoalkyl, $C_3$-$C_{10}$ haloalkylaminoalkyl, $C_5$-$C_{10}$ cycloalkylaminoalkyl, $C_4$-$C_{10}$ dialkylaminoalkyl, $C_4$-$C_{10}$ halodialkylaminoalkyl, $C_6$-$C_{10}$ cycloalkyl(alkyl)aminoalkyl, $C_2$-$C_{10}$ alkylcarbonyl, $C_2$-$C_{10}$ haloalkylcarbonyl, $C_4$-$C_{10}$ cycloalkylcarbonyl, $C_2$-$C_{10}$ alkoxycarbonyl, $C_2$-$C_{10}$ haloalkoxycarbonyl, $C_4$-$C_{10}$ cycloalkoxycarbonyl, $C_3$-$C_{10}$ alkoxyalkylcarbonyl, $C_3$-$C_{10}$ alkoxyalkoxycarbonyl, $C_2$-$C_{10}$ (alkylthio)carbonyl, $C_2$-$C_{10}$ alkoxy(thiocarbonyl), $C_2$-$C_{10}$ alkyl(thiocarbonyl), $C_2$-$C_{10}$ alkylthio(thiocarbonyl), $C_2$-$C_{10}$ alkylaminocarbonyl, $C_4$-$C_{10}$ cycloalkylaminocarbonyl, $C_3$-$C_{10}$ dialkylaminocarbonyl, $C_2$-$C_{10}$ alkylamino(thiocarbonyl), $C_3$-$C_{10}$ dialkylamino(thiocarbonyl), $C_2$-$C_{10}$ alkylsulfonylaminocarbonyl, $C_2$-$C_{10}$ haloalkylsulfonylaminocarbonyl, $C_3$-$C_{10}$ alkoxy(alkyl)aminocarbonyl or —$(CR^{15a}R^{15b})_mR^{16}$;

each $R^{15a}$ and $R^{15b}$ is independently H, halogen, $C_1$-$C_5$ alkyl, $C_1$-$C_5$ haloalkyl or $C_1$-$C_5$ alkoxy; or a geminal pair of $R^{15a}$ and $R^{15b}$ are taken together with the carbon atom to which they are attached to form —C(=O)— or a $C_3$-$C_6$ cycloalkyl or $C_3$-$C_6$ halocycloalkyl ring; or $R^{15a}$ and $R^{15b}$ attached to adjacent carbon atoms are taken together with the carbon atoms to which they are attached to form a $C_3$-$C_6$ cycloalkyl or $C_3$-$C_6$ halocycloalkyl ring;

each $R^{16}$ is independently phenyl, $C_3$-$C_8$ cycloalkyl, $C_3$-$C_8$ cycloalkenyl, $C_3$-$C_8$ cycloalkoxy, $C_3$-$C_8$ cycloalkenyloxy, 5- or 6-membered heteroaromatic ring or naphthalenyl or 8-, 9- or 10-membered heteroaromatic bicyclic ring system; or a 5- or 6-membered heterocyclic nonaromatic ring, optionally including ring members selected from the group consisting of C(=O), C(=S), C(=$NR^4$), $SiR^{5a}R^{5b}$ and $S(=O)_p(=NR^4)_q$; each ring or ring system optionally substituted with up to 5 substituents independently selected from $R^{17}$ on carbon atom ring members and $R^8$ on nitrogen atom ring members; provided that when $R^{12}$ is —$(CR^{15a}R^{15b})_mR^{16}$ and m is 0, then $R^{16}$ is other than $C_3$-$C_8$ cycloalkoxy or $C_3$-$C_8$ cycloalkenyloxy;

each $R^{17}$ is independently halogen, $C_1$-$C_6$ alkyl, $C_2$-$C_6$ alkenyl, $C_2$-$C_6$ alkynyl, $C_3$-$C_6$ cycloalkyl, $C_4$-$C_{10}$ alkylcycloalkyl, $C_3$-$C_6$ halocycloalkyl, $C_1$-$C_6$ haloalkyl, $C_2$-$C_6$ haloalkenyl, cyano, nitro, $C_1$-$C_6$ alkoxy, $C_3$-$C_8$ cycloalkoxy, $C_3$-$C_8$ halocycloalkoxy, $C_1$-$C_6$ haloalkoxy, $C_1$-$C_6$ alkylthio, $C_1$-$C_6$ alkylsulfinyl, $C_1$-$C_6$ alkylsulfonyl, $C_1$-$C_6$ haloalkylthio, $C_1$-$C_6$ haloalkylsulfinyl, $C_1$-$C_6$ haloalkylsulfonyl, $C_1$-$C_6$ alkylamino, $C_2$-$C_6$ dialkylamino, $C_2$-$C_6$ alkylcarbonyl, $C_2$-$C_6$ alkoxycarbonyl, $C_2$-$C_6$ alkylaminocarbonyl, $C_3$-$C_6$ dialkylaminocarbonyl, $C_3$-$C_6$ trialkylsilyl, phenyl, naphthalenyl or a 5- or 6-membered heteroaromatic ring;

each m is independently 0, 1 or 2;

each $R^{10}$ is independently H, $C_1$-$C_5$ alkyl, $C_2$-$C_5$ alkenyl, $C_2$-$C_5$ alkynyl, $C_3$-$C_6$ cycloalkyl, $C_3$-$C_6$ halocycloalkyl, $C_1$-$C_5$ haloalkyl, $C_2$-$C_5$ haloalkenyl, $C_2$-$C_5$ haloalkynyl, $C_2$-$C_5$ alkoxyalkyl, $C_2$-$C_5$ alkylcarbonyl or $C_1$-$C_5$ alkoxy;

each $R^{13a}$ and $R^{13b}$ is independently H, —CN, —C(=O)OR$^{18}$, $C_1$-$C_6$ alkyl, $C_2$-$C_6$ alkenyl, $C_2$-$C_6$ alkynyl, $C_3$-$C_8$ cycloalkyl, $C_3$-$C_8$ halocycloalkyl, $C_3$-$C_8$ cycloalkenyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ alkylamino, $C_2$-$C_6$ dialkylamino, $C_2$-$C_6$ alkylaminoalkyl, $C_2$-$C_6$ haloalkylaminoalkyl, $C_4$-$C_6$ cycloalkylaminoalkyl, $C_3$-$C_6$ dialkylaminoalkyl, $C_3$-$C_6$ halodialkylaminoalkyl, $C_5$-$C_{10}$ cycloalkyl(alkyl)aminoalkyl, $C_1$-$C_6$ alkoxy, $C_1$-$C_6$ haloalkoxy, $C_3$-$C_{10}$ cycloalkoxy, $C_1$-$C_{10}$ alkylthio, $C_1$-$C_{10}$ haloalkylthio, $C_3$-$C_{10}$ cycloalkylthio, $C_3$-$C_{10}$ trialkylsilyl or $C_3$-$C_{10}$ halotrialkylsilyl; or a phenyl or 5-or 6-membered heteroaromatic ring, a 8-, 9-or 10-membered heteroaromatic bicyclic ring system, or a 5-or 6-membered heterocyclic nonaromatic ring optionally including ring members selected from the group consisting of NR$^3$, C(=O), C(=S), C(=NR$^4$), SiR$^{5a}$R$^{5b}$ and S(=O)$_p$(=NR$^4$)$_q$, each ring or ring system optionally substituted on carbon ring members with 1 to 5 substituents selected from the group consisting of $C_1$-$C_3$ alkyl, halogen, —CN and $C_1$-$C_3$ alkoxy; or $R^{13a}$ and $R^{13b}$ are taken together with the carbon to which they are attached to form a 3-to 6-membered ring, said ring optionally including ring members selected from the group consisting of NR$^3$, C(=O), C(=S), C(=NR$^4$), SiR$^{5a}$R$^{5b}$ or S(=O)$_p$(=NR$^4$)$_q$ and optionally substituted on carbon ring members with 1 to 4 substituents selected from the group consisting of $C_1$-$C_2$ alkyl, halogen, —CN and $C_1$-$C_2$ alkoxy;

each $R^{14a}$ and $R^{14b}$ is independently H, —CN, —C(=O)OR$^{18}$, $C_1$-$C_6$ alkyl, $C_2$-$C_6$ alkenyl, $C_2$-$C_6$ alkynyl, $C_3$-$C_8$ cycloalkyl, $C_3$-$C_8$ halocycloalkyl, $C_3$-$C_8$ cycloalkenyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ alkylamino, $C_2$-$C_6$ dialkylamino, $C_2$-$C_6$ alkylaminoalkyl, $C_2$-$C_6$ haloalkylaminoalkyl, $C_4$-$C_6$ cycloalkylaminoalkyl, $C_3$-$C_6$ dialkylaminoalkyl, $C_3$-$C_6$ halodialkylaminoalkyl, $C_5$-$C_{10}$ cycloalkyl(alkyl)aminoalkyl, $C_1$-$C_6$ alkoxy, $C_1$-$C_6$ haloalkoxy, $C_3$-$C_{10}$ cycloalkoxy, $C_1$-$C_{10}$ alkylthio, $C_1$-$C_{10}$ haloalkylthio, $C_3$-$C_{10}$ cycloalkylthio, $C_3$-$C_{10}$ trialkylsilyl or $C_3$-$C_{10}$ halotrialkylsilyl; or a phenyl or 5-or 6-membered heteroaromatic ring, a 8-, 9-or 10-membered heteroaromatic bicyclic ring system, or a 5-or 6-membered heterocyclic nonaromatic ring, optionally including ring members selected from the group consisting of NR$^3$, C(=O), C(=S), C(=NR$^4$), SiR$^{5a}$R$^{5b}$ or S(=O)$_p$(=NR$^4$)$_q$ each ring or ring system optionally substituted on carbon ring members with 1 to 5 substituents selected from the group consisting of $C_1$-$C_3$ alkyl, halogen, —CN and $C_1$-$C_3$ alkoxy; or $R^{14a}$ and $R^{14b}$ are taken together with the carbon to which they are attached to form a 3-to 6-membered ring, said ring optionally including ring members selected from the group consisting of NR$^3$, C(=O), C(=S), C(=NR$^4$), SiR$^{5a}$R$^{5b}$ or S(=O)$_p$(=NR$^3$)$_q$ and optionally substituted on carbon ring members with 1 to 4 substituents selected from the group consisting of $C_1$-$C_2$ alkyl, halogen, —CN and $C_1$-$C_2$ alkoxy;

p and q are independently 0, 1 or 2 in each instance of S(=O)$_p$(=NR$^4$)$_q$, provided that the sum of p and q is 0, 1 or 2; and each $R^{18}$ is independently $C_1$-$C_6$ alkyl, $C_1$-$C_6$ haloalkyl, $C_3$-$C_6$ cycloalkyl, $C_4$-$C_7$ cycloalkylalkyl or $C_4$-$C_7$ alkylcycloalkyl.

2. A compound of claim 1 wherein each $R^2$ is independently H, halogen, cyano, hydroxy, —CHO, $C_1$-$C_3$ alkyl or $C_1$-$C_3$ alkoxy;

J is a phenyl or 5-or 6-membered heteroaromatic ring, a naphthalenyl ring system, or a 5-or 6-membered nonaromatic carbocyclic or heterocyclic ring, optionally including ring members selected from the group consisting of C(=O) or C(=S), each ring or ring system optionally substituted with 1 to 5 substituents independently selected from R$^7$ on carbon atom ring members and R$^8$ on nitrogen atom ring members;

each $R^7$ is independently halogen, $C_1$-$C_3$ alkyl or $C_1$-$C_3$ alkoxy;

$R^1$ is —NR$^{9a}$R$^{9b}$, —NR$^{10}$—NR$^{11a}$R$^{11b}$ or —OR$^{12}$;

each $R^{9a}$ and $R^{11a}$ is independently H, $C_1$-$C_{10}$ alkyl, $C_2$-$C_{10}$ alkenyl, $C_2$-$C_{10}$ alkynyl, $C_1$-$C_{10}$ haloalkyl, $C_2$-$C_{10}$ alkoxyalkyl, $C_1$-$C_{10}$ hydroxyalkyl or —(CR$^{15a}$R$^{15b}$)$_m$R$^{16}$;

each $R^{9b}$ and $R^{11b}$ is independently H, $C_1$-$C_{10}$ alkyl, $C_2$-$C_{10}$ alkenyl, $C_2$-$C_{10}$ alkynyl, $C_1$-$C_{10}$ haloalkyl or —(CR$^{15a}$R$^{15b}$)$_m$R$^{16}$;

$R^{12}$ is H, $C_1$-$C_{10}$ alkyl, $C_2$-$C_{10}$ alkenyl, $C_2$-$C_{10}$ alkynyl, $C_1$-$C_{10}$ haloalkyl, $C_2$-$C_{10}$ haloalkenyl or —(CR$^{15a}$R$^{15b}$)$_m$R$^{16}$;

each $R^{15a}$ and $R^{15b}$ is independently H, halogen or $C_1$-$C_5$ alkyl;

each $R^{16}$ is independently phenyl, $C_3$-$C_8$ cycloalkyl, $C_3$-$C_8$ cycloalkenyl, 5-or 6-membered heteroaromatic ring or naphthalenyl or 8-, 9-or 10-membered heteroaromatic bicyclic ring system; or a 5-or 6-membered heterocyclic nonaromatic ring, optionally including ring members selected from the group consisting of C(=O), C(=S), C(=NR$^4$), SiR$^{5a}$R$^{5b}$ and S(=O)$_p$(=NR$^4$)$_q$; each ring or ring system optionally substituted with up to 3 substituents independently selected from R$^{17}$ on carbon atom ring members and R$^8$ on nitrogen atom ring members;

m is 0 or 1;

each $R^{17}$ is independently halogen, $C_1$-$C_6$ alkyl, $C_2$-$C_6$ alkenyl, $C_2$-$C_6$ alkynyl, $C_3$-$C_6$ cycloalkyl, $C_4$-$C_{10}$ alkylcycloalkyl, $C_3$-$C_6$ halocycloalkyl, $C_1$-$C_6$ haloalkyl or cyano; or phenyl or 5-or 6-membered heteroaromatic ring; and $R^{10}$ is H, $C_1$-$C_5$ alkyl or $C_1$-$C_5$ haloalkyl.

3. A compound of claim 2 wherein

J is a phenyl or a 5-or 6-membered heteroaromatic ring, each ring optionally substituted up to 2 substituents independently selected from R$^7$ on carbon atom ring members and R$^8$ on nitrogen atom ring members;

each $R^7$ is independently halogen or $C_1$-$C_3$ alkyl;

$R^1$ is —NR$^{9a}$R$^{9b}$ or —NR$^{10}$NR$^{11a}$R$^{11b}$;

each $R^{9a}$ and $R^{11a}$ is independently $C_1$-$C_6$ alkyl, $C_2$-$C_6$ alkoxyalkyl, $C_1$-$C_6$ hydroxyalkyl or —(CR$^{15a}$R$^{15b}$)$_m$R$^{16}$;

each $R^{9b}$ and $R^{11b}$ is independently H, $C_1$-$C_{10}$ alkyl, $C_1$-$C_{10}$ haloalkyl or —(CR$^{15a}$R$^{15b}$)$_m$R$^{16}$;

m is 0;

each $R^{16}$ is independently $C_3$-$C_8$ cycloalkyl or phenyl, each optionally substituted up to 2 substituents independently selected from R$^{17}$;

$R^{17}$ is halogen, $C_1$-$C_6$ alkyl or cyano; and $R^{10}$ is H or methyl.

4. A compound of claim 3 wherein $R^2$ is H;

J is a phenyl or thiophene ring optionally substituted with up to 2 substituents independently selected from R$^7$;

each R⁷ is independently F or CH₃;
R¹ is —NR⁹ᵃR⁹ᵇ;
R⁹ᵃ is independently isopropyl or cyclopropyl; and
R⁹ᵇ is independently H.

5. A compound of claim 4 wherein
J is a phenyl or thiophene ring optionally substituted with up to 1 substituent selected from F and CH₃.

6. The compound of claim 1 which is selected from the group:
N-cyclopropyl-4-[2-(4-fluorophenyl)-6,7-dihydro-4H-pyrazolo[5,1-c][1,4]oxazin-3-yl]-2-pyrimidinamine,
4-[2-(4-fluorophenyl)-6,7-dihydro-4H-pyrazolo[5,1-c][1,4]oxazin-3-yl]-N-(1-methylethyl)-2-pyrimidinamine,
2-[[4-[2-(4-fluorophenyl)-6,7-dihydro-4H-pyrazolo[5,1-c][1,4]oxazin-3-yl]-2-pyrimidinyl]amino]-1-propanol,
4-(6,7-dihydro-2-phenyl-4H-pyrazolo[5,1-c][1,4]oxazin-3-yl)-N-(1-methylethyl)-2-pyrimidinamine,
N-cyclopropyl-4-(6,7-dihydro-2-phenyl-4H-pyrazolo[5,1-c][1,4]oxazin-3-yl)-2-pyrimidinamine, and
N-cyclopropyl-4-[6,7-dihydro-2-(3-thienyl)-4H-pyrazolo[5,1-c][1,4]oxazin-3-yl]-2-pyrimidinamine.

7. A method of preparing a compound of claim 1, comprising:
contacting a compound of Formula 1a

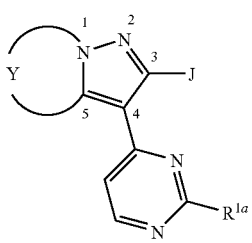

1a with a compound of Formula 2
or a reducing agent:
wherein
R¹ is halogen, —SCH₃, S(=O)CH₃, —S(=O)₂CH₃, —OS(=O)₂CH₃, —OS(=O)₂CF₃ or —OS(=O)₂Ph-p-CH₃; and
(a) when R¹ is other than hydrogen, then the compound of Formula 1a is contacted with the compound of Formula 2 in the presence of a base; and
(b) when R¹ is hydrogen, then R¹ᵃ is halogen and the compound of Formula 1a is contacted with the reducing agent.

8. A compound selected from Formula 1a, N-oxides, and salts thereof,

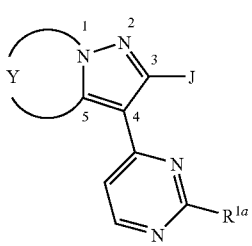

1a wherein
R¹ᵃ is halogen, —SCH₃, —S(=O)CH₃, —S(=O)₂CH₃, —OS(=O)₂CH₃, —OS(=O)₂CF₃ or —OS(=O)₂Ph-p-CH₃;

Y is

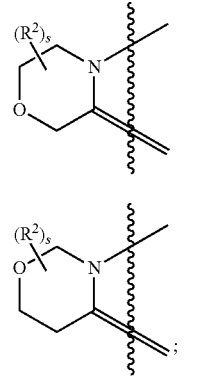

H-4 or

H-8 s is an integer from 0 to 4;
each R² is independently H, halogen, cyano, hydroxy, —CHO, —NHCHO, —N₃, —N=C=O, —N=C=S, —SH, —C(=O)NH₂, —C(=O)NHCN, —C(=O)OR⁶, —C(=O)NHOR⁶ᵃ, C₁-C₅ alkyl, C₂-C₅ alkenyl, C₂-C₅ alkynyl, C₃-C₆ cycloalkyl, C₃-C₆ halocycloalkyl, C₃-C₆ cycloalkenyl, C₁-C₅ haloalkyl, C₁-C₅ alkoxy, C₁-C₅ haloalkoxy, C₃-C₆ cycloalkoxy, C₂-C₅ alkenyloxy, C₃-C₅ haloalkenyloxy, C₂-C₅ alkynyloxy, C₂-C₅ alkylcarbonyl, C₂-C₅ alkylcarbonyloxy, C₂-C₅ haloalkylcarbonyloxy, C₃-C₅ alkoxycarbonylalkoxy, C₁-C₅ alkylthio, C₁-C₅ haloalkylthio, C₃-C₆ cycloalkylthio, C₂-C₅ alkyl(thiocarbonyl), C₂-C₅ alkylthio(thiocarbonyl), C₁-C₅ alkylsulfinyl, C₁-C₅ haloalkylsulfinyl, C₃-C₆ cycloalkylsulfinyl, C₁-C₅ alkylsulfonyl, C₁-C₅ haloalkylsulfonyl, C₃-C₆ cycloalkylsulfonyl, C₃-C₅ trialkylsilyl, C₃-C₅ halotrialkylsilyl, C₁-C₅ alkylamino, C₂-C₅ haloalkylamino, C₃-C₆ cycloalkylamino, C₂-C₅ dialkylamino or C₃-C₅ halodialkylamino;
each R³ is independently H, —CN, —C(=O)NH₂, —C(=O)NHCN, —CHO, —NHCHO, —C(=O)OR⁶, —C(=O)NHOR⁶ᵃ, hydroxy, C₁-C₅ alkyl, C₂-C₅ alkenyl, C₂-C₅ alkynyl, C₃-C₆ cycloalkyl, C₃-C₆ halocycloalkyl, C₃-C₆ cycloalkenyl, C₄-C₁₀ cycloalkylalkyl, C₄-C₇ alkylcycloalkyl, C₅-C₇ alkylcycloalkylalkyl, C₁-C₅ haloalkyl, C₂-C₅ alkylcarbonyl, C₂-C₅ haloalkylcarbonyl, C₄-C₇ cycloalkylcarbonyl, C₂-C₆ alkoxycarbonyl, C₂-C₆ haloalkoxycarbonyl, C₄-C₇ cycloalkoxycarbonyl, C₃-C₆ alkoxyalkylcarbonyl, C₃-C₆ alkoxyalkoxycarbonyl, C₂-C₆ (alkylthio)carbonyl, C₂-C₆ alkoxy(thiocarbonyl), C₂-C₆ alkyl(thiocarbonyl), C₂-C₆ alkylthio(thiocarbonyl), C₂-C₆ alkylaminocarbonyl, C₄-C₇ cycloalkylaminocarbonyl, C₃-C₆ dialkylaminocarbonyl, C₂-C₆ alkylamino(thiocarbonyl), C₃-C₆ dialkylamino(thiocarbonyl), C₃-C₆ alkoxy(alkyl)aminocarbonyl, C₁-C₅ alkoxy, C₁-C₅ haloalkoxy, C₁-C₅ alkylthio, C₁-C₅ haloalkylthio, C₃-C₆ cycloalkylthio, C₁-C₅ alkylaminosulfonyl, C₃-C₅ trialkylsilyl or C₃-C₅ halotrialkylsilyl;
each R⁴ is independently H, cyano, amino, hydroxy, C₁-C₆ alkyl, C₃-C₁₀ cycloalkyl, C₂-C₆ alkylcarbonyl, C₂-C₆ haloalkylcarbonyl, C₁-C₆ alkoxy, phenyl or benzoyl;
each R⁵ᵃ and R⁵ᵇ is independently C₁-C₅ alkyl, C₂-C₅ alkenyl, C₂-C₅ alkynyl, C₃-C₅ cycloalkyl, C₃-C₆ halocycloalkyl, C₄-C₁₀ cycloalkylalkyl, C₄-C₇ alkylcycloalkyl, C₅-C₇ alkylcycloalkylalkyl, C₁-C₅ haloalkyl, C₁-C₅ alkoxy or C₁-C₅ haloalkoxy;

each $R^6$ is independently H, $C_1$-$C_6$ alkyl, $C_1$-$C_6$ haloalkyl, $C_3$-$C_6$ cycloalkyl, $C_4$-$C_7$ cycloalkylalkyl, $C_4$-$C_7$ alkylcycloalkyl or benzyl;

each $R^{6a}$ is independently $C_1$-$C_6$ alkyl, $C_1$-$C_6$ haloalkyl, $C_3$-$C_6$ cycloalkyl, $C_4$-$C_7$ cycloalkylalkyl or $C_4$-$C_7$ alkylcycloalkyl;

J is a phenyl or 5-or 6-membered heteroaromatic ring or a naphthalenyl or 8-to 10-membered heteroaromatic bicyclic ring system, each ring or ring system optionally substituted with up to 5 substituents independently selected from $R^7$ on carbon atom ring members and $R^8$ on nitrogen atom ring members; or J is a 5-or 6-membered nonaromatic carbocyclic or heterocyclic ring, optionally including ring members selected from the group consisting of C(=O), C(=S), C(=NR$^4$), SiR$^{5a}$R$^{5b}$ and S(=O)$_p$(=NR$^4$)$_q$, each ring optionally substituted with 1 to 5 substituents independently selected from $R^7$ on carbon atom ring members and $R^8$ on nitrogen atom ring members;

each $R^7$ is independently halogen, $C_1$-$C_6$ alkyl, $C_2$-$C_6$ alkenyl, $C_2$-$C_6$ alkynyl, $C_3$-$C_6$ cycloalkyl, $C_3$-$C_6$ halocycloalkyl, $C_4$-$C_7$ alkylcycloalkyl, $C_1$-$C_6$ haloalkyl, $C_2$-$C_6$ haloalkenyl, cyano, nitro, $C_1$-$C_6$ alkoxy, $C_1$-$C_6$ haloalkoxy, $C_1$-$C_6$ alkylthio, $C_1$-$C_6$ alkylsulfinyl, $C_1$-$C_6$ alkylsulfonyl, $C_1$-$C_6$ haloalkylthio, $C_1$-$C_6$ haloalkylsulfinyl, $C_1$-$C_6$ haloalkylsulfonyl, $C_1$-$C_6$ alkylamino, $C_2$-$C_6$ dialkylamino, $C_2$-$C_6$ alkylcarbonyl, $C_2$-$C_6$ alkoxycarbonyl, $C_2$-$C_6$ alkylaminocarbonyl, $C_3$-$C_6$ dialkylaminocarbonyl or $C_3$-$C_6$-trialkylsilyl;

$R^8$ is $C_1$-$C_3$ alkyl; and p and q are independently 0, 1 or 2, in each instance of S(=O)$_p$(=NR$^3$)$_q$, provided that the sum of p and q is 0, 1 or 2.

9. A compound of claim 8 wherein
$R^{1a}$ is halogen or —S(=O)$_2$CH$_3$.

10. A compound of claim 9 wherein
$R^{1a}$ is Cl or —S(=O)$_2$CH$_3$.

11. The compound of claim 8 which is 2-(4-fluorophenyl)-4,5-dihydro-3-[2-(methylsulfonyl)-4-pyrimidinyl]-7H-pyrazolo[1,5-c][1,3]oxazine.

12. A fungicidal composition comprising (a) a compound of claim 1; and (b) at least one other fungicide.

13. A fungicidal composition comprising (a) a fungicidally effective amount of a compound of claim 1; and (b) at least one additional component selected from the group consisting of surfactants, solid diluents and liquid diluents.

14. A method for controlling plant diseases caused by fungal plant pathogens comprising applying to the plant or portion thereof, or to the plant seed, a fungicidally effective amount of a compound of claim 1.

* * * * *